(12) United States Patent
Gaertig et al.

(10) Patent No.: US 8,361,780 B2
(45) Date of Patent: Jan. 29, 2013

(54) BIOLOGICAL SYSTEM AND ASSAY FOR IDENTIFYING MODULATORS OF TUBULIN LIGASES

(75) Inventors: Jacek Gaertig, Athens, GA (US); Dorota Wloga, Legionowo (PL); Swati M. Suryavanshi, Pittsburgh, PA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 241 days.

(21) Appl. No.: 12/658,487

(22) Filed: Feb. 5, 2010

(65) Prior Publication Data
US 2010/0261220 A1 Oct. 14, 2010

Related U.S. Application Data

(63) Continuation-in-part of application No. 11/479,098, filed on Jun. 30, 2006, now abandoned.

(60) Provisional application No. 60/695,776, filed on Jun. 30, 2005.

(51) Int. Cl.
*C12N 1/10* (2006.01)
*C12N 15/74* (2006.01)
*C12Q 1/02* (2006.01)
*C12P 1/00* (2006.01)

(52) U.S. Cl. .......... 435/258.1; 435/29; 435/471; 435/41

(58) Field of Classification Search ................ 435/258.1, 435/29, 471, 41
See application file for complete search history.

(56) References Cited

U.S. PATENT DOCUMENTS

| | | | |
|---|---|---|---|
| 6,846,481 | B1 | 1/2005 | Gaertig et al. |
| 2003/0027192 | A1 | 2/2003 | Gorovsky et al. |
| 2005/0106164 | A1 | 5/2005 | Gaertig et al. |
| 2007/0031927 | A1 | 2/2007 | Gaertig et al. |

FOREIGN PATENT DOCUMENTS
WO  WO 00/46381 A1  8/2000

OTHER PUBLICATIONS

Janke et al., Tubulin polyglutamylase enzymes are members of the TTL domain protein family. Science, vol. 308: 1758-1762.*
Wloga et al., Glutamylation on a-tubulin is not essential but affects the assembly and functions of a subset of microtubules in *Tetrahymena thermophila* Eukaryotic Cell, 2008, vol. 7 (8): 1362-1372.*
Wloga et al., TTLL3 is tubulin glycine ligase that regulates the assembly of cilia. Developmental Cell, 2009, vol. 16: 867-876.*
Wloga et al., Hyperglutamylation of tubulin can either stabilize or destabilize microtubules in the same cell. Eukaryotic Cell, 2010, Vo. 9 (1): 184-193.*
Abal et al., "Centrioles resist forces applied on centrosomes during G2/M transition," Jun. 2005 *Biol. Cell* 97:425-434.
Adoutte et al., "Microtubule diversity in ciliated cells: evidence for its generation by post-translational modification in the axonemes of Paramecium and quail oviduct cells," 1991 *Biol. Cell* 71:227-245.
Alexander et al., "Characterization of posttranslational modifications in neuron-specific class III beta-tubulin by mass spectrometry," Jun. 1, 1991 *Proc. Natl. Acad. Sci. USA* 88:4685-4689.
Artymiuk et al., "Biotin carboxylase comes into the fold," Feb. 1996 *Nat. Struct. Biol.* 3:128-132.
Attwell et al., "A temperature-sensitive mutation affecting synthesis of outer arm dyneins in *Tetrahymena thermophila*," Mar.-Apr. 1992 *J. Protozool.* 39, 261-266.
Audebert et al., "Reversible Polyglutamylation of α- and β-Tubulin and Microtubule Dynamics in Mouse Brain Neurons," Jun. 1993 *Mol. Biol. Cell* 4:615-626.
Audebert et al., "Developmental regulation of polyglutamylated alpha- and beta-tubulin in mouse brain neurons," Aug. 1994 *J. Cell Sci.* 107(Pt. 8):2313-2322.
Backofen et al., "Cloning and characterization of the mammalian-specific nicolin 1 gene (*NICN1*) encoding a nuclear 24 kDa protein," Nov. 2002 *Eur. J. Biochem.* 269(21):5240-5245.
Bacon et al., "A Fast Algorithm for Rendering Space-Filling Molecule Pictures," 1988 *J. Mol. Graph.* 6:219-220.
Bagdasarian and Bagdasarian, "Chapter 18: Gene Cloning and Expression," in *Methods for General and Molecular Bacteriology*, Gerhardt et al. (eds.). American Society for Microbiology: Washington, D.C.; 1994. Title page, publisher's page, and pp. 406-417.
Barlow et al., "Paclitaxel-dependent mutants have severely reduced microtubule assembly and reduced tubulin synthesis," Sep. 1, 2002 *J. Cell Sci.* 115:3469-3478.
Bhattacharyya et al., "Tubulin, hybrid dimers, and tubulin S. Stepwise charge reduction and polymerization," Aug. 25, 1985 *J. Biol. Chem.* 260:10208-10216.
Bobinnec et al., "Glutamylation of Centriole and Cytoplasmic Tubulin in Proliferating Non-neuronal Cells," 1998 *Cell Motil. Cytoskeleton* 39:223-232.
Bobinnec et al., "Centriole Disassembly in vivo and Its Effect on Centrosome Structure and Function in Vertebrate Cells," Dec. 1998 *J. Cell Biol.* 143(6):1575-1589.
Bonnet et al., "Differential Binding Regulation of Microtubule-associated Proteins MAP1A, MAP1B, and MAP2 by Tubulin Polyglutamylation," Apr. 2001 *J. Biol. Chem.* 276(16):12839-12848.
Boucher et al., "Polyglutamylation of Tubulin as a Progressive Regulator of in Vitro Interactions between the Microtubule-associated Protein Tau and Tubulin,"1994, *Biochemistry*, Oct. 33(41):12471-12477.
Bradbury et al., "Histone deacetylases in acute myeloid leukaemia show a distinctive pattern of expression that changes selectively in response to deacetylase inhibitors," Oct. 2005 *Leukemia* 19(10):1751-1759.
Bré et al., "Glutamylated Tubulin Probed in Ciliates With the Monoclonal Antibody GT335," 1994 *Cell Motility and the Cytoskeleton* 27(4):337-349.
Bré et al., "Axonemal tubulin polyglycylation probed with two monoclonal antibodies: widespread evolutionary distribution, appearance during spermatozoan maturation and possible function in motility," Apr. 1996 *J. Cell Sci.* 109:727-738.

(Continued)

Primary Examiner — Ganapathirama Raghu
(74) Attorney, Agent, or Firm — Mueting Raasch & Gebhardt, P.A.

(57) ABSTRACT

*Tetrahymena* is used as a host cell in a biological assay for identification of modulators of tubulin ligases.

16 Claims, 44 Drawing Sheets

OTHER PUBLICATIONS

Bré et al., "Tubulin polyglycylation: differential posttranslational modification of dynamic cytoplasmic and stable axonemal microtubules in paramecium," Sep. 1998 *Mol. Biol. Cell* 9:2655-2665.

Bressac et al., "A massive new posttranslational modification occurs on axonemal tubulin at the final step of speimatogenesis in *Drosophila*," Aug. 1995 *Eur. J Cell Biol.* 67:346-355.

Brooks et al., "CHARMM: A Program for Macromolecular Energy, Minimization, and Dynamic Calculations," 1983 *J Comp. Chem.* 4(2):187-217.

Brown et al., "Hypoxia Regulates Assembly of Cilia in Suppressors of Tetrahymena Lacking an Intraflagellar Transport Subunit Gene," Aug. 2003 *Mol. Biol. Cell* 14:3192-3207. Available online May 3, 2003.

Bucher et al., "A Flexible Motif Search Technique Based on Generalized Profiles," 1996 *Comput Chem.* 20(1):3-23.

Burdine and Schier, "Conserved and divergent mechanisms in left-right axis formation," Apr. 1, 2000 *Genes Dev.* 14:763-776.

Bylund, et al., "Replication Protein A-Directed Unloading of PCNA by the Ctf18 Cohesion Establishment Complex," Jul. 2005 *Mol. Biol. Cell* 25(13):5445-5455.

Callen et al., "Isolation and characterization of libraries of monoclonal antibodies directed against various forms of tubulin in *Paramecium*," 1994 *Biol. Cell* 81:95-119.

Campbell et al., "Mutation of a Novel Gene Results in Abnormal Development of Spermatid Flagella, Loss of Intermale Aggression and Reduced Body Fat in Mice," Sep. 2002 *Genetics* 162:307-320.

Carter et al., "Structure and functional role of dynein's microtubule-binding domain," Dec. 12, 2008 *Science* 322:1691-1695.

Cassidy-Hanley et al., "Germline and Somatic Transformation of Mating *Tetrahymena thermophila* by Particle Bombardment," May 1997 *Genetics* 146:135-147.

Cheung et al., "A small-molecule inhibitor of skeletal muscle myosin II," Jan. 2002 *Nat. Cell. Biol.* 4:83-88. Available online Dec. 17, 2001.

Cheung et al., "AIDS-Related Malignancies: Emerging Challenges in the Era of Highly Active Antiretroviral Therapy," Jun.-Jul. 2005 *The Oncologist; Lymphoma* 10:412-426.

Chilcoat, et al., "Granule Lattice Protein 1 (Grl1p), an Acidic, Calcium-Binding Protein in *Tetrahymena thermophila* Dense-Core Secretory Granules, Influences Granule Size, Shape, Content Organization, and Release but Not Protein Sorting or Condensation," Dec. 1996 *J Cell Biol.* 135(6 part 2):1775-1787.

Chomczynski et al., "Short technical reports. Modification of the TRI Reagent™ Procedure for Isolation of RNA from Polysaccharide-and Proteoglycan-Rich Sources," Dec. 1995 *Biotechniques* 19(6):942-945.

Collins et al., "*Tetrahymena Thermophia*," May 2005 *Curr Biol.* 15(9):R317-318.

Crosa et al., "Chapter 16: Plasmids," in *Methods for General and Molecular Bacteriology*, Gerhardt et al. (eds.). American Society for Microbiology: Washington, D.C.; 1994. Title page, publisher's page, and pp. 365-386.

Dave et al., "DYF-1 is required for assembly of the axoneme in *Tetrahymena thermophila*," Sep. 2009 *Eukaryot. Cell* 8:1397-1406. Available online Jul. 6, 2009.

Davenport et al., "Disruption of intraflagellar transport in adult mice leads to obesity and slow-onset cystic kidney disease," Sep. 18, 2007 *Curr. Biol.* 17:1586-1594. Available online Sep. 6, 2007.

Dayringer et al., "Interactive program for visualization and modelling of proteins, nucleic acids and small molecules," Jun. 1986 *J. Mol. Graphics* 4(2):82-87.

de Bruijn and Rossback, "Chapter 17: Transposon Mutagenesis," in *Methods for General and Molecular Bacteriology*, Gerhardt et al. (eds.). American Society for Microbiology: Washington, D.C.; 1994. Title page, publisher's page, and pp. 387-405.

Dentler, "Structures linking the tips of ciliary and flagellar microtubules to the membrane," Apr. 1980 *J. Cell Sci.* 42:207-220.

Dideberg et al., "Tubulin tyrosine ligase: a shared fold with the glutathione synthetase ADP-forming family," Feb. 1998 *Trends Biochem. Sci.* 23:57-58.

Duan and Gorovsky, "Both carboxy-terminal tails of alpha- and beta-tubulin are essential, but either one will suffice," Feb. 19, 2002 *Curr. Biol.* 12:313-316.

Dupuis, "The beta-tubulin genes of *Paramecium* are interrupted by two 27 by introns," Oct. 1992 *EMBO J.* 11:3713-3719.

Dupuis-Williams et al., "The tubulin gene family of *Paramecium*: characterization and expression of the alpha PT1 and alpha PT2 genes which code for alpha-tubulins with unusual C-terminal amino acids, GLY and ALA," 1996 *Biol. Cell* 87:83-93.

Dymek et al., "PF15p is the *Chlamydomonas* homologue of the Katanin p80 subunit and is required for assembly of flagellar central microtubules," Aug. 2004 *Eukaryot. Cell* 3:870-879.

Edde et al., "Posttranslational Glutamylation of α-Tubulin," Jan. 1990 *Science* 247(4938):83-85.

Eisen, et al., "Macronuclear Genome Sequence of the Ciliate *Tetrahymena thermophila*, a Model Eukaryote," Online publication Aug. 29, 2006; DOI:10.1371/journalpbio.0040286. [Retrieved on Dec. 13, 2006]. Retrieved from the Internet: <URL:biology.plosjournals.org/perlserv/?request=get-document&doi=10.1371/joumal.pbio.0040286>; 77 pages.

Eisen et al., "Macronuclear Genome Sequence of the Ciliate *Tetrahymena thermophila*, a Model Eukaryote," Sep. 2006. *PloS Biol.* 4(9)(e286):1620-1642.

Eisenstadt et al., "Chapter 13: Gene Mutation," in *Methods for General and Molecular Bacteriology*, Gerhardt et al. (eds.). American Society for Microbiology: Washington, D.C.; 1994. Title page, publisher's page, and pp. 297-316.

Ersfeld et al., "Characterization of the Tubulin-Tyrosine Ligase," Feb. 1993 *J. Cell Biol.* 120(3):725-732.

Essner et al., "Kupffer's vesicle is a ciliated organ of asymmetry in the zebrafish embryo that initiates left-right development of the brain, heart and gut," Mar. 2005 *Development* 132:1247-1260. Available online Feb. 16, 2005.

Fahmy, "Study identifies critical 'traffic engineer' of the nervous system," *Franklin News* Sep. 8, 2010. Available online [retrieved on Jun. 26, 2012]. Retrieved from the Internet: <http://www.franklin.uga.edu/news/articles/1000/traffic_engineer.html>; 2 pages.

Felsenstein, "An Alternating Least Squares Approach to Inferring Phylogenies from Pairwise Distances," Mar. 1997 *Systematic Biology* 46(1):101-111.

Fennell et al., "Isotype expression, post-translational modification and stage-dependent production of tubulins in erythrocytic *Plasmodium falciparum*," Apr. 2008 *Int. J. Parasitol.* 38:527-539.

Fleury et al., "Where and when is microtubule diversity generated in *Paramecium*? Immunological properties of microtubular networks in the interphase and dividing cells," 1995 *Protoplasma* 189:37-60.

Fouquet et al., "Differential distribution of glutamylated tubulin during spermatogenesis in mammalian testis," 1994 *Cell Motil. Cytoskeleton* 27:49-58.

Fraering et al.,"Purification and Characterization of the Human γ-Secretase Complex," Aug. 2004 *Biochemistry* 43(30):9774-9789. Available online Jul. 10, 2004.

Fujiu et al., "Reorganization of Microtubules in the Amitotically Dividing Macronucleus of *Tetrahymena*," May 2000 *Cell Motil. Cytoskeleton* 46(1):17-27.

Gaertig et al., "Spatio-temporal reorganization of intracytoplasmic microtubules is associated with nuclear selection and differentiation during the developmental process in the ciliate *Tetrahymena thermophila*," 1992 *Protoplasma* 167:74-87.

Gaertig et al., "Perspectives on tubulin isotype function and evolution based on the observation that *Tetrahymena thermophila* microtubules contain a single α- and γ-tubulin," 1993 *Cell Motil. Cytoskeleton* 25: 243-53.

Gaertig et al., "Surface display of a parasite antigen in the ciliate *Tetrahymena thermophila*," May 1999 *Nat. Biotechnol.* 17:462-465.

Gaertig, "Molecular Mechanisms of Microtubular Organelle Assembly in *Tetrahymena*," May-Jun. 2000 *J. Eukaryotic Microbiol.* 47(3):185-190.

Gaertig, Jacek, "Role of Tubulin Post-Translational Modification in Functional Adaptation of Microtubules," Grant Abstract, Grant No. MBC-0235826, Award No. 0235826 [online]. National Science Foundation, NSF Cellular Systems Program, continuing grant, project dates Apr. 17, 2003 to Apr. 30, 2007 (estimated) [retrieved on Nov. 8, 2006]. Retrieved from the Internet: <URL:www.nsf.gov/awardsearch/showAward.do?AwardNumber=0235826>; 3 pgs.

Gaertig and Wloga, "Chapter 4. Ciliary tubulin and its post-translational modifications," in *Current Topics in Developmental Biology: Ciliary Function in Mammalian Development*, Yoder (ed.). Academic Press: San Diego, CA; 2008. Title page, publisher's page, and pp. 83-109.

Gagnon et al., "The polyglutamylated lateral chain of alpha-tubulin plays a key role in flagellar motility," Jun. 1996. *J. Cell Sci.* 109(Pt 6):1545-1553.

Galperin et al., "A diverse superfamily of enzymes with ATP-dependent carboxylate-amine/thiol ligase activity," Dec. 1997 *Protein Sci.* 6(12):2639-2643.

Galtier et al., "SEAVIEW and PHYLO_WIN: two graphic tools for sequence alignment and molecular phylogeny," Dec. 1996 *Comput. Appl. Biosci.* 12(6):543-548.

Gee et al., "An extended microtubule-binding structure within the dynein motor domain," Dec. 11, 1997 *Nature* 390:636-639.

Gorovsky et al., "Chapter 16. Isolation of micro- and macronuclei of *Tetrahymena pyriformis*," in Methods *Cell Biol.* vol. IX. Prescott (Ed.). Academic Press: New York, NY; 1975. Title page, publisher's page, and pp. 311-327.

Haddad et al., "Analysis of Exocytosis Mutants Indicates Close Coupling between Regulated Secretion and Transcription Activation in *Tetrahymena*," Sep. 1997 *Proc. Natl. Acad. Sci.* U S A 94:10675-10680.

Haggarty et al., "Domain-Selective Small-Molecule Inhibitor of Histone Deacetylase 6 (HDAC6)-Mediated Tubulin Deacetylation," Apr. 2003 *Proc. Natl. Acad. Sci.* U.S.A. 100(8):4389-4394.

Hagiwara et al., "Mechanism of Taxane Neurotoxicity," Jan. 2004 *Breast Cancer* 11(1):82-85.

Hai et al., "Chapter 28: Knockout Heterokaryons Enable Facile Mutagenic Analysis of Essential Genes in *Tetrahymena*," in *Methods in Cell Biology*, vol. 62. Academic Press: New York, NY; 1999. pp. 513-531.

Han et al., "Intraflagellar transport is required in *Drosophila* to differentiate sensory cilia but not sperm," Sep. 30, 2003 *Curr. Biol.* 13:1679-1686.

Hara et al., "A Pseudo-Michaelis Quaternary Complex in the Reverse Reaction of a Ligase: Structure of *Escherichia coli* B Glutathione Synthetase Complexed with ADP, Glutathione, and Sulfate at 2.0 Å Resolution," Sep. 1996 *Biochemistry* 35:11967-11974.

Hennenfent et al., "Novel formulations of taxanes: a review. Old wine in a new bottle?" May 2006 *Annals of Oncology* 17(5):735-749.

Hennessey et al., "Inner arm dynein 1 is essential for $Ca^{++}$-dependent ciliary reversals in *Tetrahymena thermophila*," Dec. 2002 *Cell Motil. Cytoskeleton* 53:281-288. Available online Oct. 11, 2002.

Hansen and Zeiske, "Development of the olfactory organ in the zebrafish, *Brachydanio rerio*," Jul. 8, 1993 *J Comp. Neurol.* 333:289-300.

Hideshima et al., "Small-molecule inhibition of proteasome and aggresome function induces synergistic antitumor activity in multiple myeloma," Jun. 2005 *Proc. Natl. Acad. Sci.* USA 102(24):8567-8572.

Hofmann et al., "The FHA domain: a putative nuclear signalling domain found in protein kinases and transcription factors," Sep. 1995 *Trends Biochem. Sci.* 20:347-349.

Holleran et al., "Centractin (ARP1) Associates with Spectrin Revealing a Potential Mechanism to Link Dynactin to Intracellular Organelles," Dec. 1996 *J. Cell Biol.* 135(6 Pt. 2):1815-1829.

Hoyle et al., "Axoneme-dependent tubulin modifications in singlet microtubules of the *Drosophila* sperm tail," Apr. 2008 *Cell Motil. Cytoskeleton* 65:295-313. Available online Jan. 18, 2008.

Hubbert et al., "HDAC6 is a microtubule-associated deacetylase," May 2002 *Nature* 417:455-458.

Iftode et al., "Tubulin polyglycylation: a morphogenetic marker in ciliates," Dec. 2000 *Biol. Cell* 92:615-628.

Ikegami et al., "TTLL7 is a mammalian beta-tubulin polyglutamylase required for growth of MAP2-positive neurites," Oct. 13, 2006 *J Biol. Chem.* 281(41):30707-30716. Epub Aug. 9, 2006.

Ikegami et al., "Loss of alpha-tubulin polyglutamylation in ROSA22 mice is associated with abnormal targeting of KIF1A and modulated synaptic function," Feb. 27, 2007 *Proc. Natl. Acad. Sci.* USA 104:3213-3218. Available online Feb. 20, 2007.

Ikegami et al., "TTLL10 is a protein polyglycylase that can modify nucleosome assembly protein 1," Apr. 2, 2008 *FEBS Lett.* 582:1129-1134. Available online Mar. 10, 2008.

Ikegami and Setou, "TTLL10 can perform tubulin glycylation when co-expressed with TTLL8," Jun. 18, 2009 *FEBS Lett.* 583:1957-1963. Available online May 8, 2009.

Jeanmougin et al., "Multiple sequence alignment with Clustal X," Oct. 1998 *Trends Biochem. Sci.* 23:403-405.

Jerka-Dziadosz et al., "Cellular polarity in ciliates: persistence of global polarity in a disorganized mutant of *Tetrahymena thermophila* that disrupts cytoskeletal organization," Jun. 1995 *Dev. Biol.* 169:644-661.

Jerka-Dziadosz et al., "The dynamics of filamentous structures in the apical band, oral crescent, fission line and the postoral meridional filament in *Tetrahymena thermophila* revealed by monoclonal antibody 12G9," May 2001 *Protist* 152:53-67.

Kamiya, "Functional diversity of axonemal dyneins as studied in *Chlamydomonas* mutants," 2002 *Int. Rev. Cytol.* 219:115-155.

Kann et al., "Differential distribution of glutamylated tubulin in the flagellum of mouse spermatozoa," Jun. 1995 *Tissue Cell* 27:323-329.

Kann et al., "Glutamylated Tubulin: Diversity of Expression and Distribution of Isoforms," May 2003 *Cell Motil. Cytoskeleton* 55(1):14-25.

Kisselev, "Polypeptide release factors in prokaryotes and eukaryotes: same function, different structure," 2002 *Structure* 10:8-9.

Knipling et al., "Preparation and properties of pure tubulin S," 1999 *Cell Motil. Cytoskeleton* 43:63-71.

Kotani et al., "Mechanical properties of inner-arm dynein-f (dynein I1) studied with in vitro motility assays," Aug. 1, 2007 *Biophys. J.* 93:886-894. Available online May 11, 2007.

Kovacs et al., "HDAC6 Regulates Hsp90 Acetylation and Chaperone-Dependent Activation of Glucocorticoid Receptor," May 2005 *Mol. Cell* 18:601-607.

Kozminski et al., "A motility in the eukaryotic flagellum unrelated to flagellar beating," Jun. 15, 1993 *Proc. Natl. Acad. Sci.* USA 90:5519-5523.

Kozminski et al., "The *Chlamydomonas* kinesin-like protein FLA10 is involved in motility associated with the flagellar membrane," Dec. 1995 *J. Cell Biol.* 131:1517-1527.

Kramer-Zucker et al., "Cilia-driven fluid flow in the zebrafish pronephros, brain and Kupffer's vesicle is required for normal organogenesis," Apr. 2005 *Development* 132:1907-1921.

Kraulis, "MOLSCRIPT: a program to produce both detailed and schematic plots of protein structures," 1991 *J. Appl. Crystallog* 24:946-950.

Kreitzer et al., "Detyrosination of Tubulin Regulates the Interaction of Intermediate Filaments with Microtubules In Vivo via a Kinesin-dependent Mechanism," Apr. 1999 *Mol. Biol. Cell* 10:1105-1118.

Kubo et al., "Tubulin polyglutamylation regulates axonemal motility by modulating activities of inner-arm dyneins," Mar. 9, 2010 *Curr. Biol.* 20:441-445. Available online Feb. 25, 2010.

Larcher et al., "Interaction of kinesin motor domains with alpha- and beta-tubulin subunits at a tau-independent binding site. Regulation by polyglutamylation," Sep. 6, 1996 *J. Biol. Chem.* 271:22117-22124.

Lechtreck and Geimer, "Distribution of polyglutamylated tubulin in the flagellar apparatus of green flagellates," Nov. 2000 *Cell Motil. Cytoskeleton* 47:219-235.

LeDizet and Piperno, "Detection of acetylated alpha-tubulin by specific antibodies," in *Methods in Enzymology* vol. 196—*Molecular Motors and the Cytoskeleton*. Vallee (Ed.). Academic Press: Sand Diego, CA; 1991. Title page and pp. 264-274.

Leroux et al., "Protein folding: Versatility of the cytosolic chaperonin TriC/CCT," Apr. 2000 *Curr Biol.* 10(7):R260-R264.

Leszczynski et al., "The lattice constant of a nonperfect crystal measured by X-ray diffraction," 1993 *J. Appl. Crystallog.* 26:280-283.

Letunic et al., "SMART 6: recent updates and new developments," Jan. 2009 *Nucleic Acids Res.* 37:D229—D232. Available online Oct. 31, 2008.

Lopez-Fanarraga et al., "Review: Postchaperonin Tubulin Folding Cofactors and Their Role in Microtubule Dynamics," Aug. 2001 *J. Struct Biol*. 135(2):219-229.

Lu et al., "The *Caenorhabditis elegans* Microtubule-severing Complex MEI-1/MEI-2 Katanin Interacts Differently with Two Superficially Redundant β-Tubulin Isotypes," Jan. 2004 *Mol. Biol. Cell* 15:142-150.

Ludmann, "Biochemical analysis of a mutant *Tetrahymena* lacking outer dynein arms," Sep.-Oct. 1993 *J. Euk. Microbiol*. 40:650-660.

Ludueña, "Multiple Forms of Tubulin: Different Gene Products and Covalent Modifications," 1988 *Int. Review Cytol*. 178:207-275.

Maeda et al., "Large-scale analysis of gene function in *Caenorhabditis elegans* by high-throughput RNAi," Feb. 2001 *Curr. Biol*. 11(3):171-176.

Marcus et al., "The Synergistic Combination of the Farnesyl Transferase Inhibitor Lonafamib and Paclitaxel Enhances Tubulin Acetylation and Requires a Functional Tubulin Deacetylase," May 2005 *Cancer Res*. 65(9):3883-3893.

Mary et al., "Class I and IVa beta-tubulin isotypes expressed in adult mouse brain are glutamylated," Oct. 10, 1994 *FEBS Lett*. 353:89-94.

Mary et al., "Posttranslational modifications in the C-terminal tail of axonemal tubulin from sea urchin sperm," Apr. 26, 1996 *J. Biol. Chem*. 271:9928-9933.

Matsuyama et al., "In vivo destabilization of dynamic microtubules by HDAC6-mediated deacetylation," Dec. 2002, *EMBO J*. 21(24):6820-6831.

McGrath et al., "Regulation and Evolution of the Single Alpha-Tubulin Gene of the Ciliate *Tetrahymena thermophila*," 1994 *Cell Motil.Cytoskeleton* 27(3):272-283.

McNally and Vale, "Identification of katanin, an ATPase that severs and disassembles stable microtubules," Nov. 1993 *Cell* 75:419-429.

Million et al., "Polyglutamylation and polyglycylation of α- and β-tubulins during in vitro ciliated cell differentiation of human respiratory epithelial cells," Dec. 1999 *J. Cell Sci*. 112(pt. 23):4357-4366.

Mukai et al., "Recombinant mammalian tubulin polyglutamylase TTLL7 performs both initiation and elongation of polyglutamylation on beta-tubulin through a random sequential pathway," Feb. 10, 2009 *Biochemistry* 48:1084-1093.

Multigner et al., "The A and B tubules of the outer doublets of sea urchin sperm axonemes are composed of different tubulin variants," 1996 *Biochemistry* 35:10862-10871.

National Center for Biotechnology Information, National Library of Medicine, National Institutes of Health, GenBank Locus Q8NG68, Accession No. Q8NG68, "Tubulin-tyrosine ligase (TTL)," [online]. Bethesda, MD [retrieved on Dec. 20, 2006]. Retrieved from the Internet: <URL:ncbi.nlm.nih.gov/entrez/viewer.fcgi?db=protein&val=47117358>; 3 pgs.

National Center for Biotechnology Information, National Library of Medicine, National Institutes of Health, GenBank Locus NP_036395, Accession No. NP_036395, "tubulin tyrosine ligase-like family, member 1 isoform a [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=11068135>; 2 pgs.

National Center for Biotechnology Information, National Library of Medicine, National Institutes of Health, GenBank Locus AAH30650, Accession No. AAH30650, "TTLL2 protein [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=45710086>; 2 pgs.

National Center for Biotechnology Information, National Library of Medicine, National Institutes of Health, GenBank Locus T12515, Accession No. T12515, "hypothetical protein DKFZp434B103.1—human," [online]. Bethesda, MD [retrieved on Dec. 14, 2006]. Retrieved from the Internet: <URL:ncbi.nlm.nih.gov/entrez/viewer.fcgi?db=protein&val=7512526>; 2 pgs.

National Center for Biotechnology Information, National Library of Medicine, National Institutes of Health, GenBank Locus NP_055455, Accession No. NP_055455, "tubulin tyrosine ligase-like family, member 4 [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=41281415>; 2 pgs.

National Center for Biotechnology Information, National Library of Medicine, National Institutes of Health, GenBank Locus NP_055887, Accession No. NP_055887, "tubulin tyrosine ligase-like family, member 5 [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=50658079>; 2 pgs.

National Center for Biotechnology Information, National Library of Medicine, National Institutes of Health, GenBank Locus BAC05032, Accession No. BAC05032, "unnamed protein product [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=21757131>; 3 pgs.

National Center for Biotechnology Information, National Library of Medicine, National Institutes of Health, GenBank Locus AAH60878, Accession No. AAH60878, "TTLL7 protein [*Homo sapiens*]," [online]. Bethesda, MD [retrieved on Dec. 16, 2006]. Retrieved from the Internet: <URL:ncbi.nlm.nih.gov/entrez/viewer.fcgi?db=protein&val38173831=>; 3 pgs.

National Center for Biotechnology Information, National Library of Medicine, National Institutes of Health, GenBank Locus XP_104657, Accession No. XP_104657, "PREDICTED: Similar to CG11323-PA [*Homo sapiens*]," [online]. Bethesda, MD [retrieved on Dec. 16, 2006]. Retrieved from the Internet: <URL:ncbi.nlm.nih.gov/entrez/viewer.fcgi?db=protein&val=113429469>; 2 pgs.

National Center for Biotechnology Information, National Library of Medicine, National Institutes of Health, GenBank Locus XP_092778, Accession No. XP_092778, "PREDICTED: Similar to RIKEN cDNA 4930509O20 [*Homo sapiens*]," [online] Bethesda, MD [retrieved on Dec. 16, 2006]. Retrieved from the Internet: <URL:ncbi.nlm.nih.gov/entrez/viewer.fcgi?db=protein&val=27485696>; 2 pgs.

National Center for Biotechnology Information, National Library of Medicine, National Institutes of Health, GenBank Locus BAC85781, Accession No. BAC85781, "unnamed protein product [*Homo sapiens*]," [online]. Bethesda, MD [retrieved on Dec. 16, 2006]. Retrieved from the Internet: <URL:ncbi.nlm.nih.gov/entrez/viewer.fcgi?db=protein&val=34529838>; 2 pgs.

National Center for Biotechnology Information, National Library of Medicine, National Institutes of Health, GenBank Locus AAM81328, Accession No. AAM81328, "unknown [*Homo sapiens*]," [online] Bethesda, MD [retrieved on Dec. 14, 2006]. Retrieved from the Internet: <URL:ncbi.nlm.nih.gov/entrez/viewer.fcgi?db=protein&val=21914242>; 2 pgs.

National Center for Biotechnology Information, National Library of Medicine, National Institutes of Health, GenBank Locus AAH01070, Accession No. AAH01070, "Tubulin tyrosine ligase-like family, member 12 [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=12654481>; 2 pgs.

National Center for Biotechnology Information, National Library of Medicine, National Institutes of Health, GenBank Locus XP_496092, Accession No. XP_496092, "PREDICTED: similar to RIKKEN cDNA 1700111A04 [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=51472533>; 2 pgs.

National Center for Biotechnology Information, National Library of Medicine, National Institutes of Health, GenBank Locus NP_729025, Accession No. NP_729025, "CG32238-PA [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24657931>; 4 pgs.

National Center for Biotechnology Information, National Library of Medicine, National Institutes of Health, GenBank Locus NP_733081, Accession No. NP_733081, "CG31108-PA [*Drosophila melanogaster*]," [online] Bethesda, MD [retrieved on Dec. 14, 2006]. Retrieved from the Internet: <URL:ncbi.nlm.nih.gov/entrez/viewer.fcgi?db=protein&val=24649931>; 4 pgs.

National Center for Biotechnology Information, National Library of Medicine, National Institutes of Health, GenBank Locus NP_723643, Accession No. NP_723643, "CG16833-PC, isoform C [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24583598>; 4 pgs.

National Center for Biotechnology Information, National Library of Medicine, National Institutes of Health, GenBank Locus NP_725916, Accession No. NP_725916, "CG16716-PA, isoform A [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24655878>; 4 pgs.

National Center for Biotechnology Information, National Library of Medicine, National Institutes of Health, GenBank Locus NP_609068, Accession No. NP_609068, "CG11201-PA [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24582312>; 4 pgs.

National Center for Biotechnology Information, National Library of Medicine, National Institutes of Health, GenBank Locus NP_609069, Accession No. NP_609069, "CG11323-PA [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24582314>; 4 pgs.

National Center for Biotechnology Information, National Library of Medicine, National Institutes of Health, GenBank Locus NP_573197, Accession No. NP_573197, "CG8918-PA [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24642736>; 4 pgs.

National Center for Biotechnology Information, National Library of Medicine, National Institutes of Health, GenBank Locus NP_651549, Accession No. NP_651549, "CG5987-PA [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24650577>; 4 pgs.

National Center for Biotechnology Information, National Library of Medicine, National Institutes of Health, GenBank Locus NP_650021, Accession No. NP_650021, "CG4089-PA [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24645782>; 4 pgs.

National Center for Biotechnology Information, National Library of Medicine, National Institutes of Health, GenBank Locus NP_722946, Accession No. NP_722946, "CG3964-PB, isoform B [*Drosophila melanogaster*]," [online]. Bethesda, MD [retrieved on Dec. 14, 2006]. Retrieved from the Internet: <URL:ncbi.nlm.nih.gov/entrez/viewer.fcgi?db=protein&val=24581551>; 4 pgs.

National Center for Biotechnology Information, National Library of Medicine, National Institutes of Health, GenBank Locus NP_610325, Accession No. NP_610325, "CG1550-PA [*Drosophila melanogaster*]," [online] Bethesda, MD [retrieved on Dec. 14, 2006]. Retrieved from the Internet: <URL:ncbi.nlm.nih.gov/entrez/viewer.fcgi?db=protein&val=24586383>; 4 pgs.

National Center for Biotechnology Information, National Library of Medicine, National Institutes of Health, GenBank Locus NP_009652, Accession No. NP_009652, "P-body associated protein; Pbylp [*Saccharomyces cerevisiae*]," [online]. Bethesda, MD [retrieved on Dec. 14, 2006]. Retrieved from the Internet: <URL:ncbi.nlm.nih.gov/entrez/viewer.fcgi?db=protein&val=6319570>; 2 pgs.

National Center for Biotechnology Information, National Library of Medicine, National Institutes of Health, GenBank Locus NP_177879, Accession No. NP_177879, "tubulin—tyrosine ligase family protein [*Arabidopsis thaliana*]," [online]. Bethesda, MD [retrieved on Dec. 14, 2006]. Retrieved from the Internet: <URL:ncbi.nlm.nih.gov/entrez/viewer.fcgi?db=protein&val=30699268>; 2 pgs.

National Center for Biotechnology Information, National Library of Medicine, National Institutes of Health, GenBank Locus CAB95431, Accession No. CAB95431, "conserved hypothetical protein [*Trypanosoma brucei*]," [online]. Bethesda, MD [retrieved on Dec. 14, 2006]. Retrieved from the Internet: <URL:ncbi.nlm.nih.gov/entrez/viewer.fcgi?db=protein&val=9366669>; 2 pgs.

National Center for Biotechnology Information, National Library of Medicine, National Institutes of Health, GenBank Locus XM_340623, Accession No. XM_340623, "*Trypanosoma brucei* tubulin-tyrosine ligase, putative (Tb927.2.5250) mRNA, complete cds.," [online]. Bethesda, MD [retrieved on Dec. 14, 2006]. Retrieved from the Internet: <URL:ncbi.nlm.nih.gov/entrez/viewer.fcgi?db=nuccore&val=33944952>; 2 pgs.

National Center for Biotechnology Information, National Library of Medicine, National Institutes of Health, GenBank Locus NP_505918, Accession No. NP_505918, "C55A6.2 [*Caenorhabditis elegans*]," [online]. Bethesda, MD [retrieved on Dec. 14, 2006]. Retrieved from the Internet: <URL:ncbi.nlm.nih.gov/entrez/viewer.fcgi?db=protein&val=25155100>; 3 pgs.

National Center for Biotechnology Information, National Library of Medicine, National Institutes of Health, GenBank Locus CAA87425, Accession No. CAA87425, "Hypothetical protein ZK1128.6a [*Caenorhabditis elegans*]," [online]. Bethesda, MD [retrieved on Dec. 14, 2006]. Retrieved from the Internet: <URL:ncbi.nlm.nih.gov/entrez/viewer.fcgi?db=protein&val=18376580>; 2 pgs.

National Center for Biotechnology Information, National Library of Medicine, National Institutes of Health, GenBank Locus AAL06035, Accession No. AAL06035, "Hypothetical protein H23L24.3a [*Caenorhabditis elegans*]," [online]. Bethesda, MD [retrieved on Dec. 14, 2006]. Retrieved from the Internet: <URL:ncbi.nlm.nih.gov/entrez/viewer.fcgi?db=protein&val=15718609>; 4 pgs.

National Center for Biotechnology Information, National Library of Medicine, National Institutes of Health, GenBank Locus CAA94900, Accession No. CAA94900, "Hypothetical protein K07C5.7 [*Caenorhabditis elegans*]," [online]. Bethesda, MD [retrieved on Dec. 14, 2006]. Retrieved from the Internet: <URL:ncbi.nlm.nih.gov/entrez/viewer.fcgi?db=protein&val=22265881>; 2 pgs.

National Center for Biotechnology Information, National Library of Medicine, National Institutes of Health, GenBank Locus CAA87783, Accession No. CAA87783, "Hypothetical protein D2013.9 [*Caenorhabditis elegans*]," [online]. Bethesda, MD [retrieved on Dec. 14, 2006]. Retrieved from the Internet: <URL:ncbi.nlm.nih.gov/entrez/viewer.fcgi?db=protein&val=3876933>; 2 pgs.

National Center for Biotechnology Information, National Library of Medicine, National Institutes of Health, GenBank Locus EAA40434, Accession No. EAA40434, "GLP_43_54366_55577 [*Giardia lamblia* ATCC 50803]," [online]. Bethesda, MD [retrieved on Dec. 14, 2006]. Retrieved from the Internet: <URL:ncbi.nlm.nih.gov/entrez/viewer.fcgi?db=protein&val=29248911>; 2 pgs.

National Center for Biotechnology Information, National Library of Medicine, National Institutes of Health, GenBank Locus EAA40412, Accession No. EAA40412, "GLP_43_15991_17301 [*Giardia lamblia* ATCC 50803]," [online]. Bethesda, MD [retrieved on Dec. 14, 2006]. Retrieved from the Internet: <URL:ncbi.nlm.nih.gov/entrez/viewer.fcgi?db=protein&val=29248889>; 2 pgs.

National Center for Biotechnology Information, National Library of Medicine, National Institutes of Health, GenBank Locus EAA38012, Accession No. EAA38012, "GLP_618_12970_14472 [*Giardia lamblia* ATCC 50803]," [online]. Bethesda, MD [retrieved on Dec. 14, 2006]. Retrieved from the Internet: <URL:ncbi.nlm.nih.gov/entrez/viewer.fcgi?db=protein&val=29246415>; 2 pgs.

National Center for Biotechnology Information, National Library of Medicine, National Institutes of Health, GenBank Locus EAA38969, Accession No. EAA38969, "GLP_205_13412_15397 [*Giardia lamblia* ATCC 50803]," [online]. Bethesda, MD [retrieved on Dec. 14, 2006]. Retrieved from the Internet: <URL:ncbi.nlm.nih.gov/entrez/viewer.fcgi?db=protein&val=29247406>; 2 pgs.

National Center for Biotechnology Information, National Library of Medicine, National Institutes of Health, GenBank Locus EAA37058, Accession No. EAA37058, "GLP_223_2566_4779 [*Giardia lamblia* ATCC 50803]," [online] Bethesda, MD [retrieved on Dec. 14, 2006]. Retrieved from the Internet: <URL:ncbi.nlm.nih.gov/entrez/viewer.fcgi?db=protein&val=29245419>; 2 pgs.

National Center for Biotechnology Infonnation, National Library of Medicine, National Institutes of Health, GenBank Locus EAA38326, Accession No. EAA38326, "GLP_251_3885_7112 [*Giardia lamblia* ATCC 50803]," [online]. Bethesda, MD [retrieved on Dec. 14, 2006]. Retrieved from the Internet: <URL:ncbi.nlm.nih.gov/entrez/viewer.fcgi?db=protein&val=29246741>; 2 pgs.

National Center for Biotechnology Information, National Library of Medicine, National Institutes of Health, GenBank Locus EAA39544, Accession No. EAA39544, "GLP_203_36475_34036 [*Giardia lamblia* ATCC 50803]," [online]. Bethesda, MD [retrieved on Dec. 14, 2006]. Retrieved from the Internet: <URL:ncbi.nlm.nih.gov/entrez/viewer.fcgi?db=protein&val=29247999>; 2 pgs.

National Center for Biotechnology Information, National Library of Medicine, National Institutes of Health, GenBank Locus AAH16574, Accession No. AAH16574, "Lrrc49 protein [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=16741525>; 3 pgs.

National Center for Biotechnology Information, National Library of Medicine, National Institutes of Health, GenBank Locus 2GFB_A, Accession No. 2GFB_A, "ChainA, Igg2a Fab Fragment (Cnj206)," [online]. Bethesda, MD [retrieved on Dec. 14, 2006]. Retrieved from the Internet: <URL:ncbi.nlm.nih.gov/entrez/viewer.fcgi?db=protein&val=640171>; 3 pgs.

National Center for Biotechnology Information, National Library of Medicine, National Institutes of Health, GenBank Locus XP_203706, Accession No. XP_203706, "RIKEN cDNA5730494M16 [*Mus musculus*]," [online]. Bethesda, MD [retrieved on Dec. 14, 2006]. Retrieved from the Internet: <URL:ncbi.nlm.nih.gov/entrez/viewerfcgi?db=protein&val=25029762>; 2 pgs.

National Center for Biotechnology Information, National Library of Medicine, National Institutes of Health, GenBank Locus NM_180678, Accession No. NM_180678, "*Mus musculus* glycyl-tRNA synthetase (Gars), mRNA," [online] Bethesda, MD [retrieved on Dec. 14, 2006]. Retrieved from the Internet: <URL:ncbi.nlm.nih.gov/entrez/viewer.fcgi?db=nuccore&val=30725862>; 4 pgs.

National Center for Biotechnology Information, National Library of Medicine, National Institutes of Health, GenBank Locus XP_289692, Accession No. XP_289692, "similar to Ig gamma-2B chain C region secreted form [*Mus musculus*]," [online]. Bethesda, MD [retrieved on Dec. 14, 2006]. Retrieved from the Internet: <URL:ncbi.nhn.nih.gov/entrez/viewer.fcgi?db=protein&val=28523035>; 2 pgs.

National Center for Biotechnology Information, National Library of Medicine, National Institutes of Health, GenBank Locus XP_130960, Accession No. XP_130960, "fibrinogen, B beta polypeptide [*Mus musculus*]," [online] Bethesda, MD [retrieved on Dec. 14, 2006]. Retrieved from the Internet: <URL:ncbi.nlm.nih.gov/entrez/viewer.fcgi?db=protein&val=20872398>; 2 pgs.

National Center for Biotechnology Information, National Library of Medicine, National Institutes of Health, GenBank Locus AAK53870, Accession No. AAK53870, "immunoglobulin heavy chain constant region [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=14091948>; 2 pgs.

National Center for Biotechnology Information, National Library of Medicine, National Institutes of Health, GenBank Locus BAA81879, Accession No. BAA81879, "chaperonin containing TCP-1 theta subunit [*Mus musculus*]," [online] Bethesda, MD [retrieved on Dec. 14, 2006]. Retrieved from the Internet: <URL:ncbi.nlm.nih.gov/entrez/viewer.fcgi?db=protein&val=5295992>; 2 pgs.

National Center for Biotechnology Information, National Library of Medicine, National Institutes of Health, GenBank Locus 542723, Accession No. S42723, "matricin—mouse," [online]. Bethesda, MD [retrieved on Dec. 14, 2006]. Retrieved from the Internet: <URL:ncbi.nlm.nih.gov/entrez/viewer.fcgi?db=protein&val=631730>; 2 pgs.

National Center for Biotechnology Information, National Library of Medicine, National Institutes of Health, GenBank Locus NP_005727, Accession No. NP_005727, "ARP1 actin-related protein 1 homolog A centractin alpha [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=5031569>; 3 pgs.

National Center for Biotechnology Information, National Library of Medicine, National Institutes of Health, GenBank Locus NP_006112, Accession No. NP_006112, "keratin 1 [*Homo sapiens*]," [online]. Bethesda, MD [retrieved on Dec. 14, 2006]. Retrieved from the Internet: <URL:ncbi.nlm.nih.gov/entrez/viewer.fcgi?db=protein&val=17318569>; 4 pgs.

National Center for Biotechnology Information, National Library of Medicine, National Institutes of Health, GenBank Locus NP_031663, Accession No. NP_031663, "chaperonin subunit 5 (epsilon) [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=6671702>; 3 pgs.

National Center for Biotechnology Information, National Library of Medicine, National Institutes of Health, GenBank Locus NP_033968, Accession No. NP_033968, "chaperonin subunit 6a (zeta) [*Mus musculus*]," [online] Bethesda, MD [retrieved on Dec. 14, 2006]. Retrieved from the Internet: <URL:ncbi.nlm.nih.gov/entrez/viewer.fcgi?db=protein&val=6753324>; 3 pgs.

National Center for Biotechnology Information, National Library of Medicine, National Institutes of Health, GenBank Locus NP_033970, Accession No. NP_033970, "chaperonin subunit 8 (theta) [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=6753328>; 2 pgs.

National Center for Biotechnology Information, National Library of Medicine, National Institutes of Health, GenBank Locus NP_079725, Accession No. NP_079725, "nicolin 1 [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=13384852>; 2 pgs.

National Center for Biotechnology Information, National Library of Medicine, National Institutes of Health, GenBank Locus NP_080899, Accession No. NP_080899, "nudix (nucleoside diphosphate linked moiety X)—type motif 21 [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=13386106>; 2 pgs.

National Center for Biotechnology Information, National Library of Medicine, National Institutes of Health, GenBank Locus NP_683736, Accession No. NP_683736, "hypothetical protein LOC110012 [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=22507341>; 2 pgs.

National Center for Biotechnology Information, National Library of Medicine, National Institutes of Health, GenBank Locus NP_849200, Accession No. NP_849200, "tubulin tyrosine ligase-like 1 [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=30725861>; 2 pgs.

National Center for Biotechnology Information, National Library of Medicine, National Institutes of Health, GenBank Locus NP_031600, Accession No. NP_031600, "complement component 1, q subcomponent, gamma polypeptide [*Mus musculus*]," [online]. Bethesda, MD [retrieved on Dec. 14, 2006]. Retrieved from the Internet: <URL:ncbi.nlm.nih.gov/entrez/viewer.fcgi?db=protein&val=6671652>; 2 pgs.

National Science Foundation News, Press Release 05-077 "Researchers Identify Proteins that Direct Intracellular Transport and Locomotion," [online] National Science Foundation, Arlington, VA, May 13, 2005 [retrieved on Dec. 12, 2006]. Retrieved from the Internet: <URL:www.nsf.gov/news/newssumm.jsp?cntnid=104178>; 4 pgs.

Nilsson, "Effects of DMSO on vacuole formation, contractile vacuole function, and nuclear division in *Tetrahymena pyriformis* GL," Oct. 1974 *J. Cell Sci.* 16(1):39-47.

Nogales et al., "Structure of the alpha beta tubulin dimer by electron crystallography," Jan. 8, 1998 *Nature* 391:199-202.

Nogales et al., "High-Resolution Model of the Microtubule," Jan. 1999 *Cell* 96(1):79-88.

O'Connor et al. "Two Purified Domains of Telomerase Reverse Transcriptase Reconstitute Sequence-specific Interactions with RNA," Apr. 2005 *J. Biol. Chem.* 280(17):17533-17539. Available online Feb. 24, 2005.

O'Farrell et al., "High Resolution Two-Dimensional Electrophoresis of Basic as Well as Acidic Proteins," Dec. 1977 *Cell* 12:1133-1141.

Okagaki and Kamiya, "Microtubule sliding in mutant *Chlamydomonas* axonemes devoid of outer or inner dynein arms," Nov. 1986 *J. Cell Biol.* 103:1895-1902.

Ovechkina et al., "K-Loop Insertion Restores Microtubule Depolymerizing Activity of a 'Neckless' MCAK Mutant," Nov. 2002 *J. Cell Biol.* 159(4):557-562.

Pathak et al., "The zebrafish fleer gene encodes an essential regulator of cilia tubulin polyglutamylation," Nov. 2007 *Mol. Biol. Cell* 18:4353-4364. Available online Aug. 29, 2007.

Pazour et al., "Proteomic analysis of a eukaryotic cilium," Jul. 5, 2005 *J. Cell Biol.* 170:103-113.

Péchart et al., "Composition and organization of tubulin isoforms reveals a variety of axonemal models," Dec. 1999 *Biol. Cell* 91:685-697.

Piperno et al., "Microtubules containing acetylated alpha-tubulin in mammalian cells in culture," Feb. 1987 *J. Cell Biol.* 104:289-302.

Plessmann et al., "Posttranslational modifications of α-tubulin of *Toxoplasma gondii*," Nov. 2004 *Parasitol. Res.* 94(5):386-389. Available online Oct. 2, 2004.

Popodi et al., "The proximal region of the beta-tubulin C-terminal tail is sufficient for axoneme assembly," Sep. 2005 *Cell Motil. Cytoskeleton* 62:48-64.

Prathapam et al., "A telomerase holoenzyme protein enhances telomerase RNA assembly with telomerase reverse transcriptase," Mar. 2005 *Nat. Struct. Mol. Biol.* 12(3):252-257. Available online Feb. 6, 2005.

Preston et al., "The Phylogenetic Distribution of Tubulin: Tyrosine Ligase," 1979 *J. Mol. Evol.* 13:233-244.

Priel et al., "Transitions in microtubule C-termini conformations as a possible dendritic signaling phenomenon," Dec. 2005 *Eur.Biophys. J.* 35:40-52. Available online Sep. 24, 2005.

Provence and Curtiss III, "Chapter 14: Gene Transfer in Gram-Negative Bacteria," in *Methods for General and Molecular Bacteriology*, Gerhardt et al. (eds.). American Society for Microbiology: Washington, D.C.; 1994. Title page, publisher's page, and pp. 317-347.

Raff et al., "Axoneme beta-tubulin sequence determines attachment of outer dynein arms," Jun. 24, 2008 *Curr. Biol.* 18:911-914.

Raybin et al., "Modification of Tubulin by Tyrosylation in Cells and Extracts and Its Effect on Assembly in vitro," May 1977 *J. Cell Biol.* 73(2):492-504.

Redeker et al. "Structure of tubulin C-terminal domain obtained by subtilisin treatment: The major α and β tubulin isotypes from pig brain are glutamylated," Nov. 1992 *FEBS Lett.* 313(2):185-192.

Redeker et al., "Polyglycylation of Tubulin: A Posttranslational Modification in Axonemal Microtubules," Dec. 1994 *Science* 266(5191):1688-1691.

Redeker et al., "Posttranslational modifications of the C-terminus of alpha-tubulin in adult rat brain: alpha 4 is glutamylated at two residues," Oct. 20, 1998 *Biochemistry* 37:14838-14844.

Redeker et al., "Posttranslational Modification of Brain Tubulins from the Antarctic Fish *Notothenia coriiceps*: Reduced C-Terminal Glutamylation Correlates with Efficient Microtubule Assembly at Low Temperature," Sep. 2004 *Biochemistry* 43:12265-12274.

Redeker et al., "Mutations of Tubulin Glycylation Sites Reveal Cross-talk between the C Termini of α- and β-Tubulin and Affect the Ciliary Matrix in *Tetrahymena*," Jan. 2005 *J. Biol. Chem.* 280(1):596-606.

Regnard et al., "Tubulin Polyglutamylase: Partial Purification and Enzymatic Properties," Jun. 1998 *Biochemistry* 37(23):8395-8404.

Regnard et al., "Tubulin polyglutamylase: isozymic variants and regulation during the cell cycle in HeLa cells," Dec. 1999 *J Cell Sci.* 112(Pt. 23):4281-4289.

Regnard et al., "Polyglutamylation of Nucleosome Assembly Proteins," May 2000 *J. Biol. Chem.* 275(21):15969-15976.

Regnard et al., "Characterisation of PGs1, a subunit of a protein complex co-purifying with tubulin polyglutamylase," Oct. 2003 *J. Cell Sci.* 116(20):4181-4190.

Ring et al., "Taxanes in the treatment of early breast cancer," Dec. 2005 *Cancer Treat. Rev.* 31(8):618-627. Available online Nov. 2, 2005.

Rogowski, Krzysztof Janusz, "Functions of Tubulin Polymodifications and Identification of the Responsible Enzymes," Ph.D. Dissertation, Department of Cellular Biology, University of Georgia, 178 pgs (available Jul. 27, 2005).

Rogowski et al., "Evolutionary divergence of enzymatic mechanisms for posttranslational polyglycylation," Jun. 12, 2009 *Cell* 137:1076-1087.

Roll-Mecak and Vale, "Structural basis of microtubule severing by the hereditary spastic paraplegia protein spastin," Jan. 17, 2008 *Nature* 451:363-367.

Rosenbaum, "Cytoskeleton: Functions for tubulin modifications at last," Nov. 2000 *Current Biol.* 10(21):R801-R803.

Ross and Fygenson, "Mobility of taxol in microtubule bundles," Jun. 2003 *Biophys. J.* 84:3959-3967.

Rüdiger et al., "Class II tubulin, the major brain β tubulin isotype is polyglutamylated on glutamic acid residue 435," Aug. 1992 *FEBS Lett.* 308(1):101-105.

Rüdiger et al., "Beta tubulin of bull sperm is polyglycylated," May 8, 1995 *FEBS Lett.* 364:147-151.

Rüdiger et al., "Monoclonal antibody ID5: epitope characterization and minimal requirements for the recognition of polyglutamylated α- and β-tubulin," Jan. 1999 *Eur. J. Cell Biol.* 78:15-20.

Rüegsegger et al., "Human Pre-mRNA Cleavage Factor I_m I_s Related to Spliceosomal SR Proteins and Can Be Reconstituted In Vitro from Recombinant Subunits," Jan. 1998 *Mol. Cell* 1:243-253.

Sackett et al., "Tubulin subunit carboxyl termini determine polymerization efficiency," Jan. 10, 1985 *J. Biol. Chem.* 260:43-45.

Saji et al., "Significance of HDAC6 regulation via estrogen signaling for cell motility and prognosis in estrogen receptor-positive breast cancer," Jun. 2005 *Oncogene* 24:4531-4539.

Sakakibara et al., "Inner-arm dynein c of *Chlamydomonas* flagella is a single-headed processive motor," Aug. 5, 1999 *Nature* 400:586-590.

Sale and Satir, "Direction of active sliding of microtubules in *Tetrahymena* cilia," May 1977 *Proc. Natl. Acad. Sci. USA* 74:2045-2049.

Sale, Winfield S., "Functional Substructure of Flagellar Dynein," Grant Abstract, Grant No. R37GM051173 [online]. National Institute of General Medical Sciences, National Institutes of Health; project dates Jul. 1, 1985 to Mar. 31, 2013 [retrieved on Apr. 28, 2012]. Retrieved from the Internet: <http://projectreporter.nih.gov/project_info_description.cfm?aid=8065461&icde=1230881 5>; 2 pgs.

Sambrook et al., *Molecular Cloning: A Laboratory Manual.*, Cold Spring Harbor Laboratory Press: Plainview, NY; 1989. Title page, publisher's page, and table of contents; 32 pages.

Saoudi et al., "Stabilization and bundling of subtilisin-treated microtubules induced by microtubule associated proteins," Jan. 1995 *J. Cell Sci.*108(Pt. 1):357-367.

Schafer et al., "Ultrastructural Analysis of the Dynactin Complex: An Actin-Related Protein is a Component of a Filament that Resembles F-Actin," Jul. 1994 *J Cell Biol.* 126(2):403-412.

Schliwa and van Blerkom, "Structural interaction of cytoskeletal components," Jul. 1981 *J. Cell Biol.* 90:222-235.

Schroder et al., "Purification of Brain Tubulin-Tyrosine Ligase by Biochemical and Immunological Methods," Jan. 1985 *J. Cell Biol.* 100(1):276-281.

Schneider et al., "Subpellicular and flagellar microtubules of *Trypanosoma brucei* are extensively glutamylated," Feb. 1997 *J. Cell Sci.* 110:431-437.

Schneider et al., "Posttranslational modifications of trichomonad tubulins; identification of multiple glutamylation sites," Jun. 16, 1998 *FEBS Lett.* 429:399-402.

ScienceDaily: "Newly Identified Enzyme Group Converts Protein into Cellular Traffic Signal," [online]. ScienceDaily LLC, Jun. 2, 2005 [retrieved on Dec. 12, 2006]. Retrieved from the Internet: <URL:www.sciencedaily.com/releases/2005/05/050527105307>; 3 pgs.

Seetharam and Satir, "High speed sliding of axonemal microtubules produced by outer arm dynein," Feb. 2005 *Cell Motil. Cytoskeleton* 60:96-103.

Serrador et al.,"HDAC6 Deacetylase Activity Links the Tubulin Cytoskeleton with Immune Synapse Organization," Apr. 2004 *Immunity* 20:417-428.

Serrano et al., "Involvement of the carboxyl-terminal domain of tubulin in the regulation of its assembly," Oct. 1984 *Proc. Natl. Acad. Sci. USA* 81:5989-5993.

Shang et al., "*Tetrahymena thermophila* contains a conventional gamma-tubulin that is differentially required for the maintenance of different microtubule-organizing centers," Sep. 30, 2002 *J. Cell Biol.* 158:1195-1206.

Shang et al., "A robust inducible-repressible promoter greatly facilitates gene knockouts, conditional expression, and overexpression in homologous and heterologous genes in *Tetrahymena thermophila*," Mar. 2002 *Proc. Natl. Acad. Sci. USA* 99(6):3734-3739.

Sharma et al., "Katanin regulates dynamics of microtubules and biogenesis of motile cilia," Sep. 10, 2007 *J. Cell Biol.* 178:1065-1079.

Skiniotis et al., "Modulation of kinesin binding by the C-termini of tubulin," Mar. 2004 *EMBO J.* 23(5):989-999. Available online Feb. 19, 2004.

Smith et al., "A beta-tubulin mutation selectively uncouples nuclear division and cytokinesis in *Tetrahymena thermophila*," Oct. 2004 *Eukaryot. Cell* 3:1217-1226.

Smith et al., "Robust method for proteome analysis by MS/MS using an entire translated genome: demonstration on the ciliome of Tetrahymena thermophila," May-Jun. 2005 *J. Proteome Res.* 4:909-919.

Sullenger, "Revising messages traveling along the cellular information superhighway," 1995 *Chem. & Biol.* 2:249-253.

Summers and Gibbons, "Adenosine triphosphate-induced sliding of tubules in trypsin-treated flagella of sea-urchin sperm," Dec. 1971 *Proc. Natl. Acad. Sci. USA* 68:3092-3096.

Suprenant et al., "Multiple forms of tubulin in the cilia and cytoplasm of *Tetrahymena thermophila*," Oct. 1985 *Proc. Natl. Acad Sci. USA* 82:6908-6912.

Suryavanshi et al., "Tubulin Glutamylation regulates ciliary motility by altering inner dynein arm activity," Mar. 9, 2010 *Curr. Biol.* 20:435-440. Available online on Feb. 25, 2010.

Suryavanshi, Swati, "In vivo significance of tubulin Glutamylation generated by TTLL6 E-ligases," Ph.D. Dissertation, Department of Cellular Biology, University of Georgia, 221 pgs; cover date Aug. 2010.

Thazhath et al., "Polyglycylation domain of β-tubulin maintains axonemal architecture and affects cytokinesis in *Tetrahymena*," Mar. 2002 *Nat. Cell Biol.* 4(3):256-259. Available online Feb. 19, 2002.

Thazhath et al., "Cell Context-specific Effects of the β-Tubulin Glycylation Domain on Assembly and Size of Microtubular Organelles," Sep. 2004 *Mol. Biol. Cell* 15:4136-4147.

Trichet et al., "Characterization of the human tubulin tyrosine ligase-like 1 gene (*TTLL1*) mapping to 22q13.1," Oct. 2000 *Gene* 257(1):109-117.

Turkewitz et al., "Functional genomics: the coming of age for *Tetrahymena thermophila*," Jan. 2002 *Trends in Genetics* 18(1):35-40.

Ueno et al., "Dynein pulls microtubules without rotating its stalk," Dec. 16, 2008 *Proc. Natl. Acad. Sci. USA* 105:19702-19707. Available online Dec. 8, 2008.

UGA News Service, News Release "Newly identified enzyme group converts protein into cellular traffic," [online]. University of Georgia Office of Public Affairs, May 17, 2005 [retrieved on Dec. 12, 2006]. Retrieved from the Internet: <URL:www.uga.edu/news-bin/artman/exec/view.cgi?archive=8&num=3111>; 3 pgs.

Vale and Toyoshima, "Rotation and translocation of microtubules in vitro induced by dyneins from *Tetrahymena* cilia," Feb. 12, 1988 *Cell* 52:459-469.

Valenzuela-Fernández et al., "Histone Deacetylase 6 Regulates Human Immunodeficiency Virus Type 1 Infection," Nov. 2005 *Mol. Biol. Cell* 16(11):5445-5454. Available online Sep. 7, 2005.

van Dijk et al., "A targeted multienzyme mechanism for selective microtubule polyglutamylation," May 10, 2007 *Mol. Cell* 26:437-448.

Verhey and Gaertig, "The tubulin code," Sep. 1, 2007 *Cell Cycle* 6:2152-2160. Available online Jun. 26, 2007.

Vinh et al., "Structural characterization by tandem mass spectrometry of the posttranslational polyglycylation of tubulin," Mar. 9, 1999 *Biochemistry* 38:3133-3139.

Weber et al., "Polyglycylation of tubulin in the diplomonad *Giardia lamblia*, one of the oldest eukaryotes," Sep. 1996, *FEBS Lett.*, 393(1):27-30.

Webster et al., "Microtubules are acetylated in domains that turn over slowly," Jan. 1989 *J. Cell Sci.* 92:57-65.

Westermann et al., "Identification of CfNek, a novel member of the NIMA family of cell cycle regulators, as a polypeptide copurifying with tubulin polyglutamylation activity in Crithidia," 2002 *J. Cell. Sci.* 115:5003-5011.

Westermann et al., "Post-Translational Modifications Regulate Microtubule Function," Dec. 2003 *Nat. Rev. Mol. Cell Biol.* 4(12):938-947.

Williams et al., "Chapter 42: Isolation and Fractionation of the *Tetrahymena* Cytoskeleton and Oral Apparatus," in *Methods in Cell Biology*, vol. 47, Academic Press, New York, NY (1995), pp. 301-306.

Wishart et al., "A single mutation converts a novel phosphotyrosine binding domain into a dual-specificity phosphatase," 1995 *J. Biol. Chem.* 270:26782-26785.

Witkowski et al., "Conversion of a b-ketoacyl synthase to a malonyl decarboxylase by replacement of the active-site cysteine with glutamine," 1999 *Biochemistry* 38:11643-11650.

Wloga et al., "Members of the NIMA-related Kinase Family Promote Disassembly of Cilia by Multiple Mechanisms," *Mol. Biol. Cell*, on-line publication Apr. 12, 2006; on-line publication with supplemental materials Apr. 26, 2006 [retrieved on Dec. 13, 2006]. Retrieved from the Internet: <URL:www.molbiolcell.org/cgi/content/full/17/6/2799?ijkey=f53591ad20994828502401a5d11af973da8db8db>; 84 pages.

Wloga et al., "Members of the NIMA-related Kinase Family Promote Disassembly of Cilia by Multiple Mechanisms," Jun. 2006 *Mol. Biol. Cell* 17(6):2799-2810.

Wolff et al., "Distribution of glutamylated α and β-tubulin in mouse tissues using a specific monoclonal antibody, GT335," Dec. 1992 *Eur. J. Cell Biol.* 59(2):425-432.

Wood et al., "Targeted gene disruption of dynein heavy chain 7 of *Tetrahymena thermophila* results in altered ciliary waveform and reduced swim speed," Sep. 1, 2007 *J Cell Sci.* 120:3075-3085. Available online Aug. 7, 2007.

Wuitschick et al., "Analysis of Genomic G +C Content, Codon Usage, Initiator Codon Context and Translation Termination Sites in *Tetrahymena thermophila*," May-Jun. 1999 *J. Eukaryot. Microbiol.* 46(3):239-247.

Xia et al, "Polyglycylation of Tubulin is Essential and Affects Cell Motility and Division in *Tetrahymena thermophila*," May 2000 *J. Cell Biol.* 149(5):1097-1106.

Xie et al., "Endoplasmic reticulum retention signal-dependent glycylation of the Hsp70/Grp170-related Pgp1p in *Tetrahymena*," Mar. 2007 *Eukaryot. Cell* 6:388-397. Available online Dec. 22, 2006.

Yelon, "Cardiac patterning and morphogenesis in zebrafish," Dec. 2001 *Dev. Dyn.* 222:552-563.

\* cited by examiner

GFP        ID5 mAb (polyglutamylation (>3E))

TTLL6A-$\Delta_{CT}$-GFP+Cd        Control

```
TtTTLL1         GGKWSLQSLRYYLEMVYGMANKCFDDINNIIIMSLKSVQSII-INDK-HCFEMYGYDILIDENCKPWLIEINASPSLFVTGKVDKELKTELIKNVYQIVIPDDW
DmCG32238       GGKWSVQNLALYLEGTRGVTDRLPGAISWLIVHSLRAVAPVM-ASDR-HCFECGYDIIIDNALKPWLVEVNASPSLTSTTVNDRILKYKLIDNILSVVLPPDG
HsTTLL1         GGKWTVSNLRLYLESTRGVTSKLFDEIHWIIVQSLKAVAPVM-NNDK-HCFECYGYDIIDDKLKPWLIEVNASPSLTSSTANDRILKYNLINDTLNIAVPNGE
DmCG8918        GGKWPLQNLWLYLDSLRGVSDMLWSRITATIRHSLDAVAPVM-ANDR-HCFEVYGYDIIIDNNLKPWLIEINTSPSMHSTTTNDRMLKSRLIDNVLDVVVPPNC
GlEAA40434      GGKWDIENLKLYISAHYGAVNKCFEKILFTLIHSLKAVQSSM-VFSK-SSFECYGYDILIDSRLHPWLLEVNASPSLTCSTDADRLMKCKLLDDVLKIIIPRNF
Tb05.6E7.8      GGKWTLANLLLFIQGRFGAADWLMHGIEFVIYHSLRALESVM-FNDR-HCFELYGYDILVDSQLRPHLIEVNSSPSLSTTTVSDRLLKEEVLQDVLQVVFPPDF
TtTTLL9         GGKWLLQTLKLYLISKYGKVSEAFYQIQQIIIKALQAVQKVM-INDK-RCFELYGFDILFDAQLKPWLLEVNASPSMTANTQVDSELKISVLDDTFTIIDIERI
HsTTLL9         GCKWTLQRFRQYLASKHGAVETLFRDIDNIFVKSLQSVQKVI-ISDK-HCFELYGYDILIDQDLKPWLLEVNASPSLTASSQEDYELKTCLLEDTLHVVDMEAR
CeF25C8         GLKWSLPKLFRFFKSVHGKLSKTMNDLTNVIIESLKSVQNLI-IQ---------------------VNASPSLTASSQEDFELKYRILNHMIDVLDIEKK
GlEAA40412      GAKWSLFQLGCYLETIYGQIDIMFLRIEQLIIRSLQAVANDM-IKSL-CMFEIYGFDVMLDSSLKPWLIEINASPSLSADTREDSIVKRRMLHDAISILGVDVP
TtTTLL6a        GHKRSLTSVLQLLEDQGHDVNLWKDIKRVLIKTIISAQPTLAHHYKSMCFEILGFDIILDSHLKPWVLEVNHTPSFSTDTPLDSYIKKNTIRDSLKLMNCTCK
GlEAA38012      GSKWGLQAVWDKIVEDGGDLQKIREDINDIFVKTILAVLPTLQHTYMSNCYEVLGFDIMIDSLFKPWLIEVNRSPSFTCDTPLDMRIKETLIDAVLDVINVTNG
DmCG16716       DSKWKLSAFNKWLVDHNYDVGEFWASVDDAIIKTLISAWPTLKHNYNVASFQLLGFDILVDWKLKPYILEVNRTPSLSADESVDMEVKRPLIRDTLNMLSTALV
DmCG5987        GSKRKLSAINNWMRRHNYDVEEFWSNVDDVIIKTVLSAWPVLKHNYHAACFEILGFDILVDWKLKPYILEVNRSPSPHTNEQVDREVKRPLIRDTLNLVSTVLA
HsTTLL6a        GSKWKLSTFSAYLEDHSYNVEQIWRDIEDVIIKTLISAHPIIRHNYHTACFEILGFDILLDHKLKPWLLEVNHSPSFSTDSRLDKEVKDGLLYDTLVLINLESC
TtTTLL4a        GSKWSLTALKAKYKQMGINVDELFGRIKDIIIKTCISAEPQMLDIVAKNCFELYGFDILIDSSLKPWILEVNVCPSLSSSSPLDRKIRHSLLVDVLNIIGTPY
CeZK1128.6      VPKWTLHHLWEHFDEMGVDREKIQREIEEVIIKAFISTEKPIREHMSRICYELFGIDIILDEDYKPWLLEVNISPSLHSGTPLDVSVKAPLAKDVLNLAGVYVP
HsTTLL4         GHKWALKALWNYLSQKGVNSDAIWEKIKDVVVKTIISSEPYVTSLLKMSCHELFGFDIMLDENLKPWVLEVNISFSLHSSSPLDISIKGQMIRDLLNLAGFVLP
DmCG16833       GHKWTIKSLWTYLANRGVRTDCLWEALRSLVLRTILAGENGINSMIRASCFELFGFDVILDSDLVPWLLEVNISPSLHSELPLDAHVKAPLVQGVLNTALYNVP
DmCG3964        GHKWTLQSLWSCLENRGVNTKRLWATLRNLVIKGIVSGESGLNRMYRQNCFELFGFDVLLDENLVPWLLEINISPSLHSELPLDLHVKGPLIQAVLNTALYQVP
TtTTLL14a       GNMWSFQQLWEFLEANYQFKKKIVSKIKDIIWLTFCSVKKKINQYDRKFCFEIPGFDFIIDEELNSWLIEVNTNPAIDECSQLLKTLIPRALDDALKLTIDQIF
TtTTLL14h       GNRLPLKEGLQYIFDTQFYEKHIYPRMKDLIIDLVRSCEQEM-FKSKKNCFELYGFDFIIDEDLRVWLIEANKNPGFGLPTEKARKLIDEMVDELLRLTIDQDY
Tb927.2.5250    GNELWFEEVGAYLHEVYRLEDRILPQIASIIIRTLLAARAEL-QVLENQCFQLFGYDVIVDEGLSVMLLEINGSPG------VASKYLQPLVREIIKLVDGGEA
HsTTL           GNEMFFKEFNQYLTSALNLESSILLQIKHIIRNCLLSVEPAISTK-HLQSFQLFGFDFMVDEELKVWLIEVNGAPA------CAQKLYAELCQGIVDIAISSVF
HsTTLL8         HNMWTSTRFQEYLQRQGRWGSVIYPSMKKAIAHAMKVAQDHV-EP-RKNSFELYGADFVLGRDFRPWLIEINSSPTMHPSTPVTAQLCAQVQEDTIKVAVD---
HsTTLL3         DNMWSSQRFQAHLQEMGAWSTIIVPGMKDAVIHALQTSQDTV-QC-RKASFELYGYDVILDSTLKPWLLEVNSPSLACDAPLDSLLKIKASMISDMFTVVGFVCQ
TtTTLL10a       DSHWELHKFESALKQQYNIQIKIYNQMKKASAYLFKGLEQYF-NV-FTANFQIFGLDFMFDEDFNQYFIEVNEIPQLLGQTSTHRNVCPEIVSQQLDSSLYAN-
TtTTLL12a       LKQIHYDEFIEEFEKEYTKWAAIHDKIKTMVKELFMAVYKKY---PGMNCRGSYGMDVMINGTFPQPKLLELTFSPDCERACKYHPHFFNDMFKLFFLNDQEHPN
DmCG1550        LHHVKCDDFLTLWQEQYPDWSALEQQICSMLLEVLQCASQAD--PPCGQSRALYAADIMLEKLMEPQLLEINWTPDCKRACDYYPDFFNDIFRLLFLDEENDDS
HsTTLL12        LKQVHCEEFIPEFEKQYPPWTDVQAEIFRAFTELFQVACAKP--PPLGSSRAMYAVDLMLRRVMQPQILEVNFNPDCERACRYHPTFFNDVFSTLFLDQPGGCH
CeD2013.9       ILQMKCENFIETIEKAYPQWSEVQKDINLTIRKAIEAAAKEE--APRGQSRAMYGVDIMLNDVIKSTLLEINFMPDTTRACQYYPDFADTVFETLFLDEIDPTK
DmCG11323       ENMWDCYSFQAYLRQIGKWKLERIFPGMRKAIVGCMLASQENM---DRRNTFELFGADFMICENFYPWLIEINSSPDLGATTSVTARMCPQCLEDVVKVVIDRRT
TtTTLL6e        ASKRTMQVTWEQIVKAGYDKEEILGNIEDLICKFLASMHPYL-LYNYQKRFHVLGFDILLDDKGKPWFLEVNANPSFNIEHEVYQPDGKKKVEQSPLDKYVKCR
DmCG31108       GHKWTLSALLRHLKLQSCDTRQLMLNIEDLIKAVLACAQSI-ISACRNCFELYGFDIIIDNALKPWLLEINLSPSMGVDSPLDTKVKSCLMADLLTCVGIPAY
CeC55A6.2       GHKWTLGALLRYVENEGKDAKLLMLRIEDLIVKSLLSIQNSV-ATASRTNFELFGFDVLVDQALKPWLLEVNLSPSLACDAPLDSLLKTRLIADLLNLACVPLL
HsTTLL5         GNKWSMSAMLRYLKQEGRDTTALMAHVEDLIIKTIISAELAI-ATACKSCFELYGFDVLIDSTLKPWLLEVNLSPSLACDAPLDLKIKASMISDMFTVVGFVCQ
HsTTLL2         GCKWTLSRFFSYLRSWDVDDLLLWKKIHRMVILTILAIAPSV--PFAANCFELFGFDILINDNLKPWLLEVNYSPALTLDCSTDVLVKRKLVHDIIDLIYLNGL
HsTTLL7         GSKRSIKWFTEFLQANQHDVAKFWSDISELVVKTLIVAEPHV-LHAYRVCFEVLGFDILLDRKLKPWLLEINRAPSFGTDQKIDYDVKRGVLLNALKLLNIRTS
TtTTLL2         GTKISLKMLQEKFRQKGIDWDKIWIQVQEIIVKSVLACQADI--PNNPNCFEIFGYDIIIDSSLKCCLLEINSSPSLARDFIIDDLLIKQQMIDDAIDLVSPVQF
TtTTLL15c       G-KTREQFMSSFSYQHTLKEGSVFNDFIPSVFRNYINTVLFS------RLYEMYAPDILVKDNMKPYILEYNTNPRMVNTSYFVHGWNVQTIKDIVLINMAQVR
Tb03.5L5.580    RNCFELFLEHYINGLVGRWERVLHRIDRCILLTVLSGLENL-----RKASFELYGVCVDVLLKVIPIPVLMEVNIMPSLSTHYSLDQCVGNFVADMLTLVGLTAG
DmCG11201       NNMWSLDQFKNYLRIMGASWSKTYNGFKQNLVAVVMASLDET------NAFELYGCDFMLDEHYNPILIEINSTFDLSPSTEITARICPMVLKDCIRVVVDLPK
Tb927.1.1550    ASKWTLSALESHFNKHGLDWDIGTMKQIHDILVKVLLSVQPHV---KAESCFEVYGVDVLLKVIPIPVLMEVNIMPSLSTHYSLDQCVGNFVADMLTLVGLTAG
Tb06.2N9.120    HLKKSMEELWNHIDSLCPFTSDHVWNSIAQVIVKTLLAVRSM--SKGVKSFFELYGFDMMLDSSLKPWLVEVNTLPSLASTSTFDYTVKTNIISDLLNLAMIEPF
CeH23L24.3      GSKRLLSTVFHQLESRGVKCKRLWHDIKLILVRTTLAMLPEIMLHYEHQCFQIMGFDVMIREDGTPILLEVNAAPSLTADHIEGGQRVRSIVDEVIKIPLVRDT
HsTTLL11        GSKRTFSSILCRLSSKGVDIKKVWSDIISVVIKTVIALTPELKVFYCSPCFQVTI------------------ASSQPAFPALTGLKRALWLRVG----------
GlEAA38969      GNMLHFRDLDVQMSVSDDFTSFIWPVMKRIMAAVLVAFGKAVLGAHACGCFELFGFDFMISNGYRPILIEINSNPCLALSSVVSWELLPKMLDDLMDLTIDKLF
TtTTLL3b        DLMMSQEQFAQYLKETEGFYEEIQPKLKQMVIQSLKSCQDQV--GARKNSMEFIGYDFMIDSNYQPWLIEINSSPSMEYSTSITEELVQRVLQDTTKVIVDYSM
DmCG4089        FGGSMRTVFEAYVRDQGKDPAQIWPQVEHIVRTTIAAKEKDI-VNILRNFFDLMRFDLPIDEDLKVPFLMEANMSPNLSSAHFKPNSLLYEQVLYSVFNLVGIRP
HsTTLL10        HTVMSMEHLNRYISDTFWVFTTLKKRMQQIMAHCFLAAKPKL--DCKLGYFDLIGCCDFLIDDNFKVWLLEMNSNPSLFCDSDFDFRTKHHRVLMDVFRLLEPYVP
Tb09.211.1170   CLSDLREFLDKNVENGRRVWEKVLSSCDDVVIKAFLSIEHEVVERLRKGCFELYGLDLMADDQYNVRLIEVNIMPSLATGTPLDKAVKSRMLAHLLTLIRVVPH
Tb11.02.4640    GNKRNFKFTNEWLESCGKSVEQFWARVAHVICKTILVAQPQI-ANVYNSCFEVLGFDILVDNKMKPWLMEVNHTFPSLVTDTFPLDYEVKHALISEVMDILDVKVT
Tb10.61.3050    GCKYGLRNLRQYITASCGVQAQKLFDDIQNMILRSLNAVQRVIVQDKHCFELYGYDIMIDSDLHPWLIETNASFSLSAETPADYHLKFNLLEDMFNVVDLEKR
Tb11.02.0020    DHDFIVKEFNEEYASSGYGEAAWEKIAYPKILKMLREAFGMVVTRGGDHRCRAMYGVDVMLRTERCVETGALTLEPSLLEITFYHPTFFNDIFHTLFLRDPTNMT
ScYbr094wp      VLEF---DSIEEIPNERKSIKEQIHSITNDVFLAAVNVNRLM--QPLPNAFETYIGDFLIDSNYEVKLLEINAPSPFVFQKGDLKNLIDELFDDTVKYCVTPIF
HsTTLL13        GSKRKLSTLNIWLQEHSYNPGELWGDIEDIIIKTIISAHSVL-RHNYRACFEILGFDILLDHKLKPWLLEVNHSPSFTTDSCLDQEVKDALLCDAMTLVNLRGC
AtAt1g77550     VREFEQEHNVKWMDIHEKVKQVIRAVFEAAALAHPEMQSP--------KSRAMYGVDVMLDSSFEPKILEVTYCPCDCMRACKYDMETIDGKGIVKGGDFFNNVF
CeK07C5.7       QKMSFKSTIDSYLGMQGMDTSKIWLQIRNIIGEVFRTQQTKM-LMSLQQYFELSRFDFVVDDQLNVFLMEANMSPNLSSGHFKQNQILYEQVLMNIFSLTGIST
```

Figure 13C

SEQUENCE LISTING

<160> NUMBER OF SEQ ID NOS: 132

<210> SEQ ID NO 1
<211> LENGTH: 34
<212> TYPE: DNA
<213> ORGANISM: artificial
<220> FEATURE:
<223> OTHER INFORMATION: primer

<400> SEQUENCE: 1
attttatgag ctccaccatc ttttattttg cttt                              34

<210> SEQ ID NO 2
<211> LENGTH: 35
<212> TYPE: DNA
<213> ORGANISM: artificial
<220> FEATURE:
<223> OTHER INFORMATION: primer

<400> SEQUENCE: 2
taaataagga tccacacaaa atagataaaa aggag                             35

<210> SEQ ID NO 3
<211> LENGTH: 33
<212> TYPE: DNA
<213> ORGANISM: artificial
<220> FEATURE:
<223> OTHER INFORMATION: primer

<400> SEQUENCE: 3
attttatatc gatttgttaa accagcatca cga                               33

```
<210> SEQ ID NO 4
<211> LENGTH: 35
<212> TYPE: DNA
<213> ORGANISM: artificial
<220> FEATURE:
<223> OTHER INFORMATION: primer

<400> SEQUENCE: 4
taaataactc gagaaaatta aatgtctggc tggat                              35

<210> SEQ ID NO 5
<211> LENGTH: 8
<212> TYPE: PRT
<213> ORGANISM: artificial
<220> FEATURE:
<223> OTHER INFORMATION: phosphorylated peptide
<220> FEATURE:
<221> NAME/KEY: MOD_RES
<222> LOCATION: (3)..(3)
<223> OTHER INFORMATION: PHOSPHORYLATION

<400> SEQUENCE: 5

Arg Pro Ser Val Pro Met Ala Arg
1               5

<210> SEQ ID NO 6
<211> LENGTH: 316
<212> TYPE: PRT
<213> ORGANISM: Escherichia coli

<400> SEQUENCE: 6

Met Ile Lys Leu Gly Ile Val Met Asp Pro Ile Ala Asn Ile Asn Ile
1               5                   10                  15

Lys Lys Asp Ser Ser Phe Ala Met Leu Leu Glu Ala Gln Arg Arg Gly
                20                  25                  30

Tyr Glu Leu His Tyr Met Glu Met Gly Asp Leu Tyr Leu Ile Asn Gly
            35                  40                  45

Glu Ala Arg Ala His Thr Arg Thr Leu Asn Val Lys Gln Asn Tyr Glu
    50                  55                  60

Glu Trp Phe Ser Phe Val Gly Glu Gln Asp Leu Pro Leu Ala Asp Leu
65                  70                  75                  80

Asp Val Ile Leu Met Arg Lys Asp Pro Pro Phe Asp Thr Glu Phe Ile
                85                  90                  95

Tyr Ala Thr Tyr Ile Leu Glu Arg Ala Glu Glu Lys Gly Thr Leu Ile
            100                 105                 110

Val Asn Lys Pro Gln Ser Leu Arg Asp Cys Asn Glu Lys Leu Phe Thr
        115                 120                 125

Ala Trp Phe Ser Asp Leu Thr Pro Glu Thr Leu Val Thr Arg Asn Lys
    130                 135                 140

Ala Gln Leu Lys Ala Phe Trp Glu Lys His Ser Asp Ile Ile Leu Lys
145                 150                 155                 160

Pro Leu Asp Gly Met Gly Gly Ala Ser Ile Phe Arg Val Lys Glu Gly
                165                 170                 175

Asp Pro Asn Leu Gly Val Ile Ala Glu Thr Leu Thr Glu His Gly Thr
            180                 185                 190

Arg Tyr Cys Met Ala Gln Asn Tyr Leu Pro Ala Ile Lys Asp Gly Asp
        195                 200                 205

Lys Arg Val Leu Val Val Asp Gly Glu Pro Val Pro Tyr Cys Leu Ala
    210                 215                 220

Arg Ile Pro Gln Gly Gly Glu Thr Arg Gly Asn Leu Ala Ala Gly Gly
225                 230                 235                 240
```

```
Arg Gly Glu Pro Arg Pro Leu Thr Glu Ser Asp Trp Lys Ile Ala Arg
                245                 250                 255

Gln Ile Gly Pro Thr Leu Lys Glu Lys Gly Leu Ile Phe Val Gly Leu
            260                 265                 270

Asp Ile Ile Gly Asp Arg Leu Thr Glu Ile Asn Val Thr Ser Pro Thr
            275                 280                 285

Cys Ile Arg Glu Ile Glu Ala Glu Phe Pro Val Ser Ile Thr Gly Met
            290                 295                 300

Leu Met Asp Ala Ile Glu Ala Arg Leu Gln Gln Gln
305                 310                 315

<210> SEQ ID NO 7
<211> LENGTH: 366
<212> TYPE: PRT
<213> ORGANISM: Mouse

<400> SEQUENCE: 7

Ala Gly Arg Val Lys Trp Val Thr Asp Ile Glu Lys Ser Val Leu Ile
1               5                   10                  15

Asn Asn Phe Glu Lys Arg Gly Trp Ile Gln Val Thr Glu Asn Glu Asp
            20                  25                  30

Trp Asn Phe Tyr Trp Met Ser Val Gln Thr Ile Arg Asn Val Phe Ser
        35                  40                  45

Val Glu Thr Gly Tyr Arg Leu Ser Asp Asp Gln Ile Val Asn His Phe
    50                  55                  60

Pro Asn His Tyr Glu Leu Thr Arg Lys Asp Leu Met Val Lys Asn Ile
65                  70                  75                  80

Lys Arg Tyr Arg Lys Glu Leu Glu Lys Glu Gly Ser Pro Leu Ala Glu
                85                  90                  95

Lys Asp Glu Asn Gly Lys Tyr Leu Tyr Leu Asp Phe Val Pro Val Thr
            100                 105                 110

Tyr Met Leu Pro Ala Asp Tyr Asn Leu Phe Val Glu Glu Phe Arg Lys
        115                 120                 125

Ser Pro Ser Ser Thr Trp Ile Met Lys Pro Cys Gly Lys Ala Gln Gly
    130                 135                 140

Lys Gly Ile Phe Leu Ile Asn Lys Leu Ser Gln Ile Lys Lys Trp Ser
145                 150                 155                 160

Arg Asp Ser Lys Thr Ser Ser Phe Val Ser Gln Ser Thr Lys Glu Ala
                165                 170                 175

Tyr Val Ile Ser Val Tyr Ile Asn Asn Pro Leu Leu Ile Gly Gly Arg
            180                 185                 190

Lys Phe Asp Leu Arg Leu Tyr Val Leu Val Ser Thr Tyr Arg Pro Leu
        195                 200                 205

Arg Cys Tyr Met Tyr Lys Leu Gly Phe Cys Arg Phe Cys Thr Val Lys
    210                 215                 220

Tyr Thr Pro Ser Thr Ser Glu Leu Asp Asn Met Phe Val His Leu Thr
225                 230                 235                 240

Asn Val Ala Ile Gln Lys His Gly Glu Asp Tyr Asn His Ile His Gly
                245                 250                 255

Gly Lys Trp Thr Val Asn Asn Leu Arg Leu Tyr Leu Gly Ser Thr Arg
            260                 265                 270

Gly Arg Glu Val Thr Ser Lys Leu Phe Asp Glu Ile His Trp Ile Ile
        275                 280                 285

Val Gln Ser Leu Lys Ala Val Ala Pro Val Met Asn Asn Asp Lys His
    290                 295                 300
```

```
Cys Phe Glu Cys Tyr Gly Tyr Asp Ile Ile Ile Asp Lys Leu Lys
305                 310                 315                 320

Pro Trp Leu Ile Glu Val Asn Ala Ser Pro Ser Leu Thr Ser Ser Thr
                325                 330                 335

Ala Asn Asp Arg Ile Leu Lys Tyr Asn Leu Ile Asn Asp Thr Leu Asn
            340                 345                 350

Ile Ala Val Pro Asn Gly Glu Ile Pro Asp Cys Lys Trp Asn
            355                 360                 365

<210> SEQ ID NO 8
<211> LENGTH: 319
<212> TYPE: PRT
<213> ORGANISM: Tetrahymena

<400> SEQUENCE: 8

Lys Lys Leu Lys Tyr Lys Thr Asp Phe Asp Lys Cys Val Leu Thr Asp
1               5                   10                  15

Asn Phe Ala Ala Arg Gly Trp Thr Arg Cys Gly Asp Lys Asp Asp Trp
            20                  25                  30

Asn Ile Tyr Trp Ala Thr Val Trp Asn Val Arg Asn Ile Phe Ile Arg
            35                  40                  45

Leu Asn Asp Met Gln Ile Ile Asn His Phe Pro Asn His Tyr Glu Leu
50                  55                  60

Thr Arg Lys Asp Leu Met Val Lys Asn Phe Lys Arg Tyr Lys Lys Glu
65                  70                  75                  80

Leu Tyr Leu Tyr Leu Asp Phe Ile Pro Gln Thr Phe Thr Leu Pro Gly
                85                  90                  95

Glu Tyr Ser Leu Phe Val Glu Glu Phe His Arg Asn Pro Asn Ala Thr
            100                 105                 110

Trp Ile Val Lys Pro Ala Ser Arg Ser Gln Gly Lys Gly Ile Phe Leu
            115                 120                 125

Leu Arg Lys Ile Gln Gln Leu Lys Lys Lys Glu Ala Tyr Val Val Ser
130                 135                 140

Arg Tyr Ile Asp Asn Pro Leu Leu Val Gly Gly Arg Lys Phe Asp Leu
145                 150                 155                 160

Arg Ile Tyr Ala Leu Val Thr Ser Tyr Arg Pro Leu Lys Val Tyr Leu
                165                 170                 175

Tyr Ala Met Gly Phe Gly Arg Phe Cys Asn Glu Gln Tyr Thr Gln Asp
            180                 185                 190

Ile Met Asp Asn Met Phe Ile His Leu Thr Asn Val Ala Ile Gln Lys
            195                 200                 205

Phe Ser Asp Lys Tyr Ser Glu Lys His Gly Gly Lys Trp Ser Leu Gln
210                 215                 220

Ser Leu Arg Tyr Tyr Leu Glu Met Val Tyr Gly Met Ala Asn Lys Cys
225                 230                 235                 240

Phe Asp Asp Ile Asn Asn Ile Ile Ile Met Ser Leu Lys Ser Val Gln
                245                 250                 255

Ser Ile Ile Ile Asn Asp Lys His Cys Phe Glu Met Tyr Gly Tyr Asp
            260                 265                 270

Ile Leu Ile Asp Glu Asn Cys Lys Pro Trp Leu Ile Glu Ile Asn Ala
            275                 280                 285

Ser Pro Ser Leu Thr Val Thr Gly Lys Val Asp Lys Glu Leu Lys Thr
290                 295                 300

Glu Leu Ile Lys Asn Val Tyr Gln Ile Val Ile Pro Asp Asp Trp
305                 310                 315
```

<210> SEQ ID NO 9
<211> LENGTH: 319
<212> TYPE: PRT
<213> ORGANISM: Drosophila melanogaster

<400> SEQUENCE: 9

Leu Lys Ile Gly Phe Cys Thr Asp Leu Asp Lys Ser Val Leu Val Asn
1               5                   10                  15

Asn Phe Glu Lys Arg Gly Trp His Gln Val Asn Gly Asp Asp Asp Trp
            20                  25                  30

His Phe Tyr Trp Ala Gly Val Gln Thr Cys Arg Asn Ile Phe Tyr Arg
        35                  40                  45

Met His Asp Asn Gln Met Ile Asn His Phe Pro Asn His Tyr Glu Leu
    50                  55                  60

Ser Arg Lys Asp Leu Leu Val Lys Asn Ile Lys Arg Tyr Arg Lys Asp
65                  70                  75                  80

Leu Tyr Leu Tyr Leu Asp Phe Val Pro Thr Thr Phe Val Leu Pro Ala
                85                  90                  95

Asp Tyr Asn Met Phe Val Glu Glu Tyr Arg Lys Phe Pro Leu Ser Thr
            100                 105                 110

Trp Ile Met Lys Pro Cys Gly Lys Ser Gln Gly Ala Gly Ile Phe Leu
        115                 120                 125

Ile Asn Lys Leu Ser Lys Leu Lys Lys Ser Tyr Val Ile Ser
    130                 135                 140

Arg Tyr Ile Asp Asn Pro Leu Leu Ile Gly Gly Lys Lys Phe Asp Leu
145                 150                 155                 160

Arg Leu Tyr Val Leu Val Ala Ser Phe Arg Pro Leu Lys Ala Tyr Leu
                165                 170                 175

Phe Lys Gln Gly Phe Cys Arg Phe Cys Thr Val Lys Tyr Asp Thr Ser
            180                 185                 190

Val Leu Asp Asn Met Tyr Val His Leu Thr Asn Val Ser Val Gln Lys
        195                 200                 205

His Gly Gly Glu Tyr Asn Thr Leu His Gly Gly Lys Trp Ser Val Gln
    210                 215                 220

Asn Leu Ala Leu Tyr Leu Glu Gly Thr Arg Gly Val Thr Asp Arg Leu
225                 230                 235                 240

Phe Gly Ala Ile Ser Trp Leu Ile Val His Ser Leu Arg Ala Val Ala
                245                 250                 255

Pro Val Met Ala Ser Asp Arg His Cys Phe Glu Cys Tyr Gly Tyr Asp
            260                 265                 270

Ile Ile Ile Asp Asn Ala Leu Lys Pro Trp Leu Val Glu Val Asn Ala
        275                 280                 285

Ser Pro Ser Leu Thr Ser Thr Thr Val Asn Asp Arg Ile Leu Lys Tyr
    290                 295                 300

Lys Leu Ile Asp Asn Ile Leu Ser Val Val Leu Pro Pro Asp Gly
305                 310                 315

<210> SEQ ID NO 10
<211> LENGTH: 319
<212> TYPE: PRT
<213> ORGANISM: Homo sapiens

<400> SEQUENCE: 10

Gly Lys Val Lys Trp Val Thr Asp Ile Glu Lys Ser Val Leu Ile Asn
1               5                   10                  15

Asn Phe Glu Lys Arg Gly Trp Val Gln Val Thr Glu Asn Glu Asp Trp

-continued

```
            20                  25                  30
Asn Phe Tyr Trp Met Ser Val Gln Thr Ile Arg Asn Val Phe Tyr Arg
         35                  40                  45

Leu Ser Asp Asp Gln Ile Val Asn His Phe Pro Asn His Tyr Glu Leu
     50                  55                  60

Thr Arg Lys Asp Leu Met Val Lys Asn Ile Lys Arg Tyr Arg Lys Glu
 65                  70                  75                  80

Leu Tyr Leu Tyr Leu Asp Phe Val Pro Val Thr Tyr Met Leu Pro Ala
                 85                  90                  95

Asp Tyr Asn Leu Phe Val Glu Glu Phe Arg Lys Ser Pro Ser Ser Thr
                100                 105                 110

Trp Ile Met Lys Pro Cys Gly Lys Ala Gln Gly Lys Gly Ile Phe Leu
            115                 120                 125

Ile Asn Lys Leu Ser Gln Ile Lys Lys Lys Glu Ala Tyr Val Ile Ser
        130                 135                 140

Leu Tyr Ile Asn Asn Pro Leu Leu Ile Gly Gly Arg Lys Phe Asp Leu
145                 150                 155                 160

Arg Leu Tyr Val Leu Val Ser Thr Tyr Arg Pro Leu Arg Cys Tyr Met
                165                 170                 175

Tyr Lys Leu Gly Phe Cys Arg Phe Cys Thr Val Lys Tyr Thr Pro Ser
                180                 185                 190

Thr Leu Asp Asn Met Phe Val His Leu Thr Asn Val Ala Ile Gln Lys
            195                 200                 205

His Gly Glu Asp Tyr Asn His Ile His Gly Gly Lys Trp Thr Val Ser
        210                 215                 220

Asn Leu Arg Leu Tyr Leu Glu Ser Thr Arg Gly Val Thr Ser Lys Leu
225                 230                 235                 240

Phe Asp Glu Ile His Trp Ile Ile Val Gln Ser Leu Lys Ala Val Ala
                245                 250                 255

Pro Val Met Asn Asn Asp Lys His Cys Phe Cys Tyr Gly Tyr Asp
                260                 265                 270

Ile Ile Ile Asp Asp Lys Leu Lys Pro Trp Leu Ile Glu Val Asn Ala
            275                 280                 285

Ser Pro Ser Leu Thr Ser Ser Thr Ala Asn Asp Arg Ile Leu Lys Tyr
        290                 295                 300

Asn Leu Ile Asn Asp Thr Leu Asn Ile Ala Val Pro Asn Gly Glu
305                 310                 315
```

<210> SEQ ID NO 11
<211> LENGTH: 317
<212> TYPE: PRT
<213> ORGANISM: Drosophila melanogaster

<400> SEQUENCE: 11

```
Asn Gly Ile Tyr Tyr Ser Thr Asp Trp Asp Lys Ser Ala Leu Val Ser
 1               5                  10                  15

Asn Phe Gln Lys Arg Gly Trp Leu Gln Val Pro Ser Phe Asn Glu Trp
            20                  25                  30

Asn Phe Tyr Trp Ala Cys Thr Gln Asn Cys Arg Tyr Ile Phe Tyr Arg
         35                  40                  45

Met Arg Ser Asp Gln Val Ile Asn His Phe Pro Asn Ser Ile Glu Leu
     50                  55                  60

Ser Arg Lys Asp Leu Leu Ile Lys Asn Ile Lys Arg Tyr Arg Lys Asp
 65                  70                  75                  80

Leu Tyr Lys His Leu Asp Ile Ile Pro Met Thr Phe Val Leu Pro Ser
```

```
            85                  90                  95
Asp Tyr Gln Met Phe Val Glu Val Phe His Arg Asn Pro Ala Ser Thr
            100                 105                 110

Trp Ile Val Lys Pro Cys Ser Lys Ser Gln Gly Val Gly Ile Tyr Leu
            115                 120                 125

Val Asn Lys Leu Ser Lys Leu Lys Arg Asp Thr Cys Val Ile Ser
            130                 135                 140

Lys Tyr Ile Asp Asn Pro Leu Leu Ile Gly Gly Lys Lys Phe Asp Leu
145                 150                 155                 160

Arg Leu Phe Val Leu Val Thr Thr Phe Asn Pro Leu Lys Ala Tyr Leu
                165                 170                 175

Tyr Lys Glu Gly Phe Cys Arg Phe Cys Thr Glu Lys Tyr Asp Glu Ile
                180                 185                 190

Asp Asn Val Phe Met His Leu Thr Asn Val Ser Ile Gln Lys Thr Asn
                195                 200                 205

Gln Glu Tyr Asn Ser Ile His Gly Gly Lys Trp Pro Leu Gln Asn Leu
                210                 215                 220

Trp Leu Tyr Leu Asp Ser Leu Arg Gly Val Ser Asp Met Leu Trp Ser
225                 230                 235                 240

Arg Ile Thr Ala Thr Ile Arg His Ser Leu Asp Ala Val Ala Pro Val
                245                 250                 255

Met Ala Asn Asp Arg His Cys Phe Glu Val Tyr Gly Tyr Asp Ile Ile
                260                 265                 270

Ile Asp Asn Asn Leu Lys Pro Trp Leu Ile Glu Ile Asn Thr Ser Pro
                275                 280                 285

Ser Met His Ser Thr Thr Thr Asn Asp Arg Met Leu Lys Ser Arg Leu
                290                 295                 300

Ile Asp Asn Val Leu Asp Val Val Pro Pro Asn Cys
305                 310                 315

<210> SEQ ID NO 12
<211> LENGTH: 318
<212> TYPE: PRT
<213> ORGANISM: Giardia lamblia

<400> SEQUENCE: 12

Pro Pro Ile Lys Tyr Arg Ile Asp Cys Glu Lys Tyr Ala Val Ile Ser
1               5                   10                  15

Asn Phe Glu Lys Arg Gly Trp Gln Arg Thr Ser Gly Ser Asp Trp Asn
                20                  25                  30

Ile Tyr Trp Ala Pro Val Ala Val Val Gln Lys Met Phe Ser Arg Pro
                35                  40                  45

Thr Asp Ala Gln Ile Val Asn His Phe Pro Asn His Tyr Glu Leu Thr
            50                  55                  60

Arg Lys Asp Leu Ile Val Arg Asn Met Arg Lys Tyr Arg Lys Asp Leu
65              70                  75                  80

Lys Ala Tyr Ile Asp Phe Ile Pro Leu Thr Tyr Leu Leu Pro Ser Glu
                85                  90                  95

Ser Thr Met Phe Ala Glu Glu Leu Lys Gly Asn Lys Lys Thr Pro Phe
                100                 105                 110

Ile Leu Lys Pro Ala Gly Ser Ala Gln Gly Arg Gly Ile Glu Leu Ile
                115                 120                 125

Ser Arg Met Ala Gln Phe Lys Lys Arg Thr Ile Tyr Leu Ala Ser Lys
                130                 135                 140

Tyr Ile Asn Arg Pro Leu Leu Val Gly Asn Lys Lys Phe Asp Ile Arg
```

```
                145                 150                 155                 160
Met Tyr Val Leu Val Thr Ser Tyr Ser Pro Leu Lys Ala Tyr Ile Tyr
                    165                 170                 175

Gln His Ala Phe Cys Arg Phe Cys Thr Val Glu Tyr Ser Leu Asp Pro
            180                 185                 190

Leu Ser Asn Pro Phe Val His Leu Thr Asn Val Ala Val Gln Lys His
        195                 200                 205

Gly Glu Ala Tyr Asn Ser Arg His Gly Gly Lys Trp Asp Ile Glu Asn
    210                 215                 220

Leu Lys Leu Tyr Ile Ser Ala His Tyr Gly Ala Val Asn Lys Cys Phe
225                 230                 235                 240

Glu Lys Ile Leu Phe Thr Leu Ile His Ser Leu Lys Ala Val Gln Ser
                245                 250                 255

Ser Met Val Phe Ser Lys Ser Ser Phe Glu Cys Tyr Gly Tyr Asp Ile
            260                 265                 270

Leu Ile Asp Glu Arg Leu His Pro Trp Leu Leu Glu Val Asn Ala Ser
        275                 280                 285

Pro Ser Leu Thr Cys Ser Thr Asp Ala Asp Arg Leu Met Lys Cys Lys
    290                 295                 300

Leu Leu Asp Asp Val Leu Lys Ile Ile Ile Pro Arg Asn Phe
305                 310                 315

<210> SEQ ID NO 13
<211> LENGTH: 320
<212> TYPE: PRT
<213> ORGANISM: Trypanosoma brucei

<400> SEQUENCE: 13

Met Leu Arg Tyr Arg Thr Asp Leu Asp Lys His Val Ile His Phe Ala
1               5                   10                  15

Phe Arg Arg Phe Pro Arg Ser Val Glu Ile Val Glu Asp Glu Glu Asp
            20                  25                  30

Trp His Phe Phe Trp Met Ser Val Gly Arg Val Arg Ser Leu Phe Tyr
        35                  40                  45

Arg Leu Ser Asp Ser Gln Ile Ile Asn His Phe Pro Asn His Tyr Glu
    50                  55                  60

Leu Thr Arg Lys Asp Leu Met Tyr Lys Asn Ile Lys Lys Tyr Ile Lys
65                  70                  75                  80

Asp Pro Leu Arg Phe Ala Asp Cys Val Pro Ile Thr Tyr Asn Ile Pro
                85                  90                  95

Asn Asp Leu Ala Met Phe Glu Glu Glu Phe Arg Arg Gln Pro Gly Ser
            100                 105                 110

Thr Trp Ile Val Lys Pro Thr Ser Arg Ser Gln Gly Arg Gly Ile Phe
        115                 120                 125

Leu Ile Asn Arg Leu Ser Gln Leu Lys Lys Met Asn Ser Phe Val Val
    130                 135                 140

Ser Lys Tyr Ile Arg Asp Pro Leu Leu Ile Gly Gly Lys Lys Phe Asp
145                 150                 155                 160

Leu Arg Leu Tyr Val Leu Val Thr Ser Phe Lys Pro Leu Val Ala Tyr
                165                 170                 175

Leu His Asp Gln Gly Phe Ala Arg Phe Cys Ala Thr Arg Tyr Val Ala
            180                 185                 190

Asn Ala Asp Glu Asp Leu Cys Ser His Leu Thr Asn Val Ala Leu Gln
        195                 200                 205

Lys Gly Glu Lys Glu Tyr Asn Ala Ser His Gly Gly Lys Trp Thr Leu
```

```
            210                 215                 220
Ala Asn Leu Leu Leu Phe Ile Gln Gly Arg Phe Gly Ala Ala Asp Trp
225                 230                 235                 240

Leu Met His Gly Ile Glu Phe Val Ile Tyr His Ser Leu Arg Ala Leu
                245                 250                 255

Glu Ser Val Met Phe Asn Asp Arg His Cys Phe Glu Leu Tyr Gly Tyr
                260                 265                 270

Asp Ile Leu Val Asp Ser Gln Leu Arg Pro His Leu Ile Glu Val Asn
                275                 280                 285

Ser Ser Pro Ser Leu Ser Thr Thr Thr Val Ser Asp Arg Leu Leu Lys
290                 295                 300

Glu Glu Val Leu Gln Asp Val Leu Gln Val Val Phe Pro Pro Asp Phe
305                 310                 315                 320

<210> SEQ ID NO 14
<211> LENGTH: 317
<212> TYPE: PRT
<213> ORGANISM: Tetrahymena

<400> SEQUENCE: 14

Ser Ser Ile Lys Phe Lys Thr Thr Phe Lys Asn Cys Ile Leu Glu Ser
1               5                   10                  15

Met Lys Arg Arg Gln Trp Lys Glu Ala Glu Phe Asp Asp Trp Asp Leu
                20                  25                  30

Asn Trp Ala Glu Lys Glu Trp Ile Leu Asp Val Met Ala His Val Ser
                35                  40                  45

Ser Asn Gln Arg Val Asn His Tyr Arg Asn Phe Ser Glu Leu Cys Arg
50                  55                  60

Lys Asp Leu Leu Ile Lys Asn Ile Lys Lys Tyr Lys Lys Thr Leu Ala
65                  70                  75                  80

Ala Leu Tyr Asn Phe Thr Pro Leu Thr Tyr Asn Leu Pro Ser Glu Tyr
                85                  90                  95

Ser Ile Phe Cys Glu Glu Phe Lys Lys Val Asn Ser Gln Leu Trp Ile
                100                 105                 110

Met Lys Pro Ile Gly Lys Ala Gln Gly Lys Gly Ile Phe Leu Phe Arg
                115                 120                 125

Asn Ile Lys Glu Ile Gly Asn Ala Asp Pro Tyr Val Val Gln Lys Tyr
130                 135                 140

Ile Ala Asp Pro Leu Leu Ile Gly Gly Lys Lys Phe Asp Met Arg Ile
145                 150                 155                 160

Tyr Ala Leu Cys Val Ser Tyr Gln Pro Leu Thr Val Tyr Leu Tyr Arg
                165                 170                 175

Thr Gly Phe Ala Arg Phe Thr His His Arg Tyr Asp Leu Glu Asp Ile
                180                 185                 190

Ser Asn Ala Tyr Val His Leu Thr Asn Val Ala Ile Gln Lys Thr Ser
                195                 200                 205

Glu Asn Tyr Asp Glu Lys Leu Gly Gly Lys Trp Leu Leu Gln Thr Leu
210                 215                 220

Lys Leu Tyr Leu Ile Ser Lys Tyr Gly Lys Val Ser Glu Ala Phe Tyr
225                 230                 235                 240

Gln Ile Gln Gln Ile Ile Lys Ala Leu Gln Ala Val Gln Lys Val
                245                 250                 255

Met Ile Asn Asp Lys Arg Cys Phe Glu Leu Tyr Gly Phe Asp Ile Leu
                260                 265                 270

Phe Asp Ala Gln Leu Lys Pro Trp Leu Leu Glu Val Asn Ala Ser Pro
```

```
                275                 280                 285
Ser Met Thr Ala Asn Thr Gln Val Asp Ser Glu Leu Lys Ile Ser Val
290                 295                 300

Leu Asp Asp Thr Phe Thr Ile Ile Asp Ile Glu Arg Ile
305                 310                 315

<210> SEQ ID NO 15
<211> LENGTH: 304
<212> TYPE: PRT
<213> ORGANISM: Homo sapiens

<400> SEQUENCE: 15

Ala Ser Ile Arg Phe Lys Thr Thr Leu Met Asn Thr Leu Met Asp Val
1               5                   10                  15

Leu Arg His Arg Pro Gly Trp Val Glu Val Lys Asp Glu Gly Glu Trp
                20                  25                  30

Asp Phe Tyr Trp Cys Asp Val Ser Trp Leu Arg Glu Asn Phe Thr Tyr
            35                  40                  45

Met Asp Glu His Val Arg Ile Ser His Phe Arg Asn His Tyr Glu Leu
        50                  55                  60

Thr Arg Lys Asn Tyr Met Val Lys Asn Leu Lys Arg Phe Arg Lys Gln
65                  70                  75                  80

Leu Ala Ala Lys Cys Asp Phe Phe Pro Lys Thr Phe Glu Met Pro Cys
                85                  90                  95

Glu Tyr His Leu Phe Val Glu Glu Phe Arg Lys Asn Pro Gly Ile Thr
            100                 105                 110

Trp Ile Met Lys Pro Val Ala Arg Ser Gln Gly Lys Gly Ile Phe Leu
        115                 120                 125

Phe Arg Arg Leu Lys Asp Ile Val Asp Val Glu Asn Tyr Val Ala Gln
    130                 135                 140

Arg Tyr Ile Glu Asn Pro Tyr Leu Ile Gly Gly Arg Lys Phe Asp Leu
145                 150                 155                 160

Arg Val Tyr Val Leu Val Met Ser Val Phe Ala Glu Cys Leu Leu Trp
                165                 170                 175

Ser Gly His Arg Arg Gln Asp Val His Leu Thr Asn Val Ala Val Gln
            180                 185                 190

Lys Thr Ser Pro Asp Tyr His Pro Lys Lys Gly Cys Lys Trp Thr Leu
        195                 200                 205

Gln Arg Phe Arg Gln Tyr Leu Ala Ser Lys His Gly Ala Val Glu Thr
    210                 215                 220

Leu Phe Arg Asp Ile Asp Asn Ile Phe Val Lys Ser Leu Gln Ser Val
225                 230                 235                 240

Gln Lys Val Ile Ile Ser Asp Lys His Cys Phe Glu Leu Tyr Gly Tyr
                245                 250                 255

Asp Ile Leu Ile Asp Gln Asp Leu Lys Pro Trp Leu Leu Glu Val Asn
            260                 265                 270

Ala Ser Pro Ser Leu Thr Ala Ser Ser Gln Glu Asp Tyr Glu Leu Lys
        275                 280                 285

Thr Cys Leu Leu Glu Asp Thr Leu His Val Val Asp Met Glu Ala Arg
    290                 295                 300

<210> SEQ ID NO 16
<211> LENGTH: 294
<212> TYPE: PRT
<213> ORGANISM: Caenorhabditis elegans

<400> SEQUENCE: 16
```

```
Lys Lys Ile Leu Phe Lys Cys Ala Leu Thr Asn Thr Ile Ser Asp Val
1               5                   10                  15

Leu Thr Asn Arg Glu Gly Trp Ala Gln Thr Gln Gly Asp Asp Trp Gln
            20                  25                  30

Phe Phe Trp Val Thr Arg Glu Trp Met Thr Thr Cys Tyr His Lys Phe
        35                  40                  45

Ser Glu Lys Gln Met Ile Cys His Phe Arg Asn Asp Phe Glu Leu Thr
50                  55                  60

Arg Lys Asp Phe Leu Ile Lys Asn Tyr Lys Ala Arg Lys Ala Lys
65              70                  75                  80

Val Ser Glu Phe Asn Phe Leu Pro Ser Ser Tyr Val Leu Pro Thr Glu
                85                  90                  95

Tyr His Leu Phe Val Glu Glu Phe Arg Lys Tyr Pro Asn Thr Ile Trp
            100                 105                 110

Ile Met Lys Pro Val Ala Gly Ala Gln Gly Lys Gly Ile Phe Leu Phe
        115                 120                 125

Arg Lys Leu Lys His Val Gln Glu Ala Leu Pro Tyr Val Val Gln Cys
130                 135                 140

Tyr Val His Asn Pro Tyr Leu Val Gly Gly Lys Lys Phe Asp Val Arg
145                 150                 155                 160

Ile Tyr Val Leu Val Thr Ser Phe Arg Pro Leu Asn Ala Trp Val His
                165                 170                 175

Arg Glu Gly Phe Ala Arg Phe Ser His Ser Arg Tyr Ser Thr Asp Ser
            180                 185                 190

Val Asp Asp Ala Phe Val His Leu Thr Asn Val Ala Val Ala Lys Thr
        195                 200                 205

Ala Ala Asp Tyr Asp Pro Glu Arg Gly Leu Lys Trp Ser Leu Pro Lys
        210                 215                 220

Leu Phe Arg Phe Phe Lys Ser Val His Gly Lys Leu Ser Lys Thr Met
225                 230                 235                 240

Asn Asp Leu Thr Asn Val Ile Ile Glu Ser Leu Lys Ser Val Gln Asn
                245                 250                 255

Leu Ile Ile Gln Val Asn Ala Ser Pro Ser Leu Thr Ala Ser Ser Gln
            260                 265                 270

Glu Asp Phe Glu Leu Lys Tyr Arg Ile Leu Asn His Met Ile Asp Val
        275                 280                 285

Leu Asp Ile Glu Lys Lys
        290

<210> SEQ ID NO 17
<211> LENGTH: 318
<212> TYPE: PRT
<213> ORGANISM: Giardia lamblia

<400> SEQUENCE: 17

Lys Pro Ile Arg Tyr Tyr Thr Thr Phe Arg Asn Thr Ile Trp Thr Val
1               5                   10                  15

Leu Gln Glu Arg Gly Trp Glu Gln Val Ser Asn Asp Thr Asp Trp Asn
            20                  25                  30

Phe Ile Trp Ala Ser Val Glu Trp Ile Ser Glu Arg Phe Ser His Val
        35                  40                  45

Pro Asp Thr Lys Phe Val Asn His Phe Arg Asn Phe Tyr Ile Leu Thr
50                  55                  60

Arg Lys Asp Leu Met Ala Lys Asn Leu Lys Ala Ala Arg Arg Asn Leu
65              70                  75                  80
```

```
Gly Asp Leu Phe Asp Phe Val Pro Ala Asn Phe Ile Leu Pro Met Glu
                85                  90                  95

Phe Gly Met Ile Thr Glu Phe Asn Arg Lys Gln Thr Thr Pro Leu Tyr
            100                 105                 110

Ile Val Lys Pro Ser Cys Arg Ala Gln Gly Lys Gly Ile Phe Ile Cys
        115                 120                 125

Gly Tyr Ser Asp Leu Tyr Thr Glu Ala Leu Tyr Val Val Gln Lys Tyr
    130                 135                 140

Leu Asp Asn Pro Leu Val Val Cys Gly His Lys Phe Asp Leu Arg Ile
145                 150                 155                 160

Tyr Cys Leu Val Glu Ser Phe Gln Pro Leu Val Ala Trp Ile Cys Arg
                165                 170                 175

Glu Gly Phe Ala Arg Phe Ser Leu Arg Pro Phe Thr Ala Asn Ala Thr
            180                 185                 190

Arg Asp Leu Glu Val His Leu Thr Asn Val Ala Ile Gln Lys Asn Ser
        195                 200                 205

Thr Asn Tyr Asp Ser Arg Ala Asp Gly Ala Lys Trp Ser Leu Phe Gln
    210                 215                 220

Leu Gly Cys Tyr Leu Glu Thr Ile Tyr Gly Gln Ile Asp Ile Met Phe
225                 230                 235                 240

Leu Arg Ile Glu Gln Leu Ile Ile Arg Ser Leu Gln Ala Val Ala Asn
                245                 250                 255

Asp Met Ile Lys Ser Leu Cys Met Phe Glu Ile Tyr Gly Phe Asp Val
            260                 265                 270

Met Leu Asp Ser Ser Leu Lys Pro Trp Leu Ile Glu Ile Asn Ala Ser
        275                 280                 285

Pro Ser Leu Ser Ala Asp Thr Arg Glu Asp Ser Ile Val Lys Arg Arg
    290                 295                 300

Met Leu His Asp Ala Ile Ser Ile Leu Gly Val Asp Val Pro
305                 310                 315

<210> SEQ ID NO 18
<211> LENGTH: 324
<212> TYPE: PRT
<213> ORGANISM: Tetrahymena

<400> SEQUENCE: 18

Gln Thr Leu Val Leu Asn Val Ala Asp Thr Lys Tyr Pro Val Val Lys
1               5                   10                  15

Phe Val Gly Lys Lys Ile Phe Lys Trp Lys Leu Ala Tyr Asp Met Glu
            20                  25                  30

Asp Phe Asp Ile Phe Trp Thr Asp Asn Ala Val Gln Pro Glu Gln Leu
        35                  40                  45

Gly Arg Met Gln Pro Tyr Gln Lys Ile Asn His Phe Pro Gly Met Phe
    50                  55                  60

Ser Leu Ala Arg Lys Asn His Leu Ala Arg Asn Leu Met Lys Met Arg
65                  70                  75                  80

Lys Gln Phe Pro Asp Gln Tyr Lys Phe Phe Pro Gln Thr Trp Leu Leu
                85                  90                  95

Pro Ala Glu Tyr Asn Asp Phe Lys Asn Gln Phe Glu Lys Ser Arg Ser
            100                 105                 110

Lys Ile Phe Ile Val Lys Pro Glu Ala Ser Cys Gln Gly Arg Gly Ile
        115                 120                 125

Phe Leu Thr Arg Ser Leu Asp Asp Leu Asn Pro Ser Asp His Tyr Val
    130                 135                 140
```

```
Val Gln Arg Tyr Leu Asn Lys Pro Tyr Leu Ile Asp Gly Leu Lys Phe
145                 150                 155                 160

Asp Phe Arg Leu Tyr Val Leu Leu Ala Gly Cys Asp Pro Leu Arg Ile
                165                 170                 175

Tyr Leu Tyr Tyr Glu Gly Leu Thr Arg Phe Ala Thr Glu Lys Tyr Gln
            180                 185                 190

Glu Val Asn Ile Glu Asp Met Cys Met His Leu Thr Asn Tyr Ala Ile
        195                 200                 205

Asn Lys Asp Asn Pro Asn Phe Lys Phe Asn Lys Asp Gly His Lys Arg
    210                 215                 220

Ser Leu Thr Ser Val Leu Gln Leu Leu Glu Asp Gln Gly His Asp Val
225                 230                 235                 240

Asn Lys Leu Trp Lys Asp Ile Lys Arg Val Leu Ile Lys Thr Ile Ile
                245                 250                 255

Ser Ala Gln Pro Thr Leu Ala His His Tyr Lys Ser Met Cys Phe Glu
                260                 265                 270

Ile Leu Gly Phe Asp Ile Ile Leu Asp Ser His Leu Lys Pro Trp Val
            275                 280                 285

Leu Glu Val Asn His Thr Pro Ser Phe Ser Thr Asp Thr Pro Leu Asp
        290                 295                 300

Ser Tyr Ile Lys Lys Asn Thr Ile Arg Asp Ser Leu Lys Leu Met Asn
305                 310                 315                 320

Cys Thr Cys Lys

<210> SEQ ID NO 19
<211> LENGTH: 322
<212> TYPE: PRT
<213> ORGANISM: Giardia lamblia

<400> SEQUENCE: 19

Arg Arg Ile Arg Val Cys Leu Asp Tyr Cys Lys Tyr Ser Val Ile His
1               5                   10                  15

Glu Ile Cys Glu Arg Arg Gly Trp Arg Gln Val Gly Glu Ser Asp Asp
            20                  25                  30

Trp Asn Leu Leu Trp Ser Asp Arg Ser Val Thr Ala Glu Arg Val Met
        35                  40                  45

Arg Met Lys Val Tyr Gln Arg Ile Asn His Phe Pro Ser Met Tyr Glu
    50                  55                  60

Ile Thr Arg Lys Asp Thr Leu Ala Lys Asn Leu Asn Lys Ile Arg Lys
65                  70                  75                  80

Leu Met Pro Asp Glu Tyr Asp Phe Tyr Pro Met Ser Phe Tyr Leu Pro
                85                  90                  95

Ala Asp Ser Ala Glu Met Arg Gln Tyr Ile Ser Lys Ala Pro Ser Val
            100                 105                 110

Tyr Ile Thr Lys Pro Val Ala Ser Cys Gln Gly Arg Gly Ile Arg Leu
        115                 120                 125

Phe Lys Asn Ile Asp Ser Ile Asp Thr Thr Glu Pro Gln Val Val Gln
    130                 135                 140

Glu Tyr Val Ser Lys Pro Tyr Leu Ile Gly Gly Leu Lys Phe Asp Leu
145                 150                 155                 160

Arg Met Tyr Val Leu Val Ser Val Ala Pro Leu Arg Leu Leu Val
                165                 170                 175

Tyr Glu Asp Gly Met Ala Arg Phe Ala Thr Glu Pro Tyr Ala Glu Pro
            180                 185                 190
```

```
Thr Met Lys Lys Thr Tyr Met His Leu Thr Asn Tyr Ala Ile Asn Lys
        195                 200                 205

Arg Asn Glu Asn Phe Ile Phe Asn Ala Glu Gly Ser Lys Trp Gly Leu
    210                 215                 220

Gln Ala Val Trp Asp Lys Ile Val Glu Asp Gly Gly Asp Leu Gln Lys
225                 230                 235                 240

Ile Arg Glu Asp Ile Asn Asp Ile Phe Val Lys Thr Ile Leu Ala Val
                245                 250                 255

Leu Pro Thr Leu Gln His Thr Tyr Met Ser Asn Cys Tyr Glu Val Leu
            260                 265                 270

Gly Phe Asp Ile Met Ile Asp Ser Leu Phe Lys Pro Trp Leu Ile Glu
        275                 280                 285

Val Asn His Ser Pro Ser Phe Thr Cys Asp Thr Pro Leu Asp Met Arg
    290                 295                 300

Ile Lys Glu Thr Leu Ile Asp Ala Val Leu Asp Val Ile Asn Val Thr
305                 310                 315                 320

Asn Gly

<210> SEQ ID NO 20
<211> LENGTH: 321
<212> TYPE: PRT
<213> ORGANISM: Drosophila melanogaster

<400> SEQUENCE: 20

Arg Leu Ser Val Cys Val Glu His Thr Arg Phe Gln Leu Val Ala Lys
1               5                   10                  15

Val Thr Arg Asn Met Gly Phe Gln His Val Pro Glu His Arg Leu Trp
            20                  25                  30

Asn Ile Gln Trp Ser Asp Ser Thr Pro His His Asp Leu Leu Arg Asn
        35                  40                  45

Met Lys Arg Phe Gln Gln Ile Asn His Phe Pro Gly Met Val Glu Ile
    50                  55                  60

Cys Arg Lys Asp Leu Leu Ser Arg Asn Leu Asn Arg Met Leu Lys Met
65                  70                  75                  80

Phe Pro Gly Asp Tyr Arg Ile Phe Pro Lys Thr Trp Leu Met Pro Thr
                85                  90                  95

Asp Ala Tyr Asp Val Ala Ile Tyr Ala Asn Lys His Lys Arg Thr Phe
            100                 105                 110

Ile Leu Lys Pro Tyr Ser Ala Gly Gln Gly Arg Gly Ile Trp Ile Thr
        115                 120                 125

Thr Asp Leu Arg Thr Val Gly Lys Arg Glu Lys Leu Ile Cys Gln Thr
    130                 135                 140

Tyr Ile Glu Arg Pro Leu Leu Ile Asp Gly Tyr Lys Phe Asp Leu Arg
145                 150                 155                 160

Val Tyr Thr Leu Val Thr Ser Val Asp Pro Leu Arg Ile Phe Val Tyr
                165                 170                 175

Asn Glu Gly Leu Ala Arg Phe Ala Thr Gln Lys Tyr Val Pro Pro Thr
            180                 185                 190

Ser His Asn Val Phe Met His Leu Thr Asn Tyr Cys Leu Asn Arg Arg
        195                 200                 205

Asn Ser Gln Tyr Met Val Gly Asn Gly Ser Lys Arg Lys Leu Ser
    210                 215                 220

Ala Phe Asn Lys Trp Leu Val Asp His Asn Tyr Asp Val Gly Glu Phe
225                 230                 235                 240

Trp Ala Ser Val Asp Asp Ala Ile Ile Lys Thr Leu Ile Ser Ala Trp
```

```
                     245                 250                 255
Pro Thr Leu Lys His Asn Tyr Asn Val Ala Ser Phe Gln Leu Leu Gly
            260                 265                 270

Phe Asp Ile Leu Val Asp Trp Lys Leu Lys Pro Tyr Ile Leu Glu Val
            275                 280                 285

Asn His Thr Pro Ser Leu Ser Ala Asp Glu Ser Val Asp Met Glu Val
            290                 295                 300

Lys Arg Pro Leu Ile Arg Asp Thr Leu Asn Met Leu Ser Thr Ala Leu
305                 310                 315                 320

Val

<210> SEQ ID NO 21
<211> LENGTH: 321
<212> TYPE: PRT
<213> ORGANISM: Drosophila melanogaster

<400> SEQUENCE: 21

Lys Ser Thr Ile Cys Val Ser Asn Ser Arg Tyr Ala Met Ile Gly Lys
1               5                   10                  15

Ile Ser Lys Thr Leu Gly Tyr Lys Leu Val Lys Glu Ser Lys Met Trp
            20                  25                  30

Asn Ile Leu Trp Ser Asp Ser Phe Pro Gly Val Glu Leu Phe Lys Asn
        35                  40                  45

Met Lys Arg Phe Gln Gln Ile Asn His Phe Pro Gly Met Ile Glu Ile
    50                  55                  60

Cys Arg Lys Asp Leu Leu Ser Arg Asn Leu Asn Arg Met Leu Lys Ile
65                  70                  75                  80

Phe Pro Gln Asp Tyr Lys Ile Phe Pro Lys Thr Trp Met Leu Pro Ala
                85                  90                  95

Asp Tyr Gly Asp Ala Met Asn Tyr Ala Leu Asn His Lys Arg Thr Phe
            100                 105                 110

Ile Leu Lys Pro Asp Ser Gly Ala Gln Gly Arg Gly Ile Trp Leu Thr
        115                 120                 125

Asn Asp Leu Lys Thr Ile Gly Pro His Glu Arg Leu Ile Cys Gln Thr
    130                 135                 140

Tyr Ile His Arg Pro Leu Leu Ile Asp Gly Tyr Lys Phe Asp Leu Arg
145                 150                 155                 160

Val Tyr Thr Leu Ile Thr Ser Val Asp Pro Leu Arg Ile Phe Val Tyr
                165                 170                 175

Asn Glu Gly Leu Ala Arg Phe Ala Thr Asn Lys Tyr Val Glu Pro Thr
            180                 185                 190

Ala Asn Asp Leu Tyr Met His Leu Thr Asn Tyr Ser Val Asn Lys Arg
        195                 200                 205

Asn Ser His Tyr Glu Leu Cys Asp Asn Gly Ser Lys Arg Lys Leu Ser
    210                 215                 220

Ala Ile Asn Asn Trp Met Arg Arg His Asn Tyr Asp Val Glu Glu Phe
225                 230                 235                 240

Trp Ser Asn Val Asp Asp Val Ile Ile Lys Thr Val Leu Ser Ala Trp
                245                 250                 255

Pro Val Leu Lys His Asn Tyr His Ala Ala Cys Phe Glu Ile Leu Gly
            260                 265                 270

Phe Asp Ile Leu Val Asp Trp Lys Leu Lys Pro Tyr Ile Leu Glu Val
        275                 280                 285

Asn His Ser Pro Ser Phe His Thr Asn Glu Gln Val Asp Arg Glu Val
    290                 295                 300
```

```
Lys Arg Pro Leu Ile Arg Asp Thr Leu Asn Leu Val Ser Thr Val Leu
305                 310                 315                 320

Ala

<210> SEQ ID NO 22
<211> LENGTH: 320
<212> TYPE: PRT
<213> ORGANISM: Homo sapiens

<400> SEQUENCE: 22

Arg Leu Val Ile Asn Leu Ser Ser Cys Arg Tyr Glu Ser Val Arg Arg
1               5                   10                  15

Ala Ala Gln Gln Tyr Gly Phe Arg Glu Gly Gly Glu Asp Asp Asp Trp
                20                  25                  30

Thr Leu Tyr Trp Thr Asp Tyr Ser Val Ser Leu Glu Arg Val Met Glu
        35                  40                  45

Met Lys Ser Tyr Gln Lys Ile Asn His Phe Pro Gly Met Ser Glu Ile
    50                  55                  60

Cys Arg Lys Asp Leu Leu Ala Arg Asn Met Ser Arg Met Leu Lys Met
65                  70                  75                  80

Phe Pro Lys Asp Phe Arg Phe Pro Arg Thr Trp Cys Leu Pro Ala
                85                  90                  95

Asp Trp Gly Asp Leu Gln Thr Tyr Ser Arg Ser Arg Lys Asn Lys Thr
            100                 105                 110

Tyr Ile Cys Lys Pro Asp Ser Gly Cys Gln Gly Lys Gly Ile Phe Ile
            115                 120                 125

Thr Arg Thr Val Lys Glu Ile Lys Pro Gly Asp Met Ile Cys Gln
        130                 135                 140

Leu Tyr Ile Ser Lys Pro Phe Ile Ile Asp Gly Phe Lys Phe Asp Leu
145                 150                 155                 160

Arg Ile Tyr Val Leu Val Thr Ser Cys Asp Pro Leu Arg Ile Phe Val
                165                 170                 175

Tyr Asn Glu Gly Leu Ala Arg Phe Ala Thr Thr Ser Tyr Ser Arg Pro
            180                 185                 190

Cys Leu Asp Asp Ile Cys Met His Leu Thr Asn Tyr Ser Ile Asn Lys
            195                 200                 205

His Ser Ser Asn Phe Ser Arg Asp Gly Ser Lys Arg Lys Leu Ser Thr
        210                 215                 220

Phe Ser Ala Tyr Leu Glu Asp His Ser Tyr Asn Val Glu Gln Ile Trp
225                 230                 235                 240

Arg Asp Ile Glu Asp Val Ile Ile Lys Thr Leu Ile Ser Ala His Pro
                245                 250                 255

Ile Ile Arg His Asn Tyr His Thr Ala Cys Phe Glu Ile Leu Gly Phe
            260                 265                 270

Asp Ile Leu Leu Asp His Lys Leu Lys Pro Trp Leu Leu Glu Val Asn
            275                 280                 285

His Ser Pro Ser Phe Ser Thr Asp Ser Arg Leu Asp Lys Glu Val Lys
        290                 295                 300

Asp Gly Leu Leu Tyr Asp Thr Leu Val Leu Ile Asn Leu Glu Ser Cys
305                 310                 315                 320

<210> SEQ ID NO 23
<211> LENGTH: 321
<212> TYPE: PRT
<213> ORGANISM: Tetrahymena
```

-continued

<400> SEQUENCE: 23

Phe Asn Leu Lys Tyr Lys Ile Asn Gly Glu Asn Pro Tyr Lys Cys Val
1               5                   10                  15

Val Lys Ala Phe Glu Glu Ala Gly Phe Glu Met Thr Glu Glu Asn Asp
            20                  25                  30

Trp Asn Cys Val Trp Ser Leu Pro Lys Lys Asp Arg Val Lys Phe Met
        35                  40                  45

Asn Gln Phe Gln Lys Gln Asn His Phe Pro Gly Cys Trp Asn Leu Gly
    50                  55                  60

Arg Lys Asp Phe Met Trp Arg Cys Leu Asn Arg Val Lys Arg Lys Cys
65                  70                  75                  80

Pro Lys Glu Met Asp Phe Val Pro Asn Thr Tyr Leu Leu Cys Asn Asp
                85                  90                  95

Trp Asp Arg Phe Leu Ala Arg Arg Asp Glu Ala Ser Lys Thr Leu Trp
            100                 105                 110

Ile Leu Lys Pro Ala Asp Gln Ala Cys Gly Arg Gly Val Lys Val Ile
        115                 120                 125

Ser Lys Thr Thr Lys Val Lys Arg Lys Ser Asn Arg Ile Ile Cys Asp
    130                 135                 140

Tyr Ile Ala Asn Pro His Leu Ile Asn Gly Leu Lys Tyr Asp Leu Arg
145                 150                 155                 160

Leu Tyr Val Leu Val Thr Ser Tyr Asp Pro Leu Arg Ile Tyr Leu Tyr
                165                 170                 175

Glu Glu Gly Leu Thr Arg Phe Ala Thr Glu Lys Tyr Asn Thr Asn Thr
            180                 185                 190

Ile Ser Lys Arg Phe Val His Leu Thr Asn Tyr Ser Val Asn Lys His
        195                 200                 205

Ala Lys Lys Phe Val Lys Asn Thr Asn Gly Ser Lys Trp Ser Leu Thr
    210                 215                 220

Ala Leu Lys Ala Lys Tyr Lys Gln Met Gly Ile Asn Val Asp Glu Leu
225                 230                 235                 240

Phe Gly Arg Ile Lys Asp Ile Ile Lys Thr Cys Ile Ser Ala Glu
                245                 250                 255

Pro Gln Met Leu Asp Ile Val Ala Lys Asn Cys Phe Glu Leu Tyr Gly
            260                 265                 270

Phe Asp Ile Leu Ile Asp Ser Ser Leu Lys Pro Trp Ile Leu Glu Val
        275                 280                 285

Asn Val Cys Pro Ser Leu Ser Ser Ser Pro Leu Asp Arg Lys Ile
    290                 295                 300

Lys His Ser Leu Leu Val Asp Val Leu Asn Ile Ile Gly Ile Thr Pro
305                 310                 315                 320

Tyr

<210> SEQ ID NO 24
<211> LENGTH: 321
<212> TYPE: PRT
<213> ORGANISM: Caenorhabditis elegans

<400> SEQUENCE: 24

Ala Arg Leu Thr Trp Cys His Asn Ser Leu Leu Pro Ile Val Met Arg
1               5                   10                  15

Gln Thr Leu Ala Ala Ser His Phe Thr Val Val Asp Glu Ser Leu Phe
            20                  25                  30

Tyr Val Gly Tyr Trp Gly Arg His Leu Lys Ser Ala Gly Tyr Arg Ala
        35                  40                  45

```
Leu Gln Pro His Gln Lys Val Asn His Phe Pro Gly Ala Phe His Ile
     50                  55                  60

Gly Arg Lys Asp Arg Leu Trp Met His Ile Arg Lys Gln Gln Glu Arg
 65                  70                  75                  80

Phe Glu Gly Glu Phe Asp Ile Met Pro Phe Thr Tyr Ile Leu Pro Thr
                 85                  90                  95

Asp Arg Gln Glu Leu Leu Lys Tyr Leu Glu Thr Asp Ala Ser Arg His
                100                 105                 110

Val Ile Val Lys Pro Pro Ala Ser Ala Arg Gly Thr Gly Ile Ser Val
            115                 120                 125

Thr Arg Lys Pro Lys Asp Phe Pro Thr Thr Ala Thr Leu Val Ala Gln
130                 135                 140

His Tyr Ile Glu Arg Pro Leu Thr Ile Asn Arg Ala Lys Phe Asp Leu
145                 150                 155                 160

Arg Leu Tyr Ala Tyr Val Pro Thr Phe Glu Pro Leu Arg Val Tyr Ile
                165                 170                 175

Tyr Asp Gln Gly Leu Val Arg Phe Ala Ser Val Pro Tyr Ser His Ser
                180                 185                 190

Val Ile Ser Asn Lys Tyr Met His Leu Thr Asn Tyr Ser Ile Asn Lys
            195                 200                 205

Leu Ala Glu Ala Asp Gly Val Ala Asn Val Pro Lys Trp Thr Leu His
210                 215                 220

His Leu Trp Glu His Phe Asp Glu Met Gly Val Asp Arg Glu Lys Ile
225                 230                 235                 240

Gln Arg Glu Ile Glu Glu Val Ile Ile Lys Ala Phe Ile Ser Thr Glu
                245                 250                 255

Lys Pro Ile Arg Glu His Met Ser Arg Ile Cys Tyr Glu Leu Phe Gly
                260                 265                 270

Ile Asp Ile Ile Leu Asp Glu Asp Tyr Lys Pro Trp Leu Leu Glu Val
            275                 280                 285

Asn Ile Ser Pro Ser Leu His Ser Gly Thr Pro Leu Asp Val Ser Val
290                 295                 300

Lys Ala Pro Leu Ala Lys Asp Val Leu Asn Leu Ala Gly Val Tyr Val
305                 310                 315                 320

Pro

<210> SEQ ID NO 25
<211> LENGTH: 322
<212> TYPE: PRT
<213> ORGANISM: Homo sapiens

<400> SEQUENCE: 25

Lys Leu Leu Arg Trp Lys Met Ser Thr Val Thr Pro Asn Ile Val Lys
 1               5                  10                  15

Gln Thr Ile Gly Arg Ser His Phe Lys Ile Ser Lys Arg Asn Asp Asp
                20                  25                  30

Trp Leu Gly Cys Trp Gly His His Met Lys Ser Pro Ser Phe Arg Ser
            35                  40                  45

Ile Arg Glu His Gln Lys Leu Asn His Phe Pro Gly Ser Phe Gln Ile
 50                  55                  60

Gly Arg Lys Asp Arg Leu Trp Arg Asn Leu Ser Arg Met Gln Ser Arg
 65                  70                  75                  80

Phe Lys Lys Glu Phe Ser Phe Pro Gln Ser Phe Ile Leu Pro Gln
                 85                  90                  95
```

-continued

Asp Ala Lys Leu Leu Arg Lys Ala Trp Glu Ser Ser Arg Gln Lys
            100                 105                 110

Trp Ile Val Lys Pro Pro Ala Ser Ala Arg Gly Ile Gly Ile Gln Val
        115                 120                 125

Ile His Lys Trp Ser Gln Leu Pro Lys Arg Arg Pro Leu Leu Val Gln
    130                 135                 140

Arg Tyr Leu His Lys Pro Tyr Leu Ile Ser Gly Ser Lys Phe Asp Leu
145                 150                 155                 160

Arg Ile Tyr Val Tyr Val Thr Ser Tyr Asp Pro Leu Arg Ile Tyr Leu
                165                 170                 175

Phe Ser Asp Gly Leu Val Arg Phe Ala Ser Cys Lys Tyr Ser Pro Ser
            180                 185                 190

Met Leu Gly Asn Lys Phe Met His Leu Thr Asn Tyr Ser Val Asn Lys
        195                 200                 205

Lys Asn Ala Glu Tyr Gln Ala Asn Ala Asp Gly His Lys Trp Ala Leu
    210                 215                 220

Lys Ala Leu Trp Asn Tyr Leu Ser Gln Lys Gly Val Asn Ser Asp Ala
225                 230                 235                 240

Ile Trp Glu Lys Ile Lys Asp Val Val Val Lys Thr Ile Ile Ser Ser
                245                 250                 255

Glu Pro Tyr Val Thr Ser Leu Leu Lys Met Ser Cys His Glu Leu Phe
            260                 265                 270

Gly Phe Asp Ile Met Leu Asp Glu Asn Leu Lys Pro Trp Val Leu Glu
        275                 280                 285

Val Asn Ile Ser Pro Ser Leu His Ser Ser Pro Leu Asp Ile Ser
    290                 295                 300

Ile Lys Gly Gln Met Ile Arg Asp Leu Leu Asn Leu Ala Gly Phe Val
305                 310                 315                 320

Leu Pro

<210> SEQ ID NO 26
<211> LENGTH: 322
<212> TYPE: PRT
<213> ORGANISM: Drosophila melanogaster

<400> SEQUENCE: 26

Arg Val Leu Lys Trp Arg Ile Thr Asn Ile Met Pro Lys Val Val Arg
1               5                   10                  15

Leu Ile Leu Ala Asn Ser Gly Met Arg Met Leu Lys Lys Thr Asn Asp
            20                  25                  30

Trp Met Gly Val Trp Gly Lys His Leu Lys Ser Pro Cys Phe Lys Ala
        35                  40                  45

Ile Arg Ser Tyr Gln Lys Ile Asn His Leu Pro Gly Ser Phe Arg Ile
    50                  55                  60

Gly Arg Lys Asp Ser Cys Trp Lys Asn Leu Gln Arg Gln Met Gly Lys
65                  70                  75                  80

His Asn Lys Glu Phe Gly Phe Met Pro Arg Thr Tyr Ile Ile Pro Asn
                85                  90                  95

Asp Leu Gly Ala Leu Arg Arg His Trp Pro Lys Tyr Ala Gln Thr Lys
            100                 105                 110

Trp Ile Ile Lys Pro Pro Ala Ser Ala Arg Gly Ala Gly Ile Arg Val
        115                 120                 125

Ile Asn Arg Trp Gly Gln Ile Pro Lys Arg Arg Pro Leu Ile Val Gln
    130                 135                 140

Lys Tyr Ile Glu Arg Pro Leu Leu Ile Asn Gly Ser Lys Phe Asp Leu

```
                145                 150                 155                 160
Arg Leu Tyr Val Leu Val Thr Ser Val Asn Pro Leu Arg Val Phe Met
                    165                 170                 175

Tyr His Asn Gly Leu Ala Arg Phe Ala Ser Val Lys Tyr Ser Ala Lys
                180                 185                 190

Thr Leu Asn Asp Arg Cys Met His Leu Thr Asn Tyr Ser Ile Asn Lys
            195                 200                 205

Phe Ser Ser Asn Tyr Ser Lys Asn Glu Asp Gly His Lys Trp Thr Ile
        210                 215                 220

Lys Ser Leu Trp Thr Tyr Leu Ala Asn Arg Gly Val Arg Thr Asp Cys
225                 230                 235                 240

Leu Trp Glu Ala Leu Arg Ser Leu Val Leu Arg Thr Ile Leu Ala Gly
                245                 250                 255

Glu Asn Gly Ile Asn Ser Met Ile Arg Ala Ser Cys Phe Glu Leu Phe
            260                 265                 270

Gly Phe Asp Val Ile Leu Asp Ser Asp Leu Val Pro Trp Leu Leu Glu
        275                 280                 285

Val Asn Ile Ser Pro Ser Leu His Ser Glu Leu Pro Leu Asp Ala His
    290                 295                 300

Val Lys Ala Pro Leu Val Gln Gly Val Leu Asn Thr Ala Leu Tyr Asn
305                 310                 315                 320

Val Pro

<210> SEQ ID NO 27
<211> LENGTH: 322
<212> TYPE: PRT
<213> ORGANISM: Drosophila melanogaster

<400> SEQUENCE: 27

Arg Val Leu Lys Trp Lys Leu Ser Pro Val Met Pro Lys Ile Val Lys
1               5                   10                  15

Arg Val Val Leu Asn Ser Gly Phe Arg Ile Ile Lys Asn Thr Thr Asp
                20                  25                  30

Trp Met Ala Val Trp Glu Lys His Met Lys Ser Pro Gly Phe Arg Thr
            35                  40                  45

Ile Arg Ser His Gln Lys Tyr Asn His Ile Pro Gly Ser Phe Arg Ile
        50                  55                  60

Gly Arg Lys Asp Thr Met Trp Arg Ser Ile Tyr Asn Asn Met Lys Lys
65                  70                  75                  80

Phe Lys Lys Glu Phe Gly Phe Met Gln Lys Ser Tyr Ile Met Pro Asp
                85                  90                  95

Asp Leu Glu Ser Leu Arg Gln Val Trp Pro Lys Asn Ala Ser Thr Lys
            100                 105                 110

Trp Ile Val Lys Pro Pro Ala Ser Ala Arg Gly Thr Gly Ile Arg Ile
        115                 120                 125

Val Asn Lys Trp Ser Gln Phe Pro Lys Asp Arg Pro Leu Val Val Gln
    130                 135                 140

Lys Tyr Ile Glu Arg Pro Leu Leu Ile Asn Asp Asn Lys Phe Asp Met
145                 150                 155                 160

Arg Leu Tyr Val Val Leu Thr Ser Ile Asn Pro Leu Arg Ile Tyr Met
                165                 170                 175

Tyr Lys Asp Gly Leu Ala Arg Phe Ala Ser Val Lys Tyr Ser Ser Glu
            180                 185                 190

Leu Leu Asp Glu Arg Cys Met His Leu Thr Asn Tyr Ser Ile Asn Lys
        195                 200                 205
```

```
Phe Ser Gln Asn Tyr Ala Lys Asn Glu Asp Gly His Lys Trp Thr Leu
    210                 215                 220

Gln Ser Leu Trp Ser Cys Leu Glu Asn Arg Gly Val Asn Thr Lys Arg
225                 230                 235                 240

Leu Trp Ala Thr Leu Arg Asn Leu Val Ile Lys Gly Ile Val Ser Gly
                245                 250                 255

Glu Ser Gly Leu Asn Arg Met Tyr Arg Gln Asn Cys Phe Glu Leu Phe
                260                 265                 270

Gly Phe Asp Val Leu Leu Asp Glu Asn Leu Val Pro Trp Leu Leu Glu
            275                 280                 285

Ile Asn Ile Ser Pro Ser Leu His Ser Glu Leu Pro Leu Asp Leu His
        290                 295                 300

Val Lys Gly Pro Leu Ile Gln Ala Val Leu Asn Thr Ala Leu Tyr Gln
305                 310                 315                 320

Val Pro

<210> SEQ ID NO 28
<211> LENGTH: 324
<212> TYPE: PRT
<213> ORGANISM: Tetrahymena

<400> SEQUENCE: 28

Leu Leu Lys Phe Tyr Val Gly Gly Asn Asn Gly Glu Arg Ile Arg
1               5                   10                  15

Lys Leu Met Leu Lys Arg Glu Gly Trp Val Glu Thr Lys Asp Pro Thr
                20                  25                  30

Phe Val Asn Phe Lys Trp Gln Gln Thr Thr Arg Gly Tyr Lys Tyr Glu
                35                  40                  45

Glu Asn Thr Ser Tyr Lys Gln Val Val Asn His Phe Glu Phe His Lys
50                  55                  60

Glu Ile Thr Asn Lys Gln Tyr Leu Val Lys Asn Leu Met Ser Phe Ala
65                  70                  75                  80

Glu Ser Met Gln Asn Val Phe Asp Ile Thr Pro Leu Thr Tyr Val Ile
                85                  90                  95

Asp Phe Ile Leu Asn Asn Phe Leu Lys Phe Glu Met Asn Met Pro
                100                 105                 110

Tyr Met Trp Leu Leu Lys Pro Thr Phe Leu Asn Arg Gly Arg Gly Ile
                115                 120                 125

His Val Phe Asn Ser Leu Ala Ser Leu Glu Lys Ala Ser Gln Phe Val
            130                 135                 140

Ile Gln Lys Tyr Ile Glu Lys Pro Leu Leu Ile Asn Lys Arg Lys Phe
145                 150                 155                 160

Asp Ile Arg Val Trp Ala Leu Val Leu Ile Leu Phe Tyr Tyr Leu Phe
                165                 170                 175

Gln Ile Lys Arg Glu Gly Tyr Met Arg Leu Ser Ser Ser Glu Phe Ser
                180                 185                 190

Thr Asp Glu Leu Asp Asn Leu Phe Ile His Leu Thr Asn Asn Ala Ile
            195                 200                 205

Gln Lys Tyr Ser Asp Asn Tyr Gly Gln Phe Glu Asn Gly Asn Met Trp
210                 215                 220

Ser Phe Gln Gln Leu Trp Glu Phe Leu Glu Ala Asn Tyr Gln Phe Lys
225                 230                 235                 240

Lys Lys Ile Val Ser Lys Ile Leu Asp Ile Ile Trp Leu Thr Phe Cys
                245                 250                 255
```

```
Ser Val Lys Lys Ile Asn Gln Tyr Asp Arg Lys Phe Cys Phe Glu
            260                 265                 270

Ile Phe Gly Phe Asp Phe Leu Ile Asp Glu Glu Leu Asn Ser Trp Leu
            275                 280                 285

Ile Glu Val Asn Thr Asn Pro Ala Ile Asp Glu Cys Ser Gln Leu Leu
290                 295                 300

Lys Thr Leu Ile Pro Arg Ala Leu Asp Asp Ala Leu Lys Leu Thr Ile
305                 310                 315                 320

Asp Gln Ile Phe

<210> SEQ ID NO 29
<211> LENGTH: 319
<212> TYPE: PRT
<213> ORGANISM: Tetrahymena

<400> SEQUENCE: 29

Val Tyr Lys Phe Ile Val Tyr Pro Gly Asn Asn Ser Phe Val Ile Arg
1               5                   10                  15

Glu Ala Leu Leu Lys Arg Gly Asn Trp Lys Glu Val Gln Tyr Asp Asp
            20                  25                  30

Glu Ile Asp Phe Ile Trp Ser Pro Asn Ser Leu Ser Thr Lys Glu Lys
        35                  40                  45

Asn Pro Asn His Gln Ile Val Ile Asn His Phe Glu Asn Asn Gln Ser
    50                  55                  60

Leu Thr Thr Lys Ser Asp Met Ile Lys Ala Leu Asn Asn His Tyr Arg
65                  70                  75                  80

Lys Asn Tyr Asn Val Phe His Ser Ile Pro Ala Thr Tyr Val Leu Ile
                85                  90                  95

Val Asp Gln Arg Asp Phe Gln Ile Lys Phe Asn Glu Ile Ser Lys Asn
            100                 105                 110

Ile Trp Ile Leu Lys Pro Asp Asn Met Ser Gln Gly Lys Gly Ile Glu
        115                 120                 125

Ile Phe Gln Ser Leu Lys Ala Ile Leu Ser Phe Ser Lys Trp Val Ile
    130                 135                 140

Gln Lys Tyr Ile Glu Arg Pro Leu Leu Tyr Asn Gly Arg Lys Phe Asp
145                 150                 155                 160

Leu Arg Val Trp Val Leu Leu Thr Asn Lys Gly Glu Leu Phe Val Tyr
                165                 170                 175

Lys Asn Gly Tyr Leu Arg Thr Ser Ser Ser Lys Tyr Ser Met Gln Thr
            180                 185                 190

Phe Asn Glu Ala Val His Leu Thr Asn Trp Ser Leu Gln Lys Gly Leu
        195                 200                 205

Pro Ser Tyr Glu Lys His Glu Gln Gly Asn Arg Leu Pro Leu Lys Glu
    210                 215                 220

Gly Leu Gln Tyr Ile Phe Asp Thr Gln Phe Tyr Glu Lys His Ile Tyr
225                 230                 235                 240

Pro Arg Met Lys Asp Leu Ile Ile Asp Leu Val Arg Ser Cys Glu Gln
                245                 250                 255

Glu Met Phe Lys Ser Lys Lys Asn Cys Phe Glu Leu Tyr Gly Phe Asp
            260                 265                 270

Phe Ile Ile Asp Glu Asp Leu Arg Val Trp Leu Ile Glu Ala Asn Lys
        275                 280                 285

Asn Pro Gly Phe Gly Leu Pro Thr Glu Lys Ala Arg Lys Leu Ile Asp
    290                 295                 300

Glu Met Val Asp Glu Leu Leu Arg Leu Thr Ile Asp Gln Asp Tyr
```

```
                305                 310                 315

<210> SEQ ID NO 30
<211> LENGTH: 309
<212> TYPE: PRT
<213> ORGANISM: Trypanosoma brucei

<400> SEQUENCE: 30

Ala Ala Pro Arg Phe Phe Leu Gly Glu Ser Asn Phe Ser Val Tyr Glu
1               5                   10                  15

Glu Met Ala Arg Gln Leu Lys Glu Met Gly Trp Cys Glu Val Arg Ser
            20                  25                  30

Lys Gly Trp Leu Pro Thr Cys Asp Val Ile Leu Gly Asp Ser Arg Tyr
        35                  40                  45

Ser Gly Ser Arg Trp Leu Asn Tyr Phe Arg Gly Ser His Arg Leu Thr
    50                  55                  60

Leu Lys Ala Ser Met Ala Arg Leu Leu Gln Lys Ala Asp Ser Thr Cys
65                  70                  75                  80

Gly Glu Trp Met Pro Arg Ser Tyr Val Leu Gly Gly Asp Arg Glu Ala
                85                  90                  95

Phe Leu Glu His Ala Val Arg Asp Pro Thr Gln Val Trp Ile Ile Lys
            100                 105                 110

Pro Ser Ser Gly Cys Lys Gly Lys Asp Ile Val Leu Thr Arg Ser Val
        115                 120                 125

Ala Glu Leu Glu Val Arg Arg Ile Tyr Leu Val Gln Gln Tyr Val Gln
    130                 135                 140

Arg Pro Leu Leu Tyr Arg Gly Arg Lys Phe Asp Met Arg Val Trp Ala
145                 150                 155                 160

Leu Leu Lys Ser Pro Tyr Thr Ile Tyr Ala Phe Thr Lys Gly Ser Cys
                165                 170                 175

Arg Thr Ser Ser Ser Pro Tyr Asp Pro Asp Asp Ile Glu Asp Tyr Leu
            180                 185                 190

Val His Leu Thr Asn His Cys Leu Gln Glu Asp Ala Pro Glu Phe Gly
        195                 200                 205

Gln Tyr Glu Glu Gly Asn Glu Leu Trp Phe Glu Glu Val Gly Ala Tyr
    210                 215                 220

Leu His Glu Val Tyr Arg Leu Glu Asp Arg Ile Leu Pro Gln Ile Ala
225                 230                 235                 240

Ser Ile Ile Ile Arg Thr Leu Leu Ala Ala Arg Ala Glu Leu Gln Val
                245                 250                 255

Leu Glu Asn Gln Cys Phe Gln Leu Phe Gly Tyr Asp Val Ile Val Asp
            260                 265                 270

Glu Gly Leu Ser Val Met Leu Leu Glu Ile Asn Gly Ser Pro Gly Val
        275                 280                 285

Ala Ser Lys Tyr Leu Gln Pro Leu Val Arg Glu Ile Ile Lys Leu Val
    290                 295                 300

Asp Gly Gly Glu Ala
305

<210> SEQ ID NO 31
<211> LENGTH: 313
<212> TYPE: PRT
<213> ORGANISM: Homo sapiens

<400> SEQUENCE: 31

Met Tyr Thr Phe Val Val Arg Asp Glu Asn Ser Ser Val Tyr Ala Glu
1               5                   10                  15
```

```
Val Ser Arg Leu Leu Ala Thr Gly His Trp Lys Arg Leu Arg Asn
         20                  25                  30

Pro Arg Phe Asn Leu Met Leu Gly Glu Arg Asn Arg Leu Pro Phe His
             35                  40                  45

Glu Pro Gly Leu Val Gln Leu Val Asn Tyr Tyr Arg Gly Ala Asp Lys
 50                  55                  60

Leu Cys Arg Lys Ala Ser Leu Val Lys Leu Ile Lys Thr Ser Pro Glu
 65                  70                  75                  80

Leu Ala Glu Ser Cys Thr Trp Phe Pro Glu Ser Tyr Val Ile Tyr Pro
                 85                  90                  95

Asp Glu Arg Glu Phe Phe Leu Ala Ser Tyr Asn Arg Lys Lys Asn Val
             100                 105                 110

Trp Ile Ala Lys Ser Ser Ala Gly Ala Lys Gly Glu Gly Ile Leu Ile
             115                 120                 125

Ser Ser Glu Ala Ser Glu Leu Leu Asp Gly Gln Val His Val Ile Gln
 130                 135                 140

Lys Tyr Leu Glu His Pro Leu Leu Gly His Arg Lys Phe Asp Ile
 145                 150                 155                 160

Arg Ser Trp Val Leu Val Asp His Gln Tyr Asn Ile Tyr Leu Tyr Arg
                 165                 170                 175

Glu Gly Val Leu Arg Thr Ala Ser Glu Pro Tyr His Val Asp Asn Phe
             180                 185                 190

Gln Asp Lys Thr Cys His Leu Thr Asn His Cys Ile Gln Lys Tyr Ser
             195                 200                 205

Lys Asn Tyr Gly Lys Tyr Glu Glu Gly Asn Glu Met Phe Phe Lys Glu
 210                 215                 220

Phe Asn Gln Tyr Leu Thr Ser Ala Leu Asn Leu Glu Ser Ser Ile Leu
 225                 230                 235                 240

Leu Gln Ile Lys His Ile Ile Arg Asn Cys Leu Leu Ser Val Glu Pro
                 245                 250                 255

Ala Ile Ser Thr Lys His Leu Gln Ser Phe Gln Leu Phe Gly Phe Asp
                 260                 265                 270

Phe Met Val Asp Glu Glu Leu Lys Val Trp Leu Ile Glu Val Asn Gly
                 275                 280                 285

Ala Pro Ala Cys Ala Gln Lys Leu Tyr Ala Glu Leu Cys Gln Gly Ile
 290                 295                 300

Val Asp Ile Ala Ile Ser Ser Val Phe
 305                 310

<210> SEQ ID NO 32
<211> LENGTH: 296
<212> TYPE: PRT
<213> ORGANISM: Homo sapiens

<400> SEQUENCE: 32

Gln Thr Arg Leu Leu Gln Gly Arg Gly Gly Leu Ala Val Pro Gly Leu
 1               5                  10                  15

Leu Gln Val Leu Ile Thr Val Glu Gln Ser Cys His Pro Glu Pro
             20                  25                  30

Val Arg Val Thr Ala Gly Val Leu Gly Ala Pro Leu Ala Leu Thr Pro
             35                  40                  45

Val Leu Gln Pro Pro Cys Gln Asp Val Met Gly Ser Pro Pro Gly Leu
 50                  55                  60

His Ser Ser Glu Ser Gln Arg Ala Leu Gly Gln Leu Leu Cys Gln Ala
 65                  70                  75                  80
```

Leu Leu Asn Arg Asp Ile Asp Gly Leu Arg Asn Ile Trp Ile Ile Lys
            85                  90                  95

Pro Ala Ala Lys Ser Arg Gly Arg Asp Ile Val Cys Met Asp Arg Val
            100                 105                 110

Glu Glu Ile Leu Glu Asp Asn Lys Trp Val Val Gln Lys Tyr Ile Glu
            115                 120                 125

Thr Pro Leu Leu Ile Cys Asp Thr Lys Phe Asp Ile Arg Gln Trp Phe
    130                 135                 140

Leu Val Thr Asp Trp Asn Pro Leu Thr Ile Trp Phe Tyr Lys Glu Ser
145                 150                 155                 160

Tyr Leu Arg Phe Ser Thr Gln Arg Phe Ser Leu Asp Lys Leu Asp Ser
                165                 170                 175

Ala Ile His Leu Cys Asn Asn Ala Val Gln Lys Tyr Leu Lys Asn Asp
            180                 185                 190

Val Gly Arg Ser Pro His Asn Met Trp Thr Ser Thr Arg Phe Gln Glu
            195                 200                 205

Tyr Leu Gln Arg Gln Gly Arg Trp Gly Ser Val Ile Tyr Pro Ser Met
    210                 215                 220

Lys Lys Ala Ile Ala His Ala Met Lys Val Ala Gln Asp His Val Glu
225                 230                 235                 240

Pro Arg Lys Asn Ser Phe Glu Leu Tyr Gly Ala Asp Phe Val Leu Gly
                245                 250                 255

Arg Asp Phe Arg Pro Trp Leu Ile Glu Ile Asn Ser Ser Pro Thr Met
            260                 265                 270

His Pro Ser Thr Pro Val Thr Ala Gln Leu Cys Ala Gln Val Gln Glu
            275                 280                 285

Asp Thr Ile Lys Val Ala Val Asp
    290                 295

<210> SEQ ID NO 33
<211> LENGTH: 320
<212> TYPE: PRT
<213> ORGANISM: Homo sapiens

<400> SEQUENCE: 33

Leu Cys Leu Asn Leu Arg Asn Leu Pro Trp Phe Asp Glu Val Asp Ala
1               5                   10                  15

Asn Ser Phe Phe Pro Arg Cys Tyr Cys Leu Gly Ala Glu Asp Asp Phe
            20                  25                  30

Ile Glu Asp Phe Trp Leu Thr Ala Ala Arg Asn Val Leu Lys Leu Gln
        35                  40                  45

Pro Lys Lys Gln Glu Lys Asn Pro Val Leu Val Ser Pro Glu Phe Val
    50                  55                  60

Asp Glu Ala Leu Cys Ala Cys Glu Glu Tyr Leu Ser Asn Leu Ala His
65                  70                  75                  80

Met Asp Glu Ala Pro Leu Tyr Leu Thr Pro Glu Gly Trp Ser Leu Phe
                85                  90                  95

Leu Glu Gly Ala Glu Leu Arg His Leu Asp Thr Gln Val Gln Arg Asn
            100                 105                 110

Ile Trp Ile Val Lys Pro Gly Ala Lys Ser Arg Gly Arg Gly Ile Met
        115                 120                 125

Cys Met Asp His Leu Glu Glu Met Leu Lys Asp Gly Lys Trp Val Val
    130                 135                 140

Gln Lys Tyr Ile Glu Arg Pro Leu Leu Ile Phe Gly Thr Lys Phe Asp
145                 150                 155                 160

```
Leu Arg Gln Trp Phe Leu Val Thr Asp Trp Asn Pro Leu Thr Val Trp
                165                 170                 175

Phe Tyr Arg Asp Ser Tyr Ile Arg Phe Ser Thr Gln Pro Phe Ser Leu
            180                 185                 190

Lys Asn Leu Asp Asn Ser Val His Leu Cys Asn Asn Ser Ile Gln Lys
        195                 200                 205

His Leu Glu Asn Ser Cys His Arg His Pro Asp Asn Met Trp Ser Ser
210                 215                 220

Gln Arg Phe Gln Ala His Leu Gln Glu Met Gly Ala Trp Ser Thr Ile
225                 230                 235                 240

Ile Val Pro Gly Met Lys Asp Ala Val Ile His Ala Leu Gln Thr Ser
                245                 250                 255

Gln Asp Thr Val Gln Cys Arg Lys Ala Ser Phe Glu Leu Tyr Gly Ala
            260                 265                 270

Asp Phe Val Phe Gly Glu Asp Phe Gln Pro Trp Leu Ile Glu Ile Asn
        275                 280                 285

Ala Ser Pro Thr Met Ala Pro Ser Thr Ala Val Thr Ala Arg Leu Cys
    290                 295                 300

Ala Gly Val Gln Ala Asp Thr Leu Arg Val Val Ile Asp Arg Met Leu
305                 310                 315                 320

<210> SEQ ID NO 34
<211> LENGTH: 315
<212> TYPE: PRT
<213> ORGANISM: Tetrahymena

<400> SEQUENCE: 34

Asn Asp Thr Lys Tyr Lys Ile Phe Ser Tyr Asp Tyr Asp Phe Arg Leu
1               5                   10                  15

Lys Arg Ile Ile His Gln Cys Val Ser Asn Tyr Lys Tyr His Tyr Gln
                20                  25                  30

Ala Asp Leu Leu Tyr Leu Glu Pro Ile Cys Asp Gln Asn Ser Asn Ile
            35                  40                  45

Leu Ile Gln Asn Leu Thr Ile Tyr Asn Phe Leu Met Asn Ser Asp Ile
        50                  55                  60

Val Asn Asn Lys Leu His Phe Tyr Gln Ile Ala His Gln Leu Asp Gln
65                  70                  75                  80

Glu Asn Phe Ser Leu Ser Lys Phe Leu Pro Lys Thr Tyr Ala Phe Asn
                85                  90                  95

Leu Gln Glu Glu Glu Phe Met Asn Leu Leu Ser Glu Met Trp Ile
            100                 105                 110

Ser Lys Pro Leu Asp Gln Leu Gly Gly Lys Gly Ile Lys Val Tyr Gln
        115                 120                 125

Asn Ser Ser Gln Ile Lys Glu Asp Gln Gln Val Ile Val Gln Arg Tyr
    130                 135                 140

Ile Gln Asn Pro Leu Leu Val Asn Lys Lys Phe Asp Ile Arg Ser
145                 150                 155                 160

Tyr Val Ile Val Val Ser Thr Asp Pro Tyr Ile Val Tyr Phe Leu Asn
                165                 170                 175

Gly Tyr Val Arg Leu Thr Ile Asn Asp Tyr Asn Lys Asn Asp Thr Asp
            180                 185                 190

Leu Leu Thr His Leu Val Asn Thr Asn Ile Gln Lys His Pro Gln
        195                 200                 205

Phe Asn Ser Lys Lys Asp Asp Ser His Trp Glu Leu His Lys Phe Glu
    210                 215                 220
```

Ser Ala Leu Lys Gln Gln Tyr Asn Ile Gln Ile Lys Ile Tyr Asn Gln
225                 230                 235                 240

Met Lys Lys Ala Ser Ala Tyr Leu Phe Lys Gly Leu Glu Gln Tyr Phe
                245                 250                 255

Asn Val Phe Thr Ala Asn Phe Gln Ile Phe Gly Leu Asp Phe Met Phe
            260                 265                 270

Asp Glu Asp Phe Asn Gln Tyr Phe Ile Glu Val Asn Glu Ile Pro Gln
        275                 280                 285

Leu Leu Gly Gln Thr Ser Thr His Arg Asn Val Cys Pro Glu Ile Val
    290                 295                 300

Ser Gln Gln Leu Asp Ser Ser Leu Tyr Ala Asn
305                 310                 315

<210> SEQ ID NO 35
<211> LENGTH: 307
<212> TYPE: PRT
<213> ORGANISM: Tetrahymena

<400> SEQUENCE: 35

Leu Asn Asp Thr Leu Pro Lys Gln Thr Pro Leu Lys Val Ile Thr Asp
1               5                   10                  15

Asn Ser Leu Val Ser Glu Tyr Leu Thr Ala Pro Glu Phe Gln Leu Cys
            20                  25                  30

Glu Ala Asn Val Ile Phe Leu Thr His Cys Phe Glu Glu Thr Ile Arg
        35                  40                  45

Asp His Tyr Met Thr Lys Phe Cys Asn Gln Phe Pro Asp Glu Cys His
    50                  55                  60

Ile Val Gln Lys Asn His Leu Ala Asp Thr Val Phe Ser Thr Leu Gly
65                  70                  75                  80

Gln Val Asp Trp Ile Gln Pro Thr Tyr Asn Leu Lys Thr Gln Met Asn
                85                  90                  95

Glu Phe Val Gly Glu Tyr Lys Arg Arg Arg Asn Asn Val Trp Ile Ile
            100                 105                 110

Lys Ala Phe Asn Leu Ala Arg Ser Leu Asp Met Ile Val Thr Asp Asn
        115                 120                 125

Leu Asp Gln Ile Ile Arg Thr Leu Pro Arg Leu Ala Gln Lys Tyr Ile
    130                 135                 140

Thr Asn Pro Val Thr Leu Phe Gly Lys Lys Ile Asp Leu Arg Tyr Ile
145                 150                 155                 160

Val Ser Val Arg Ser Leu Glu Pro Phe Glu Val Phe Ile Tyr Lys Val
                165                 170                 175

Phe Trp Ile Arg Thr Ser Asn Asn Asp Phe Thr Asn Asp Tyr Arg Glu
            180                 185                 190

Ile Tyr Glu Thr His Phe Thr Val Met Asn Tyr Gly Lys Lys Leu Lys
        195                 200                 205

Gln Ile His Tyr Asp Glu Phe Ile Glu Glu Phe Glu Lys Glu Tyr Thr
    210                 215                 220

Lys Trp Ala Ala Ile His Asp Lys Ile Lys Thr Met Val Lys Glu Leu
225                 230                 235                 240

Phe Met Ala Val Tyr Lys Lys Tyr Pro Gly Met Asn Cys Arg Gly Ser
                245                 250                 255

Tyr Gly Met Asp Val Met Ile Asn Gly Thr Phe Gln Pro Lys Leu Leu
            260                 265                 270

Glu Leu Thr Phe Ser Pro Asp Cys Glu Arg Ala Cys Lys Tyr His Pro
        275                 280                 285

His Phe Phe Asn Asp Met Phe Lys Leu Phe Leu Asn Asp Gln Glu
    290                 295                 300

His Pro Asn
305

<210> SEQ ID NO 36
<211> LENGTH: 315
<212> TYPE: PRT
<213> ORGANISM: Drosophila melanogaster

<400> SEQUENCE: 36

Pro Leu Pro Ala Arg Ser Arg Cys Asp Pro Leu Lys Val Tyr Ala Glu
1               5                   10                  15

Tyr Glu Val Val Arg Arg His Leu Thr Ser Ser Glu Phe Ile Leu Val
            20                  25                  30

Glu Ala Asp Val Leu Trp Leu Thr His His Phe Lys Asn Phe Glu Asp
        35                  40                  45

Ala Asp Arg Ser Pro Gly Lys Phe Ile Asn Gln Phe Pro Phe Glu Tyr
    50                  55                  60

Val Ile Thr Ile Lys Asp Leu Leu Ser Ile Val Gly Arg Arg Ala Ala
65                  70                  75                  80

Lys Glu His Glu Thr Phe Pro Ala Trp Leu Pro Thr Thr Tyr Asn Leu
                85                  90                  95

Ser Thr Glu Val Lys Glu Phe Ala Ala Tyr Tyr Gln Thr Arg Ala Ala
            100                 105                 110

Asn His Trp Ile Ile Lys Pro Trp Asn Leu Ala Arg Gly Leu Asp Thr
        115                 120                 125

His Ile Thr Asp Asn Ile Lys Gln Ile Val Arg Thr Gly Pro Lys Ile
    130                 135                 140

Ala Gln Lys Tyr Ile Glu Arg Pro Val Leu Phe Gly Ser Val Lys Phe
145                 150                 155                 160

Asp Ile Arg Tyr Val Ile Leu Leu Lys Ser Val Lys Pro Leu Lys Ala
                165                 170                 175

Tyr Ile His Arg Lys Phe Phe Leu Arg Phe Ala Asn His Pro Phe Thr
            180                 185                 190

Leu Asp His Phe Asp Asp Tyr Glu Lys His Tyr Thr Val Met Asn Tyr
        195                 200                 205

Gln Thr Glu Ala Gln Leu His His Val Lys Cys Asp Asp Phe Leu Thr
    210                 215                 220

Leu Trp Gln Glu Gln Tyr Pro Asp Trp Ser Ala Leu Glu Gln Gln Ile
225                 230                 235                 240

Cys Ser Met Leu Leu Glu Val Leu Gln Cys Ala Ser Gln Ala Asp Pro
                245                 250                 255

Pro Cys Gly Gln Ser Arg Ala Leu Tyr Ala Ala Asp Ile Met Leu Glu
            260                 265                 270

Lys Leu Met Glu Pro Gln Leu Leu Glu Ile Asn Trp Thr Pro Asp Cys
        275                 280                 285

Lys Arg Ala Cys Asp Tyr Tyr Pro Asp Phe Phe Asn Asp Ile Phe Arg
    290                 295                 300

Leu Leu Phe Leu Asp Glu Glu Asn Asp Asp Ser
305                 310                 315

<210> SEQ ID NO 37
<211> LENGTH: 313
<212> TYPE: PRT
<213> ORGANISM: Homo sapiens

```
<400> SEQUENCE: 37

Asn Pro Val Val His Pro His Gly His Ile Phe Lys Val Tyr Thr Asp
1               5                   10                  15

Val Gln Gln Val Ala Ser Ser Leu Thr His Pro Arg Phe Thr Leu Thr
            20                  25                  30

Asp Ala Asp Ile Leu Phe Asn Phe Ser His Phe Lys Asp Tyr Arg Lys
        35                  40                  45

Ser Gln Glu Arg Pro Gly Val Leu Asn Gln Phe Pro Cys Glu Asn
    50                  55                  60

Leu Leu Thr Val Lys Asp Cys Leu Ala Ser Ile Ala Arg Arg Ala Gly
65                  70                  75                  80

Gly Pro Glu Gly Pro Pro Trp Leu Pro Arg Thr Phe Asn Leu Arg Thr
                85                  90                  95

Glu Leu Pro Gln Phe Val Ser Tyr Phe Gln Gln Arg Glu Arg Asn His
            100                 105                 110

Trp Ile Cys Lys Pro Trp Asn Leu Ala Arg Ser Leu Asp Thr His Val
            115                 120                 125

Thr Lys Ser Leu His Ser Ile Ile Arg Ser Thr Pro Lys Val Val Ser
130                 135                 140

Lys Tyr Ile Glu Ser Pro Val Leu Phe Gly Lys Val Lys Phe Asp Ile
145                 150                 155                 160

Arg Tyr Ile Val Leu Leu Arg Ser Val Arg Pro Leu Arg Leu Phe Val
                165                 170                 175

Tyr Asp Val Phe Trp Leu Arg Phe Ser Asn Arg Ala Phe Ala Leu Asn
            180                 185                 190

Asp Leu Asp Asp Tyr Glu Lys His Phe Thr Val Met Asn Tyr Asp Pro
        195                 200                 205

Asp Val Val Leu Lys Gln Val His Cys Glu Glu Phe Ile Pro Glu Phe
    210                 215                 220

Glu Lys Gln Tyr Pro Pro Trp Thr Asp Val Gln Ala Glu Ile Phe Arg
225                 230                 235                 240

Ala Phe Thr Glu Leu Phe Gln Val Ala Cys Ala Lys Pro Pro Leu
                245                 250                 255

Gly Ser Ser Arg Ala Met Tyr Ala Val Asp Leu Met Leu Arg Arg Val
            260                 265                 270

Met Gln Pro Gln Ile Leu Glu Val Asn Phe Asn Pro Asp Cys Glu Arg
        275                 280                 285

Ala Cys Arg Tyr His Pro Thr Phe Phe Asn Asp Val Phe Ser Thr Leu
    290                 295                 300

Phe Leu Asp Gln Pro Gly Gly Cys His
305                 310

<210> SEQ ID NO 38
<211> LENGTH: 311
<212> TYPE: PRT
<213> ORGANISM: Caenorhabditis elegans

<400> SEQUENCE: 38

Thr Ser Leu Pro Ile Leu Lys Lys Arg Lys Ile Lys Val Tyr Ala Asp
1               5                   10                  15

Asp Thr Gln Leu Thr Glu His Leu Lys Asn His Lys Val Glu Tyr Val
            20                  25                  30

Lys Ala Asp Val Ile Trp Met Ile Lys His Phe His Asp Tyr Lys Gln
        35                  40                  45
```

Ser Glu Glu Asn Pro Cys Gly Met Ile Asn Gln Phe Pro Phe Glu Ser
            50                  55                  60

Cys Ile Thr Val Lys Asp Leu Leu Ala Ala Cys Ala Met Arg Asp Pro
 65                  70                  75                  80

Ala Lys Asn Asp Trp Tyr Gln Leu Thr Tyr Asn Leu Asn Thr Gln Leu
                85                  90                  95

Pro Glu Phe Val Ala Arg Phe Gln Asn Arg Glu Leu Asn Val Trp Ile
            100                 105                 110

Val Lys Pro Trp Asn Leu Ala Arg Gly Met Asp Met Thr Val Thr Glu
            115                 120                 125

Asp Leu Asn Gln Ile Ile Arg Thr Gly Pro Lys Ile Val Cys Glu Tyr
130                 135                 140

Ile Pro Arg Pro Leu Leu Phe Asn Lys Val Lys Phe Asp Leu Arg Tyr
145                 150                 155                 160

Ile Val Phe Leu Asn Gly Ile Ala Pro Val Thr Ala Tyr Val Tyr Asn
                165                 170                 175

Arg Phe Trp Ile Arg Phe Ala Ile Asn Glu Phe Ser Leu Ser Asn Phe
            180                 185                 190

Glu Asp Val Glu Thr His Phe Thr Val Phe Asn Tyr Leu Asp Lys Glu
            195                 200                 205

Lys Ile Leu Gln Met Lys Cys Glu Asn Phe Ile Glu Thr Ile Glu Lys
210                 215                 220

Ala Tyr Pro Gln Trp Ser Glu Val Gln Lys Asp Ile Asn Leu Thr Ile
225                 230                 235                 240

Arg Lys Ala Ile Glu Ala Ala Lys Glu Glu Ala Pro Arg Gly Gln
                245                 250                 255

Ser Arg Ala Met Tyr Gly Val Asp Ile Met Leu Asn Asp Val Ile Lys
            260                 265                 270

Ser Thr Leu Leu Glu Ile Asn Phe Met Pro Asp Thr Thr Arg Ala Cys
            275                 280                 285

Gln Tyr Tyr Pro Asp Phe Ala Asp Thr Val Phe Glu Thr Leu Phe Leu
            290                 295                 300

Asp Glu Ile Asp Pro Thr Lys
305                 310

<210> SEQ ID NO 39
<211> LENGTH: 308
<212> TYPE: PRT
<213> ORGANISM: Drosophila melanogaster

<400> SEQUENCE: 39

Met Thr Ile Asn Lys Phe His Arg Ala Pro Phe Thr Ser Lys Glu Gly
 1               5                  10                  15

Leu Cys Ser Gln Leu Arg Asp Phe His Trp Phe Phe Glu Glu Gly Thr
             20                  25                  30

Ala Glu Met Tyr Pro Glu Glu Leu Gly Glu Phe Ile Glu Asn Phe Lys
         35                  40                  45

Leu Thr Ala Cys Val Ala Phe Leu Arg Ala Met Leu Cys Lys Tyr His
 50                  55                  60

Lys Gln Gly Ser Asp Ala Val Phe Ser Cys Ser Gly Lys Ile Pro Tyr
 65                  70                  75                  80

Ser Ala Ile Asp Phe Ala Asp Trp Asp Ala Phe Leu Phe Gln His Gln
                 85                  90                  95

Gln Leu Val Asn Asn Met Trp Ile Val Lys Pro Ala Asn Lys Cys Arg
            100                 105                 110

```
Gly Arg Gly Ile Ile Leu Met Asp Asn Leu Lys Lys Ile Leu Gly Lys
            115                 120                 125

Ser Arg Tyr Val Val Gln Lys Tyr Ile Glu Arg Pro Leu Ile Leu Phe
        130                 135                 140

Gln Thr Lys Phe Asp Ile Arg Gln Trp Phe Leu Ile Thr Asn Thr Gln
145                 150                 155                 160

Pro Leu Val Val Trp Phe Tyr Arg Glu Ser Tyr Leu Arg Phe Ser Ser
                165                 170                 175

Gln Glu Tyr Ser Leu Ser Asn His His Glu Ser Val His Leu Thr Asn
            180                 185                 190

Tyr Ala Ile Gln Lys Lys Tyr Thr Asn Gly Lys Arg Asp Lys Arg Glu
        195                 200                 205

Asn Met Trp Asp Cys Tyr Ser Phe Gln Ala Tyr Leu Arg Gln Ile Gly
210                 215                 220

Lys Trp Leu Glu Arg Ile Phe Pro Gly Met Arg Lys Ala Ile Val Gly
225                 230                 235                 240

Cys Met Leu Ala Ser Gln Glu Asn Met Asp Arg Arg Asn Thr Phe Glu
                245                 250                 255

Leu Phe Gly Ala Asp Phe Met Ile Cys Glu Asn Phe Tyr Pro Trp Leu
            260                 265                 270

Ile Glu Ile Asn Ser Ser Pro Asp Leu Gly Ala Thr Thr Ser Val Thr
        275                 280                 285

Ala Arg Met Cys Pro Gln Cys Leu Glu Asp Val Val Lys Val Val Ile
290                 295                 300

Asp Arg Arg Thr
305

<210> SEQ ID NO 40
<211> LENGTH: 319
<212> TYPE: PRT
<213> ORGANISM: Tetrahymena

<400> SEQUENCE: 40

Val Ile Lys Val Asn Thr Ser Lys Ser Arg Ser Glu Leu Lys Leu Leu
1               5                   10                  15

Arg Ile Leu Ile Asp Lys Asn Gly Trp Lys Glu Thr Phe Gly Tyr Glu
            20                  25                  30

Lys Ile Leu Trp Ser Gly Leu Ser Met Asn Gly Glu Gln Leu Ala Tyr
        35                  40                  45

Asp Glu Ile Cys Val Asn Arg Tyr Pro Gln Met Glu Glu Leu Ala His
    50                  55                  60

Lys Lys Thr Thr Gly Tyr Phe Leu Asn Leu Phe Arg Glu Tyr Phe Pro
65                  70                  75                  80

Glu His Phe Asp Phe Phe Pro Lys Thr Phe Leu Ile Pro Glu Gln Met
                85                  90                  95

Asp Glu Leu Lys Gln Glu Tyr Lys Lys Asn Ser Lys Lys Leu Cys Ile
            100                 105                 110

Ala Lys Pro Ser Ser Gly Cys Gln Gly Asp Gly Ile Lys Leu Ile Glu
        115                 120                 125

Gly Ile Lys Asp Leu Pro Ile Ala Asn Gln Leu Val Val Gln Glu Tyr
    130                 135                 140

Ile Asn Asn Pro Met Leu Ile Gln Gly Lys Lys Phe Asp Leu Arg Leu
145                 150                 155                 160

Tyr Val Leu Ile Ser Ser Leu Asp Pro Leu Ile Val Tyr Leu His Asp
                165                 170                 175
```

```
Glu Gly Leu Ala Arg Phe Cys Thr Glu Pro Tyr Lys Pro Ser Ile
            180                 185                 190

Asn Asn Ser Tyr Met His Leu Thr Asn Tyr Ser Leu Asn Lys Asn Asn
        195                 200                 205

Pro Asn Phe Lys Leu Pro Thr Glu Ala Ser Lys Arg Thr Met Gln Val
    210                 215                 220

Thr Trp Glu Gln Ile Val Lys Ala Gly Tyr Asp Lys Glu Glu Ile Leu
225                 230                 235                 240

Gly Asn Ile Glu Asp Leu Ile Cys Lys Phe Leu Ala Ser Met His Pro
                245                 250                 255

Tyr Leu Leu Tyr Asn Tyr Gln Lys Arg Phe His Val Leu Gly Phe Asp
            260                 265                 270

Ile Leu Leu Asp Asp Lys Gly Lys Pro Trp Phe Leu Glu Val Asn Ala
        275                 280                 285

Asn Pro Ser Phe Asn Ile Glu His Glu Val Tyr Gln Pro Asp Gly Lys
    290                 295                 300

Lys Lys Val Glu Gln Ser Pro Leu Asp Lys Tyr Val Lys Cys Arg
305                 310                 315

<210> SEQ ID NO 41
<211> LENGTH: 320
<212> TYPE: PRT
<213> ORGANISM: Drosophila melanogaster

<400> SEQUENCE: 41

Lys Leu Lys Ile Thr Tyr Lys Phe His Gln Thr Glu Thr Lys Leu Leu
1               5                   10                  15

Arg Lys Leu Phe Asn Val His Gly Leu Thr Glu Val Gln Gly Glu Asn
            20                  25                  30

Asn Leu Leu Trp Thr Gly Val His Met Lys Leu Asp Ile Val Arg Asn
        35                  40                  45

Leu Ala Pro Tyr Gln Arg Val Asn His Phe Pro Arg Ser Tyr Glu Met
    50                  55                  60

Thr Arg Lys Asp Arg Leu Tyr Lys Asn Ile Glu Arg Met Gln His Leu
65                  70                  75                  80

Arg Met Lys His Phe Asp Ile Val Pro Gln Thr Phe Val Leu Pro Ile
                85                  90                  95

Glu Ser Arg Asp Leu Val Val Ala His Asn Lys His Arg Gly Pro Trp
            100                 105                 110

Ile Val Lys Pro Ala Ala Ser Ser Arg Gly Arg Gly Ile Phe Ile Val
        115                 120                 125

Asn Ser Pro Asp Gln Ile Pro Gln Asp Glu Gln Ala Val Val Ser Lys
    130                 135                 140

Tyr Ile Val Asp Pro Leu Cys Ile Asp Gly His Lys Cys Asp Leu Arg
145                 150                 155                 160

Val Tyr Val Leu Val Thr Ser Phe Asp Pro Leu Ile Ile Tyr Leu Tyr
                165                 170                 175

Glu Glu Gly Ile Val Arg Leu Ala Thr Val Lys Tyr Asp Arg His Ala
            180                 185                 190

Leu Trp Asn Pro Cys Met His Leu Cys Asn Tyr Ser Ile Asn Lys Tyr
        195                 200                 205

His Ser Asp Tyr Ile Arg Ser Ser Asp Gly His Lys Trp Thr Leu Ser
    210                 215                 220

Ala Leu Leu Arg His Leu Lys Leu Gln Ser Cys Asp Thr Arg Gln Leu
225                 230                 235                 240
```

```
Met Leu Asn Ile Glu Asp Leu Ile Ile Lys Ala Val Leu Ala Cys Ala
            245                 250                 255

Gln Ser Ile Ile Ser Ala Cys Arg Asn Cys Phe Glu Leu Tyr Gly Phe
            260                 265                 270

Asp Ile Leu Ile Asp Asn Ala Leu Lys Pro Trp Leu Leu Glu Ile Asn
            275                 280                 285

Leu Ser Pro Ser Met Gly Val Asp Ser Pro Leu Asp Thr Lys Val Lys
            290                 295                 300

Ser Cys Leu Met Ala Asp Leu Leu Thr Cys Val Gly Ile Pro Ala Tyr
305                 310                 315                 320

<210> SEQ ID NO 42
<211> LENGTH: 320
<212> TYPE: PRT
<213> ORGANISM: Caenorhabditis elegans

<400> SEQUENCE: 42

Arg Leu Arg Leu Thr Phe Lys Met Met Arg Ser Asp Ser Arg Leu Ile
1               5                   10                  15

Arg Thr Met Cys His Ser His Gly Phe Met Gln Cys Ser Ser Lys Asn
            20                  25                  30

Asn Val Ile Trp Met Gly Ala Pro Val Lys Ser Val Arg Met Arg Glu
        35                  40                  45

Leu Met Pro Trp Gln Arg Leu Asn Gln Phe Pro Arg Ser Thr Glu Leu
    50                  55                  60

Thr Lys Lys Asp Arg Leu Tyr Glu Asn Ile Glu Arg Ser Lys Ser Ile
65                  70                  75                  80

Phe Glu Ser Phe Asp Phe Ile Pro Glu Phe Tyr Val Thr Pro Arg Glu
                85                  90                  95

Asn Arg Lys Met Glu Asn Ala Phe Val Arg Val Ala Lys Gly Glu Phe
            100                 105                 110

Ile Val Lys Pro Thr Asn Ser Arg Gln Gly Lys Gly Ile Phe Phe Ala
        115                 120                 125

Asn Ser Met Ala Asp Ile Pro Ala Glu Gly Pro Leu Leu Val Ser Arg
    130                 135                 140

Tyr Leu Lys Asp Pro Tyr Leu Val Asn Asn His Lys Phe Asp Leu Arg
145                 150                 155                 160

Ile Tyr Val Ala Val Thr Ser Phe Tyr Pro Leu Val Ala Tyr Val Tyr
                165                 170                 175

Ser Glu Gly Leu Ala Arg Leu Ala Ser Arg Pro Tyr Asp Thr Ser Ala
            180                 185                 190

Asp Ser Asn Glu Tyr Val His Leu Thr Asn Tyr Ser Ile Asn Lys Asn
        195                 200                 205

Ser Thr Ser Phe Val Arg Asn Glu Ser Gly His Lys Trp Thr Leu Gly
    210                 215                 220

Ala Leu Leu Arg Tyr Val Glu Asn Glu Gly Lys Asp Ala Lys Leu Leu
225                 230                 235                 240

Met Leu Arg Ile Glu Asp Leu Ile Val Lys Ser Leu Leu Ser Ile Gln
                245                 250                 255

Asn Ser Val Ala Thr Ala Ser Arg Thr Asn Phe Glu Leu Phe Gly Phe
            260                 265                 270

Asp Val Leu Val Asp Gln Ala Leu Lys Pro Trp Leu Leu Glu Val Asn
        275                 280                 285

Leu Ser Pro Ser Leu Ala Cys Asp Ala Pro Leu Asp Ser Leu Leu Lys
    290                 295                 300
```

```
Thr Arg Leu Ile Ala Asp Leu Leu Asn Leu Ala Cys Val Pro Leu Leu
305                 310                 315                 320
```

<210> SEQ ID NO 43
<211> LENGTH: 320
<212> TYPE: PRT
<213> ORGANISM: Homo sapiens

<400> SEQUENCE: 43

```
Arg Tyr His Leu Ser Tyr Lys Ile Val Arg Thr Asp Ser Arg Leu Val
1               5                   10                  15

Arg Ser Ile Leu Thr Ala His Gly Phe His Glu Val His Pro Ser Ser
                20                  25                  30

Asn Leu Met Trp Thr Gly Ser His Leu Lys Pro Phe Leu Leu Arg Thr
            35                  40                  45

Leu Ser Glu Ala Gln Lys Val Asn His Phe Pro Arg Ser Tyr Glu Leu
        50                  55                  60

Thr Arg Lys Asp Arg Leu Tyr Lys Asn Ile Ile Arg Met Gln His Thr
65                  70                  75                  80

His Phe Lys Val Phe His Ile Leu Pro Gln Thr Phe Leu Leu Pro Ala
                85                  90                  95

Glu Tyr Ala Glu Phe Cys Asn Ser Tyr Ser Lys Asp Arg Gly Pro Trp
            100                 105                 110

Ile Val Lys Pro Val Ala Ser Ser Arg Gly Arg Gly Val Tyr Leu Ile
        115                 120                 125

Asn Asn Pro Asn Gln Ile Ser Leu Glu Glu Asn Ile Leu Val Ser Arg
    130                 135                 140

Tyr Ile Asn Asn Pro Leu Leu Ile Asp Asp Phe Lys Phe Asp Val Arg
145                 150                 155                 160

Leu Tyr Val Leu Val Thr Ser Tyr Asp Pro Leu Val Ile Tyr Leu Tyr
                165                 170                 175

Glu Glu Gly Leu Ala Arg Phe Ala Thr Val Arg Tyr Asp Gln Gly Ala
            180                 185                 190

Ile Arg Asn Gln Phe Met His Leu Thr Asn Tyr Ser Val Asn Lys Lys
        195                 200                 205

Ser Gly Asp Tyr Val Ser Cys Asp Asp Gly Asn Lys Trp Ser Met Ser
    210                 215                 220

Ala Met Leu Arg Tyr Leu Lys Gln Glu Gly Arg Asp Thr Thr Ala Leu
225                 230                 235                 240

Met Ala His Val Glu Asp Leu Ile Ile Lys Thr Ile Ile Ser Ala Glu
                245                 250                 255

Leu Ala Ile Ala Thr Ala Cys Lys Ser Cys Phe Glu Leu Tyr Gly Phe
            260                 265                 270

Asp Val Leu Ile Asp Ser Thr Leu Lys Pro Trp Leu Leu Glu Val Asn
        275                 280                 285

Leu Ser Pro Ser Leu Ala Cys Asp Ala Pro Leu Asp Leu Lys Ile Lys
    290                 295                 300

Ala Ser Met Ile Ser Asp Met Phe Thr Val Val Gly Phe Val Cys Gln
305                 310                 315                 320
```

<210> SEQ ID NO 44
<211> LENGTH: 322
<212> TYPE: PRT
<213> ORGANISM: Homo sapiens

<400> SEQUENCE: 44

```
Leu Lys Pro Leu Val Phe Arg Val Asp Glu Thr Thr Pro Ala Val Val
```

-continued

Gln Ser Val Leu Leu Glu Arg Gly Trp Asn Lys Phe Asp Lys Gln Glu
1               5                   10                  15

Asp Trp Asn Leu Tyr Trp Arg Thr Ser Ser Phe Arg Met Thr Glu His
            20                  25                  30

Asn Ser Val Lys Pro Trp Gln Gln Leu Asn His His Pro Gly Thr Thr
35                      40                  45

Lys Leu Thr Arg Lys Asp Cys Leu Ala Lys His Leu Lys His Met Arg
50                  55                  60

Arg Met Tyr Thr Ser Leu Tyr Gln Phe Ile Pro Leu Thr Phe Val Met
65                      70                  75                  80

Pro Asn Asp Tyr Thr Lys Phe Val Ala Glu Tyr Phe Gln Glu Arg Gln
                85                  90                  95

Ser Tyr Trp Ile Cys Lys Pro Ala Glu Leu Ser Arg Gly Arg Gly Ile
                    100                 105                 110

Leu Ile Phe Ser Asp Phe Lys Asp Phe Ile Phe Asp Asp Met Tyr Ile
            115                 120                 125

Val Gln Lys Tyr Ile Ser Asn Pro Leu Leu Ile Gly Arg Tyr Lys Cys
130                 135                 140

Asp Leu Arg Ile Tyr Val Cys Val Thr Gly Phe Lys Pro Leu Thr Ile
145                     150                 155                 160

Tyr Val Tyr Gln Glu Gly Leu Val Arg Phe Ala Thr Glu Lys Phe Asp
                165                 170                 175

Leu Ser Asn Leu Gln Asn Asn Tyr Ala His Leu Thr Asn Ser Ser Ile
                    180                 185                 190

Asn Lys Ser Gly Ala Ser Tyr Glu Lys Ile Lys Glu Gly Cys Lys Trp
            195                 200                 205

Thr Leu Ser Arg Phe Phe Ser Tyr Leu Arg Ser Trp Asp Val Asp Asp
210                 215                 220

Leu Leu Leu Trp Lys Lys Ile His Arg Met Val Ile Leu Thr Ile Leu
225                     230                 235                 240

Ala Ile Ala Pro Ser Val Pro Phe Ala Ala Asn Cys Phe Glu Leu Phe
                245                 250                 255

Gly Phe Asp Ile Leu Ile Asn Asp Asn Leu Lys Pro Trp Leu Leu Glu
                    260                 265                 270

Val Asn Tyr Ser Pro Ala Leu Thr Leu Asp Cys Ser Thr Asp Val Leu
            275                 280                 285

Val Lys Arg Lys Leu Val His Asp Ile Ile Asp Leu Ile Tyr Leu Asn
290                 295                 300

Gly Leu
305                     310                 315                 320

<210> SEQ ID NO 45
<211> LENGTH: 321
<212> TYPE: PRT
<213> ORGANISM: Homo sapiens

<400> SEQUENCE: 45

Lys Gly Thr Ile Thr Ala Asn Val Gly Ala Lys Phe Glu Ile Val
1               5                   10                  15

Arg Leu Val Ile Asp Glu Met Gly Phe Met Lys Thr Pro Asp Glu Asp
            20                  25                  30

Asn Leu Ile Trp Cys Asp Ser Ala Val Gln Gln Glu Lys Ile Ser Glu
        35                  40                  45

Leu Gln Asn Tyr Gln Arg Ile Asn His Phe Pro Gly Met Gly Glu Ile
    50                  55                  60

```
Cys Arg Lys Asp Phe Leu Ala Arg Asn Met Thr Lys Met Ile Lys Ser
 65                  70                  75                  80

Arg Pro Leu Asp Tyr Thr Phe Val Pro Arg Thr Trp Ile Phe Pro Ala
                 85                  90                  95

Glu Tyr Thr Gln Phe Gln Asn Tyr Val Lys Glu Leu Lys Lys Lys Thr
            100                 105                 110

Phe Ile Val Lys Pro Ala Asn Gly Ala Met Gly His Gly Ile Ser Leu
        115                 120                 125

Ile Arg Asn Gly Asp Lys Leu Pro Ser Gln Asp His Leu Ile Val Gln
130                 135                 140

Glu Tyr Ile Glu Lys Pro Phe Leu Met Glu Gly Tyr Lys Phe Asp Leu
145                 150                 155                 160

Arg Ile Tyr Ile Leu Val Thr Ser Cys Asp Pro Leu Lys Ile Phe Leu
                165                 170                 175

Tyr His Asp Gly Leu Val Arg Met Gly Thr Glu Lys Tyr Ile Pro Pro
            180                 185                 190

Asn Leu Thr Gln Leu Tyr Met His Leu Thr Asn Tyr Ser Val Asn Lys
        195                 200                 205

His Asn Glu His Phe Glu Arg Asp Glu Thr Gly Ser Lys Arg Ser Ile
210                 215                 220

Lys Trp Phe Thr Glu Phe Leu Gln Ala Asn Gln His Asp Val Ala Lys
225                 230                 235                 240

Phe Trp Ser Asp Ile Ser Glu Leu Val Val Lys Thr Leu Ile Val Ala
                245                 250                 255

Glu Pro His Val Leu His Ala Tyr Arg Val Cys Phe Glu Val Leu Gly
            260                 265                 270

Phe Asp Ile Leu Leu Asp Arg Lys Leu Lys Pro Trp Leu Leu Glu Ile
        275                 280                 285

Asn Arg Ala Pro Ser Phe Gly Thr Asp Gln Lys Ile Asp Tyr Asp Val
290                 295                 300

Lys Arg Gly Val Leu Leu Asn Ala Leu Lys Leu Leu Asn Ile Arg Thr
305                 310                 315                 320

Ser

<210> SEQ ID NO 46
<211> LENGTH: 318
<212> TYPE: PRT
<213> ORGANISM: Tetrahymena

<400> SEQUENCE: 46

Lys Pro Glu Val Tyr Asp Ile Ile Thr Arg Ser Phe Met Arg Lys Lys
 1               5                  10                  15

Asp Trp Phe Glu Leu Pro His Gly Leu Gln Leu Arg Thr Ser Trp Asn
                 20                  25                  30

Leu Leu Trp Thr Trp Ser Lys Pro Gln Ile Asp Phe Asn Lys Leu Leu
            35                  40                  45

Leu Phe Gln Lys Val Asn His Phe Pro Phe Asn Lys Asn Leu Val Arg
        50                  55                  60

Lys Asp Leu Leu Lys Lys Asn Phe Glu Arg Ile Thr Lys Leu Gly Ala
 65                  70                  75                  80

Gln Ala Phe Asn Ile Leu Pro Leu Thr Phe Val Leu Pro Lys Glu Tyr
                 85                  90                  95

Cys Asn Phe Ser Glu Arg Phe Tyr Glu Glu Met Leu Asn Ile Trp Ile
            100                 105                 110
```

Met Lys Pro Val Gly Lys Ser Gln Gly Arg Gly Ile Ser Leu Val Asn
            115                 120                 125

Asp Ile Ala Gln Val Val Tyr Ala Glu Pro Val Val Gln Lys Tyr
    130                 135                 140

Met Lys Asp Pro Leu Leu Leu Asp Gly Tyr Lys Phe Asp Met Arg Ile
145                 150                 155                 160

Tyr Ala Leu Ile Thr His Met Lys Pro Leu Glu Ala Phe Val Tyr Lys
                165                 170                 175

Glu Gly Phe Ala Arg Leu Ser Thr Glu Lys Tyr Gln Leu Asn Ala Ile
            180                 185                 190

Lys Asn Asn Gln Ile His Leu Thr Asn Phe Ser Ile Gln Lys His His
            195                 200                 205

Tyr Asp Pro Ala Ser Asn Asn Gly Thr Lys Ile Ser Leu Lys Met
    210                 215                 220

Leu Gln Glu Lys Phe Arg Gln Lys Gly Ile Asp Trp Asp Lys Ile Trp
225                 230                 235                 240

Ile Gln Val Gln Glu Ile Ile Val Lys Ser Val Leu Ala Cys Gln Ala
                245                 250                 255

Asp Ile Pro Asn Asn Pro Asn Cys Phe Glu Ile Phe Gly Tyr Asp Ile
            260                 265                 270

Ile Ile Asp Ser Ser Leu Lys Cys Cys Leu Leu Glu Ile Asn Ser Ser
            275                 280                 285

Pro Ser Leu Ala Arg Asp Phe Ile Ile Asp Asp Leu Ile Lys Gln Gln
    290                 295                 300

Met Ile Asp Asp Ala Ile Asp Leu Val Ser Pro Val Gln Phe
305                 310                 315

<210> SEQ ID NO 47
<211> LENGTH: 314
<212> TYPE: PRT
<213> ORGANISM: Tetrahymena

<400> SEQUENCE: 47

Asp Trp Asn Asp Gln Tyr Thr Arg Asp Ile Phe Ala Asn Phe Ser
1               5                   10                  15

Lys Val Ala Ser Glu Met Tyr Gly Trp Glu Leu Pro Ser Asp Tyr Leu
            20                  25                  30

Glu Ser Phe Ala Pro Glu Ile Asn Ile Thr Gln Tyr Tyr Phe Gln Leu
            35                  40                  45

Gly Cys Leu Phe Gln Gly Ile Asn Lys Ile Pro Ser Ser Gly Ser Phe
        50                  55                  60

Thr Arg Lys Glu Gly Leu Ser Arg Ser Tyr Arg Lys Phe Leu Thr Gln
65              70                  75                  80

Ile Met Lys Glu Phe Lys Phe Leu Pro Gln Thr Tyr Asn Leu Asn Asn
            85                  90                  95

Glu Cys Lys Asn Phe Phe Asn Tyr Val Glu Ser Glu Thr Tyr Phe Gln
        100                 105                 110

Phe Ile Ser Lys Leu Ala Asn Val His Gln Gly Lys Gly Ile Ser Val
    115                 120                 125

Val Thr Pro Ala Ile Met Glu Ala Leu Gln Asn Pro Glu Leu Val Gln
    130                 135                 140

Glu Tyr Ile Asn Asn Pro Leu Leu Leu Asn Gly Val Lys Phe Glu Val
145                 150                 155                 160

Arg Met His Phe Val Ile Ala Ser Leu Asn Pro Leu Ile Ile Tyr Ala
                165                 170                 175

```
Gln Asp Lys Ala Gly Val Ala Phe Cys Ala Leu Lys Tyr Asn Ser His
            180                 185                 190

Asp Ser Gln Ile Gln Arg His Leu Cys Val Tyr Asn Ile Ala Arg Glu
            195                 200                 205

Leu Leu Asn Leu Ser Asp Glu Glu Leu Gly Lys Thr Arg Glu Gln Phe
            210                 215                 220

Met Ser Ser Phe Ser Tyr Gln His Thr Leu Lys Glu Gly Ser Val Phe
225                 230                 235                 240

Asn Asp Phe Ile Pro Ser Val Phe Arg Asn Tyr Ile Asn Thr Val Leu
                245                 250                 255

Phe Ser Arg Leu Tyr Glu Met Tyr Ala Pro Asp Ile Leu Val Lys Asp
            260                 265                 270

Asn Met Lys Pro Tyr Ile Leu Glu Tyr Asn Thr Asn Pro Arg Met Val
            275                 280                 285

Asn Thr Ser Tyr Phe Val His Gly Trp Asn Val Gln Thr Ile Lys Asp
            290                 295                 300

Ile Val Leu Ile Asn Met Ala Gln Val Arg
305                 310

<210> SEQ ID NO 48
<211> LENGTH: 303
<212> TYPE: PRT
<213> ORGANISM: Trypanosoma brucei

<400> SEQUENCE: 48

Met Asn Ser Leu Ser Glu Thr Ile Ser Leu Leu Gly Ala Lys Cys Asn
1               5                   10                  15

Ala Ala Leu Asn Gln Ile Ile Trp Leu Asp Lys Ser Val Leu Ser Ser
            20                  25                  30

Arg Val Ala Ala Leu Ser Cys Phe His Arg Val Asn His Phe Pro Gly
        35                  40                  45

Met His Val Ile Ala Arg Lys Ala Thr Leu Phe Lys Arg Leu Met Arg
    50                  55                  60

Ile Arg Arg Gln His Arg Arg Ser Leu Asp Ala Phe Pro Trp Ser Phe
65                  70                  75                  80

Ser Pro Ser Thr Gln Leu Glu Arg Phe Ile Ser Asp Gly Arg Glu Gly
                85                  90                  95

Glu Ile Phe Ile Leu Lys Pro Asn Arg Gly Cys Glu Gly Lys Gly Ile
            100                 105                 110

Ile Ile Thr Ala Glu Pro Leu His Val Val Glu Arg Asn Glu Cys Leu
        115                 120                 125

Val Gln Gln Tyr Val Pro His Pro Leu Cys Ile Asp Arg Lys Lys Phe
    130                 135                 140

Asp Leu Arg Ile Tyr Val Leu Val Thr Ser Val Val Val Leu Gln Leu
145                 150                 155                 160

Phe Val His Lys Glu Gly Leu Val Arg Ile Cys Thr Glu Asp Tyr Ala
                165                 170                 175

Ala Pro Asn Cys Lys Arg Gln Gly Met His Leu Thr Asn Tyr Ala Val
            180                 185                 190

Asn Lys Arg Ala Gln Gly Phe Ser Val Gly Asp Val Gly Asn Lys Arg
        195                 200                 205

Asp Phe Lys Phe Leu Glu His Tyr Ile Asn Gly Leu Val Gly Arg Trp
    210                 215                 220

Glu Arg Val Leu His Arg Ile Asp Arg Cys Ile Leu Leu Thr Val Leu
225                 230                 235                 240
```

```
Ser Gly Leu Glu Asn Leu Arg Asn Cys Phe Glu Leu Gly Val Asp
            245                 250                 255

Ile Leu Leu Thr Glu Asp Leu Lys Pro Val Leu Met Glu Val Asn His
            260                 265                 270

Ser Pro Ser Leu Phe Cys Asp Ser Asp Phe Asp Phe Arg Thr Lys His
            275                 280                 285

Arg Val Leu Met Asp Val Phe Arg Leu Leu Glu Pro Tyr Val Pro
            290                 295                 300

<210> SEQ ID NO 49
<211> LENGTH: 314
<212> TYPE: PRT
<213> ORGANISM: Drosophila melanogaster

<400> SEQUENCE: 49

Arg Asn Arg Arg Ile Phe Thr Val Tyr Gly Asn Tyr His Thr Val Arg
1               5                   10                  15

Arg Ala Leu Met Arg Arg Gly Trp Leu Glu Lys Leu Pro Ala Ser Leu
            20                  25                  30

Gln Ser Met Ser Glu Asp Ala Leu Leu Glu His Ala Arg Glu Ala Val
        35                  40                  45

Val Ile Ser Lys Met Ile Asn His Phe Pro Ala Phe Phe Ile Trp Gln
50                  55                  60

Gly Lys Gly Gln Arg Asp Leu Cys Ala Glu Val Arg Pro Phe Arg Asn
65                  70                  75                  80

Gly Val Cys Gly Met Ser Tyr Pro Arg Phe Tyr Arg Leu Gly Gly Glu
            85                  90                  95

Arg Met Ala Phe Ile Glu Asp Tyr Gln Gln Thr Gln Ala Asn Leu Trp
            100                 105                 110

Ile Leu Lys Pro Gly Tyr Gln Ser Arg Gly Ile Gly Ile Val Ile Arg
            115                 120                 125

Ser Ser Leu Asp Asp Ile Leu Gln Trp Asn Lys Lys Ile Val Gln Lys
            130                 135                 140

Tyr Ile Glu Arg Pro Leu Leu Ile Tyr Arg Thr Lys Phe Asp Ile Arg
145                 150                 155                 160

Gln Tyr Met Leu Leu Thr Ile Thr Asp Thr Val Ser Ile Trp Thr Tyr
            165                 170                 175

Arg Asp Cys Tyr Leu Arg Phe Ser Ser Gln Glu Phe Thr Met Asp Asp
            180                 185                 190

Leu Arg Glu Ser Ile His Leu Thr Asn Asn Ser Val Gln Lys Arg Tyr
            195                 200                 205

Lys Asn Lys Thr Asn Arg Asp Ser Asn Asn Met Trp Ser Leu Asp Gln
        210                 215                 220

Phe Lys Asn Tyr Leu Arg Ile Met Gly Ala Ser Trp Ser Lys Thr Tyr
225                 230                 235                 240

Asn Gly Phe Lys Gln Asn Leu Val Ala Val Met Ala Ser Leu Asp
            245                 250                 255

Glu Thr Asn Ala Phe Glu Leu Tyr Gly Cys Asp Phe Met Leu Asp Glu
            260                 265                 270

His Tyr Asn Pro Ile Leu Ile Glu Ile Asn Ser Thr Pro Asp Leu Ser
            275                 280                 285

Pro Ser Thr Glu Ile Thr Ala Arg Ile Cys Pro Met Val Leu Lys Asp
            290                 295                 300

Cys Ile Arg Val Val Val Asp Leu Pro Lys
305                 310
```

<210> SEQ ID NO 50
<211> LENGTH: 317
<212> TYPE: PRT
<213> ORGANISM: Trypanosoma brucei

<400> SEQUENCE: 50

Thr Leu Ser Phe Thr Met Pro Ala Pro Ala Val Arg Phe Ser Ala Val
1               5                   10                  15

Met Cys Ala Leu Glu Arg Ala Gly Phe Val Glu Asp Thr Ser Leu Leu
            20                  25                  30

Leu Leu Lys Trp Cys Lys Arg Pro Val Arg Ser Asp Phe Ser Lys Leu
        35                  40                  45

Arg Leu Phe Gln Arg Ile Asn His Phe Pro Gly Thr Trp Arg Leu Gly
    50                  55                  60

Lys Lys Asp Glu Leu His Arg His Leu Val Ala Ala Arg Val Arg Trp
65                  70                  75                  80

Ser Glu His Met Asn Phe Phe Pro Glu Ala Trp Val Leu Pro Asp Glu
                85                  90                  95

Leu Asn Arg Val Leu Cys Ala Lys Glu Arg Gly Asn Val Phe Ile
            100                 105                 110

Ala Lys Pro Thr Thr Ala Ala Cys Gly Arg Gly Ile Gln Leu Leu Val
        115                 120                 125

Ala Gly Glu Pro Ser His Ser Ser Asn Arg Met Ile Val Gln Arg Tyr
    130                 135                 140

Val Ser Asp Pro Leu Leu Val Glu Gly Tyr Lys Phe Asp Leu Arg Leu
145                 150                 155                 160

Tyr Val Val Val Thr Ser Tyr Val Pro Leu Arg Ala Tyr Leu Tyr Thr
                165                 170                 175

Glu Gly Leu Val Arg Phe Ala Thr Ser Pro Tyr Pro Asn Asp Pro Glu
            180                 185                 190

Arg Thr Leu Thr Ala His Leu Thr Asn Phe Thr Ile Asn Lys Lys Ser
        195                 200                 205

Glu Asp Phe Phe Ser Pro Ala Gly Ala Ser Lys Trp Thr Leu Ser Ala
    210                 215                 220

Leu Glu Ser His Phe Asn Lys His Gly Leu Asp Trp Asp Gly Thr Met
225                 230                 235                 240

Lys Gln Ile His Asp Ile Leu Val Lys Val Leu Ser Val Gln Pro
                245                 250                 255

His Val Lys Ala Glu Ser Cys Phe Glu Val Tyr Gly Val Asp Val Leu
            260                 265                 270

Leu Lys Val Ile Pro Ile Pro Val Leu Met Glu Val Asn Ile Met Pro
        275                 280                 285

Ser Leu Ser Thr His Tyr Ser Leu Asp Gln Cys Val Lys Gly Asn Phe
    290                 295                 300

Val Ala Asp Met Leu Thr Leu Val Gly Leu Thr Ala Gly
305                 310                 315

<210> SEQ ID NO 51
<211> LENGTH: 323
<212> TYPE: PRT
<213> ORGANISM: Trypanosoma brucei

<400> SEQUENCE: 51

Ser Pro Met Phe Cys Ile Thr Ser Pro Ser Cys Glu Tyr Tyr Ala Leu
1               5                   10                  15

Arg Leu Pro Leu Leu Lys Ala Gly Phe Lys Arg Leu His Thr His Leu

-continued

```
                20                  25                  30
Pro Ser Asn Leu Leu Trp Gly Arg Ser Leu Met Ile Arg Pro Thr Ala
            35                  40                  45
Gln Met Val Cys Ala His Gln Arg Phe Asn His Phe Pro Arg Thr Tyr
        50                  55                  60
Thr Leu Gly Cys Lys Leu Gly Leu Ala Gln Arg Leu His Arg Val Lys
65                  70                  75                  80
Lys Ser Leu Arg Asp Val Phe Asp Phe Pro Gln Thr Trp Ile Phe
                85                  90                  95
Pro Glu Gln Lys Glu Ser Leu Met Lys Ala Met Asp Gln Ala Arg Pro
            100                 105                 110
Gln Arg Phe Ile Trp Lys Pro Ala Arg Gly Ser Cys Gly Lys Gly Ile
        115                 120                 125
Phe Val Cys Pro Gly Gly Glu Lys Asn Ser Val Asn Arg Ser Tyr Val
        130                 135                 140
Val Gln Glu Tyr Val Asp Asp Pro Leu Leu Glu Gly Arg Lys Met
145                 150                 155                 160
Asp Leu Arg Leu Tyr Val Ala Val Thr Ser Tyr Asp Pro Leu Thr Val
                165                 170                 175
Tyr Leu His Asp Glu Gly Leu Val Arg Leu Ala Val Gln Gln Tyr Asn
            180                 185                 190
Glu Gly Ala His Phe Asp Pro Phe Arg Asp Leu Thr Asn Tyr Ser Ile
        195                 200                 205
Gly Arg Lys Trp Val Lys Lys Gly Lys Gln Phe Gly His Leu Lys Lys
        210                 215                 220
Ser Met Glu Glu Leu Trp Asn His Ile Asp Ser Leu Cys Pro Thr Ser
225                 230                 235                 240
Asp His Val Trp Asn Ser Ile Ala Gln Val Ile Val Lys Thr Leu Leu
                245                 250                 255
Ala Val Lys Ser Thr Met Ser Lys Gly Val Lys Ser Phe Phe Glu Leu
            260                 265                 270
Tyr Gly Phe Asp Met Met Leu Asp Ser Ser Leu Lys Pro Trp Leu Val
        275                 280                 285
Glu Val Asn Thr Leu Pro Ser Leu Ala Ser Thr Ser Thr Phe Asp Tyr
        290                 295                 300
Thr Val Lys Thr Asn Ile Ile Ser Asp Leu Leu Asn Leu Ala Met Ile
305                 310                 315                 320
Glu Pro Phe

<210> SEQ ID NO 52
<211> LENGTH: 324
<212> TYPE: PRT
<213> ORGANISM: Caenorhabditis elegans

<400> SEQUENCE: 52

Arg Phe Thr Ile Asp Thr Ser Arg Ala Lys Ser Asn Gln Tyr Val Val
1               5                  10                  15
Ser Leu Cys Ser Lys Lys Ile Gly Ile Ile Glu Tyr Pro Asp Gly Arg
            20                  25                  30
Pro Cys Asp Val Tyr Trp His Asn Val Val Leu Ser Asp Met Asn Lys
        35                  40                  45
Ile Val Thr Ser Pro Gln Ser Arg Val Asn Lys Phe Pro Gly Met Thr
    50                  55                  60
Glu Leu Ala Lys Lys Ile Ser Leu Thr His Ser Ile Ser Met Gln
65                  70                  75                  80
```

```
Lys Leu Phe Pro Asp Glu Tyr Ala Phe Tyr Pro Asn Ser Trp Phe Leu
                85                  90                  95

Pro Ala Asp Phe His Ala Phe Tyr Arg Lys Ala Gln Ala Leu Gly Lys
            100                 105                 110

Met Trp Phe Ile Val Lys Pro Asp Glu Gly Ala Gln Gly Thr Gly Ile
        115                 120                 125

Tyr Leu Ile Asn Ser Pro Asn Gln Ile Arg Asn Asp Gln Arg Gln Leu
    130                 135                 140

Val Gln Glu Tyr Val Ala Asp Pro Leu Leu Met Asp Lys Leu Lys Phe
145                 150                 155                 160

Asp Phe Arg Val Tyr Gly Val Ile Lys Ser Ile Asn Pro Leu Ser Ile
                165                 170                 175

Tyr Val Ala Arg Glu Gly Met Ala Arg Phe Cys Thr Glu Lys Tyr Glu
            180                 185                 190

Lys Pro Asp Phe Lys Asn Leu Tyr Ala His Leu Thr Asn Tyr Ser Leu
        195                 200                 205

Asn Lys Ala Asn Glu Ala Tyr Val His Ser Asn Thr Gly Ser Lys Arg
    210                 215                 220

Leu Leu Ser Thr Val Phe His Gln Leu Glu Ser Arg Gly Val Lys Thr
225                 230                 235                 240

Lys Arg Leu Trp His Asp Ile Lys Leu Ile Leu Val Lys Thr Thr Leu
                245                 250                 255

Ala Met Leu Pro Glu Ile Met Leu His Tyr Glu His Gln Cys Phe Gln
            260                 265                 270

Ile Met Gly Phe Asp Val Met Ile Arg Glu Asp Gly Thr Pro Ile Leu
        275                 280                 285

Leu Glu Val Asn Ala Ala Pro Ser Leu Thr Ala Asp His Ile Glu Gly
    290                 295                 300

Gly Gln Arg Val Arg Ser Ile Val Asp Glu Val Ile Lys Ile Pro Leu
305                 310                 315                 320

Val Arg Asp Thr

<210> SEQ ID NO 53
<211> LENGTH: 293
<212> TYPE: PRT
<213> ORGANISM: Homo sapiens

<400> SEQUENCE: 53

Gln Arg Pro Val Thr Val Asp Ser Ser Lys Ala Arg Thr Ser Leu Asp
1               5                   10                  15

Ala Leu Lys Ile Ser Ile Arg Gln Leu Lys Trp Lys Glu Phe Pro Phe
            20                  25                  30

Pro Cys Asp Ile Tyr Trp His Gly Val Ser Phe His Asp Asn Asp Ile
        35                  40                  45

Phe Ser Gly Gln Val Asn Lys Phe Pro Gly Met Thr Glu Met Val Arg
    50                  55                  60

Lys Ile Thr Leu Ser Arg Ala Val Arg Thr Met Gln Asn Leu Phe Pro
65                  70                  75                  80

Glu Glu Tyr Asn Phe Tyr Pro Arg Ser Trp Ile Leu Pro Asp Glu Phe
                85                  90                  95

Gln Leu Phe Val Ala Gln Val Gln Met Val Lys Asp Pro Thr Phe Ile
            100                 105                 110

Val Lys Pro Asp Gly Gly Cys Gln Gly Asp Gly Ile Tyr Leu Ile Lys
        115                 120                 125
```

Asp Pro Ser Asp Ile Arg Leu Ser Arg Pro Ala Val Val Gln Glu Tyr
            130                 135                 140

Ile Cys Lys Pro Leu Leu Ile Asp Lys Leu Lys Phe Asp Ile Arg Leu
145                 150                 155                 160

Tyr Val Leu Leu Lys Ser Leu Asp Pro Leu Glu Ile Tyr Ile Ala Lys
                165                 170                 175

Asp Gly Leu Ser Arg Phe Cys Thr Glu Pro Tyr Gln Glu Pro Thr Leu
            180                 185                 190

His Arg Ile Phe Met His Leu Thr Asn Tyr Ser Leu Asn Ile His Ser
        195                 200                 205

Gly Asn Phe Ile His Ser Asp Ser Gly Ser Lys Arg Thr Phe Ser Ser
    210                 215                 220

Ile Leu Cys Arg Leu Ser Ser Lys Gly Val Asp Ile Lys Lys Val Trp
225                 230                 235                 240

Ser Asp Ile Ile Ser Val Val Ile Lys Thr Val Ile Ala Leu Thr Pro
                245                 250                 255

Glu Leu Lys Val Phe Tyr Gln Ser Thr Cys Phe Gln Val Thr Ile Ala
            260                 265                 270

Ser Ser Gln Pro Ala Phe Pro Ala Leu Thr Gly Leu Lys Arg Ala Leu
        275                 280                 285

Trp Leu Arg Val Gly
    290

<210> SEQ ID NO 54
<211> LENGTH: 317
<212> TYPE: PRT
<213> ORGANISM: Giardia lamblia

<400> SEQUENCE: 54

Val Cys Lys Tyr Ser Phe Gly Pro Gly Asn Asn Ala Ala Leu Val Glu
1               5                   10                  15

Gln Val Leu Lys Ser Arg Pro Trp Trp Thr Ser Thr Asp Asp Glu Asn
            20                  25                  30

Asn Leu Arg Trp Gln Gln Leu Thr Pro Ala Pro Met Arg Phe Cys Ser
        35                  40                  45

Thr Met Arg Arg Thr Val Phe Asn His Leu Pro Gly Asn Gly Thr Leu
    50                  55                  60

His Ser Lys Val Ser Leu Tyr Gln Ile Leu Leu Arg Lys Leu Gly Lys
65                  70                  75                  80

Pro Ala Leu Asp Phe Leu Pro Val Thr Tyr Ile Leu Thr Val Glu Arg
                85                  90                  95

Asp Lys Phe Arg Arg His Phe Ala Ala Leu Ala Ser Asn Leu Trp Ile
            100                 105                 110

Val Lys Pro Ile Gly Leu Asn Arg Gly Arg Gly Ile Lys Val Val Thr
        115                 120                 125

Asn Pro Glu Asp Ala Ile Glu Ser Met Ser Phe Ile Val Gln Lys Tyr
    130                 135                 140

Val Glu Glu Pro Phe Leu Ile Asn Gly Arg Lys Phe Asp Ile Arg Thr
145                 150                 155                 160

Tyr Ala Leu Ile Thr Ser Asp Gly Asn Ala Tyr Ile Tyr Glu Tyr Gly
                165                 170                 175

Tyr Leu Arg Leu Thr Ser Ala Lys Tyr Ser Leu Asp Thr Thr Asp Thr
            180                 185                 190

Thr Val His Leu Thr Asn Asn Ala Val Gln Lys Asn Ile His Gly Tyr
        195                 200                 205

-continued

```
Asn Gln Phe Glu Asp Gly Asn Met Leu His Phe Arg Asp Leu Asp Val
        210                 215                 220

Gln Met Ser Val Ser Asp Phe Thr Ser Phe Ile Trp Pro Val Met
225                 230                 235                 240

Lys Arg Ile Met Ala Ala Val Leu Val Ala Phe Gly Lys Ala Val Leu
                    245                 250                 255

Gly Ala His Ala Cys Gly Cys Phe Glu Leu Phe Gly Phe Asp Phe Met
                260                 265                 270

Ile Ser Asn Gly Tyr Arg Pro Ile Leu Ile Glu Ile Asn Ser Asn Pro
            275                 280                 285

Cys Leu Ala Leu Ser Ser Val Val Ser Trp Glu Leu Leu Pro Lys Met
            290                 295                 300

Leu Asp Asp Leu Met Asp Leu Thr Ile Asp Lys Leu Phe
305                 310                 315

<210> SEQ ID NO 55
<211> LENGTH: 321
<212> TYPE: PRT
<213> ORGANISM: Tetrahymena

<400> SEQUENCE: 55

Asp Pro Lys Thr Lys Val Phe Ile Ile Lys Gly Gly Tyr Gly Asp Leu
1               5                   10                  15

Arg Lys Ala Leu Gln Glu Arg Gly Trp Val Glu Asn Pro Asp Tyr Phe
                20                  25                  30

Cys Phe Asp Leu Lys Trp Thr Cys Lys Val Gln Asp Ile Asp Tyr Asp
            35                  40                  45

Asn Leu Gln Glu Asn Gln Val Val Asn His Phe Asp Asn Asn Gln Thr
50                  55                  60

Phe Thr Ser Lys Tyr Gly Leu Ala Arg Asn Leu Arg Thr Leu Ile His
65                  70                  75                  80

Ser Glu Ile Asp Val Tyr Lys Phe Pro Arg Cys Phe Asp Leu Gly
                85                  90                  95

Asp Glu Phe Glu Asp Phe Ile Glu Asn Phe Lys Val Ala Lys Ala Asn
            100                 105                 110

Ile Trp Ile Val Lys Pro Asn Phe Leu Ser Arg Gly Arg Gly Ile Lys
        115                 120                 125

Cys Phe Asn Ser Leu Asp Lys Ile Met Asp Glu Thr Gln Phe Val Val
130                 135                 140

Gln Lys Tyr Ile Glu Asn Pro Leu Leu Ile Asn Asn Lys Lys Phe Asp
145                 150                 155                 160

Met Arg Gln Trp Ala Ile Val Gln Asp Phe Cys Pro Pro Arg Ile Trp
                165                 170                 175

Phe Phe Glu Glu Cys Tyr Ile Arg Leu Cys Ser Val Glu His Asn Ile
            180                 185                 190

Asp Asp Leu Asn Asn Arg Phe Val His Leu Thr Asn Asn Ile Val Gln
        195                 200                 205

Lys Tyr Asn Lys Asp Ala Tyr Ala Asp Lys Asp Leu Met Met Ser
210                 215                 220

Gln Glu Gln Phe Ala Gln Tyr Leu Lys Glu Thr Glu Gly Phe Tyr Glu
225                 230                 235                 240

Glu Ile Gln Pro Lys Leu Lys Gln Met Val Ile Gln Ser Leu Lys Ser
                245                 250                 255

Cys Gln Asp Gln Val Gly Ala Arg Lys Asn Ser Met Gly Phe Ile Gly
            260                 265                 270
```

```
Tyr Asp Phe Met Ile Asp Ser Asn Tyr Gln Pro Trp Leu Ile Glu Ile
            275                 280                 285
Asn Ser Ser Pro Ser Met Glu Tyr Ser Thr Ser Ile Thr Glu Glu Leu
        290                 295                 300
Val Gln Arg Val Leu Gln Asp Thr Thr Lys Val Ile Val Asp Tyr Ser
305                 310                 315                 320
Met

<210> SEQ ID NO 56
<211> LENGTH: 301
<212> TYPE: PRT
<213> ORGANISM: Drosophila melanogaster

<400> SEQUENCE: 56

Tyr Ala Ile Phe Gly Arg Ser Pro Thr Glu Glu His Leu Val His Val
1               5                   10                  15
Val Asn Val Leu His Lys Phe Gly Tyr Lys Arg Val Gly Val Asn Asp
            20                  25                  30
Asn Leu Leu Trp Ala His Asp Tyr Pro Phe Leu Ser Phe Ala Lys Asn
        35                  40                  45
Leu Gly Gln His Gln Val Val Asn His Tyr Pro Gly Cys Gly Tyr Leu
    50                  55                  60
Thr Asn Lys Val Asp Leu Cys Thr Thr Gln Leu Pro Phe Leu Pro Arg
65                  70                  75                  80
Ala Phe Arg Leu Pro Ala Glu Arg Glu Phe Leu Asp Tyr Ala Arg
                85                  90                  95
Glu Asn Pro Gln Ala Leu Phe Val Gln Lys His Asn Glu His Arg His
            100                 105                 110
Ile Lys Val Arg Ala Pro Ala Asp Ile Ala Phe Gly Ser Asn Asp Ser
        115                 120                 125
Phe Val Gln Glu Phe Val Gln Arg Pro Tyr Leu Val Asp Gly His Lys
    130                 135                 140
Phe Asp Ile Gly Val Tyr Val Ile Thr Ser Val Asn Pro Leu Arg
145                 150                 155                 160
Val Tyr Ile Tyr Thr Gly Asp Val Leu Arg Tyr Cys Pro Val Lys Tyr
                165                 170                 175
His Pro Phe Asp Ala Glu Asn Val Asp Lys Tyr Ile Val Gly Asp Asp
            180                 185                 190
Tyr Leu Pro Thr Trp Glu Phe Gly Gly Ser Met Arg Thr Val Phe Glu
        195                 200                 205
Ala Tyr Val Arg Asp Gln Gly Lys Asp Pro Ala Gln Ile Trp Pro Gln
    210                 215                 220
Val Glu His Ile Val Arg Thr Thr Ile Ala Ala Lys Glu Lys Asp Ile
225                 230                 235                 240
Val Asn Ile Leu Arg Asn Phe Phe Asp Leu Met Arg Phe Asp Leu Phe
                245                 250                 255
Ile Asp Glu Asp Leu Lys Val Phe Leu Met Glu Ala Asn Met Ser Pro
            260                 265                 270
Asn Leu Ser Ser Ala His Phe Lys Pro Asn Ser Leu Leu Tyr Glu Gln
        275                 280                 285
Val Leu Tyr Ser Val Phe Asn Leu Val Gly Ile Arg Pro
    290                 295                 300

<210> SEQ ID NO 57
<211> LENGTH: 313
<212> TYPE: PRT
```

<213> ORGANISM: Homo sapiens

<400> SEQUENCE: 57

```
Pro Gly Pro Phe Phe Tyr Ile Gly Gly Ser Asn Gly Ala Thr Ile Ile
1               5                   10                  15

Ser Ser Tyr Cys Lys Ser Lys Gly Trp Gln Arg Ile His Asp Ser Arg
            20                  25                  30

Asp Tyr Thr Leu Lys Trp Cys Glu Val Lys Ser Arg Asp Ser Tyr Gly
        35                  40                  45

Glu Gln Leu Leu Asp Ala Ser Lys Val Pro Gly Gly Val Gln Ala Arg
    50                  55                  60

Leu Glu Lys Asp Ala Ala Pro Ala Leu Glu Asp Leu Pro Leu Arg
65                  70                  75                  80

Met Glu Glu Phe Phe Pro Glu Thr Tyr Arg Leu Asp Leu Glu Arg Glu
                85                  90                  95

Ala Phe Phe Thr Leu Phe Asp Glu Thr Gln Ile Trp Ile Cys Lys Pro
            100                 105                 110

Thr Ala Ser Asn Gln Gly Lys Gly Ile Phe Leu Leu Arg Asn Gln Glu
        115                 120                 125

Glu Val Ala Ala Pro Gln Ala Arg Val Val Gln Arg Tyr Ile Gln Asn
    130                 135                 140

Pro Leu Leu Val Asp Gly Arg Lys Phe Asp Val Arg Ser Tyr Leu Leu
145                 150                 155                 160

Ile Ala Cys Thr Thr Pro Tyr Met Ile Phe Phe Gly His Gly Tyr Ala
                165                 170                 175

Arg Leu Thr Leu Ser Leu Tyr Asp Pro His Ser Ser Asp Leu Gly Gly
            180                 185                 190

His Leu Thr Asn Gln Phe Met Gln Lys Ser Pro Leu Tyr Met Leu
        195                 200                 205

Leu Lys Glu His Thr Val Trp Ser Met Glu His Leu Asn Arg Tyr Ile
    210                 215                 220

Ser Asp Thr Phe Trp Val Phe Thr Thr Leu Lys Lys Arg Met Gln Gln
225                 230                 235                 240

Ile Met Ala His Cys Phe Leu Ala Ala Lys Pro Lys Leu Asp Cys Lys
                245                 250                 255

Leu Gly Tyr Phe Asp Leu Ile Gly Cys Asp Phe Leu Ile Asp Asp Asn
            260                 265                 270

Phe Lys Val Trp Leu Leu Glu Met Asn Ser Asn Pro Ala Leu His Thr
        275                 280                 285

Asn Cys Glu Val Leu Lys Glu Val Ile Pro Gly Val Val Ile Glu Thr
    290                 295                 300

Leu Asp Leu Val Leu Glu Thr Phe Arg
305                 310
```

<210> SEQ ID NO 58
<211> LENGTH: 320
<212> TYPE: PRT
<213> ORGANISM: Trypanosoma brucei

<400> SEQUENCE: 58

```
Met Cys Leu Tyr Lys Leu Gly Pro Gly Val Val Ala Phe Lys Val Val
1               5                   10                  15

Ile Asp Ala Phe Glu Ala Ser Gly Met Lys Tyr Thr Ala Ser Asn Glu
            20                  25                  30

Asn Val Ile Trp Ala Lys Arg Ala Thr Thr Tyr Ile Leu Ser His Leu
        35                  40                  45
```

Gly Pro Tyr Gln Lys Val Asn His Phe Pro Gly Thr Trp Ile Gly
          50                  55                  60

Arg Lys Asp Ser Leu Ala Thr Asn Ile Gln Lys Met Gln Arg Tyr Phe
 65                  70                  75                  80

Ile Pro Met Thr Phe Leu Leu Pro Lys Gln Arg Ser Gln Leu Glu Asp
                 85                  90                  95

Tyr Val Asn Glu Asn Pro Asp Ser Ala Asp Pro Leu Ile Phe Ile
                100                 105                 110

Val Lys Pro Ser Ala Ser Ser Cys Gly Arg Gly Ile Arg Leu Tyr Arg
                115                 120                 125

Gly Met Pro Pro Met Pro Thr Gly Ser Lys Asn Val Cys Gln Arg Tyr
            130                 135                 140

Val Gly Asn Pro Met Met Ile Phe Gly Arg Lys Phe Asp Leu Arg Leu
145                 150                 155                 160

Tyr Cys Val Val Thr Ser Phe Asp Pro Leu Arg Ile Tyr Ile Phe Asp
                165                 170                 175

Glu Gly Leu Val Arg Phe Ala Ala Gln Lys Tyr Pro Gly Met Asp Leu
                180                 185                 190

Asp Asn Val Gln Lys His Leu Thr Asn Tyr Ser Val Asn Lys Thr Ala
                195                 200                 205

Glu Leu Asn Arg Ala Ser Arg Gly Cys Leu Ser Asp Leu Arg Glu Phe
210                 215                 220

Leu Asp Lys Asn Val Glu Asn Gly Arg Arg Val Trp Glu Lys Val Leu
225                 230                 235                 240

Ser Ser Cys Asp Asp Val Val Ile Lys Ala Phe Leu Ser Ile Glu His
                245                 250                 255

Glu Val Val Glu Arg Leu Arg Lys Gly Cys Phe Glu Leu Tyr Gly Leu
                260                 265                 270

Asp Leu Met Ala Asp Asp Gln Tyr Asn Val Arg Leu Ile Glu Val Asn
            275                 280                 285

Ile Met Pro Ser Leu Ala Thr Gly Thr Pro Leu Asp Lys Ala Val Lys
        290                 295                 300

Ser Arg Met Leu Ala His Leu Leu Thr Leu Ile Arg Val Val Pro His
305                 310                 315                 320

<210> SEQ ID NO 59
<211> LENGTH: 323
<212> TYPE: PRT
<213> ORGANISM: Trypanosoma brucei

<400> SEQUENCE: 59

Pro Gln Tyr Lys Ile Val Asn Leu Ala Leu Cys Lys Tyr Pro Leu Leu
 1                   5                  10                  15

Arg Ile Ile Ala Gln Glu Asn Gly Phe Lys Ile Gln Glu Leu Glu Asp
                 20                  25                  30

Asn Phe Asn Ile Val Trp Ser Asp Thr Val Leu Pro Leu Thr Arg Leu
             35                  40                  45

Val Arg Leu Ala Asn Trp Gln Arg Thr Asn His Phe Pro Ser Met Tyr
         50                  55                  60

Leu Leu Cys Arg Lys Gly His Leu Gly Ile Thr Leu Gly Arg Met Arg
 65                  70                  75                  80

Lys Val Met Pro Ser His Tyr Ile Phe Tyr Pro Arg Thr Trp Ser Leu
                 85                  90                  95

Arg Ser Glu Arg His Gln Phe Ala Arg Phe Leu Met Ala Leu Arg Ser
                100                 105                 110

```
Lys Phe Phe Ile Met Lys Pro Asn Ser Gly Cys Gln Gly Arg Gly Ile
            115                 120                 125

Met Ile Thr Arg Asp Pro Leu Asn Ala Val Glu Asp Leu Asp Asn Ile
130                 135                 140

Val Gln Glu Tyr Ile Thr Arg Pro Leu Leu Glu Gly Arg Lys Phe
145                 150                 155                 160

Asp Leu Arg Val Tyr Val Leu Leu Thr Ser Ile Arg Ala Pro Ser Ile
                165                 170                 175

Phe Leu Phe Asn Asp Gly Leu Val Arg Gln Cys Ala Glu Leu Tyr Glu
            180                 185                 190

Arg Pro Thr Val Lys Asn Thr Cys Lys His Leu Thr Asn Tyr Ala Val
            195                 200                 205

Asn Lys His Asn Pro Glu Tyr Val Phe Asn Asp Gly Asn Lys Arg
            210                 215                 220

Asn Phe Lys Phe Phe Asn Glu Trp Leu Glu Ser Cys Gly Lys Ser Val
225                 230                 235                 240

Glu Gln Phe Trp Ala Arg Val Ala His Val Ile Cys Lys Thr Ile Leu
                245                 250                 255

Val Ala Gln Pro Gln Ile Ala Asn Val Tyr Asn Ser Cys Phe Glu Val
            260                 265                 270

Leu Gly Phe Asp Ile Leu Val Asp Asn Lys Met Lys Pro Trp Leu Met
            275                 280                 285

Glu Val Asn His Thr Pro Ser Leu Val Thr Asp Thr Pro Leu Asp Tyr
            290                 295                 300

Glu Val Lys His Ala Leu Ile Ser Glu Val Trp Asp Ile Leu Asp Val
305                 310                 315                 320

Lys Val Thr

<210> SEQ ID NO 60
<211> LENGTH: 320
<212> TYPE: PRT
<213> ORGANISM: Trypanosoma brucei

<400> SEQUENCE: 60

Gly Arg Val Gly Pro Ile Arg Phe Arg Thr Phe Leu Arg Asn Thr Val
1               5                   10                  15

Leu Asp Val Met Arg Ser Arg Gly Trp Leu Thr Asp Ser Glu Leu
                20                  25                  30

Asp Leu Phe Trp Ala Asp Val Cys Trp Ile Arg Glu Ala Tyr Val Arg
            35                  40                  45

Leu Asp Asp Ala Gln Arg Ile Asn His Phe Arg Asn His Phe Glu Leu
50                  55                  60

Thr Arg Lys Asp Leu Met Val Lys Asn Leu Lys Arg Met Arg Lys Thr
65                  70                  75                  80

Leu Ala Thr Glu Phe Asp Phe Phe Pro Thr Thr Phe Ser Leu Pro Gln
                85                  90                  95

Asp Tyr Gly Leu Phe Glu Met Glu Phe Arg Arg Gln Pro Ala Val Trp
            100                 105                 110

Ile Met Lys Pro Pro Ala Lys Ala Gln Gly Lys Gly Ile Phe Leu Phe
            115                 120                 125

Ser Lys Ile Ser Gln Ile Ser Glu Trp Arg Arg Glu Leu Ala Gln Arg
            130                 135                 140

Tyr Ile Glu Asn Pro His Leu Val Gly Gly Lys Lys Tyr Asp Leu Arg
145                 150                 155                 160
```

```
Val Tyr Val Leu Val Thr Ser Tyr Ser Pro Leu Thr Val Trp Leu His
            165                 170                 175

Arg Thr Gly Phe Ala Arg Phe Cys His Gln Arg Phe Ser Leu Lys Asp
            180                 185                 190

Ile Asp Asn Thr Phe Ile His Val Thr Asn Val Ala Val Gln Lys Thr
            195                 200                 205

Asn Pro Lys Tyr Thr Pro Ser Ser Gly Cys Lys Tyr Gly Leu Arg Asn
            210                 215                 220

Leu Arg Gln Tyr Ile Thr Ala Ser Cys Gly Val Gln Val Ala Gln Lys
225                 230                 235                 240

Leu Phe Asp Asp Ile Gln Asn Met Ile Leu Arg Ser Leu Asn Ala Val
            245                 250                 255

Gln Arg Val Ile Val Gln Asp Lys His Cys Phe Glu Leu Tyr Gly Tyr
            260                 265                 270

Asp Ile Met Ile Asp Ser Asp Leu His Pro Trp Leu Ile Glu Thr Asn
            275                 280                 285

Ala Ser Pro Ser Leu Ser Ala Glu Thr Pro Ala Asp Tyr His Leu Lys
            290                 295                 300

Phe Asn Leu Leu Glu Asp Met Phe Asn Val Val Asp Leu Glu Lys Arg
305                 310                 315                 320

<210> SEQ ID NO 61
<211> LENGTH: 319
<212> TYPE: PRT
<213> ORGANISM: Trypanosoma brucei

<400> SEQUENCE: 61

Asp Asn Arg His Gly Ala Gln Leu Ile Phe Asp His Met Trp Asn Lys
1               5                   10                  15

Val Gly Ser Tyr Arg Leu Pro Thr Ser Ala Asp Gly Asp Ser Gln
            20                  25                  30

Glu Ser Tyr Trp Phe Ile His Asp Glu Val Gly Ser Ala Ile Gln Leu
            35                  40                  45

Ser Gln Asn Leu Thr Asp Ala Asn His Phe Val Val Val Asp Leu Pro
50                  55                  60

Gln Glu Ala His Ile Val Trp Val Val His His Ser Ile Glu Gly Leu
65                  70                  75                  80

Asn Ala Gln Tyr Ile Ser Gln Phe Pro Glu Glu Ser Glu Phe Thr Ser
            85                  90                  95

Glu Thr Tyr Gly Tyr Val Asp Trp Tyr Gln Thr Ser Tyr Asp Asn Leu
            100                 105                 110

Trp Ile Ser Lys Pro Thr Asn Leu Ala Arg Ser Ile Asp Met Thr Leu
            115                 120                 125

Ser Ser Asn Leu Thr Glu Leu Leu Arg Ala Val Glu Thr Val Ile Cys
130                 135                 140

Lys Tyr Ile Ala Asn Thr Ala Thr Leu Arg Lys Arg Lys Phe Asp Leu
145                 150                 155                 160

Arg Phe Ile Val Ala Val Asn Ser Phe Thr Ser Met Glu Ala Tyr Val
            165                 170                 175

Tyr Asn Thr Phe Trp Arg Phe Ala Leu Lys Glu Tyr Ser Leu Asp Asp
            180                 185                 190

Phe Asp Cys Tyr Glu Lys His Trp Thr Val Met Asn Tyr Thr Asn Pro
            195                 200                 205

Glu Ala Leu Leu Gln Leu His Asp His Asp Phe Val Lys Glu Phe Asn
            210                 215                 220
```

```
Glu Glu Tyr Ala Ser Ser Gly Tyr Gly Glu Ala Ala Trp Glu Lys Ile
225                 230                 235                 240

Ala Tyr Pro Lys Ile Leu Lys Met Leu Arg Glu Ala Phe Gly Met Val
                245                 250                 255

Val Thr Arg Gly Gly Asp His Arg Cys Arg Ala Met Tyr Gly Val Asp
            260                 265                 270

Val Met Leu Arg Thr Glu Arg Cys Val Glu Thr Gly Ala Leu Thr Leu
        275                 280                 285

Glu Pro Ser Leu Leu Glu Ile Thr Phe Tyr His Pro Thr Phe Phe Asn
290                 295                 300

Asp Ile Phe His Thr Leu Phe Leu Arg Asp Pro Thr Asn Met Thr
305                 310                 315

<210> SEQ ID NO 62
<211> LENGTH: 302
<212> TYPE: PRT
<213> ORGANISM: Saccharomyces cerevisiae

<400> SEQUENCE: 62

Asn Arg Trp Ile Pro Ile Phe Asn Gly Pro His Ile Asn Leu Glu Asn
1               5                   10                  15

Ser Phe Ala Glu Ile Glu Asp Gly Asn Glu Ser Ser Ile Ser Phe
            20                  25                  30

Asn Trp Ala Pro Lys Phe Gly Ala His Lys Asp Ser Met Asp Lys Leu
        35                  40                  45

Met Glu Leu Pro Asn Asn Tyr Phe Thr Asn Ser Tyr Ile Tyr Arg Lys
    50                  55                  60

Ala Leu Ile Arg Lys His Phe Leu Ser His Thr Ile Gln Thr Tyr Thr
65                  70                  75                  80

Ala Lys Asn Pro Glu Ser Ile Leu Lys Lys Ala Asp Tyr Arg Glu Phe
                85                  90                  95

Leu Asp Asp Ala Leu Asp Glu Asn Trp Lys Trp Trp Ile Val Lys Pro
            100                 105                 110

Ser Met Ser Asp Lys Gly Gln Gly Ile Arg Val Phe Lys Thr Ile Glu
        115                 120                 125

Asp Leu Gln Ala Ile Phe Asp Ser Ile Ile Gln Glu Tyr Leu Thr Asn
    130                 135                 140

Pro Leu Leu Leu Ala Ser Met Asp Asn Arg Lys Phe His Ile Arg Cys
145                 150                 155                 160

Tyr Val Val Cys Arg Gly Asp Leu Phe Val Pro Leu Asp Pro Tyr Ala
                165                 170                 175

Tyr Ser Val Leu Lys Asp Leu Glu Cys His Leu Thr Asn Thr Cys Leu
            180                 185                 190

Gln Ser Lys Lys Lys Asp Lys Asp Ser Ser Val Leu Glu Phe Asp Ser
        195                 200                 205

Ile Glu Glu Ile Pro Asn Glu Arg Lys Ser Ile Lys Glu Gln Ile His
    210                 215                 220

Ser Ile Thr Asn Asp Val Phe Leu Ala Ala Val Asn Val Asn Arg Leu
225                 230                 235                 240

Asn Phe Gln Pro Leu Pro Asn Ala Phe Glu Thr Tyr Gly Val Asp Phe
                245                 250                 255

Leu Ile Asp Ser Asn Tyr Glu Val Lys Leu Leu Glu Ile Asn Ala Phe
            260                 265                 270

Pro Asp Phe Lys Gln Thr Gly Lys Asp Leu Lys Asn Leu Ile Asp Glu
        275                 280                 285
```

Leu Phe Asp Asp Thr Val Lys Tyr Cys Val Thr Pro Ile Phe
            290                 295                 300

<210> SEQ ID NO 63
<211> LENGTH: 323
<212> TYPE: PRT
<213> ORGANISM: Homo sapiens

<400> SEQUENCE: 63

Arg Arg Ser Leu Ala Ile Asn Leu Thr Asn Cys Lys Tyr Glu Ser Val
1               5                   10                  15

Arg Arg Ala Ala Gln Met Cys Gly Leu Lys Glu Val Gly Glu Asp Glu
            20                  25                  30

Glu Trp Thr Leu Tyr Trp Thr Asp Cys Ala Val Ser Leu Glu Arg Val
        35                  40                  45

Met Asp Met Lys Arg Phe Gln Lys Ile Asn His Phe Pro Gly Met Thr
    50                  55                  60

Glu Ile Cys Arg Lys Asp Leu Leu Ala Arg Asn Leu Asn Arg Met Tyr
65                  70                  75                  80

Lys Leu Tyr Pro Ser Glu Tyr Asn Ile Phe Pro Arg Thr Trp Cys Leu
                85                  90                  95

Pro Ala Asp Tyr Gly Asp Phe Gln Ser Tyr Gly Arg Gln Arg Lys Ala
            100                 105                 110

Arg Thr Tyr Ile Cys Lys Pro Asp Ser Gly Cys Gln Gly Arg Gly Ile
        115                 120                 125

Phe Ile Thr Arg Asn Pro Arg Glu Ile Lys Pro Gly Glu His Met Ile
    130                 135                 140

Cys Gln Gln Tyr Ile Ser Lys Pro Leu Leu Ile Asp Gly Phe Lys Phe
145                 150                 155                 160

Asp Met Arg Val Tyr Val Leu Ile Thr Ser Cys Asp Pro Leu Arg Ile
                165                 170                 175

Phe Thr Tyr Glu Glu Gly Leu Ala Arg Phe Ala Thr Thr Pro Tyr Met
            180                 185                 190

Glu Pro Ser Leu Asp Asn Val Cys Met His Leu Thr Asn Tyr Ala Ile
        195                 200                 205

Asn Lys His Asn Glu Asn Phe Val Arg Asp Gly Ala Gly Ser Lys Arg
    210                 215                 220

Lys Leu Ser Thr Leu Asn Ile Trp Leu Gln Glu His Ser Tyr Asn Pro
225                 230                 235                 240

Gly Glu Leu Trp Gly Asp Ile Glu Asp Ile Ile Lys Thr Ile Ile
                245                 250                 255

Ser Ala His Ser Val Leu Arg His Asn Tyr Arg Ala Cys Phe Glu Ile
            260                 265                 270

Leu Gly Phe Asp Ile Leu Leu Asp His Lys Leu Lys Pro Trp Leu Leu
        275                 280                 285

Glu Val Asn His Ser Pro Ser Phe Thr Thr Asp Ser Cys Leu Asp Gln
    290                 295                 300

Glu Val Lys Asp Ala Leu Leu Cys Asp Ala Met Thr Leu Val Asn Leu
305                 310                 315                 320

Arg Gly Cys

<210> SEQ ID NO 64
<211> LENGTH: 307
<212> TYPE: PRT
<213> ORGANISM: Arabidopsis thaliana

<400> SEQUENCE: 64

-continued

```
Leu Gln Ala Lys Ala Phe Glu Ser Lys Pro Ser Asn Pro Ser Val Ser
1               5                   10                  15

Arg Ser Ile Gln His Ser Asp Gly Ser Pro Leu Leu Val Tyr Thr Asp
            20                  25                  30

Asp Ala Asp Ile Leu Trp Thr Ser Val Gln Val Asp Glu Leu Lys
        35                  40                  45

Val Gly Ile Thr Asp Asp Gln Tyr Ile Asn Gln Phe Pro Phe Glu Ala
    50                  55                  60

Cys Leu Val Met Lys His His Leu Ala Glu Thr Ile Gln Met Gly Tyr
65                  70                  75                  80

Gly Ser Pro Lys Trp Leu Gln Pro Thr Tyr Glu Thr Gln Leu Ser Gln
                85                  90                  95

Phe Ile Gly Asp Tyr Cys Val Arg Asn Leu Trp Ile Leu Lys Pro Trp
            100                 105                 110

Asn Met Ala Arg Thr Ile Asp Thr Ser Ile Thr Asp Asn Leu Ser Ala
        115                 120                 125

Ile Ile Arg Met Met Glu Thr Ile Cys Gln Lys Tyr Ile Glu His Pro
130                 135                 140

Ala Leu Phe Lys Gly Asn Lys Phe Asp Leu Arg Tyr Val Val Leu Val
145                 150                 155                 160

Arg Ser Ile Asp Pro Leu Glu Ile Tyr Leu Ile Glu Ile Phe Trp Val
                165                 170                 175

Arg Leu Ser Asn Asn Pro Tyr Ser Leu Glu Lys Phe Phe Glu Tyr Glu
            180                 185                 190

Thr His Phe Thr Val Met Asn Tyr Gly Arg Lys Leu Asn His Lys Pro
        195                 200                 205

Thr Ala Glu Val Arg Glu Phe Glu Gln Glu His Asn Val Lys Trp Met
210                 215                 220

Asp Ile His Glu Lys Val Lys Gln Val Ile Arg Ala Val Phe Glu Ala
225                 230                 235                 240

Ala Ala Leu Ala His Pro Glu Met Gln Ser Pro Lys Ser Arg Ala Met
                245                 250                 255

Tyr Gly Val Asp Val Met Leu Asp Ser Ser Phe Glu Pro Lys Ile Leu
            260                 265                 270

Glu Val Thr Tyr Cys Pro Asp Cys Met Arg Ala Cys Lys Tyr Asp Met
        275                 280                 285

Glu Thr Ile Asp Gly Lys Gly Ile Val Lys Gly Gly Asp Phe Phe Asn
290                 295                 300

Asn Val Phe
305
```

<210> SEQ ID NO 65
<211> LENGTH: 277
<212> TYPE: PRT
<213> ORGANISM: Caenorhabditis elegans

<400> SEQUENCE: 65

```
Val Thr Gly Ser Tyr Glu Ser Ala His Thr Gly His Met Met His Ile
1               5                   10                  15

Arg Glu Met Phe Glu His Thr Gly Tyr Lys Ile Val Thr Lys Asn Glu
            20                  25                  30

Lys Trp Asp Val Met Trp His His Glu Tyr Ser Phe Thr Gln Glu Pro
        35                  40                  45

Lys Asn Ala Ser Pro Asn Gln Ile Val Asn His Val Pro Gly Ser Gly
    50                  55                  60
```

```
Phe Tyr Thr Ser Lys Val Gln Leu Ala Thr Ser Asp Leu Ser Asn Gly
 65                  70                  75                  80

Val Pro Lys Ala Phe Gln Leu Pro Ala Glu Lys Ser Lys Leu Leu Glu
                 85                  90                  95

Tyr Ala Glu Lys Asn Pro Asp Val Leu Trp Val Gln Lys Asp Asn Thr
            100                 105                 110

His Arg Asn Ile Lys Ile Lys Ser Thr Asn Asp Met Asp Leu Ser Lys
        115                 120                 125

Asn Asn Ser Phe Val Gln Lys Phe Val Asp Asn Pro Leu Leu Ile Asp
    130                 135                 140

Asn Lys Phe Cys Pro Glu Asp Tyr His Pro Phe Asp Ala Asn Asn Val
145                 150                 155                 160

Asp Lys Tyr Val Val Gly Asp Asp Tyr Thr Pro Ile Trp Glu Gln Lys
                165                 170                 175

Met Ser Phe Lys Ser Thr Ile Asp Ser Tyr Leu Gly Met Gln Gly Met
            180                 185                 190

Asp Thr Ser Lys Ile Trp Leu Gln Ile Arg Asn Ile Ile Gly Glu Val
        195                 200                 205

Phe Arg Thr Gln Gln Thr Lys Met Leu Met Ser Leu Gln Gln Tyr Phe
    210                 215                 220

Glu Leu Ser Arg Phe Asp Phe Val Val Asp Gln Leu Asn Val Phe
225                 230                 235                 240

Leu Met Glu Ala Asn Met Ser Pro Asn Leu Ser Ser Gly His Phe Lys
                245                 250                 255

Gln Asn Gln Ile Leu Tyr Glu Gln Val Leu Met Asn Ile Phe Ser Leu
            260                 265                 270

Thr Gly Ile Ser Thr
            275

<210> SEQ ID NO 66
<211> LENGTH: 12
<212> TYPE: PRT
<213> ORGANISM: Tetrahymena thermophila

<400> SEQUENCE: 66

Asn His Phe Pro Gly Met Phe Ser Leu Ala Arg Lys
1               5                   10

<210> SEQ ID NO 67
<211> LENGTH: 12
<212> TYPE: PRT
<213> ORGANISM: Tetrahymena thermophila

<400> SEQUENCE: 67

Asn His Phe Pro Asn His Tyr Glu Leu Thr Arg Lys
1               5                   10

<210> SEQ ID NO 68
<211> LENGTH: 12
<212> TYPE: PRT
<213> ORGANISM: artificial
<220> FEATURE:
<223> OTHER INFORMATION: consensus sequence
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
```

<400> SEQUENCE: 68

Asn His Phe Pro Xaa Xaa Xaa Xaa Leu Xaa Arg Lys
1               5                   10

<210> SEQ ID NO 69
<211> LENGTH: 33
<212> TYPE: DNA
<213> ORGANISM: artificial
<220> FEATURE:
<223> OTHER INFORMATION: primer

<400> SEQUENCE: 69
aataaacgcg tcatgtcata gaaagatata tat         33

<210> SEQ ID NO 70
<211> LENGTH: 36
<212> TYPE: DNA
<213> ORGANISM: artificial
<220> FEATURE:
<223> OTHER INFORMATION: primer

<400> SEQUENCE: 70
aataaacgcg tcatggataa taaataaagt gatata      36

<210> SEQ ID NO 71
<211> LENGTH: 32
<212> TYPE: DNA
<213> ORGANISM: artificial
<220> FEATURE:
<223> OTHER INFORMATION: primer

<400> SEQUENCE: 71
atatacgcgt cgcctagttg ttaaaaaaaa ag          32

<210> SEQ ID NO 72
<211> LENGTH: 34
<212> TYPE: DNA
<213> ORGANISM: artificial
<220> FEATURE:
<223> OTHER INFORMATION: primer

<400> SEQUENCE: 72
aataaacgcg tcgagtaggc aaagaagcaa taag        34

<210> SEQ ID NO 73
<211> LENGTH: 35
<212> TYPE: DNA
<213> ORGANISM: artificial
<220> FEATURE:
<223> OTHER INFORMATION: primer

<400> SEQUENCE: 73
aattacgcgt cagagttttg actggtaaaa aagtg       35

<210> SEQ ID NO 74
<211> LENGTH: 36
<212> TYPE: DNA
<213> ORGANISM: artificial
<220> FEATURE:
<223> OTHER INFORMATION: primer

<400> SEQUENCE: 74
tttaaacgcg tcattagaag aaatacaaaa aaggtc      36

```
<210> SEQ ID NO 75
<211> LENGTH: 34
<212> TYPE: DNA
<213> ORGANISM: artificial
<220> FEATURE:
<223> OTHER INFORMATION: primer

<400> SEQUENCE: 75
aattacgcgt cagagtagca ataggagtca aaag                              34

<210> SEQ ID NO 76
<211> LENGTH: 32
<212> TYPE: DNA
<213> ORGANISM: artificial
<220> FEATURE:
<223> OTHER INFORMATION: primer

<400> SEQUENCE: 76
atataggatc catacataca tacatccatt ca                                32

<210> SEQ ID NO 77
<211> LENGTH: 35
<212> TYPE: DNA
<213> ORGANISM: artificial
<220> FEATURE:
<223> OTHER INFORMATION: primer

<400> SEQUENCE: 77
tttatggatc ctcactttat tgtcactcgt ttatc                             35

<210> SEQ ID NO 78
<211> LENGTH: 32
<212> TYPE: DNA
<213> ORGANISM: artificial
<220> FEATURE:
<223> OTHER INFORMATION: primer

<400> SEQUENCE: 78
ttattggatc cttgactcct attgctactc tg                                32

<210> SEQ ID NO 79
<211> LENGTH: 31
<212> TYPE: DNA
<213> ORGANISM: artificial
<220> FEATURE:
<223> OTHER INFORMATION: primer

<400> SEQUENCE: 79
aattggatcc tcaagtctaa gaattaggct t                                 31

<210> SEQ ID NO 80
<211> LENGTH: 33
<212> TYPE: DNA
<213> ORGANISM: artificial
<220> FEATURE:
<223> OTHER INFORMATION: primer

<400> SEQUENCE: 80
tttatggatc ctcattcttc aggtgtgtac ttc                               33

<210> SEQ ID NO 81
<211> LENGTH: 30
<212> TYPE: DNA
<213> ORGANISM: artificial
<220> FEATURE:
<223> OTHER INFORMATION: primer
```

```
<400> SEQUENCE: 81
atattgggcc cgaggaagat gatgatgaga                                    30

<210> SEQ ID NO 82
<211> LENGTH: 30
<212> TYPE: DNA
<213> ORGANISM: artificial
<220> FEATURE:
<223> OTHER INFORMATION: primer

<400> SEQUENCE: 82
ataaacccgg ggctaaagaa aacataccag                                    30

<210> SEQ ID NO 83
<211> LENGTH: 30
<212> TYPE: DNA
<213> ORGANISM: artificial
<220> FEATURE:
<223> OTHER INFORMATION: primer

<400> SEQUENCE: 83
aatttactag tagccatggg ttttagaagt                                    30

<210> SEQ ID NO 84
<211> LENGTH: 30
<212> TYPE: DNA
<213> ORGANISM: artificial
<220> FEATURE:
<223> OTHER INFORMATION: primer

<400> SEQUENCE: 84
attatgagct cctttggaa gtaatgtcag                                     30

<210> SEQ ID NO 85
<211> LENGTH: 30
<212> TYPE: DNA
<213> ORGANISM: artificial
<220> FEATURE:
<223> OTHER INFORMATION: primer

<400> SEQUENCE: 85
atattgggcc cgagctaatc aaacatacga                                    30

<210> SEQ ID NO 86
<211> LENGTH: 30
<212> TYPE: DNA
<213> ORGANISM: artificial
<220> FEATURE:
<223> OTHER INFORMATION: primer

<400> SEQUENCE: 86
attatatcga tttcctagct attctggtta                                    30

<210> SEQ ID NO 87
<211> LENGTH: 30
<212> TYPE: DNA
<213> ORGANISM: artificial
<220> FEATURE:
<223> OTHER INFORMATION: primer

<400> SEQUENCE: 87
atattcccgg gaaaaagcct gatgttgaag                                    30
```

```
<210> SEQ ID NO 88
<211> LENGTH: 30
<212> TYPE: DNA
<213> ORGANISM: artificial
<220> FEATURE:
<223> OTHER INFORMATION: primer

<400> SEQUENCE: 88
atattccgcg gggctacaaa taaagtccat                                    30

<210> SEQ ID NO 89
<211> LENGTH: 22
<212> TYPE: DNA
<213> ORGANISM: artificial
<220> FEATURE:
<223> OTHER INFORMATION: primer

<400> SEQUENCE: 89
tatcttttgg actgataatg ct                                            22

<210> SEQ ID NO 90
<211> LENGTH: 20
<212> TYPE: DNA
<213> ORGANISM: artificial
<220> FEATURE:
<223> OTHER INFORMATION: primer

<400> SEQUENCE: 90
ctcttaatat ctttccacag                                               20

<210> SEQ ID NO 91
<211> LENGTH: 20
<212> TYPE: DNA
<213> ORGANISM: artificial
<220> FEATURE:
<223> OTHER INFORMATION: primer

<400> SEQUENCE: 91
agatctctaa aggaaaatgc                                               20

<210> SEQ ID NO 92
<211> LENGTH: 20
<212> TYPE: DNA
<213> ORGANISM: artificial
<220> FEATURE:
<223> OTHER INFORMATION: primer

<400> SEQUENCE: 92
ttcatgtagt tatctggttg                                               20

<210> SEQ ID NO 93
<211> LENGTH: 32
<212> TYPE: DNA
<213> ORGANISM: artificial
<220> FEATURE:
<223> OTHER INFORMATION: primer

<400> SEQUENCE: 93
atatacgcgt catgttctaa tagaattagc ag                                 32

<210> SEQ ID NO 94
<211> LENGTH: 32
<212> TYPE: DNA
<213> ORGANISM: artificial
<220> FEATURE:
<223> OTHER INFORMATION: primer
```

```
<400> SEQUENCE: 94
ataatggatc ctcatttta ttctctatag at                                32

<210> SEQ ID NO 95
<211> LENGTH: 32
<212> TYPE: DNA
<213> ORGANISM: artificial
<220> FEATURE:
<223> OTHER INFORMATION: primer

<400> SEQUENCE: 95
atatacgcgt catgttctaa tagaattagc ag                               32

<210> SEQ ID NO 96
<211> LENGTH: 34
<212> TYPE: DNA
<213> ORGANISM: artificial
<220> FEATURE:
<223> OTHER INFORMATION: primer

<400> SEQUENCE: 96
tattggatcc tcattctttt aagtaattct tgag                             34

<210> SEQ ID NO 97
<211> LENGTH: 35
<212> TYPE: DNA
<213> ORGANISM: artificial
<220> FEATURE:
<223> OTHER INFORMATION: primer

<400> SEQUENCE: 97
tttatacgcg tcatgtttag catcgatatt taagg                            35

<210> SEQ ID NO 98
<211> LENGTH: 35
<212> TYPE: DNA
<213> ORGANISM: artificial
<220> FEATURE:
<223> OTHER INFORMATION: primer

<400> SEQUENCE: 98
ttattctcga gtcattttt gtaagaagct agtac                             35

<210> SEQ ID NO 99
<211> LENGTH: 36
<212> TYPE: DNA
<213> ORGANISM: artificial
<220> FEATURE:
<223> OTHER INFORMATION: primer

<400> SEQUENCE: 99
attatacgcg tcatgagttc tttagatgaa ggttta                           36

<210> SEQ ID NO 100
<211> LENGTH: 35
<212> TYPE: DNA
<213> ORGANISM: artificial
<220> FEATURE:
<223> OTHER INFORMATION: primer

<400> SEQUENCE: 100 ttttggatc ctcatgagaa attaggtttt agatt                             35
```

```
<210> SEQ ID NO 101
<211> LENGTH: 32
<212> TYPE: DNA
<213> ORGANISM: artificial
<220> FEATURE:
<223> OTHER INFORMATION: primer

<400> SEQUENCE: 101
atatacgcgt catggataaa agttacaata ta                           32

<210> SEQ ID NO 102
<211> LENGTH: 35
<212> TYPE: DNA
<213> ORGANISM: artificial
<220> FEATURE:
<223> OTHER INFORMATION: primer

<400> SEQUENCE: 102
ataatggatc ctcacaattt tttactactt taagt                        35

<210> SEQ ID NO 103
<211> LENGTH: 38
<212> TYPE: DNA
<213> ORGANISM: artificial
<220> FEATURE:
<223> OTHER INFORMATION: primer

<400> SEQUENCE: 103
atatacgcgt catgatattg cctttttgaat actattt                     38

<210> SEQ ID NO 104
<211> LENGTH: 35
<212> TYPE: DNA
<213> ORGANISM: artificial
<220> FEATURE:
<223> OTHER INFORMATION: primer

<400> SEQUENCE: 104
atttaggatc caactgattt atcgttgatt gagtg                        35

<210> SEQ ID NO 105
<211> LENGTH: 32
<212> TYPE: DNA
<213> ORGANISM: artificial
<220> FEATURE:
<223> OTHER INFORMATION: primer

<400> SEQUENCE: 105
atatacgcgt catgagtgat cgaatatatc at                           32

<210> SEQ ID NO 106
<211> LENGTH: 36
<212> TYPE: DNA
<213> ORGANISM: artificial
<220> FEATURE:
<223> OTHER INFORMATION: primer

<400> SEQUENCE: 106
ataatggatc ctcatatttt ttaattttca tttttc                       36

<210> SEQ ID NO 107
<211> LENGTH: 32
<212> TYPE: DNA
<213> ORGANISM: artificial
<220> FEATURE:
<223> OTHER INFORMATION: primer
```

```
<400> SEQUENCE: 107
aaatagggcc ccttaaacca gcagcaacag ac                                    32

<210> SEQ ID NO 108
<211> LENGTH: 32
<212> TYPE: DNA
<213> ORGANISM: artificial
<220> FEATURE:
<223> OTHER INFORMATION: primer

<400> SEQUENCE: 108
aaatacccgg gcaagactct ctggattagg at                                    32

<210> SEQ ID NO 109
<211> LENGTH: 32
<212> TYPE: DNA
<213> ORGANISM: artificial
<220> FEATURE:
<223> OTHER INFORMATION: primer

<400> SEQUENCE: 109
aaattatcga ttgatgttta tcacaggcta ag                                    32

<210> SEQ ID NO 110
<211> LENGTH: 32
<212> TYPE: DNA
<213> ORGANISM: artificial
<220> FEATURE:
<223> OTHER INFORMATION: primer

<400> SEQUENCE: 110
aaattgagct ctgctttagt tatgtttaga ac                                    32

<210> SEQ ID NO 111
<211> LENGTH: 32
<212> TYPE: DNA
<213> ORGANISM: artificial
<220> FEATURE:
<223> OTHER INFORMATION: primer

<400> SEQUENCE: 111
aaatagggcc catcatagta gagtaacagc ct                                    32

<210> SEQ ID NO 112
<211> LENGTH: 32
<212> TYPE: DNA
<213> ORGANISM: artificial
<220> FEATURE:
<223> OTHER INFORMATION: primer

<400> SEQUENCE: 112
aaataatcga tctggtgaat gtttggttgt tg                                    32

<210> SEQ ID NO 113
<211> LENGTH: 32
<212> TYPE: DNA
<213> ORGANISM: artificial
<220> FEATURE:
<223> OTHER INFORMATION: primer

<400> SEQUENCE: 113
aaaatcccgg gtaccttgtg taagtccaga ag                                    32
```

```
<210> SEQ ID NO 114
<211> LENGTH: 35
<212> TYPE: DNA
<213> ORGANISM: artificial
<220> FEATURE:
<223> OTHER INFORMATION: primer

<400> SEQUENCE: 114
atattccgcg gtcatttttt gtaagaagct agtac                              35

<210> SEQ ID NO 115
<211> LENGTH: 31
<212> TYPE: DNA
<213> ORGANISM: artificial
<220> FEATURE:
<223> OTHER INFORMATION: primer

<400> SEQUENCE: 115
taaaccgcgg gatagcctgt cttctcctcc a                                  31

<210> SEQ ID NO 116
<211> LENGTH: 34
<212> TYPE: DNA
<213> ORGANISM: artificial
<220> FEATURE:
<223> OTHER INFORMATION: primer

<400> SEQUENCE: 116
aatagggccc gatactttaa tatcaaatac ttgc                               34

<210> SEQ ID NO 117
<211> LENGTH: 32
<212> TYPE: DNA
<213> ORGANISM: artificial
<220> FEATURE:
<223> OTHER INFORMATION: primer

<400> SEQUENCE: 117
aaatgggccc tagatgacag tattgttgat gc                                 32

<210> SEQ ID NO 118
<211> LENGTH: 31
<212> TYPE: DNA
<213> ORGANISM: artificial
<220> FEATURE:
<223> OTHER INFORMATION: primer

<400> SEQUENCE: 118
aattcccggg ttaggtctgc attgtcaaac c                                  31

<210> SEQ ID NO 119
<211> LENGTH: 31
<212> TYPE: DNA
<213> ORGANISM: artificial
<220> FEATURE:
<223> OTHER INFORMATION: primer

<400> SEQUENCE: 119
ttaaatcgat agttgagata attgatcatg c                                  31

<210> SEQ ID NO 120
<211> LENGTH: 31
<212> TYPE: DNA
<213> ORGANISM: artificial
<220> FEATURE:
<223> OTHER INFORMATION: primer
```

-continued

<400> SEQUENCE: 120
ttaagagctc ctcataaata atctaccaca c    31

<210> SEQ ID NO 121
<211> LENGTH: 34
<212> TYPE: DNA
<213> ORGANISM: artificial
<220> FEATURE:
<223> OTHER INFORMATION: primer

<400> SEQUENCE: 121
atttgggccc ttagggagtt ctgctgctaa gagt    34

<210> SEQ ID NO 122
<211> LENGTH: 33
<212> TYPE: DNA
<213> ORGANISM: artificial
<220> FEATURE:
<223> OTHER INFORMATION: primer

<400> SEQUENCE: 122
aattaatcga tacttgtagt catcatttga atc    33

<210> SEQ ID NO 123
<211> LENGTH: 32
<212> TYPE: DNA
<213> ORGANISM: artificial
<220> FEATURE:
<223> OTHER INFORMATION: primer

<400> SEQUENCE: 123
attaacccgg gccatctgct aattcaagag ga    32

<210> SEQ ID NO 124
<211> LENGTH: 34
<212> TYPE: DNA
<213> ORGANISM: artificial
<220> FEATURE:
<223> OTHER INFORMATION: primer

<400> SEQUENCE: 124
attaagagct cactgattta tcgttgattg agtg    34

<210> SEQ ID NO 125
<211> LENGTH: 32
<212> TYPE: DNA
<213> ORGANISM: artificial
<220> FEATURE:
<223> OTHER INFORMATION: primer

<400> SEQUENCE: 125
aaaaagggcc caacaaccat ccatatgaca gc    32

<210> SEQ ID NO 126
<211> LENGTH: 32
<212> TYPE: DNA
<213> ORGANISM: artificial
<220> FEATURE:
<223> OTHER INFORMATION: primer

<400> SEQUENCE: 126
aaattcccgg gccatcctag ctcaattaga ac    32

```
<210> SEQ ID NO 127
<211> LENGTH: 31
<212> TYPE: DNA
<213> ORGANISM: artificial
<220> FEATURE:
<223> OTHER INFORMATION: primer

<400> SEQUENCE: 127
tataatcgat aaggcttgca gataatgagt g                              31

<210> SEQ ID NO 128
<211> LENGTH: 31
<212> TYPE: DNA
<213> ORGANISM: artificial
<220> FEATURE:
<223> OTHER INFORMATION: primer

<400> SEQUENCE: 128
tatagagctc gggaatttga acttaacaca g                              31

<210> SEQ ID NO 129
<211> LENGTH: 25
<212> TYPE: DNA
<213> ORGANISM: artificial
<220> FEATURE:
<223> OTHER INFORMATION: morpholino

<400> SEQUENCE: 129
gtgttggtgc atgtttgagt taacc                                     25

<210> SEQ ID NO 130
<211> LENGTH: 25
<212> TYPE: DNA
<213> ORGANISM: artificial
<220> FEATURE:
<223> OTHER INFORMATION: morpholino

<400> SEQUENCE: 130
gatgtacaga gctgagattg aaaag                                     25

<210> SEQ ID NO 131
<211> LENGTH: 20
<212> TYPE: DNA
<213> ORGANISM: artificial
<220> FEATURE:
<223> OTHER INFORMATION: primer

<400> SEQUENCE: 131
cttactccac tcatacgctg                                           20

<210> SEQ ID NO 132
<211> LENGTH: 20
<212> TYPE: DNA
<213> ORGANISM: artificial
<220> FEATURE:
<223> OTHER INFORMATION: primer

<400> SEQUENCE: 132
gtcgaatgtt gatcacctcc                                           20
```

BIOLOGICAL SYSTEM AND ASSAY FOR IDENTIFYING MODULATORS OF TUBULIN LIGASES

This application is a continuation-in-part of U.S. application Ser. No. 11/479,098, filed Jun. 30, 2006, which claims the benefit of U.S. Provisional Application Ser. No. 60/695,776, filed Jun. 30, 2005, each of which is incorporated herein by reference in its entirety.

This invention was made with government support under grants from the National Science Foundation, Grant Nos. MBC-0235826 and MBC-033965, and under a grant from the National Institutes of Health, Grant No. R37GM051173. The U.S. Government has certain rights in this invention.

BACKGROUND OF THE INVENTION

Microtubules are fibers made of α-tubulin and β-tubulin dimers. Microtubules form cytoplasmic networks and serve as frameworks of important organelles, including the mitotic spindle, centrioles, cilia and bundles inside neurites. The biogenesis of microtubules involves the synthesis of tubulin polypeptides, chaperonin-assisted folding and dimerization of α-tubulin and β-tubulin, transport to the sites of assembly, nucleation, polymerization, deposition of post-translational modifications (PTMs), and binding of diverse microtubule-associated proteins (MAPs).

During mitosis, the microtubule undergoes dramatic changes to transition from an interphase monopolar organization to the bipolar spindle. Thus, tubulins are a major target of anti-cancer drugs which act by disrupting the dynamic properties of MTs during mitosis and in some cases inducing apoptosis. However currently available widely used microtubule-targeting compounds (such as vinblastine or paclitaxel) suffer from a major limitation—they target microtubules indiscriminately. Paclitaxel, for example, a compound that hyperstabilizes microtubules and blocks cells in mitosis, is currently the most widely used drug to treat ovarian, breast, lung cancers and AIDS-related Kaposi's sarcoma (Ring et al. (2005) Cancer Treat Rev 31, 618-627; Cheung et al., (2005) Oncologist 10, 412-426). However, paclitaxel produces strong side effects by affecting non-mitotic microtubules, in particular in nerve cells (Hennenfent et al. (2006). Ann Oncol. 17, 735-749). Paclitaxel also affects the bone marrow leading to hematopoietic deficiencies in ~90% of patients (Hagiwara et al. (2004) Breast Cancer 11, 82-85). Ideally, future anti-microtubule compounds should affect as few cell types as possible besides intended targets. Humans have several isotypes of α-tubulin and β-tubulin, some of which are expressed in a restricted fashion. However, tubulins are highly conserved and differ mainly in the small portion of their primary sequence near the C-terminal end (Luduena (1998) Int. Review Cytol. 178, 207-274). Thus, developing isotype-specific inhibitors for tubulin primary polypeptides is likely to be difficult.

Post-translational modifications of microtubules are ubiquitously present in eukaryotes and their physiological importance is increasingly well documented (Rosenbaum (2000) Current Biol. 10, R801-R803, Westermann et al. (2003) Nat Rev Mol Cell Biol 4, 938-947). The most studied post-translational modifications include acetylation of α-tubulin, detyrosination of α-tubulin, palmitoylation of α-tubulin, and phosphorylation, glutamylation, and glycylation of α-tubulin and β-tubulin.

Post-translational modifications are believed to function in regulating interactions of microtubules with MAPs (such as dynein and kinesin motors) (Rosenbaum (2000) Current Biol. 10, R801-R803), Westermann et al. (2003) Nat Rev Mol Cell Biol 4, 938-947). Most post-translational modifications are located on the C-terminal tails of tubulins, highly flexible acidic domains present on the surface of microtubules (Nogales et al. (1999) Cell 96, 79-88). The tails are also the major sites of interactions with kinesin and dynein motors, structural MAPs (MAP2, Tau), microtubule-severing protein katanin, and plus end-depolymerizer (MCAK) (Skiniotis et al. (2004) Embo J 23, 989-999, Ovechkina et al. (2002) J Cell Biol 159, 557-562, Lu et al. (2004) Mol Biol Cell 15, 142-150). By regulating the activity of tubulin modifying enzymes, cells can mark microtubules in specific subcellular areas to regulate binding and activity of MAPs in a localized fashion. Detyrosination of α-tubulin promotes transport of vimentin intermediate filaments mediated by kinesin-1 (Kreitzer et al. (1999) Mol. Biol. Cell 10, 1105-1118). Another post-translational modification, polyglycylation, appears to acts as a mark to regulate assembly of cilia and severing of stable cortical microtubules in *Tetrahymena* (Thazhath et al. (2002) Nature Cell Biol. 4, 256-259; Thazhath et al. (2004) Mol Biol Cell 15, 4136-4147). The basic principle of specific post-translational modifications acting alone or in combination to regulate binding of a variety of microtubule interactors is likely to be general. By analogy with the epigenetic "histone code", eukaryotic cells appear to utilize a "microtubule code" to coordinate MAPs.

Glutamylation, a conserved post-translational modification, occurs by addition of a variable number of glutamate (also known as glu or "E") residues onto specific glutamate residues of the C-terminal tail domain of α-tubulin or β-tubulin (Eddé et al. (1990) Science 247, 83-85), Weber et al. (1996) FEBS Lett. 393, 27-30). Besides tubulins only the nucleosome assembly proteins, NAP-1 and NAP-2 are known to undergo glutamylation (Regnard et al. (2000) J. Biol. Chem. 275, 15969-15976). The added glutamates form a peptide side chain using the gamma-carboxyl group of the glutamate in the primary sequence. Due to its negative charge and bulky nature, glutamate side chains have a strong structural impact on microtubules. Because the number of added glutamates changes as the function of age of microtubules and cell cycle stage, this post-translational modification is probably not a simple on/off signal. Rather, glutamylation may act like a rheostat to fine tune the function of microtubules. Tubulin glutamylation is particularly abundant on microtubules inside cellular projections including neuritis (Wolff et al. (1992) Eur. J. Cell Biol. 59, 425-432) and cilia (Bré et al. (1994) Cell Motility and the Cytoskeleton 27, 337-349). Glutamylation accumulates on microtubules of centrioles and in the central part of the mitotic spindle (Bobinnec et al. (1998) Cell Motil. Cytoskeleton 39, 223-232). Tubulin glutamylation is important in vivo. Injection of antibodies specific to glutamylated tubulin caused disassembly of centrioles in mammalian cells (Bobinnec et al. (1998) J. Cell Biol. 143, 1575-1589), suggesting that inhibitors of glutamylation could have anti-mitotic properties. A mutation of a subunit associated with the TTLL1 glutamylase in the mouse blocked assembly of sperm axonemes and affected behavior (Campbell et al. (2002) Genetics 162, 307-320). In vitro, glutamylation of microtubules strongly affects binding of kinesins and structural MAPs, MAP2 and Tau (Bonnet et al. (2000) J. Biol. Chem. 276, 12839-12848, Boucher et al. (1994) Biochemistry 33, 12471-12477).

Inhibitors of a forward post-translational modification enzyme are not known in the art. Furthermore, inhibitors are known for only one of the reverse post-translational modification enzymes, tubulin deacetylase HDAC6 (related to histone deacetylases). Overexpression of HDAC6 decreased acetylation and increased chemotactic motility of mammalian cells (Hubbert et al. (2002) Nature 417, 455-458). HDAC6 can be inhibited with trichostatin A (a broad inhibitor of deacetylases) (Matsuyama et al. (2002) Embo J 21, 6820-6831), and tubacin (a specific inhibitor) (Haggarty et al. (2003) Proc. Natl. Acad. Sci. U.S.A. 100, 4389-4394). Chemically blocking HDAC6 increased the level of acetylation on microtubules and decreased cell motility as well as disrupted localization of the p58 MAP (a Golgi-microtubule linker) in vivo (Haggarty et al. (2003) Proc. Natl. Acad. Sci. U.S.A. 100, 4389-4394). Inhibitors of HDAC6 has helped to uncover potential new functions for α-tubulin acetylation, including its role in the immune synapse formation (Serrador et al. (2004) Immunity 20, 417-428), and during infection of cells by HIV (Valenzuela-Fernandez et al. (2005) Mol Biol Cell 16, 5445-5454). HDAC6 is upregulated in the acute myeloid leukemia cells (Bradbury et al. (2005) Leukemia 19, 1751-1759), and is one of the estrogen-responsive genes in breast carcinoma. Blocking HDAC6 with tubacin inhibited estradiol-induced cell migration of breast carcinoma cells (Saji et al. (2005) Oncogene 24, 4531-4539). Tubacin also increased anti-cancer effects of other compounds, including a proteasome inhibitor, bortezomid (Hideshima et al. (2005) Proc Natl Acad Sci USA 102, 8567-8572). Although HDAC6 effects could be mediated by at least two different substrates (α-tubulin and HSP90, Kovacs et al. (2005) Mol Cell 18, 601-607), it is very likely that the effects on cell motility are microtubule-mediated. Importantly, HDAC6 is required for the synergistic inhibitory action of paclitaxel and lonafarmib (an inhibitor of farnesyltransferase) on cancer cells (Marcus et al. (2005). Cancer Res 65, 3883-3893). However, these targeting efforts are limited to one post-translational modification and specifically, to one enzyme, HDAC6 deacetylase. A general strategy for identifying post-translational modification drugs and in particular inhibitors of forward enzymes responsible for deposition of PTMs is needed.

SUMMARY OF THE INVENTION

The invention provides a biological system and assay for identification of inhibitors of enzymes responsible tubulin glutamylation.

In one aspect, the invention is directed to a biological system that includes a host protozoan, preferably a ciliate such as *Tetrahymena*, that overexpresses a tubulin glutamylase, preferably *Tetrahymena* Ttll6Ap, Ttll6Bp, Ttll6Cp, Ttll6Dp, Ttll6Ep or Ttll6Fp. In one embodiment, the *Tetrahymena* overexpresses a wild-type tubulin glutamylase. In another embodiment, the *Tetrahymena* expresses a modified tubulin glutamylase, for example a truncated form of a *Tetrahymena* tubulin glutamylase that is missing the C-terminal region responsible for targeting the glutamylase to the cilia. A modified tubulin glutamylase can include, for example, a subunit of a tubulin glutamylase or a mutated tubulin glutamylase having mutations at one or more sites, or a fusion construct that includes all or part of a tubulin glutamylase. A preferred truncated tubulin glutamylase is *Tetrahymena* Ttll6Ap-$\Delta_{710}$. Preferably, the tubulin glutamylase is under the control of a metallothionein promoter, more preferably an MTT1 promoter. MTT1 is conveniently inducible by cadmium.

The invention should be understood as including a *Tetrahymena* cell or cell line that overexpresses a wild-type or modified tubulin glutamylase as described above. In a particularly preferred embodiment, the *Tetrahymena* cell or cell line contains polynucleotide sequence encoding a wild-type or modified tubulin glutamylase that is integrated into the β-tubulin 1 (BTU1) locus. A preferred construct for use in transforming the *Tetrahymena* includes an MTT1 promoter region upstream of a region that encodes a fusion protein. The fusion protein optionally includes a marker protein, such as green fluorescent protein (GFP), followed by a tubulin glutamylase, or vice versa. Preferably, the construct encodes the marker protein followed by an in-frame coding region of a genomic sequence of the tubulin glutamylase gene, preferably the *Tetrahymena* TTLL6A gene (locus number 25.m00404 at *Tetrahymena* genome database; The Institute for Genomic Research website at www.tigr.org), or a truncated version thereof, TTLL6A-$\Delta_{710}$. A particularly preferred *Tetrahymena* is one that expresses Ttll6Ap-GFP or Ttll6Ap-$\Delta_{710}$-GFP.

In another aspect, the invention is directed to a *Tetrahymena* tubulin glutamylase, as well as a nucleic acid encoding a *Tetrahymena* tubulin glutamylase. The invention encompasses amino acid sequences having at least about 90%, preferably at least about 95%, and more preferably at least about 98% identity to the amino acid sequences described herein.

In another aspect, the invention is directed toward a high throughput in vivo assay for identification, validation and/or analysis of selective inhibitors of tubulin glutamylases. The assay is performed using a protozoan, preferably the ciliate *Tetrahymena*, a model protist with a sophisticated microtubular cytoskeleton. The *Tetrahymena* used in the in vivo assay overexpresses a tubulin glutamylase, as described herein. This assay is a phenotypic screen based on rescue from growth arrest caused by overexpression of a tubulin glutamylase enzyme in *Tetrahymena*.

In another aspect, the invention is directed toward an in vitro assay for identification, validation and/or analysis of selective inhibitors of tubulin glutamylases. This assay makes use of a glutamylation reaction using a purified *Tetrahymena* enzyme and microtubules. A variant of this assay, useful as a primary screen, employs luciferase activity as a readout signal.

Inhibitors of tubulin glutamylases are expected to be therapeutically useful to treat or prevent many diseases including cancer and disorders of central nervous system including mental diseases. They may also find utility as a male contraceptive.

Accordingly, the present invention is directed to a *Tetrahymena* cell that overexpresses a tubulin glutamylase. Preferably the *Tetrahymena* includes a polynucleotide operably encoding a tubulin glutamylase, wherein the polynucleotide is integrated into a BTU1 locus. The polynucleotide preferably includes an MTT1 promoter region upstream of a region encoding a fusion protein, which fusion protein incorporates a marker protein and a tubulin glutamylase. The marker protein is preferably an optically detectable protein; more preferably it is a fluorescent protein such as green, red or blue fluorescent protein. The tubulin glutamylase may be a wild-type or a modified tubulin glutamylase; preferably the tubulin glutamylase is *Tetrahymena* Ttll6Ap glutamylase or Ttll6Ap-$\Delta_{710}$ glutamylase. A preferred *Tetrahymena* cell is one that overexpresses *Tetrahymena* TTLL6A gene (locus number 25.m00404 at *Tetrahymena* genome database), or its truncated version, *Tetrahymena* TTLL6A-$\Delta_{710}$.

The invention further provides a method for identifying an inhibitor of tubulin glutamylase that includes contacting a *Tetrahymena* cell of the invention with a candidate inhibitor compound; and detecting an increase in cell growth and/or motility; wherein an increase in cell growth or motility is indicative of tubulin glutamylase inhibition.

In another aspect, the invention provides a genetically engineered *Tetrahymena* cell that expresses tubulin exhibiting reduced polymodification compared to a wild-type *Tet-* rahymena cell. Polymodification can take the form of, for example, polyglutamylation or polyglycylation.

In one embodiment of the genetically engineered *Tetrahymena* cell that exhibits reduced polyglutamylation, the tubulin present in the *Tetrahymena* cell has shortened glutamyl side chains compared to wild-type *Tetrahymena* tubulin. In a preferred embodiment, at least a portion of the shortened glutamyl side chains contain less than 6 glutamic acid residues, and the density, or proportion, of the glutamyl side chains containing less than 6 glutamic acid residues is increased relative to wild-type *Tetrahymena* tubulin. More preferably, at least portion of the shortened glutamyl side chains contain only one glutamic acid residue, and the density, or proportion, of the glutamyl side chains containing only one glutamic acid residue is increased relative to wild-type *Tetrahymena* tubulin.

In one embodiment of the genetically engineered *Tetrahymena* cell that exhibits reduced polyglycylation, tubulin present in the *Tetrahymena* cell lacks glycyl side chains that are present in wild-type tubulin. In a preferred embodiment, the tubulin glycylation level is less than 80%, more preferably less than 90%, and even more preferably less than 95%, of the tubulin glycylation level in wild-type *Tetrahymena* tubulin.

In another preferred embodiment of the *Tetrahymena* cell, a plurality of the tubulin glutamic acid ligase genes, preferably TTLL6 genes, or a plurality of the tubulin glycine ligase genes, preferably TTLL3 genes, of the *Tetrahymena* cell have been disrupted.

A preferred genetically engineered *Tetrahymena* cell has reduced function of at least two paralogs of TTLL6 or TTLL3. Paralogs of TTLL6 may be selected from the group consisting of TTLL6A, TTLL6B, TTLL6C, TTLL6D, TTLL6E, and TTLL6F. Paralogs of TTLL3 may be selected from the group consisting of TTLL3A, TTLL3B, TTLL3C, TTLL3D, TTLL3E, and TTLL3F. Particularly preferred genetically engineered *Tetrahymena* cells are knockout cells, and include a TTLL6A/TTLL6F knockout cell, a TTLL6A/TTLL6B/TTLL6D/TTLL6F knockout cell, a TTLL6A/TTLL6B/TTLL6D/TTLL6E/TTLL6F knock out cell, a TTLL3A/TTLL3B knockout cell, a TTLL3A/TTLL3B/TTLL3C/TTLL3D knockout cell, and a TTLL3A/TTLL3B/TTLL3C/TTLL3D/TTLL3E/TTLL3F knockout cell.

Cellular components which, in wild-type *Tetrahymena* cells, are polymodified with glutamic acid side chains and/or glycine side chains, but which, in the genetically engineered *Tetrahymena* cells of the invention, exhibit shortened or absent glutamic acid or glycine side chains, can be isolated from genetically engineered *Tetrahymena* cells of the invention and employed in in vitro assays to identify inhibitors or enhancers of glutamic acid ligases or glycine ligases. Thus, in another aspect, the invention provides an in vitro method for identifying an inhibitor or enhancer of a glutamic acid ligase or a glycine ligase, which method utilizes cellular components isolated from the genetically engineered *Tetrahymena* of the invention. Preferably, the cellular components used in the assay methods of the invention are tubulin-containing components such as axonemes, microtubules, and tubulin.

In one embodiment, the method is a method for identifying an inhibitor of a glutamic acid ligase that includes contacting a cellular component, such as an axoneme, a microtubule, a stabilized microtubule or tubulin, isolated from the *Tetrahymena* cell of the invention, with a candidate inhibitor compound and a glutamic acid ligase; and detecting a change in glutamylation of the cellular component, wherein the absence of additional glutamylation, or a slower rate of glutamylation compared to the rate observed in the absence of the candidate inhibitor compound, is indicative of a compound that inhibits glutamic acid ligase.

In another embodiment, the is a method for method for identifying an inhibitor of a glycine ligase that includes contacting a cellular component, such as an axoneme, a microtubule, a stabilized microtubule or tubulin, isolated from the *Tetrahymena* cell of the invention, with a candidate inhibitor compound and a glycine ligase; detecting a change in glycylation of the cellular component, wherein the absence of additional glycylation, or a slower rate of glycylation compared to the rate observed in the absence of the candidate inhibitor compound, is indicative of a compound that inhibits glycine ligase.

Unless otherwise specified, "a," "an," "the," and "at least one" are used interchangeably and mean one or more than one.

BRIEF DESCRIPTION OF THE DRAWINGS

FIG. 13 shows a multiple sequence alignment of TTL domains (SEQ ID NOs:8-65) of TTL and TTLL proteins.

FIGS. 38A and B show a cell expressing GFP-Ttll3Ap before (A) and after (B) induction with 2.5 μg/ml $CdCl_2$ for 5 hr, labeled by TAP952. FIG. 38C shows GFP fluorescence in GFP-Ttll3Ap-expressing cells. Scale bar, 10 μm. c, cilia; oc, oral cilia. FIG. 38D shows a fluorogram of an SDS-PAGE gel with brain microtubule proteins after in vitro glycylation with fractions enriched in overexpressed TTLL3 proteins of *Tetrahymena*. FIG. 38E shows a graph showing levels of incorporation of $^3$H-glycine (in disintegrations per min) into brain α- or β tubulin in in vitro glycylation assays. FIG. 38F shows Western blots of ciliary proteins from wild-type and cells overproducing either GFP-Ttll3Ap or GFP-DN-Ttll3Ap. FIG. 38G shows a Western blot of cells expressing either GFPTtll3Ap or GFP-DN-Ttll3Ap before (−) and after (+) cadmium induction, probed either with anti-GFP or anti-α-tubulin antibodies.

FIG. 39A-D' shows wild type and GFP-Ttll3Ap overproducing cells (marked by arrows) were induced by 2.5 μg/ml cadmium chloride for 5 hrs, mixed and processed side-by side for quantitative immunofluorescence with the following antibodies: TAP952 anti-monoglycylated tubulin (A'); AXO49 anti-polyglycylated tubulin (B'); polyG, anti-polyglycylation side chain (C') and ID5, anti-polyglutamylated tubulin (D'). Corresponding merged images with the GFP signal are shown in A-D (in A, in the wildtype control, the faint green signal corresponds to autofluorescence of food vacuoles loaded with Ink). FIG. 39A"-D" shows graphs representing the corresponding quantitative immunofluorescence analyses of the average pixel intensity of axoneme sections. N—number of analyzed cilia, P—total number of analyzed pixel. Error bars show standard deviations. Note that there is an increase in the levels of tubulin monoglycylation but not polyglycylation and decrease in the level of tubulin polyglutamylation in cilia of GFP-Ttll3Ap overproducing cells. These data are consistent with Ttll3Ap having a glycine ligase chain initiating activity but lacking chain elongating activity and negatively inhibiting tubulin glutamylation. Bar, 10 μm.

FIG. 40A-D shows WT (fed with India ink) and 3AB-KO cells (arrows) imaged side by side. (A) and (C) show immunofluorescence with TAP952 and AXO49 respectively, while (B) and (D) show the corresponding phase contrast images. Insets show higher magnifications (2.53) of boxed areas of cilia. FIG. 40E-E' shows growth curves of WT and TTLL3 knockout strains grown without (E) or with (E') 35 μM paclitaxel. Note that in (E), WT and 3AB-KO curves completely overlap. FIG. 40F shows Western blots of ciliary proteins from WT (loaded at multiple dilutions) and TTLL3 knockout strains. FIG. 40G shows a graph representing the length of cilia in WT and TTLL3 knockout cells. Error bars represent SEM. The differences between WT and 3AB-KO, 3ABCD-KO, and 3ABC-DEF-KO cells were statistically significant ($p<0.0001$). FIG. 40G'-G" shows immunofluorescence images of cilia in WT and sextuple knockout cells labeled with anti-tubulin antibodies. Images of the entire cells are shown in FIGS. 41K and L. FIG. 40H-K shows immunofluorescence with anti-total tubulin antibodies of *Tetrahymena* cells that are either WT (H and J) or 3AB-KO (I and K), and were either untreated (H-I) or treated with 25 μM paclitaxel for 4 hr (J and K).

FIG. 41A-F shows 3AB-KO (A-C) and 3ABCDEF-KO (D-F) cells were mixed with wild type cells (indicated by arrows, earlier fed with India ink for identification) and stained with the following antibodies: TAP952, tubulin monoglycylation (A, D); AXO49, tubulin polyglycylation (B, E) and ID5, tubulin polyglutamylation (C, F). FIG. 41A'-F' shows graphs contain the corresponding quantitative immunofluorescence data based on the average pixel intensity of axonemes. N—number of analyzed axonemes, P—number of analyzed pixels. Error bars show standard deviations. Note the dramatic reduction in the level of tubulin monoglycylation in both double and sextuple knockouts (A,A' D,D') and polyglycylation in the sextuple knockouts (E,E') and an increase in the level of tubulin polyglutamylation (C,C', F,F') in TTLL3 knockout cells. FIG. 41G-J shows knockouts of TTLL3 genes reduce the levels of tubulin polyglycylation in cilia. All cells were analyzed at the same gain level to visualize polyglycylated tubulin in wild type (G) and TTLL3 double (H), quadruple (I) and sextuple (J) knockout cells. Note that wild type and double knockout cells are overexposed. FIG. 41K and L shows immunofluorescence with a mixture of 12G10 anti-α-tubulin and SG anti-total tubulin antibodies of *Tetrahymena* wild type (K) and 3ABC-DEF-KO cells (L). Note the reduction in the length of cilia in TTLL3 knockout cells. The boxed areas are shown at higher magnification in FIG. 40G-G'. Bar, 10 μm.

N—number of analyzed cilia, P—number of analyzed pixels. Error bars show standard deviations. Bar, 10 µm.

Figure 43:
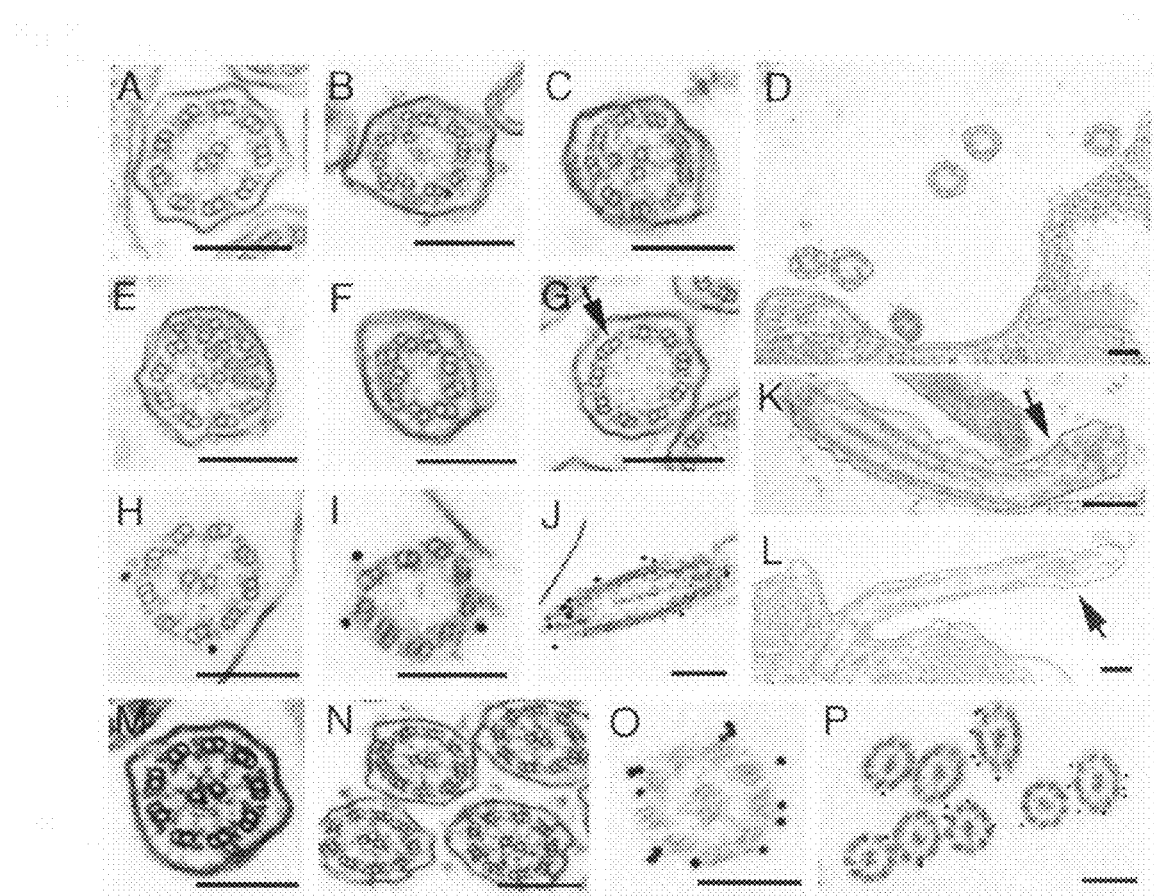

FIG. 43 shows TTLL3 proteins and tubulin glycylation are restricted to outer microtubules and dominant-negative TTLL3 disrupts the axoneme structure. FIG. 43A-G shows TEM cross-sections of axonemes of WT (A) and GFP-DN-Ttll3Ap-overproducing cells (B-G). The arrow in (G) marks an abnormal triplet. Scale bar, 0.2 µm. FIG. 43H-J shows immunogold localization of either GFPTtll3Ap (H) or GFP-DN-Ttlll3Ap (I and J) with anti-GFP antibodies. Scale bar, 0.2 µm. FIG. 43K-L shows longitudinal TEM sections of cilia of GFPDN-Ttll3Ap overproducing cells. Scale bar, 0.2 µm. FIG. 43M and N shows TEM cross-sections of axonemes of 3AB-KO (M) and 3ABCDEF-KO (N) cells. Scale bar, 0.2 µm. FIG. 43O and P shows immunogold localization of monoglycylated (O) or polyglycylated tubulin (P) in WT cells using TAP952 and AXO49 mAb, respectively. Scale bar, 0.2 µm.

Figure 44:
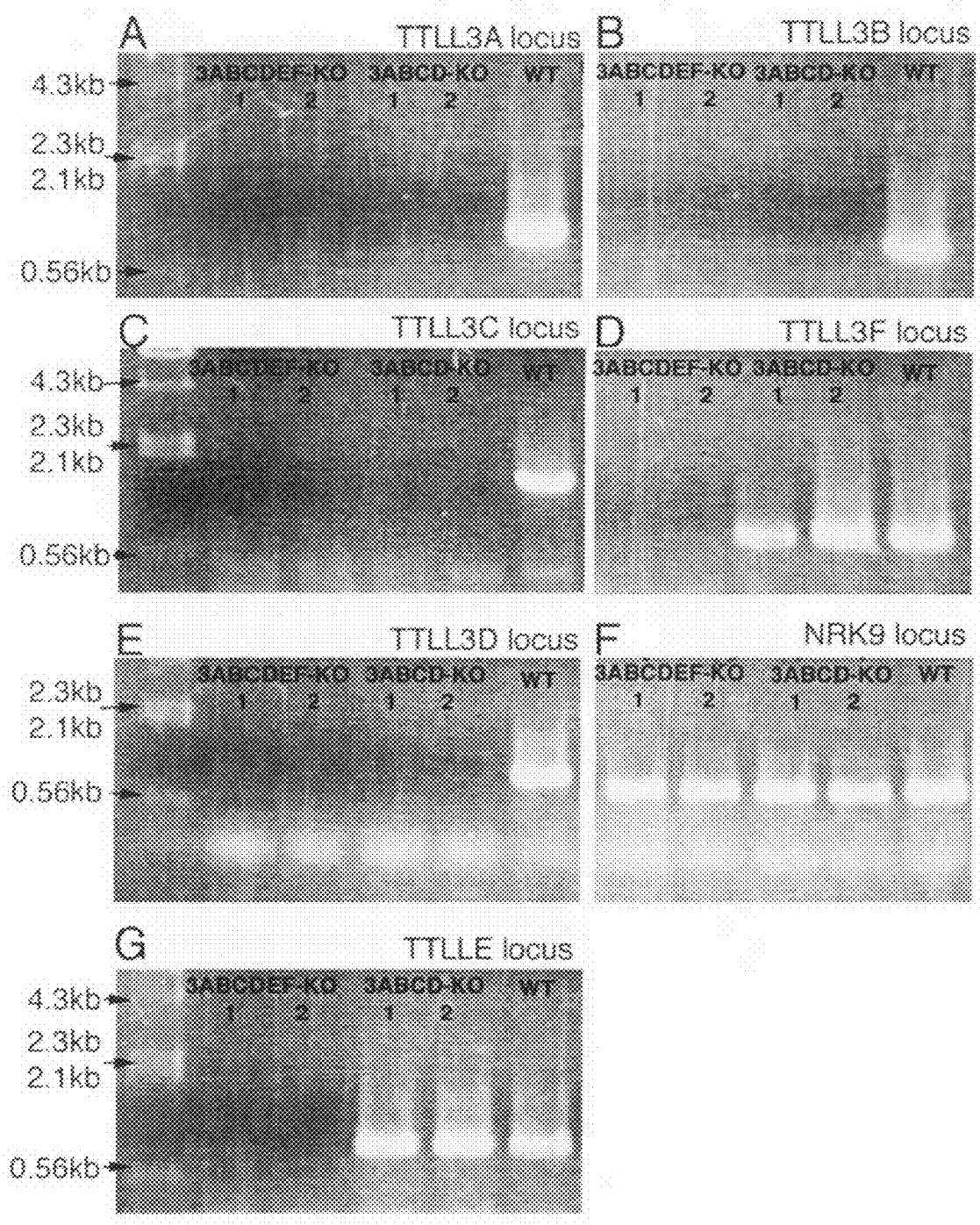

FIG. 44 shows a PCR analysis of quadruple and sextuple knockout cells. To confirm deletion of part of the TTLL3 genes in each locus, wild type, quadruple and sextuple knockout cells were analyzed by PCR with primers that amplify junctions between the targeted regions and non-targeted flanking sequences. The absence of the product indicates that a specific region has been entirely deleted in the tested strain. (A) TTLL3A locus, (B) TTLL3B locus, (C) TTLL3C locus, (D) TTLL3F locus, (E) TTLL3D locus, (F) positive control for PCR amplification of a non-targeted NRK9 locus, (G) TTLL3E locus.

Figure 45:
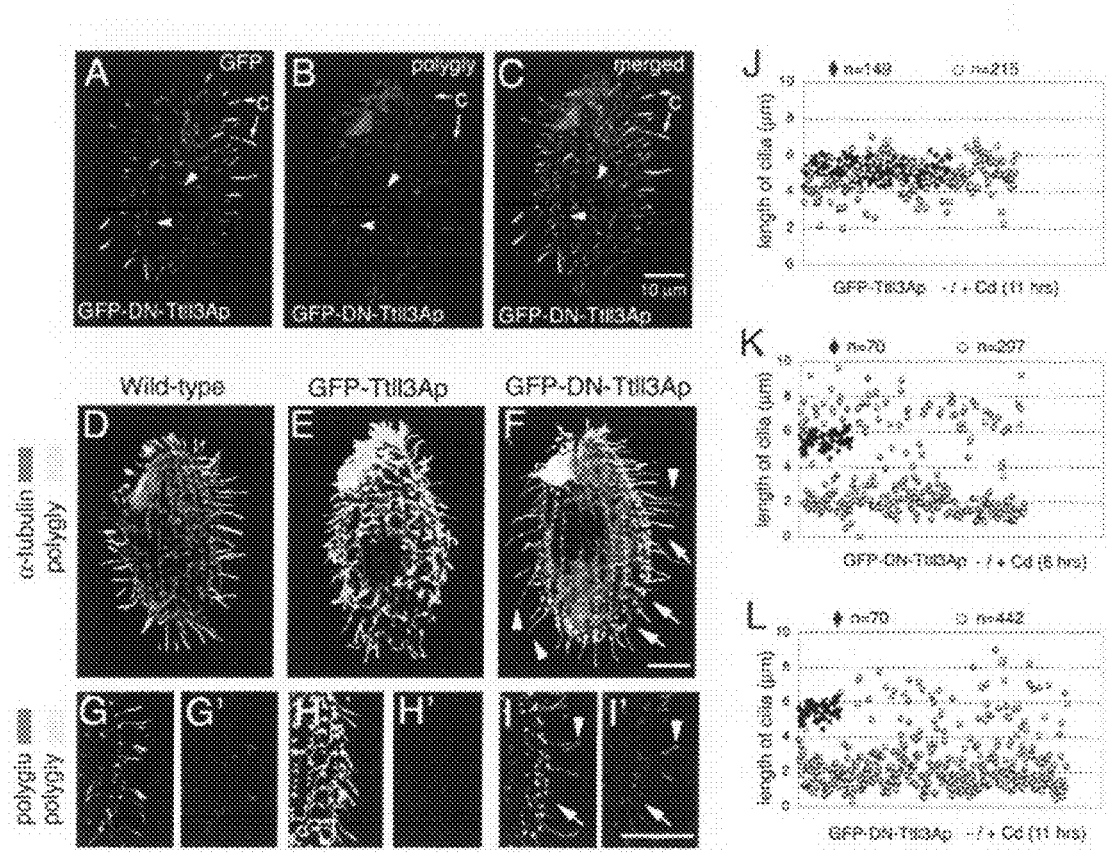

FIG. 45 shows expression of a dominant-negative TTLL3 affects ciliary length. FIG. 45A-C shows cells expressing GFP-DN-Ttll3Ap induced with 2.5 mg/ml $CdCl_2$ for 6 hr. The GFP fluorescence is shown in (A), AXO49 immunofluorescence in (B), and a merged image in (C). GFPDN-Ttlll3Ap is enriched in short, newly formed cilia (arrowheads) and in the distal segments of long preexisting cilia (arrows). FIG. 45D-F shows WT (D), GFP-Ttll3Ap-(E), and GFP-DNTfi13Ap (F)-overexpressing cells were labeled with 12G10 anti-α-tubulin and polyG antibodies. Arrows point at short, new cilia, while arrowheads mark long, pre-existing cilia. FIG. 45G-I' shows WT (G and G') and either GFP-Ttll3Ap- (H and H') or GFP-DN-Ttll3Ap (I and I')-overproducing cells were double labeled with ID5 anti-polyglutamylated tubulin and polyG antibodies. Note that short cilia and distal segments of elongated cilia in GFP-DN-Ttll3Ap cells are hypoglycylated and hyperglutamylated. Scale bar, 10 µm. FIG. 45J-L) Graphs representing the distribution of axoneme lengths in cells overexpressing either GFP-Ttll3Ap (J) or GFP-DN-Ttll3Ap (K and L) that were uninduced (black diamonds) or induced with $CdCl_2$ (white circles) for 6 (K) or 11 hr (J and L). Each data point represents a single measured axoneme.

Figure 46:
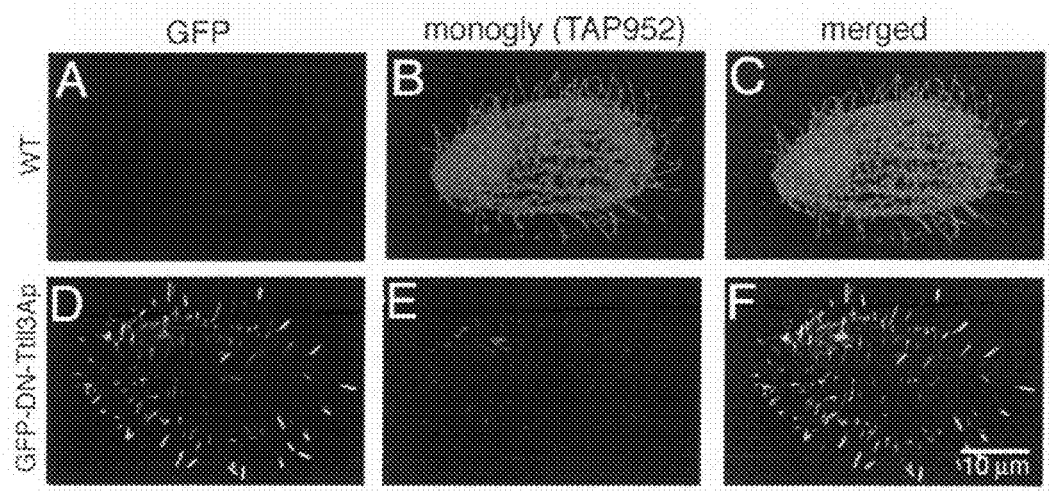

FIG. 46 shows overproduction of GFP-DN-Ttll3Ap reduces tubulin glycylation. Wild-type (A-C and G-I) and GFP-DN-Ttll3Ap (D-F) cells were induced with 2.5 µg/ml $CdCl_2$ for 6 hr and imaged at the same gain. Images of GFP or background (A and D), monoglycylation (B and E) and merged signals (C and F) are shown. The GFP-DN-Ttll3Ap cells have lower levels of tubulin monoglycylation and polyglycylation even without transgene induction probably due to leaky expression of the MTT1 promoter. In addition, after the transgene induction, the signal of monoglycylation is nearly non-detectable in locations that accumulate DN-Ttll3Ap (D-F). Bar, 10 µm.

Figure 47:
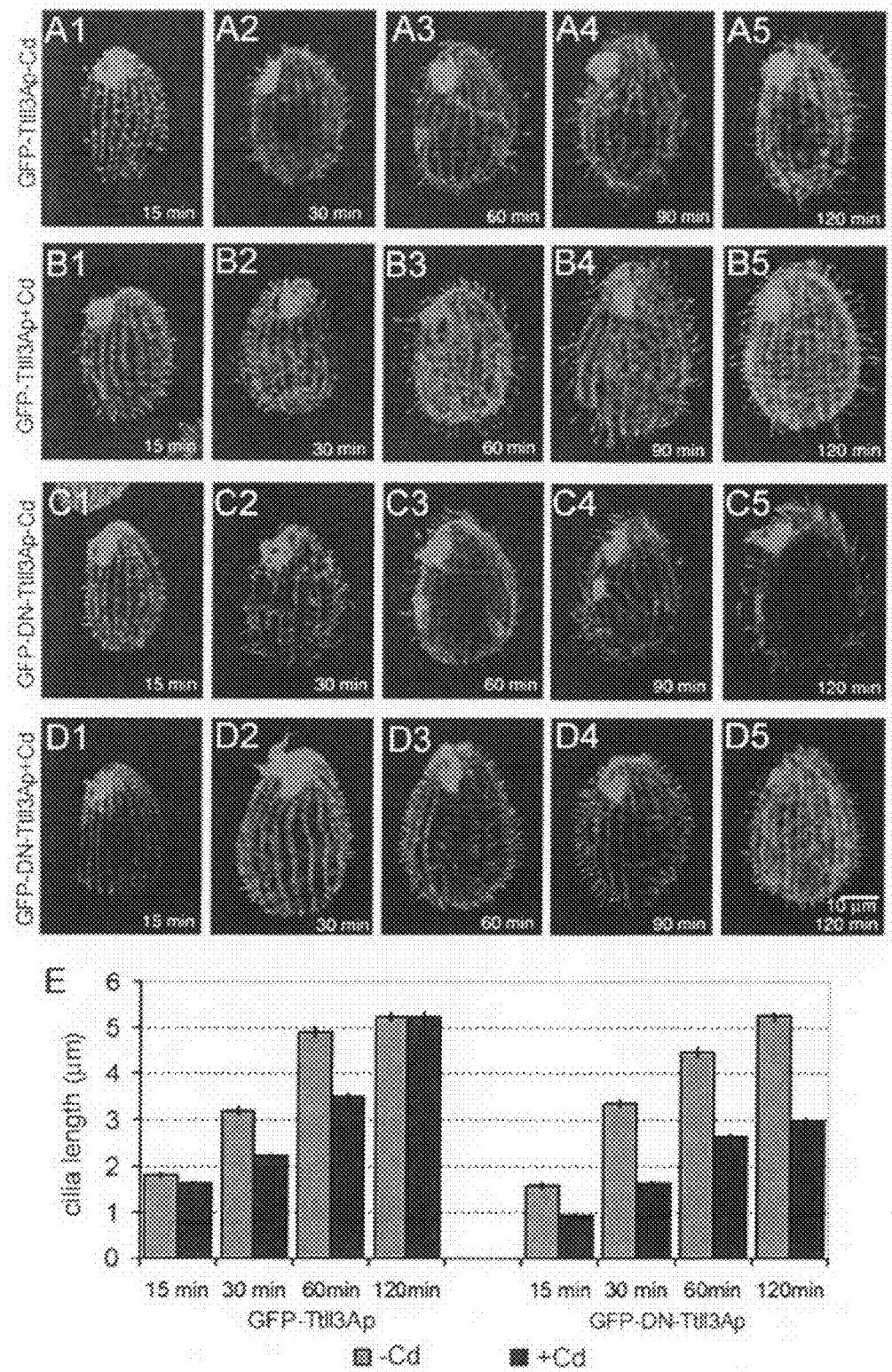

FIG. 47 shows overproduction of GFP-DN-Ttll3Ap inhibits elongation of axonemes during cilia regeneration. Uninduced (A1-A5 and C1-C5) and induced (4.5 hr, 2 µg/ml $CdCl_2$) cells (B1-B5 and D1-D5) expressing either GFP-Ttll3Ap (A1-B5) or GFP-DN-Ttll3Ap (C1-D5), were deciliated, allowed to regenerate cilia in SPP medium (A1-A5 and C1-C5) or SPP with 2.5 µg/ml $CdCl_2$ (B1-B5 and D1-D5) and analyzed by immunofluorescence using 12G10 and SG anti-tubulin antibodies within the following 15-120 min. Bar, 10 µm. E. Graphs that document the length of cilia in regenerating cells. Note that induction of DN-Ttll3Ap and not Ttll3Ap inhibits elongation of cilia.

Figure 48:
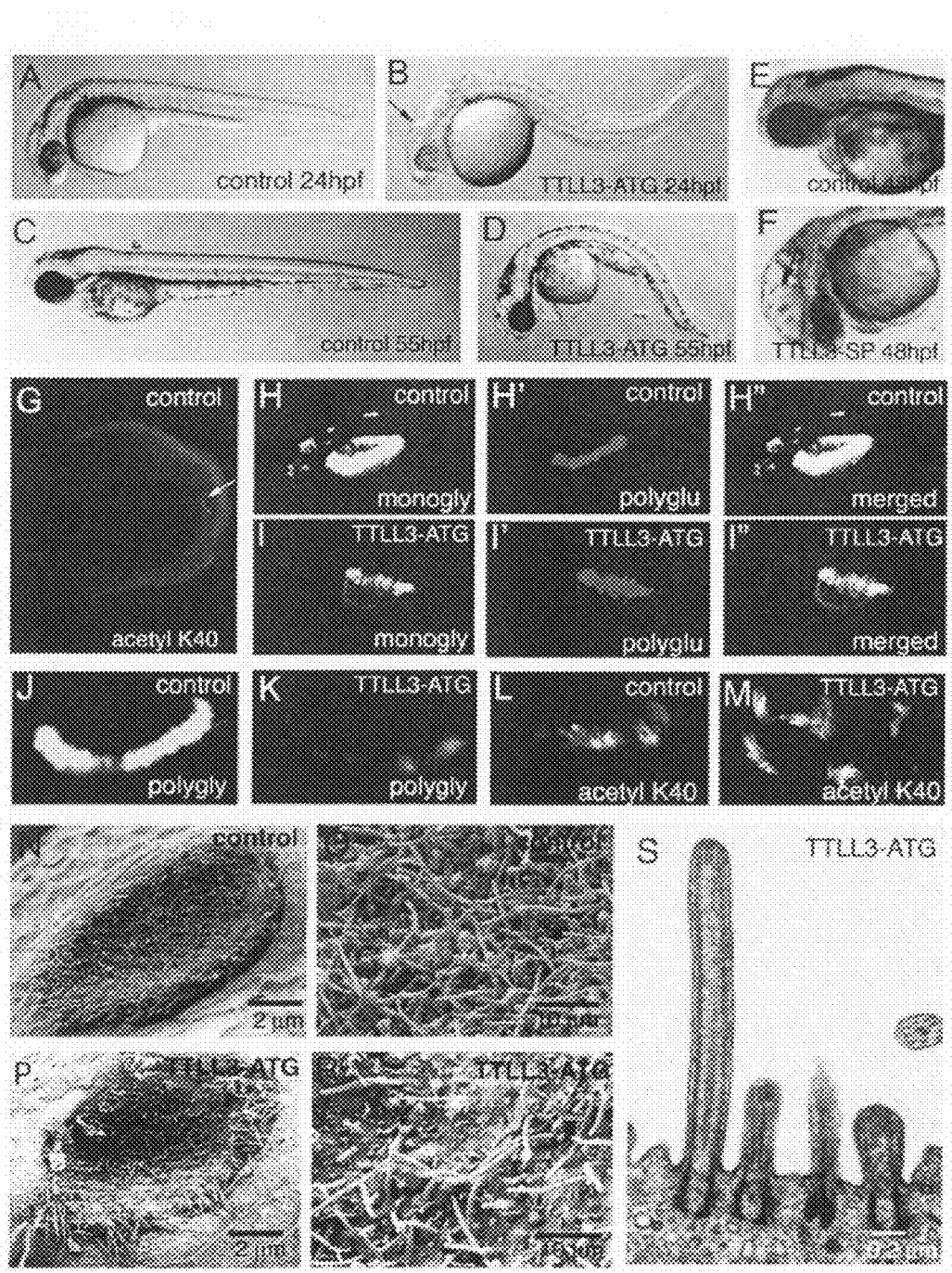

FIG. 48 shows TTLL3 is required for tubulin glycylation and cilia assembly in zebrafish. FIG. 48A-F shows images of live control and morphant embryos at 24 (A and B), 48 (E and F), and 55 hpf. FIGS. 48C and D shows hydrocephaly is apparent in TTLL3-ATG morphant embryos, as indicated by the enlarged vesicles in the hindbrain (B and F, arrows). FIG. 48G shows T=the head of a WT embryo stained by 6-11 B1 antibodies at 72 hpf (the olfactory placode is marked with an arrow). FIG. 48H-I" shows in olfactory cilia, TTLL3-ATG MOs reduce the levels of tubulin monoglycylation detected by TAP952 mAb at 72 hpf (compare [H] and [I]), but not the levels of tubulin polyglutamylation revealed by polyE antibodies (H' and I"). FIG. 48J and K shows the olfactory cilia stained with AXO49 anti-polyglycylated tubulin mAb in a control (J) and a TTLL3-ATG morphant (K) at 72 hpf. FIG. 48L and M) Olfactory cilia stained with 6-11 B-1 mAb in a control (L) and a TTLL3-ATG morphant (M) at 72 hpf. FIG. 48N-R shows SEM images of the zebrafish olfactory placode at 72 hpf in control (N and O) and a TTLL3-ATG morphant (P and R); (O) and (R) are higher magnifications of areas of placodes shown in (N) and (P). FIG. 48S shows TEM image of a fragment of the olfactory placode in the TTLL3-ATG embryo.

Figure 49:
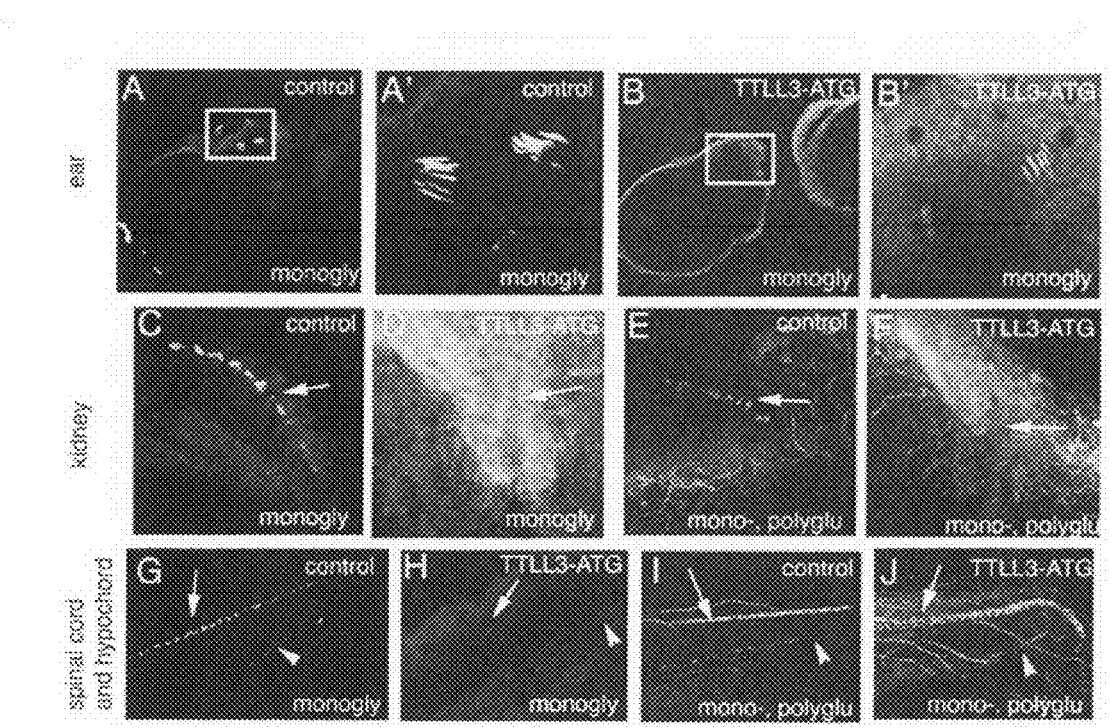

FIG. 49 shows ttll3 MOs reduce tubulin monoglycylation in zebrafish cilia. FIG. 49A-B' shows ear in a control (A and A') and a morphant fish (B and B') labeled with TAP952 mAb. (A') and (B') show higher magnifications (5×) of areas boxed in (A) and (B). FIG. 49C-F shows the pronephric duct area in control (C and E) and morphant fish (D and F) labeled with TAP952 anti-monoglycylated tubulin mAb (C and D) and GT335 anti-glutamylated tubulin mAb (E and F). Note lack of cilia staining in morphants in corresponding area (all indicated by arrows). FIG. 49G-J shows the spinal cord and hypochord area in control (G and I) and morphant fish (H and J) labeled with TAP952 (G and H) and GT335 mAb (I and J). Arrows indicate cilia in spinal cord, while arrowheads point to cilia in hypochord in control embryos (G and I). Note lack of cilia staining in morphants in corresponding regions, as indicated by arrows and arrowheads (H and J).

Figure 50:
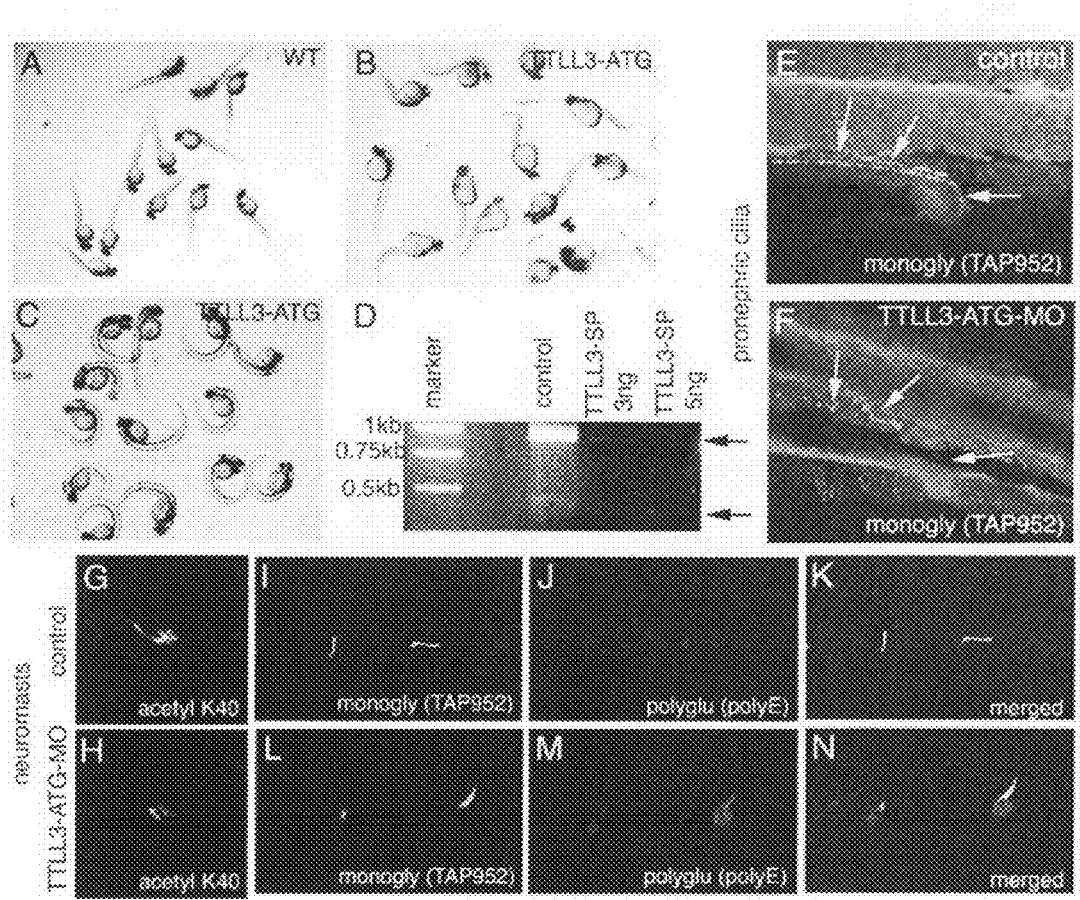

FIG. 50A-C shows a knockdown of TTLL3 expression in zebrafish changes fish morphology and affects cilia in multiple organs. Morphology of control embryos (A) and TTLL3-ATG morphants (B-C) at 48 hpf that were released manually from the chorion after 24 hpf (B) or at 72 hpf released manually from the chorion after 48 hpf (C). FIG. 50D shows results of an RT-PCR assay for TTLL3 mRNA using total RNA from control and morphants injected with 3 or 5 ng of TTLL3-SP MO. FIGS. 50E and F shows depletion of TTLL3 reduces the TAP952 signal of tubulin monoglycylation in pronephron cilia; a control embryo (E) and a TTLL3-ATG morphant (F). FIG. 50G-N shows TTLL3 depletion shortens cilia and reduces the TAP952-positive tubulin monoglycylation. G and H are images of neuromasts stained with 6-11 B-1 anti-acetylated α-tubulin antibodies in control (G) and a TTLL3-ATG morphant (H). FIG. 50I-N shows double labeling of control embryos (I-K) and TTLL3-ATG morphants (L-N) with TAP952 (I and L) and polyE anti-polyglutamylation antibodies (J and M) and merged images (K and N). Note a decrease in the level of tubulin monoglycylation and increase in the level of tubulin polyglutamylation in morphants.

Figure 51:
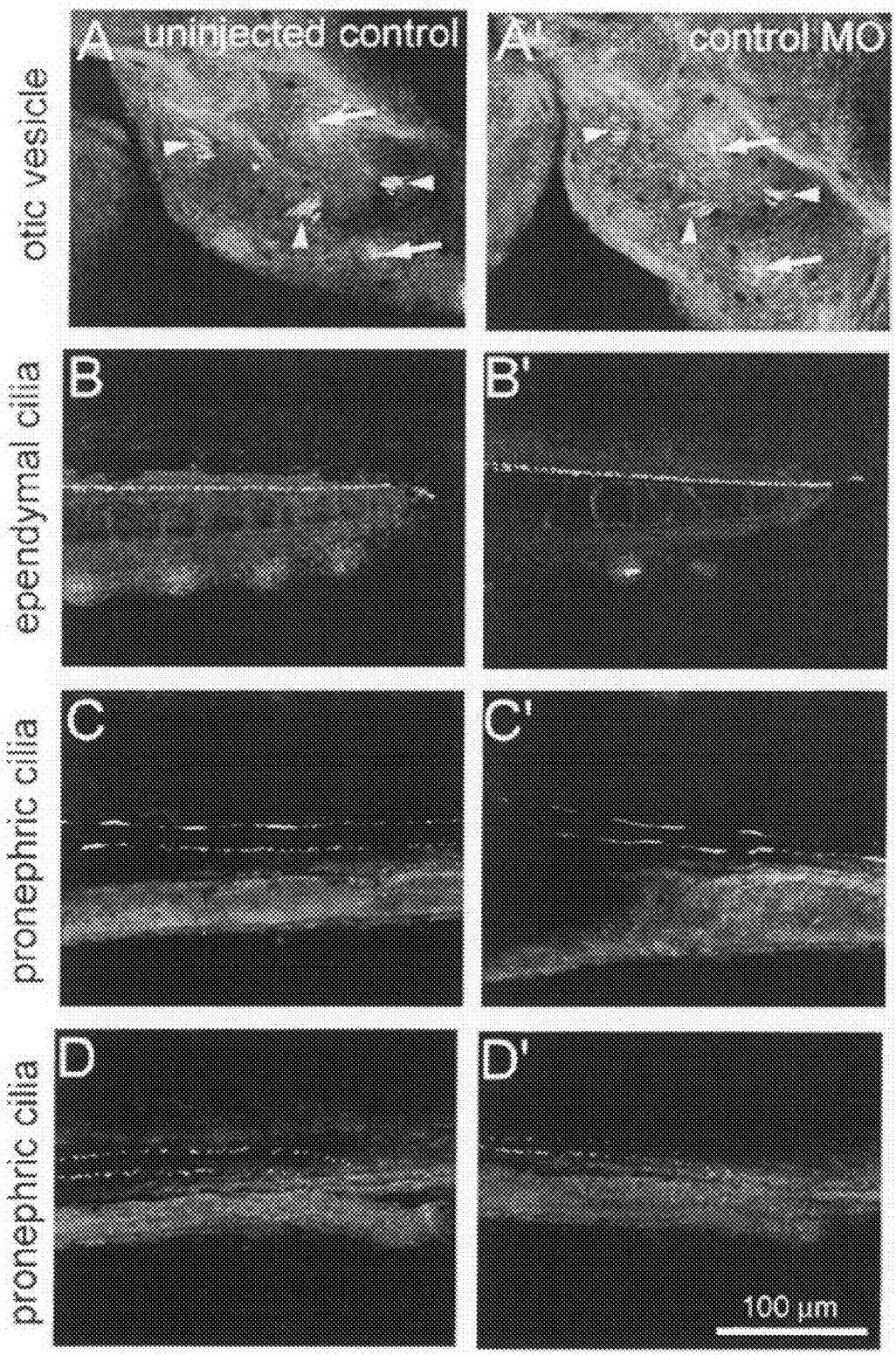

FIG. 51 shows injection of random sequence morpholinos into zebrafish embryos does not affect the levels of monoglycylation detected by TAP952. Uninjected embryos (A-D) and embryos injected with 1 ng of random sequence morpholinos (A'-D'), were fixed at 72 hpf, stained with TAP952 antibodies and the levels of tubulin monoglycylation were analyzed by immunofluoresce in cilia in the otic vesicle (arrowheads) and neuromasts (arrows) (A-A'), spinal cord (B-B') and in middle (C-C') and distal (D-D') part of the pronephric duct. Scale 100 μm.

Figure 52:
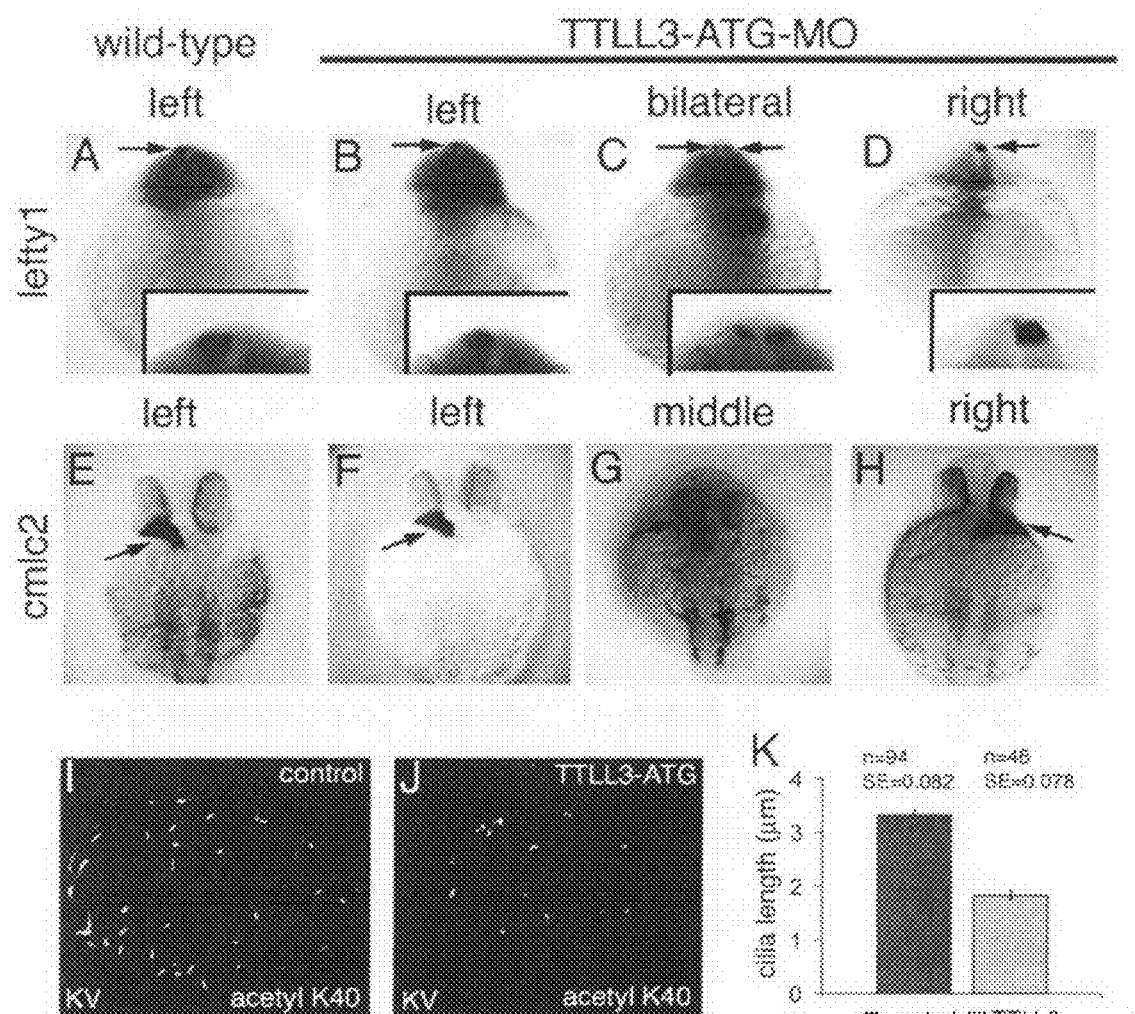

FIG. 52 shows depletion of ttll3 expression produces defects in the LR asymmetry in zebrafish. Ventral views of 22 hpf embryos stained for expression of lefty1 (A-D), or 33 hpf embryos stained for expression of cmlc2 (E-H). Insets in (A)-(D) depict 43 magnifications of the heads of embryos. In all cases, the left side of the embryo is to the left of the panel. lefty1 is normally expressed on the left side of the epiphysis (A). ttll3 morphant embryos express lefty1 on the left body side (B), or display bilateral (C) or right-sided expression (D). Arrows mark the epiphysis. In untreated embryos, cmlc2 (E) is expressed in the myocardium, which is normally located in the left lateral plate. The position of the heart field is unaltered in some TTLL3 morphants (F). Other morphants display midline (G) or right-side expression (H). Arrows in E-H mark the heart field. (I and J) Cilia in KV stained with 6-11 B-1 anti-acetylated K40 α-tubulin mAb in a control (I) and a TTLL3-ATG morphant (J) at 8-10 somite stage at 14 hpf. (K) A graph represents the average length of cilia in KV in control (n=3) and TTLL3-ATG morphants (n=3). Data are presented as means±SEM.

Figure 53:
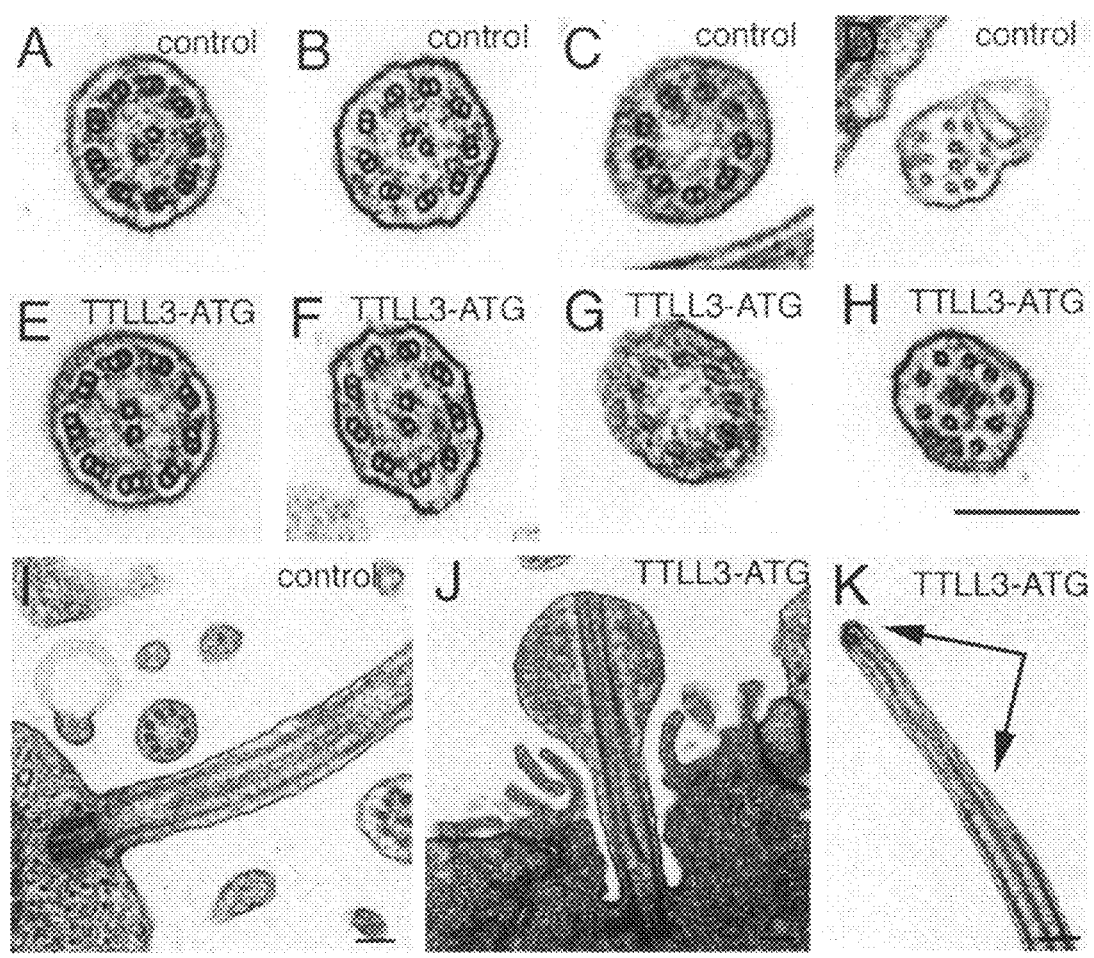

FIG. 53 shows TEM study of cilia in the olfactory placode in a control (A-D, I) and in a morphant (E-H, J-K). Note that in a control placode, there are axoneme cross-sections that have both inner and outer (A) or only inner (B) dynein arms and some cross-sections lack the central pair (C). The distal ends of control cilia were contain the A-subfiber extensions (D). Ultrastructure of the remaining few morphant cilia was normal except that longitudinal sections show that some cilia have swollen tips (J).

DETAILED DESCRIPTION OF ILLUSTRATIVE EMBODIMENTS

The present invention is directed to a new group of enzymes which regulate the assembly and dynamics of microtubules, called tubulin ligases. Two types of tubulin PTMs, known as polymodifications are glutamylation and glycylation. Glutamylation and glycylation are the addition and/or elongation of peptide branches made of either glutamyl or glycyl residues, respectively, that are attached to tubulin. The enzymes responsible for post-translational glutamylation, in which a side branch of one or more glutamic acid is added to the tubulin protein, are tubulin glutamylases, also known as and referred to herein as tubulin glutamic acid ligases or "E-ligases," wherein the "E" refers to the amino acid abbreviation for glutamic acid. The enzymes responsible for post-translational glycylation, in which a side branch of one or more glycine is added to the tubulin protein, are tubulin glycine ligases, also known as and referred to herein as tubulin glycylases or "G-ligases," wherein the "G" refers to the amino acid abbreviation for glycine. The invention is further directed to cells having reduced levels of polymodification as well as methods of using said cells.

In the following examples, overproduction of one of these enzymes in *Tetrahymena*, Ttll6Ap, using MTT1 promoter is shown to lead to cell multiplication arrest of transgenic *Tetrahymena*. Advantageously, the lethal condition brought about by overproduction of the enzyme can be used to screen for novel compounds which inhibit the enzyme, based on a rescue of the lethal phenotype associated with overproduction. Thus, the invention includes screening methods to identify inhibitors of a tubulin glutamylase, as well as compounds identified using the screening method and methods of using them.

*Tetrahymena* as a Model System

*Tetrahymena* is a free-living ciliate and a model eukaryote with a sequenced genome. *Tetrahymena* has been used in research that led to some key achievements, including the Nobel award winning discovery of self-splicing RNA, and identification of telomeres and telomerase, histone acetyltransferase, dynein, and siRNAs that guide DNA rearrangement (Turkewitz et al. (2002) Trends in Genetics 18, 35-40). The *Tetrahymena* system is well equipped for reverse genetics (by homologous DNA recombination), and biochemical studies (Collins et al. (2005) Curr Biol 15, R317-318).

*Tetrahymena* assembles a diverse set of microtubules including those forming the cell body networks, cilia, centriole-like basal bodies, and the mitotic spindle. Due to the importance of their diverse microtubules, ciliates are sensitive to perturbations in microtubule-dependent functions which result in characteristic (potentially screenable) phenotypes (Janke et al. (2005) Science 308, 1758-1762 (see Example I), Thazhath, et al. (2002) Nature Cell Biol. 4, 256-259, Fujiu et al. (2000) Cell Motil Cytoskeleton 46, 17-27).

*Tetrahymena* posttranslationally modifies its microtubules, using highly conserved post-translational modifications, including extensive glutamylation of microtubules in the basal bodies and cilia (Gaertig (2000) Microbiol. 47, 185-190). *Tetrahymena* has been in use as a model to dissect the function of post-translational modifications. The use of *Tetrahymena* led to the first report a mutant phenotype caused by lack of specific sites of post-translational modifications on tubulins (Thazhath et al. (2002) Nature Cell Biol. 4, 256-259), and the discovery of the first post-translational modification forward enzyme (Janke et al. (2005) Science 308, 1758-1762 (see Example I)).

*Tetrahymena* is attractive for high throuphput manipulations due to its: 1) rapid growth (generation time of 3 hrs), 2) low cost of culture, 3) nearly transparent culture medium, 4) ability to grow on defined medium without animal products (lowers the cost of culture and reduced the strigency of required biosafety procedures, 5) lack of pathogenicity, 6) routine culture on 96-well plates, 7) growth to high density in microdrops (compatibility with 384-1536 well plates), 8) lack of autofluorescence (no cell wall or plastids), 9) rapid cell motility (promotes mixing of assay components), 10) sensitivity to established inhibitors (e.g. cycloheximide, paclitaxel) within the concentration range similar to animal cells, 11) methods for introduction of transgenes and protein tagging, 12) targeted mutation approaches that allow for exploration of loss-of-function phenotypes, 13) inducible-repressible promoters that allow for generation of gain-of-function phenotypes, 14) large cell size—highly amenable for HT cytological profiling at low microscopic magnification, 15) advanced cellular functions shared with animal cells including sophisticated microtubule-based organelles, regulated secretion, nuclear apoptosis, DNA rearrangements, phagocytosis, and chemotactic cell motility.

Tubulin Ligases

Microtubules are filamentous structures that have a variety of important functions in living cells, e.g. in cell division, nerve cell differentiation or transport inside the cells. Microtubular networks are involved in a variety of important functions in living cells, e.g. in cell division, nerve cell differentiation or transport inside the cells. In most proliferating mammalian cells, interphase microtubules are glutamylated at a very low level, and only during mitosis.

How microtubule-associated motor proteins are regulated is not well understood. A potential mechanism for spatial regulation of motor proteins is provided by post-translational modifications of tubulin subunits that form patterns on microtubules. Microtubules are dynamic elements of the cytoskeleton that are assembled from heterodimers of α- and β-tubulin. Once assembled, tubulin subunits undergo several conserved posttranslational modifications (PTMs) that diversify the external and luminal surfaces of microtubules (Verhey and Gaertig. 2007. Cell Cycle 6:2152-2160). Two types of polymeric posttranslational modifications of α/β-tubulin occur widely in cilia and flagella. These two PTMs will be referred as "polymodifications." Polymodifications generate peptide branches of variable lengths that are attached to several acceptor sites in the C-terminal tails of α- and β-tubulin (Redeker et al., (1998) Biochemistry 37, 14838-14844; Schneider et al., (1998) FEBS Lett. 429, 399-402; Vinh et al., (1999) Biochemistry 38, 3133-3139). These modifications, conserved throughout evolution, are thought to act individually or in combination to control specific microtubule-based functions. However, their cellular functions are poorly understood. Polymodifications substantially increase the heterogeneity of the α/β-tubulin heterodimer. These tubulin polymodifications, referred to as glutamylation and glycylation, correspond to the addition of a peptide polymer consisting of several glutamates (Eddé et al., (1990) Science 247, 83-85) or glycines (Redeker et al., (1994) Science 266, 1688-1691) onto the γ-carboxyl group of a glutamate of the primary sequence of tubulin. The C-terminal tail domains of tubulin are also the major binding sites of many microtubule-associated proteins (MAPs) and MT-based molecular motors (kinesins and dyneins). It is thus highly probable that both modifications regulate the interactions between microtubules and their partners.

It appears that microtubule populations can be distinguished between different cell types as well as inside a single cell by specific polymodification patterns. The flexible parameters that could specify those patterns on microtubules are (i) the density of the modification (fraction of modified tubulins within a microtubule), (ii) the choice of the tubulin subunit (α- or β-tubulin), (iii) the length of the side chains and (iv) the modification sites occupied on the tubulin molecule.

In ciliates, both polymodification types are not only present in cilia and basal bodies (Péchart et al., (1999) Biol. Cell 91, 685-697; Adoutte et al., (1991) Biol. Cell 71, 227-245; Bré et al., (1994) Cell Motil. Cytoskeleton 27, 337-49; Iftode et al., (2000) Biol. Cell 92, 615-628), but also occur on the more dynamic intracytoplasmic microtubules (Bré et al., (1994) Cell Motil. Cytoskeleton 27, 337-49; Fleury et al., (1995) Protoplasma 189, 37-60; Bré et al., (1998) Mol. Biol. Cell 9, 2655-2665). α- and β-tubulins of ciliates are biochemically heterogeneous (Bré et al., (1994) Cell Motil. Cytoskeleton 27, 337-49; Bré et al., (1998) Mol. Biol. Cell 9, 2655-2665; Suprenant et al., (1985) Proc. Natl. Acad. Sci. USA 82, 6908-6912), suggesting that structural differences among tubulin isoforms are important in generating functionally distinct types of microtubules in a single cell. However, genetic and biochemical studies showed that in ciliates only one or two gene isotypes of α- and β-tubulin form the bulk of microtubules (Redeker et al., (1994) Science 266, 1688-1691; Dupuis, (1992) EMBO J. 11, 3713-3719; Gaertig et al., (1993) Cell Motil. Cytoskeleton 25, 243-53; McGrath et al., (1994) Cell Motil. Cytoskeleton 27, 272-283; Dupuis-Williams et al., (1996) Biol. Cell 87, 83-93). Therefore, the large number of tubulin isoforms present in ciliates is mainly the result of PTMs (see Refs. 6, 29). Thus, ciliates provide a favorable model for assessing the function of PTMs.

The modifying enzymes, tubulin glutamic acid ligases (tubulin E-ligases) and tubulin glycine ligases (tubulin G-ligases), belong to the family of proteins related to the tubulin tyrosine ligase (TTL), known as TTL-like (TTLL) proteins (Janke et al., 2005. Science 308:1758-1762; van Dijk et al., 2007. Mol. Cell 26:437-448; Wloga et al., 2008. Eukaryot. Cell 7:1362-1372). Tubulin ligases may be either chain initiating ligases or chain elongation ligases.

Figure 8:
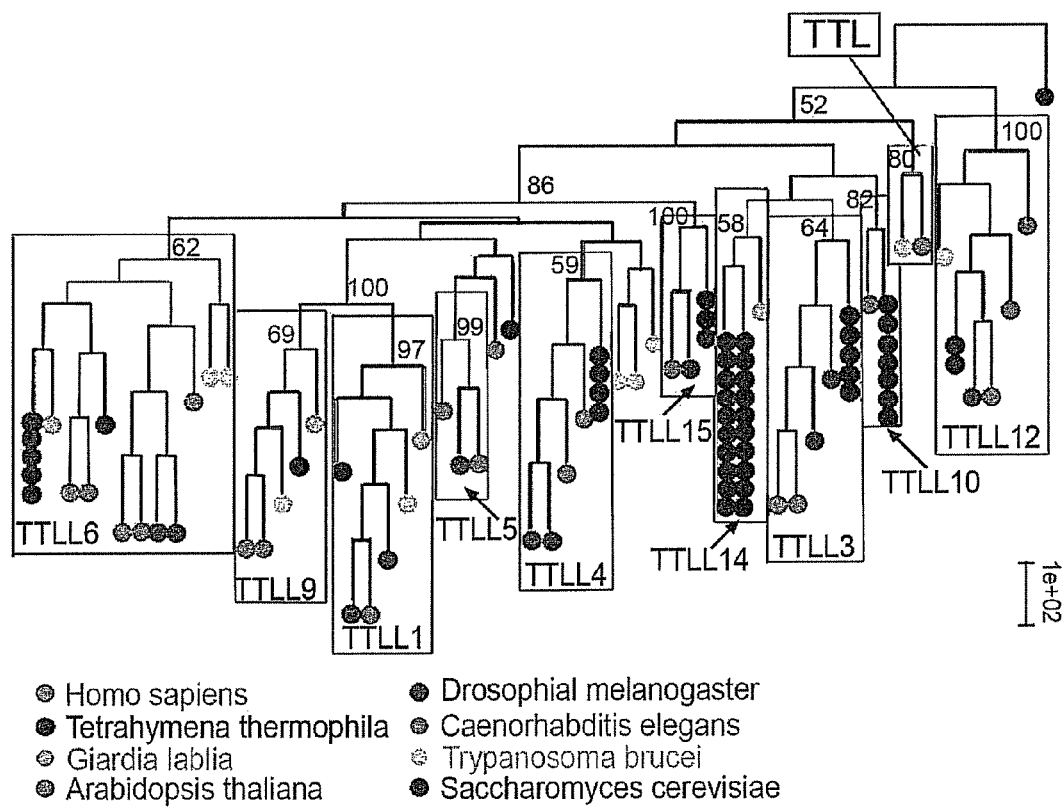
FIG. 8 shows an evolutionary tree of TTL domain proteins, based on the Neighbor-Joining method. Numbers correspond to bootstrap values for 100 repeats. Dots represent predicted TTL domain sequences in several genomes analyzed. The grey lines denote clades discussed in the paper. The yeast sequence was used as an outgroup. See FIGS. 12 and 13 for complete data.

The TTL-like proteins (TTLLs) are members of a large family of conserved eukaryotic proteins that are likely involved in PTMs such as polymodifications. Phylogenetic analyses showed that TTLLs of diverse eukaryotes belong to several conserved subtypes (example I, FIGS. 8, 12 and 13). In *Tetrahymena*, the TTLL family has over 50 genes, including a number paralogs (genes related by duplication within a genome that may evolve new functions, even if these are related to the original one). The unusually large number of TTLL genes in *Tetrahymena* and the lack of a detectable loss of function phenotype for TTLL1 (example I) suggests functional redundancy. The phylogenetic association of TTLL1, TTLL9, TTLL4, TTLL6, TTLL5 and TTLL15 protein types (86% bootstrap value; FIG. 8) suggests that these protein types are all involved in glutamylation of tubulin or possibly other proteins such as NAPs (Regnard et al., *J Biol Chem* 275, 15969 (2000)). The phylogenetic association of TTLL3, TTLL10, and TTLL14 suggests that these protein types are all involved in glycylation of tubulin or possibly other MAPs or NAPs.

Studies on several glutamic acid ligases indicate that tubulin glutamylation is important for assembly of axonemes. Hyperelongation of glutamyl side chains stabilizes cell body and destabilizes axonemal microtubules in the same cell (example IV). Further, deletion of two paralogs of a tubulin E-ligase caused severe deficiency in ciliary motility and increased the velocity of microtubule sliding in axonemes (example V).

The role of tubulin glycylation remains unknown, mainly because the modifying enzymes are yet to be discovered. In vivo, glutamic acid and glycine ligases oppose each other. Reduction in tubulin glycylation led to hyperglutamylation, likely by competing for shared modification sites on tubulin (example VII). Thus, it is likely that tubulin glycylation regulates the assembly and dynamics of axonemal microtubules and acts either directly or indirectly by inhibiting tubulin glutamylation. Thus, glycylation likely acts by competing with glutamylation for shared modification sites on tubulin.

Tubulin glutamic Acid Ligases

Until now the enzymes which deposit post-translational modifications on microtubules remained unidentified due to, among other things, difficulties in their purification. As a result of synergistic research that explored advantages of the mouse model (in collaboration with Dr. Bernard Eddé and Carsten Janke at CRBM, Montpelier, France) and *Tetrahymena*, our laboratories identified a family of glutamylases differing in substrate preferences (α-tubulin vs. β-tubulin) (Janke et al. (2005) Science 308, 1758-1762 (see Example I)).

The catalytic subunit of the major neural glutamylase is the product of the TTLL1 gene that encodes a protein with a tubulin-tyrosine ligase (TTL)-like domain. TTL is a well known reverse enzyme for another post-translational modification, tubulin detyrosination (Ersfeld et al. (1993) J. Cell Biol. 120, 725-732). TTLL1 and TTL belong to a larger family of conserved proteins with a common catalytic domain. We named these proteins "TTL-like" (TTLLs). Phylogenetic analyses identified conserved subtypes of TTLLs, that may all be involved in ligation of specific amino acids to tubulins (Janke et al. (2005) Science 308, 1758-1762 (see Example I)). Members of this novel family are structurally related to other proteins designated as ADP-forming enzymes, that display an ATP hydrolysis-dependent carboxylate-amine ligase activity. TTLL1 type proteins are associated with glutamylase activity on α-tubulin. TTLL1-mediated glutamylation is required for neurite extension in the mouse (Janke et al. (2005) Science 308, 1758-1762 (see Example I)). A mutation in the noncatalytic subunit of TTLL1 complex, PGs1, led to disruption of assembly of axonemal microtubules in murine sperm and interestingly, caused reduction in aggressive behavior in males (Campbell et al. (2002) Genetics 162, 307-320). In *Tetrahymena*, a gene knockout of Ttll1p reduced the level of α-tubulin glutamylation, which in turn was associated with slow growth, defects in specific types of microtubules including basal bodies (centriole-like structures that template cilia), and slow ciliary beating (Janke et al. (2005) Science 308, 1758-1762 (see Example I)).

Figure 9:
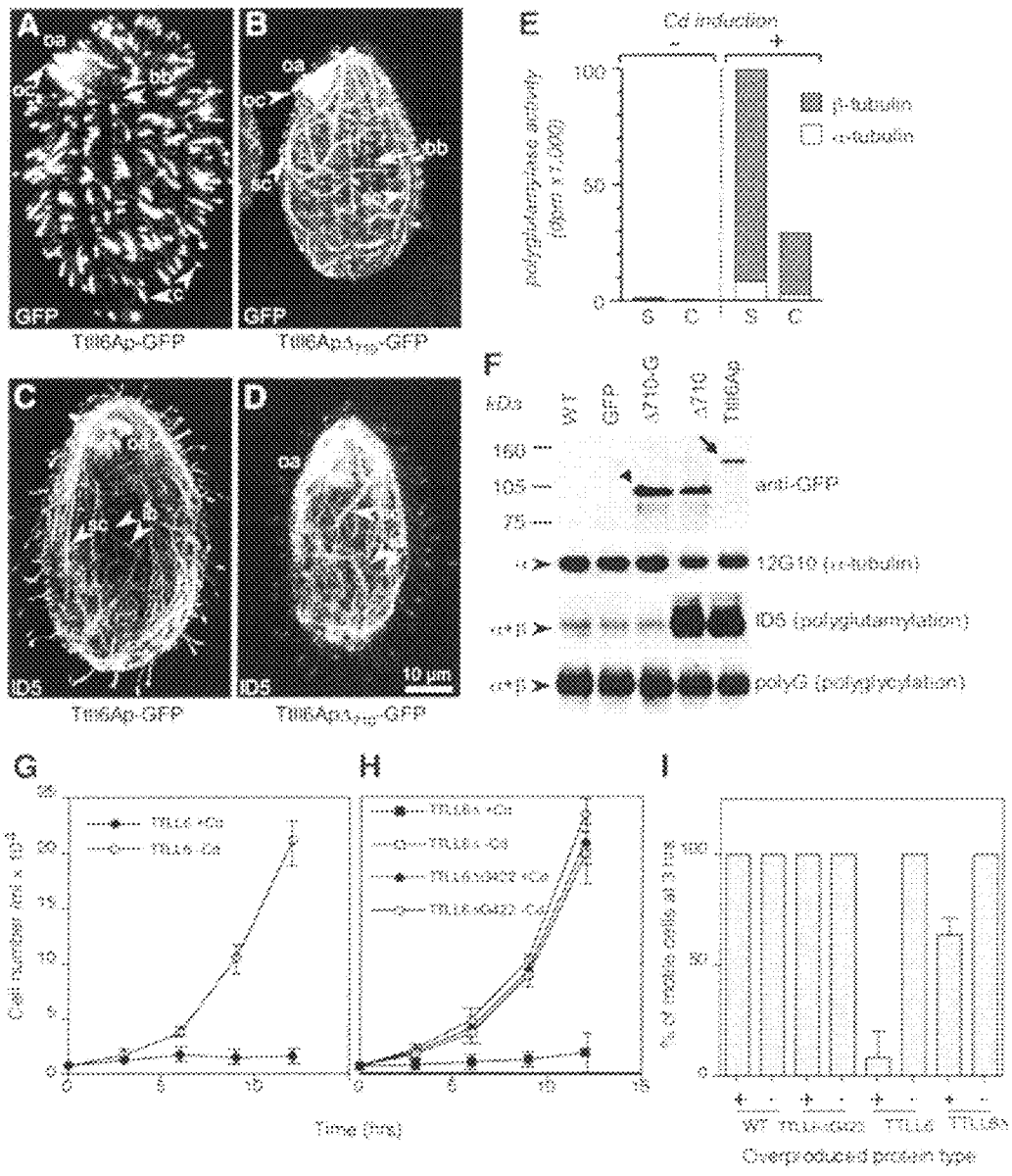
FIG. 9 shows that Ttll6p-GFP is associated with strong tubulin glutamylation in vivo and in vitro. (A-D) GFP fluorescence (A, B) and immunofluorescence images using ID5 anti-glutamylation antibody (C, D) of cells overproducing Ttll6Ap-GFP (A, C) or Ttll6ApΔ$_{710}$-GFP (B, D). The staining detected in A, B co-localized with MTs visualized by anti-α-tubulin antibodies (results not shown). Note appearance of strong glutamylation in the cell body in cells overproducing forms of Ttll6Ap, while glutamylation is restricted to cilia and basal bodies in control cells (compare with the wild type cell shown in FIG. 3C). Abbreviations: c, cilia; oc, oral cilia; oa, oral apparatus; bb, basal bodies; sc, subcortical MTs; ic, intracytoplasmic MTs. (E) Tubulin glutamylase assays using soluble (S) and cytoskeletal (C) fractions from Ttll6ApΔ$_{710}$-GFP cells grown in the absence (−) and presence (+) of cadmium for 3 hrs. (F) Immunoblots of total cells (anti-GFP) or cytoskeletons of the following strains following a 3 hr cadmium treatment: wild type (WT), cells overproducing GFP (GFP), Ttll6ApΔ$_{710}$-E422G-GFP (Δ710-G), Ttll6ApΔ$_{710}$-GFP (Δ710), and Ttll6Ap-GFP (Ttll6p). The antibodies used were: anti-GFP (GFP), anti-α-tubulin (12G10), anti-glutamylation (ID5), anti-polyglycylation (polyG). (G-I) Cells overproducing an enzymatically active Ttll6Ap and not an ATPase-deficient form fail to multiply and undergo ciliary paralysis. Growth curves on SPP medium for strains expressing Ttll6Ap-GFP (G), Ttll6ApΔ$_{710}$-GFP or Ttll6ApΔ$_{710}$-E422G-GFP (H) with or without cadmium induction. Note that only the ATPase-capable proteins reduce the growth rate. (I) The percentage of motile cells in several overproducing strains. After 3 hrs of cadmium induction 100-200 cells were scored for vigorous motility. Either extremely sluggish (showing rotations but no directional movement) or completely paralyzed cells were counted as non-motile. The data shown in all panels represent mean values from three independent experiments.

Another TTLL, TTLL6, was found to be a highly active glutamylase for β-tubulin (Janke et al. (2005) Science 308, 1758-1762 (see Example I)). A TTLL6 type protein of *Tetrahymena*, Ttll6Ap, localizes mainly to cilia. *Tetrahymena* cells overproducing Ttll6Ap-GFP showed a dramatic increase in the level of tubulin glutamylation on cilia and some cell body microtubules (compare FIG. 1, middle and right panels, with FIG. 9C). A reliable in vitro assay for glutamylation that includes tritiated glutamic acid, taxol-stabilized microtubules and ATP is available (Regnard et al. (1998) Biochemistry 37, 8395-8404, Regnard et al. (1999) J. Cell Sci 112, 4281-4289). Remarkably, crude extracts of *Tetrahymena* cells overproducing Ttll6Ap under a cadmium-inducible promoter had 100 times more of activity in vitro (as compared to non-induced cells) (Janke et al. (2005) Science 308, 1758-1762 (see Example I)). Ttll6Ap-GFP with a mutation in the predicted ATP-binding site lacked any detectable glutamylase activity. Thus, Ttll6Ap expresses well in *Tetrahymena* and large quantities of this enzyme can be produced cheaply.

Because there are several expressed paralogs, it has not yet been possible to determine what the loss of function for the Ttll6Ap-type activity is in *Tetrahymena*. A single knockout of TTLL6A gene did not produce a mutant phenotype.

Hyperglutamylation of β-Tubulin by Ttll6Ap Stabilizes Microtubules, Blocks Cells Proliferation and Inhibits Ciliary Motility in *Tetrahymena*.

Figure 1:
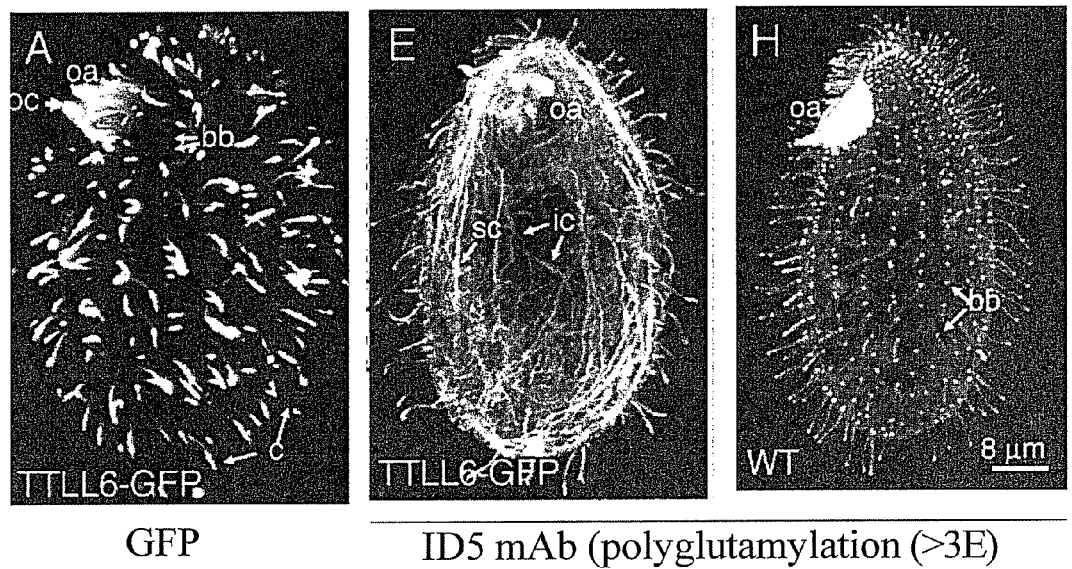
FIG. 1 shows ciliary localization of Ttll6Ap-GFP (left panel, A), immuno-fluorescence with the anti-glutamylation antibody of cells overproducing Ttll6Ap (middle panel, E) and controls (right panel, H). Abbreviations: sc, subcortical MTs; ic, intracytoplasmic MTs; oc, oral cilia; oa, oral apparatus.

A full-length Ttll6Ap localizes primarily to cilia in *Tetrahymena* (FIG. 1, left panel; Example I and FIG. 9A). When the full length Ttll6Ap-GFP was overproduced, cells stopped dividing in a few hours (Example I) and become paralyzed due to lack of ciliary beating (Example I).

Figure 2:
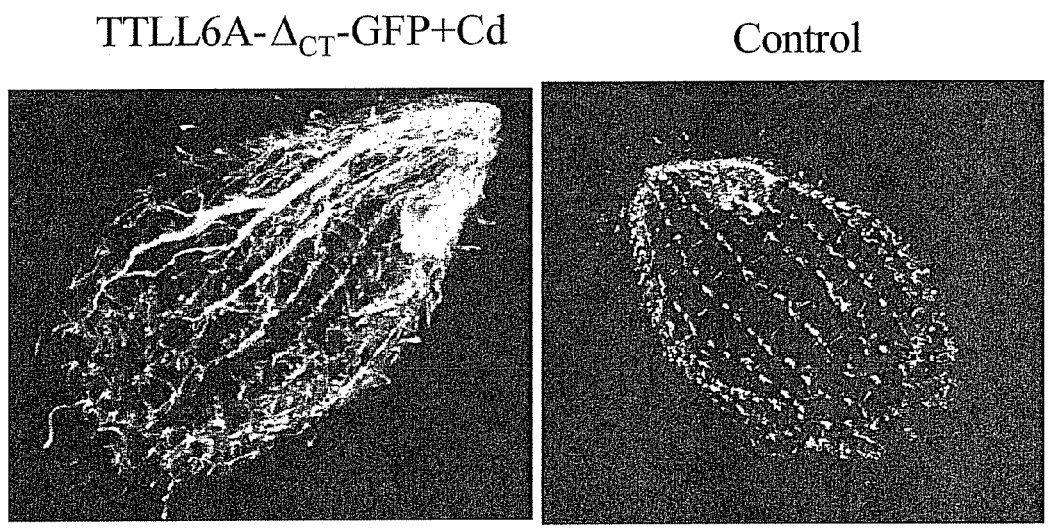
FIG. 2 shows that hyperglutamylation by Ttll6Ap-ΔCT-GFP stabilizes cytoplasmic MTs. Cells overproducing truncated Ttll6Ap-GFP or control cells were treated with 40 μM nocodazole for 30 minutes and labeled by immunofluorescence using anti-α-tubulin antibodies. Note the presence of drug-stable wavy and thick MTs in the cell body of Ttll6Ap-ΔCT cells.

A truncated but enzymatically active form of Ttll6Ap lacking 288 amino acids of its C-terminus (Ttll6Ap-$\Delta_{710}$) failed to localize to cilia and accumulated in the cell body. As Ttll6Ap-Δ710 accumulated on cell body microtubules, their appearance changed dramatically—they acquired extensive glutamylation and become thick and wavy, which indicated that these microtubules were hyperstable. Indeed we found that these microtubules were resistant to nocodazole (FIG. 2).

An inactive (ATPase-dead) variant of the truncated protein (Ttll6Ap-$\Delta_{710}$-G422) accumulated to the same level as the enzymatically active protein, but failed to hyperglutamylate and hyperstabilize cell body microtubules. The ATPase-dead variant did not have any effect on cell growth and motility (Example I). This experiment indicates that the ATP-binding site within the TTL homology domain of the glutamylases is one of the preferred target region for development of specific inhibitors.

The above observations argue that the observed phenotypic effects of active Ttll6tAp are mediated by its glutamylation activity and not by the mere binding to microtubules. Importantly, excessive glutamylation on β-tubulin strongly inhibits cell multiplication and ciliary motility. The biological assay of the invention takes advantage of these effects, because a glutamylase inhibitor will rescue the host organism from a lethal condition, restoring growth and, where a full length glutamylase is used such that it localizes to the cilia, cell motility. Of course, glutamylation on b-tubulin may be required for cell viability. Therefore, the inhibitor would need to be applied in a range of concentrations to find its concentration that titrates out the overproduced enzyme but does not deplete the total activity below the endogenous level. It should be noted that cells overproducing Ttll6Ap-$\Delta_{cT}$ also ceased dividing, but the effect on ciliary motility was relatively mild because this isoform cannot be targeted to cilia (Example I). This is advantageous because the truncated Ttll6Ap variant is especially useful in the cell-based, biological assay to avoid sedimentation of paralyzed cells to the well bottom that could disturb the uniformity of signal strength across the well.

Tubulin Glycine Ligases

An analysis of ciliary tubulin from the protist *Paramecium* led to the discovery of polyglycylation, which consisted of an additional lateral chain of up to 34 glycine units on both axonemal tubulin subunits (Redeker et al., Science. 1994; 266:1688-1691). Since then, studies on polyglycylation, using either mass spectrometry (Rüdiger et al., FEBS Lett. 1995; 364:147-151; Mary et al., J Biol Chem. 1996; 271: 9928-9933; Multigner et al., Biochemistry. 1996; 35:10862-10871; Weber et al., FEBS Lett. 1996; 393:27-30) or two anti-glycylated tubulin monoclonal antibodies (mAbs), TAP 952 and AXO 49 (Bré et al., J Cell Sci. 1996; 109:727-738), have involved principally axonemes of various cell types. mAbs, TAP 952 and AXO 49, serve as complementary tools for detection of mono- and polyglycylated tubulin (Bre et al., 1998 Mol. Biol. Cell 9(9):2655-2665). Taken together, the data suggest that axonemal tubulin could be the preferred substrate for polyglycylation. This would contrast with the broad occurrence of polyglutamylation in both cytoplasmic (Eddé et al., Science. 1990; 247:83-85; Alexander et al., Proc Natl Acad Sci USA. 1991; 88:4685-4689; Redeker et al., FEBS Lett. 1992; 313:185-192; Rüdiger et al., FEBS Lett. 1992; 308:101-105; Wolff et al., Eur J Cell Biol. 1992; 59:425-432; Mary et al., FEBS Lett. 1994; 353:89-94) and axonemal tubulin (Bré et al., Cell Motil Cytoskeleton. 1994; 27:337-349; Fouquet et al., Cell Motil Cytoskeleton. 1994; 27:49-58; Mary et al., J Biol Chem. 1996; 271:9928-9933; Schneider et al., J Cell Sci. 1997; 110:431-437). Therefore, polyglycylation is likely a selective marker of the most stable microtubules.

The role of tubulin glycylation remains largely unknown, mainly because the modifying enzymes are yet to be discovered. TTLL3 proteins act as tubulin glycine ligases with chain-initiating activity. *Tetrahymena* TTLL3 is a tubulin glycine ligase (G-ligase) with a chain-initiating activity. *Tetrahymena* cells lacking all TTLL3 genes have shortened axonemes that are resistant to paclitaxel, indicating that tubulin glycylation changes the lattice properties of axonemal microtubules. Deletion of TTLL3 in zebrafish development by morpholino (MO)-based depletion studies indicate that TTLL3 is required for either elongation or stability of axonemes. In both organisms, a reduction in tubulin glycylation led to hyperglutamylation (example VII). Thus, glycylation could act by competing with glutamylation for shared modification sites on tubulin.

Cells

Cells useful in the method of the invention include but not limited to animal, plant, yeast, protozoan, and bacterial cells. Unicellular eukaryotic cells, such as protozoan cells, are preferred. Even more preferably, the cell of the present invention is a ciliated cell. Examples of ciliated cells include, without limitation, *Tetrahymena, Paramecium, Plasmodium*, and *Chlamydomonas*. An example of a particularly preferred cell for use in the method of the invention is *Tetrahymena*. Also included in the present invention are cellular components, such as axonemes, microtubules or tublin, derived from the cells.

Cells useful in the present invention have been engineered to result in reduced levels of polymodification. Preferred types of polymodification in the present invention include, without limitation, polyglutamylation and polyglycylation.

Preferably, the reduced level of polymodification in the cell of the present invention is a result of the disruption of a tubulin ligase gene (e.g., via a "knockout" of a gene), such that the modification is reduced when compared to a wild type cell (i.e., a cell that does not have a disruption in a tubulin ligase gene). Methods of disrupting or altering levels of polymodification can be effected at any level of gene expression (e.g., DNA replication, transcription, translation, or post-translationally) of a tubulin ligase and are routine and well known in the art. For example, enzymatic function can be inhibited when the enzyme is targeted by a molecular inhibitor, such as an antibody or a small molecule inhibitor. Translation of an RNA message into an enzyme can be disrupted, for example, by introducing a small interfering RNA, a short-hairpin RNA, a morpholino, or a hybridization probe into the cell. Transcription of a gene encoding an enzyme can be disrupted, for example, by targeting the gene with a molecular inhibitor or physically altering the gene to prevent or confound gene replication or transcription. Cells can be engineered through the introduction of polynucleotides, as well as the directed mutagenesis of coding regions. Common gene disruption techniques include mutagenesis, gene deletion or knock-out, and heterologous gene transformation. Such methods are well known in the art; see, e.g., Sambrook et al, *Molecular Cloning: A Laboratory Manual.*, Cold Spring Harbor Laboratory Press (1989), and *Methods for General and Molecular Bacteriology,* (eds. Gerhardt et al.) American Society for Microbiology, chapters 13-14 and 16-18 (1994). Optionally, the cell may have multiple gene disruptions. The multiplicity of disruptions may occur from engineering more than one disruption in a single cell or from engineering the disruptions in separate cells and crossing the cells to obtain progeny harboring multiple disruptions.

A particularly useful cell having reduced levels of polymodification is a cell that has been engineered to "knock out" a gene encoding a tubulin ligase. In one embodiment, at least two paralogs of a tubulin glutamic acid ligase gene are disrupted. Non-limiting examples of tubulin glutamic acid ligase genes are TTLL1, TTLL9, TTLL4, TTLL6, TTLL5 and TTLL15. Preferably, the knocked out tubulin glutamic acid ligase gene is the TTLL6 gene. Preferred cells of the present invention include, without limitation, cells having a disruption of the TTLL6A and F paralogs, such as a TTLL6A/TTLL6F knockout cell (e.g, cell line "6AF-KO" as described in Example V), cells having a disruption of the TTLL6A, B, D, and F paralogs, such as a TTLL6A/TTLL6B/TTLL6D/TTLL6F knockout cell (e.g., cell line "6ABDF-KO" as described in Example VI), or cells having a disruption of the TTLL6A, B, D, E, and F paralogs, such as a TTLL6A/TTLL6B/TTLL6C/TTLL6D/TTLL6E/TTLL6F knockout cell (e.g., cell line "6ABDEF-KO" as described in Example VI).

Deletion of TTLL6A and TTLL6F genes from *Tetrahymena* produces double knockout (KO) cells (termed herein 6AF-KO cells) that have cilia with microtubule axonemes that have greatly shortened side chains. The shortened glutamyl side chains may be, but are not necessarily, as short as a single glutamic acid residue. Axonemes isolated from 6AF-KO cells, as well as microtubule preparations and tubulin preparations derived therefrom, are well-suited for use as substrates for in vitro glutamylation reactions using purified or crude enzymes that have glutamyl side chain elongase activity, such as Ttll6Ap and similar enzymes.

It should be noted that *Tetrahymena* and other organisms have a large number of TTLL genes (~50), including TTLL1, TTLL9, that potentially could encode tubulin glutamic acid ligases and be functionally redundant with TTLL6. It was thus entirely unexpected that the deletion of just the TTLL6A and 6F genes, from among the many TTLL genes present in *Tetrahymena*, would lead such a significant loss of tubulin glutamylation in cilia.

Advantageously, due to its high growth rate and inexpensive methods of culture, *Tetrahymena* with deletions of TTLL6A and 6F is an excellent source of axonemes and other tubulin-containing structures for in vitro assay for tubulin glutamylation at an industrial scale for the purpose of screening for compounds that either enhance or inhibit the reaction. Moreover, the deletion of five TTLL genes simultaneously (TTTL6A, B, D, E and F, to produce a strain termed herein 6ABDEF-KO), was found to produce *Tetrahymena* cells evidencing further reduction in the levels of tubulin polyglutamylation, and thus could provide an even lower background signal in axonemes and other tubulin-containing structures used for in vitro assays.

In another embodiment, the cell of the invention has at least two paralogs of a tubulin glycine ligase gene disrupted. Non-limiting examples of tubulin glycine ligases are TTLL3, TTLL10, and TTLL14. Preferably, the knocked out tubulin glycine ligase gene is a TTLL3 gene. Preferred cells include, without limitation, cells having a disruption of the TTLL3A and B paralogs, such as a TTLL3A/TTLL3B knockout (e.g., cell line "3AB-KO" as described in Example VII), cells having a disruption of the TTLL3A, B, C, and D paralogs, such as a TTLL3A/TTLLL3B/TTLL3C/TTLL3D knockout cell (e.g., cell line "3ABCD-KO" as described in Example VII), or cells having a disruption of the TTLL3A, B, C, D, E, and F paralogs, such a TTLL3A/TTLL3B/TTLL3C/TTLL3D/TTLL3E/TTLL3F knockout cell (e.g., cell line "3ABCDEF-KO" as described in Example VII).

Antibodies that bind to axonemes, microtubules and tubulin isolated from cells of the invention, which have utility as diagnostic reagents and have potential therapeutic uses as well, are also included in the invention.

Antibody-based Screening Assays

The invention further includes screening assays based on anti-glutamylation antibodies, which give an extremely strong signal reflecting Ttll6Ap activity (see Example I; FIG. 9C,D). Examples of antibody-based assays include cytoblot for an in vivo assay, or ELISA-type assay with plates coated with microtubules for in vitro assay.

Assays

The ciliate *Tetrahymena thermophila* has 18 types of diverse microtubules that are all assembled in a single cell. Due to its high growth rate and inexpensive methods of culture, *Tetrahymena* is an excellent model for in vivo assays as well as an ideal source for axonemes, microtubules and tubulin for use in in vitro assays on an industrial scale. The cells and methods of the present invention provide a system in which to perform high-throughput screens of the methods as described below.

The present invention thus includes both in vivo and in vitro methods for identifying compounds that enhance or inhibit a tubulin ligase reaction. In vitro methods advantageously utilize cellular components such as axonemes, microtubules or tubulins, that are isolated from the genetically engineered *Tetrahymena* cells of the invention. The cellular components useful in the in vitro assays are components that are, in a wild-type *Tetrahymena* cell, polymodified with glutamic acid and/or glycine side chains. Also included in the present invention are the enhancers and inhibitors identified using the method of the invention.

A inhibitor or enhancer compound identified by the method of the present invention may be, without limitation, a protein, a peptide, a peptide fragment, an antibody, a small molecule, a nucleic acid, a chemical compound, or any other molecule capable of inhibiting or enhancing the ligase reaction. A compound of identified by the method of the present invention may be a natural or a synthetic compound. Also included in the present invention are compositions including an inhibitor or enhancer molecule identified by the method of the present invention. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration.

In vivo assays may be performed using the cells of the present invention and may include biological assays or molecular assays. For example, a biological assay may involve phenotypic studies. Phenotypic studies typically used to examine microtubules include, but are not limited to, cell growth, cell motility, phagocytosis, and ciliary beat frequency. In one embodiment, an in vivo assay may be used as a primary screen and an in vitro assay may be used as a secondary screen, or vice versa.

In vitro assays may utilize isolated cellular components of the cells of the present invention. An "isolated" component, such as an axoneme, microtubule or tubulin, is one that has been removed from the cell. Preferably, the cellular component is purified, i.e., essentially free from any other cellular products or impurities. In vitro assays may include biological or molecular assays. For example, a molecular assay typically used to examine microtubules may include, without limitation, biochemical studies such as glutamylation assays or glycylation assays and microtubule sliding assays. For example, an in vitro assay with purified enzyme will determine whether the compound directly inhibits or enhances the ligase activity. Further assays, both in vitro and/or in vivo, can be used to determine whether the enzyme is a broad or selective modulator and whether it can act on mammalian ligases. These assays are commonly used in the field and would be known to a skilled artisan.

Assays for detecting glutamylation or glycylation are also well known in the art and are further described in the Examples, below. Glutamylation assays may include, for example, contacting the experimental sample with a suitable substrate, preferably a stabilized microtubule, under conditions that allow for glutamylation, and detecting the level of glutamylation on the substrate. Detection of glutamylation level can be accomplished using any convenient method, for example using antibody detection. Likewise, a glycylation assays may include, for example, contacting the experimental sample with a suitable substrate, preferably a stabilized microtubule, under conditions that allow for glycylation, and detecting the level of glycylation on the substrate. Optionally, the tubulin ligase assay may further include, prior to contacting the sample with the substrate, lysing the cell of the present invention and/or isolating cellular components such as the axonemes, microtubules or tubulin.

Cellular components such as axonemes, microtubules or tubulin, which have been isolated from a *Tetrahymena* cell of the invention that exhibits reduced tubulin polyglutamylation, are useful in in vitro assays for identifying inhibitors or enhancers of tubulin glutamylation. For example, a substrate, such as an as axoneme, microtubule or tubulin, can be contacted with a candidate glutamic acid ligase-inhibitor compound and a known glutamic acid ligase, preferably a tubulin glutamic acid ligase. A change in the glutamylation level of the substrate, dependent upon the presence or absence of the inhibitor compound, can be detected. The absence of additional glutamylation, or a slower rate of glutamylation in the presence of the candidate compound compared to the glutamylation rate in the absence of the candidate compound, indicates that the compound functions as a glutamic acid ligase inhibitor. Likewise, to identify an enhancer compound, an increase in glutamylation amount or rate, compared to the glutamylation rate in the absence of the candidate compound, is indicative of a compound that enhances or stimulates glutamic acid ligase activity. Optionally, the inhibitory nature of an inhibitory compound can be confirmed or further characterized or studied using in vivo assays. Advantageously, such in vivo assays can be performed in wild-type *Tetrahymena* or a *Tetrahymena* cell that has been genetically engineered to overexpress a tubulin glutamic acid ligase, such as TTLL6A.

Alternatively, a primary in vivo assay can be used to identify candidate glutamic acid ligase inhibitor compounds. In this embodiment, a *Tetrahymena* cell exhibiting reduced glycine ligase activity (and hence, hyperglutamylation) as described herein can be contacted with a candidate glutamic acid ligase-inhibitor compound, and a change in at least one of cell growth or motility can be detected. A decrease in cell growth or motility is indicative of tubulin glutamic acid inhibition. The method may further include detecting the amount of glutamylation. A decrease in glutamylation relative to an untreated cell is indicative of tubulin glutamic acid ligase inhibition.

In analogous methods, cellular components such as axonemes, microtubules or tubulin, which have been isolated from a *Tetrahymena* cell of the invention that exhibits reduced tubulin polyglycylation, are useful in in vitro assays for identifying inhibitors or enhancers of tubulin glycine ligase. For example, the method may include contacting a substrate isolated from a *Tetrahymena* cell having reduced glycine ligase activity, with a candidate glycine ligase-inhibitor compound and a known glycine ligase, preferably a tubulin glycine ligase, and detecting a change in glycylation of the substrate. A change in the glycylation level of the substrate, dependent upon the presence or absence of the inhibitor compound, can be detected. The absence of additional glycylation, or a slower rate of glycylation in the presence of the candidate compound compared to the glycylation rate in the absence of the candidate compound, indicates that the compound functions as a glycine ligase inhibitor. Likewise, to identify an enhancer compound, an increase in glycylation amount or rate, compared to the glycylation rate in the absence of the candidate compound, is indicative of a compound that enhances or stimulates glycine ligase activity. Optionally, the inhibitory nature of an inhibitor compound can be confirmed or further characterized or studied using in vivo assays. Advantageously, such in vivo assays can be performed in wild-type *Tetrahymena* or a *Tetrahymena* cell that has been genetically engineered to overexpress a tubulin glycine ligase, such as TTLL3A.

Scientific and Medical Applications

It is expected that an inhibitor of glutamylase will be of great value in assessing the function of glutamylation in diverse cell types, including those that are difficult to grow in vitro or manipulate genetically and are known to have highly glutamylated microtubules (such as ciliated epithelial cells (Million et al. (1999)). There is evidence that glutamylation affects assembly of certain organelles such as flagella (Campbell et al. (2002) Genetics 162, 307-320), centrioles (Bobinnec et al. (1998) J. Cell Biol. 143, 1575-1589), and neural bundles (Janke et al. (2005) Science 308, 1758-1762 (see Example I)). Thus, genetic means alone may not adequately assess the function of glutamylation in already assembled organelles.

Additionally, glutamylase inhibitors could find innovative uses in medicine. As noted earlier, tubulins are a major target of anti-cancer drugs. However, tubulins are highly conserved. Thus, developing isotype-specific inhibitors for tubulin primary polypeptides is likely to be difficult. The present invention provides an alternative strategy that involves targeting the post-translational modification enzymes rather then tubulins per se. Tubulin glutamylases identified herein are suitable objects for highly focused targeting strategies. Mammals have nine glutamylase enzymes (Janke et al. (2005) Science 308, 1758-1762 (see Example I)), many of which display restricted patterns of expression (see Unigene entries: Hs.91930, Hs.445826, Hs.567737 Mm.276780). Thus, a restricted chemical targeting of microtubules may be possible by inhibition of specific tubulin glutamylases.

Furthermore, ciliates are evolutionary relatives of important apicomplexan parasites (e.g., malaria-causing *Plasmodium* and *Toxoplasma*), known to extensively glutamylate pellicular microtubules (Plessmann et al. (2004) Parasitol Res 94, 386-389). Thus narrow specificity inhibitors developed against a *Tetrahymena* enzyme may be useful as anti-parasite compounds. For example, the eukaryotic parasite *Toxoplasma gondii* has highly glutamylated pellicular microtubules (Plessmann et al., (2004) Parasitol. Res. 94, 386-389) and *Toxoplasma* has several glutamylase genes. An inhibitor of a glutamylase can inhibit the growth of, or kill, for example, ciliated protozoans.

An inhibitor of glutamylase can be used in a number of diverse and medically relevant ways. For example, two glutamylases (TTLL6 and TTLL13) in humans are highly expressed in the testis and only at low level or are non-detectable in other tissues (NCBI/Unigene entry Hs.632164; Hs.91930). A mutation in the noncatalytic subunit of one glutamylase, PGs1, blocked assembly of sperm axonemes in the mouse (Campbell et al. (2002). Genetics 162, 307-320). Thus, a glutamylase inhibitor could be used as a male contraceptive, as it can be expected to interfere with the function of sperm flagellum. As shown in the following examples, one of the enzymes in *Tetrahymena* localizes to cilia, which are structures similar to flagella. Another potential application is in cancer. It is known that glutamylases modify microtubules of spindles and centrioles in dividing cells (Bobinnec et al. (1998) Cell Motility Cytoskeleton 39, 223-232). Thus, an inhibitor of a glutamylase is expected to inhibit cell proliferation.

Another potential application is as a psychiatric drug. A mutation in the non-catalytic subunit of the glutamylase was found to reduce male-male aggression in the mouse model likely based on its effect on the brain (Campbell et al. (2002). Genetics 162, 307-320). Thus, an inhibitor of glutamylation could be useful as a psychiatric drug.

EXAMPLES

The present invention is illustrated by the following examples. It is to be understood that the particular examples, materials, amounts, and procedures are to be interpreted broadly in accordance with the scope and spirit of the invention as set forth herein.

Example I

Tubulin Glutamylase Enzymes are Members of the TTL Domain Protein Family

Summary

Glutamylation of tubulin has been implicated in several functions of microtubules but the identification of the responsible enzyme(s) has been challenging. We show here that the neuronal glutamylase is a protein complex containing a tubulin tyrosine ligase-like (TTLL) protein, TTLL1. TTLL1 is a member of a large family of proteins with a TTL domain, whose members could catalyze ligations of diverse amino acids to tubulins or other substrates. In the model protist *Tetrahymena thermophila* two conserved types of glutamylases were characterized, which differ in substrate preference and subcellular localization. Janke et al. (2005) Science 308, 1758-1762.

Introduction

Polyglutamylation is an uncommon type of posttranslational modification that adds multiple glutamic acids to a γ-carboxyl group of a glutamate residue of target proteins, including tubulin and nucleosome assembly proteins NAP1 and NAP2 (Edde et al., Science 247, 83 (1990); Rüdiger et al., FEBS Lett 308, 101 (1992); Redeker et al. FEBS Lett 313, 185 (1992); Regnard et al., J Biol Chem 275, 15969 (2000)). The resulting glutamate side chains are of variable length, allowing for a graded regulation of protein-protein interactions. Glutamylation regulates the binding of neuronal microtubule (MT) associated proteins as a function of the length of the glutamate chain, suggesting that the modification is important for the organization of the neuronal MT network (Bonnet et al., J Biol Chem 276, 12839 (2001)). Tubulin glutamylation may also play a role in centriole maintenance (Bobinnec et al., J Cell Biol 143, 1575 (1998)) axoneme motility (Gagnon et al., J Cell Sci 109, 1545 (1996); Million et al., J Cell Sci 112, 4357 (1999)) and mitosis (Bobinnec et al., Cell Motil Cytoskeleton 39, 223 (1998); Regnard et al., J Cell Sci 112, 4281 (1999)).

Identification of mouse brain glutamylase. Monoclonal antibody (mAb 206), raised against a partially purified brain tubulin glutamylase fraction, immunoprecipitates the enzyme complex, including the PGs1 protein (Regnard et al., J Cell Sci 116, 4181 (2003)). Here we used gel electrophoresis followed by nano-LC-MS-MS (Liquid Chromatography-Mass Spectrometry) to identify 4 additional protein components of the same complex: p24, p33, p49 and p79 (FIG. 5A; Table I). Polyclonal antibodies were raised against recombinant proteins or peptides of p24, p32/PGs1, p33, p49 and p79 and used for co-immunoprecipitation analyses. mAb 206, anti-p32/PGs1 antibodies (L83) and anti-p79 antibodies (L80) precipitated ≧80% of the glutamylase activity (FIG. 5B) along with all 5 proteins (FIG. 5C). These 5 proteins also consistently copurified with the glutamylase activity during several purification steps (FIG. 10) and were named Glutamylase subunits PGs5, PGs1, PGs2, PGs3 and PGs4 (for p24, p32, p33, p49 and p79, respectively). Additional proteins were found in the mAb 206-immunoprecipitated fraction, including Arp1 and CF Im25 (Table I), but these did not consistently copurify with the enzyme activity.

The apparent size of the neuronal glutamylase complex (360 kDa; Regnard et al., Biochemistry 37, 8395 (1998)) is greater than the theoretical sum of the predicted molecular masses of all 5 subunits (217 kDa), suggesting that the complex contains multiples of one or more subunits. Some of the components appear on 2D gels as multiple spots at different isoelectric points, suggesting that they are themselves subject to charge-altering post-translational modifications (FIG. 5A). Indeed, PGs1 was phosphorylated on Ser 279. The 3 more acidic spots of PGs1/p32 contain the phosphorylated peptide 277-284 (RPSVPMAR (SEQ ID NO:5)) (FIG. 5A: spots 5-7). Phosphorylation site prediction (available on the world wide web at expasy.org/) indicates that 5279 can be phosphorylated by cAMP- or cGMP-dependent protein kinases. The 3 more acidic spots of PGs1/p32 contain the phosphorylated peptide 277-284 (RPSVPMAR; SEQ ID NO:5) (FIG. 5A: spots 5-7). Phosphorylation site prediction (available on the world wide web at expasy.org/) indicates that S279 can be phosphorylated by cAMP- or cGMP-dependent protein kinases.

PGs1 (a product of the mouse gene GTRGEO22) is required for sperm axoneme assembly and normal animal behavior (Campbell et al., Genetics 162, 307 (2002)) and may act in the intracellular targeting of the glutamylase complex (Regnard et al., J Cell Sci 116, 4181 (2003)). PGs3 is an ortholog of the human TTLL1 protein (Trichet et al. Gene 257, 109 (2000)). The amino acid sequence of TTLL1 exhibits 17% identity to tubulin tyrosine ligase (TTL), which catalyses the addition of tyrosine to the C-terminal glutamate of detyrosinated α-tubulin (Ersfeld et al., J Cell Biol 120, 725 (1993)). Despite obvious differences, both glutamylation and tyrosination reactions involve an amino acid addition to a glutamate residue through the formation of an amide bond. Thus, we examined the possibility that TTLL1 is the catalytic subunit of neural tubulin glutamylase.

Figure 11:
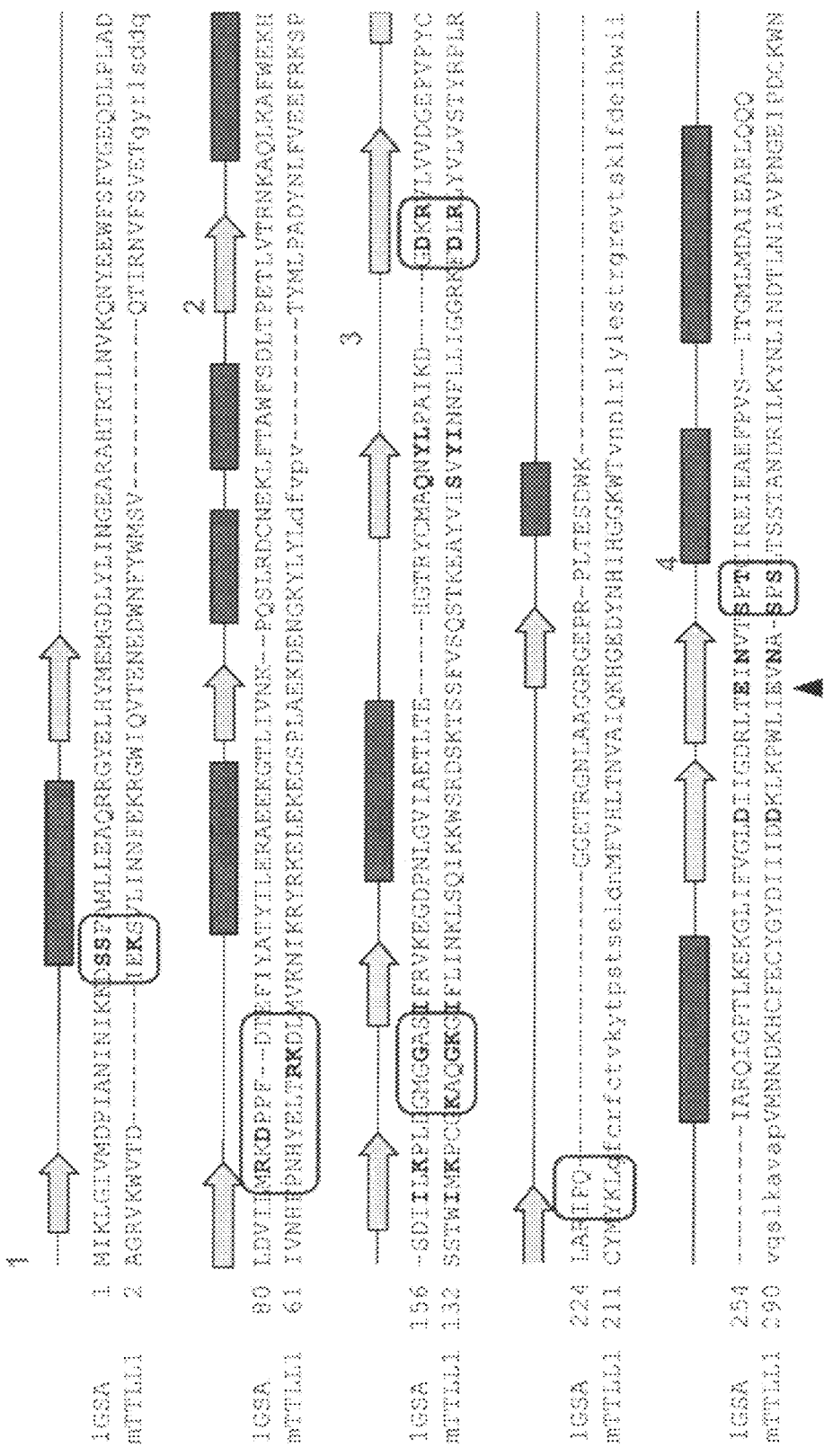
FIG. 11 shows a sequence profile alignment of 1GSA (SEQ ID NO:6) and mTTLL1 (SEQ ID NO:7) for TTLL1 modeling.

A structural model for TTLL1. The amino acid sequence of TTLL1 (PGs3) contains three conserved motifs which correspond to the ATP/Mg$^{2+}$-binding site typical of enzymes with a carboxylate-amine/thiol ligase activity, such as glutathione synthetase (Galperin et al., Protein Sci 6, 2639 (1997)). Although the overall sequence similarity between TTLL1 and the known carboxylate-amine/thiol ligase enzymes is low, we could align the ATP-binding regions, and also all major parts of TTLL1. A structural model of TTLL1 was obtained by homology-based modeling using glutathione synthetase from E. coli as a template (FIG. 6A, B). Docking of ATP and Mg$^{2+}$ into the model supports the localization of the ATP/Mg$^{2+}$-binding site (FIGS. 6B, C and FIG. 11). We were also able to fit a peptide with a glutamate side chain into the active site, which located a putative binding site for free glutamate (FIG. 6C). Thus, it is very likely that TTLL1 protein is the catalytic subunit of neural tubulin glutamylase.

Figure 3:
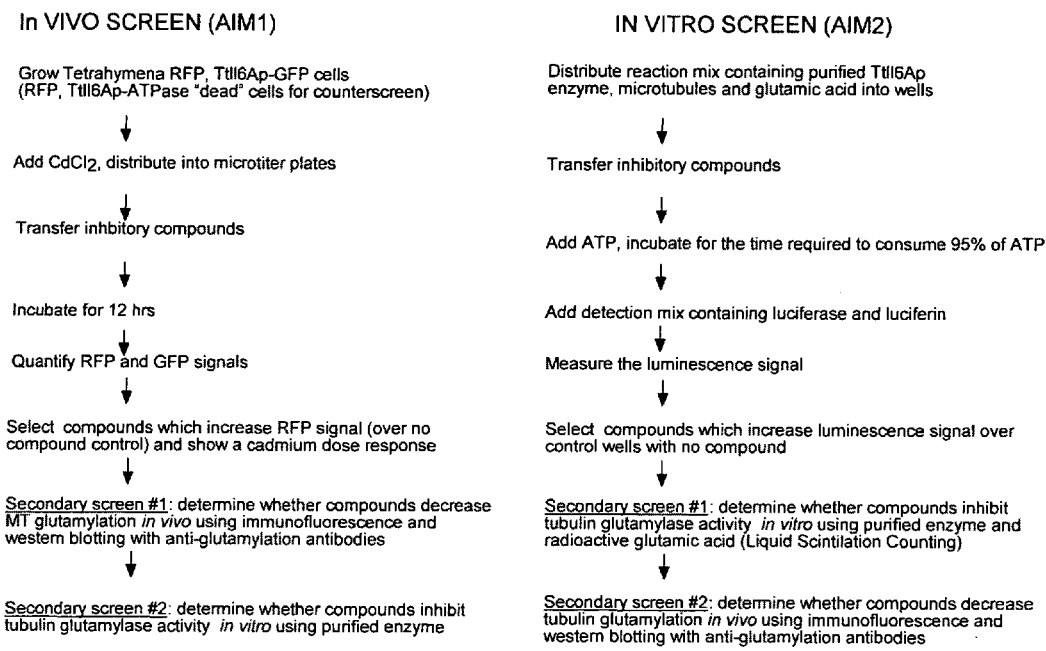
FIG. 3 shows exemplary in vivo and in vitro screens for inhibitors of glutamylases.
Figure 7:
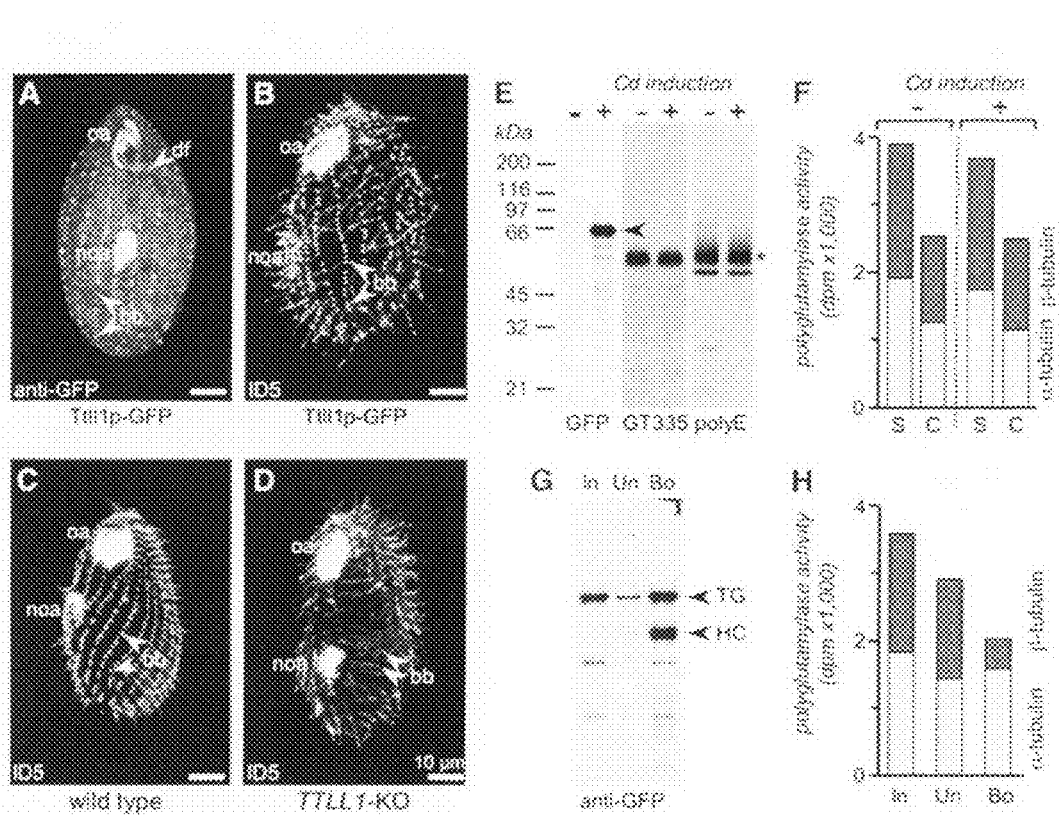
FIG. 7 shows that Ttll1p of *Tetrahymena* is associated with tubulin glutamylation. (A) A cell expressing Ttll1p-GFP, labeled by immunofluorescence using anti-GFP antibodies. (B-D) Glutamylated MTs labeled by ID5 antibody in a cell overproducing Ttll1p-GFP (B), a wild type cell (C) and a TTLL1-null cell (D). Note a strong reduction in the labeling of rows of basal bodies in D as compared to C. (E) Immunoblotting studies on total *Tetrahymena* cell extracts before (−) and after (+) 3 hrs cadmium induction of Ttll1p-GFP, analyzed with anti-GFP (GFP), anti-glutamylation GT335 and polyE antibodies (arrowhead points to Ttll1p-GFP; * marks the comigrating α- and β-tubulin bands). (F) The soluble (S) and cytoskeletal (C) fractions from cells overproducing Ttll1p-GFP (+) or non-induced controls (−) were analyzed for tubulin glutamylase activity in vitro. (G, H) Soluble fractions of cells overproducing Ttll1p-GFP were subjected to immunoprecipitation with anti-GFP antibodies. The input (In), unbound (Un) and bound (Bo) fractions were analyzed by immunoblotting with anti-GFP antibodies (G; arrowhead TG points to Ttll1p-GFP, HC to the anti-GFP heavy chain) and assayed for glutamylase activity in vitro (H). Equal volumes of input, unbound and bead fractions were analyzed by immunoblotting, while 20 times more of bead fraction was assayed for glutamylase activity. Abbreviations: oa, oral apparatus; noa, new oral apparatus prior to cell division; df, deep fiber; bb, basal bodies.

Ttll1p is associated with α-tubulin glutamylase activity in vivo. When expressed in bacteria or in various cell lines as well as in several heterologous systems, the murine TTLL1 had a strong tendency to precipitate and did not show glutamylase activity in vitro. We used a homologous protein expression system based on the ciliated protist Tetrahymena thermophila to assess the role of TTLL1-related proteins in glutamylation. Tetrahymena has a complex cytoskeleton with a large number of distinct types of MTs (Gaertig, J Eukaryot Microbiol 47, 185 (2000)). Most types of MTs in Tetrahymena are monoglutamylated, while a small subset, including MTs of the basal bodies (BBs), cilia, contractile vacuole pore (CVP) and oral deep fiber (DF), have side chains composed of two or more glutamates. Using the recently sequenced macronuclear genome of Tetrahymena, we identified the likely TTLL1 ortholog, Ttll1p (54% of amino acid sequence identity to TTLL1). Ttll1p with an N-terminal GFP was strongly overexpressed using a cadmium-inducible gene promoter (Shang et al., Proc Natl Acad Sci USA 99, 3734 (2002)). Ttll1p-GFP localized to a subset of glutamylated MT organelles: including BBs, CVPs and DF (FIG. 3A), but no increase in the level of MT glutamylation over normal level was detected (FIG. 3B, C, E), and the phenotype appeared normal. Similar results were obtained for the HA epitope C-terminally tagged protein. No change in in vitro tubulin glutamylation activity was detected in cell extracts despite the strong accumulation of Ttll1p-GFP (FIG. 7F). However, a glutamylase activity directed mostly toward α-tubulin was co-immunoprecipitated with anti-GFP antibodies from extracts of overexpressing cells (FIG. 7G, H). The overexpressed protein apparently can replace a part of the endogenous Ttll1p but may not function alone. Based on the data obtained for the murine homolog, it is likely that Ttll1p also acts in a complex and that other subunits are limiting. We also constructed cells completely lacking the TTLL1 gene, using gene disruption. The TTLL1-null cells had a normal phenotype, but showed a strong reduction in tubulin glutamylation in the BBs (FIG. 7C, D), confirming that Ttll1p is involved in glutamylation but also suggesting that there are additional glutamylase activities in this organism that do not require Ttll1p.

Figure 12:
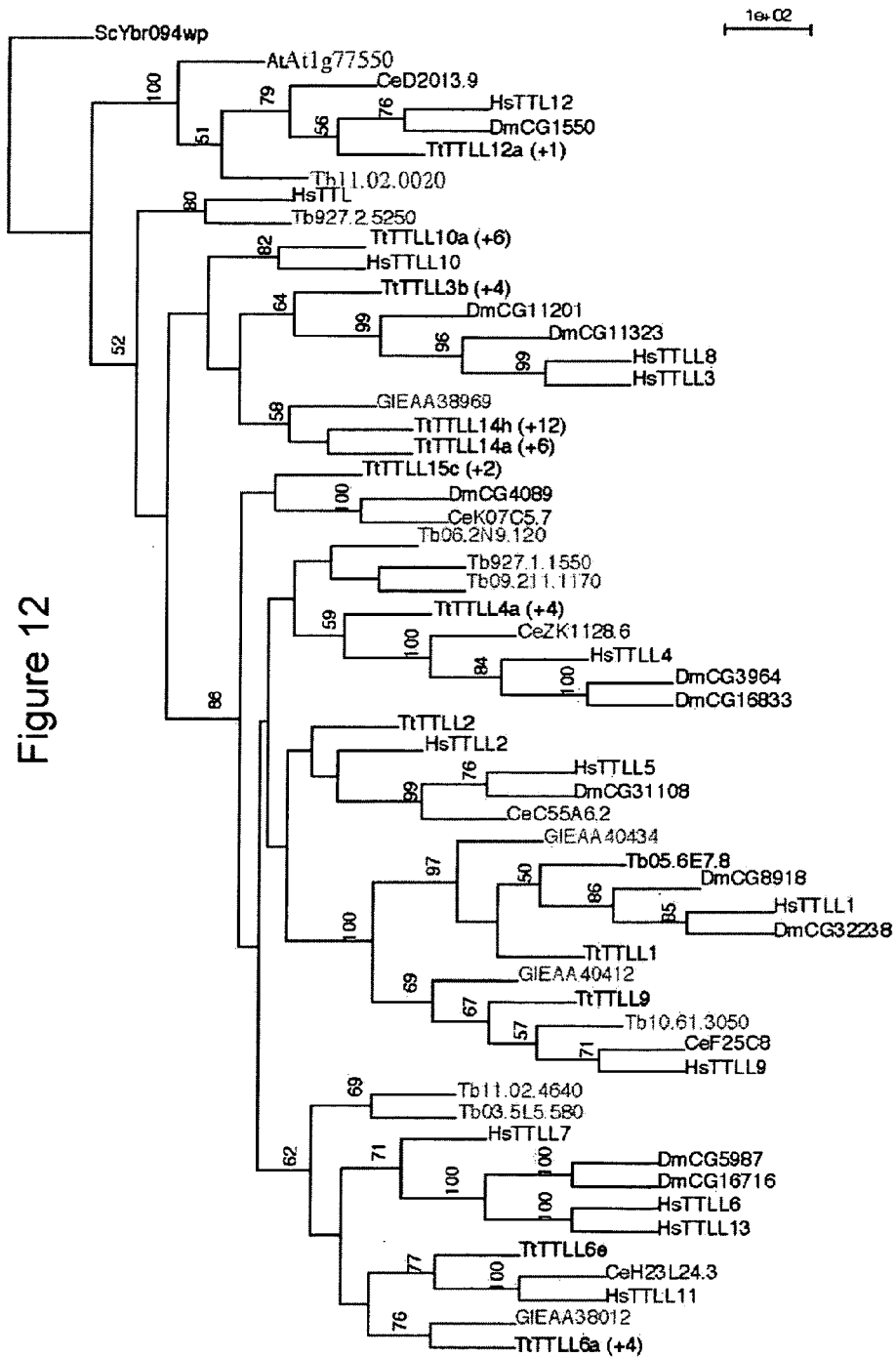
FIG. 12 shows a phylogenetic analysis of predicted protein gene sequences containing a TTL domain.

The TTLL family. TTLL1 and TTL are members of a large family of conserved eukaryotic proteins with a TTL homology domain, raising the possibility that other members of this family are also involved in glutamylation or other types of posttranslational amino acid ligations. Phylogenetic analyses showed that TTL-like proteins (TTLLs) of diverse eukaryotes belong to several conserved subtypes (FIGS. 8, 12 and 13). We used the HsTTLL1 sequence (Trichet et al., Gene 257, 109 (2000)) as a template for tBLASTn searches to identify all TTLL loci of Tetrahymena and several other model eukaryotes. Phylogenetic analyses revealed 10 clades of TTLLs, 8 of which contain mammalian proteins. Tetrahymena has between 1-7 sequences in most groups, and one clade of 20 ciliate-specific TTLLs. Among the genomes surveyed, only Trypanosoma has a close homolog of the mammalian TTL, which may be why an enzymatic activity of TTL was not detected in invertebrates (Preston et al., J Mol Evol 13, 233 (1979)) and Tetrahymena (Raybin et al., J Cell Biol 73, 492 (1977)).

Tetrahymena Ttll6Ap is a β-tubulin-preferring glutamylase. The Tetrahymena TTLL6A sequence belongs to a clade related to TTLL1 type (FIGS. 8 and 13). Overproduced Ttll6Ap-GFP localized mainly to cilia, with a small amount associated with BBs and cell body MTs (FIG. 9A). Overproduction of Ttll6Ap-GFP led to a strong increase in glutamylation in cilia, and on cell body MTs (FIG. 9C; compare FIG. 7C). A strong increase in tubulin glutamylation (but not in polyglycylation) was also detected in whole cells using immunoblotting (FIG. 9F).

A truncated variant lacking the 286 C-terminal amino acids, Ttll6apΔ$_{710}$-GFP localized predominantly to the cell body with strong preference for subcortical (SC) MTs that extend from the apical end of the cell and run below the BBs (FIG. 9B). Consistently, overexpression of Ttll6ApΔ$_{710}$-GFP led to a strong increase in glutamylation on MTs in the cell body and to a much lesser extent in cilia (FIG. 9D). Thus, the 286 C-terminal amino acids of Ttll6Ap are required for preferential targeting to cilia.

We used the truncated version of Ttll6Ap for biochemical studies, due to the increased presence of this variant in the soluble/cytosolic pool, as compared to the full-length protein. Extracts of cells overexpressing Ttll6ApΔ$_{710}$-GFP showed a 100-fold increase in in vitro glutamylase activity for β-tubulin and a 10-fold increase for α-tubulin compared to non-induced cells (FIG. 9E). This activity co-purified with Ttll6ApΔ$_{710}$-GFP protein under all conditions tested (FIG. 14A-C). No in vitro activity toward NAP proteins was detected. Thus, Ttll6Ap is a tubulin glutamylase displaying a strong preference for the β-tubulin subunit.

Increased glutamylation affects cell growth and motility. *Tetrahymena* cells overexpressing Ttll6Ap-GFP ceased to multiply in a few hours following cadmium-induction (FIG. 9G) and most had paralyzed cilia (FIG. 9I), indicating that excessive glutamylation inhibits cell proliferation and ciliary dynein-based motility. Cells overexpressing the truncated protein also ceased to proliferate but the effect on ciliary motility was much weaker, in accordance with the altered protein localization pattern (FIG. 9H, I). These effects did not occur when a mutation in the predicted ATP binding site (E422G) of the TTL homology domain was introduced (FIG. 11). Compared to the ATPase-active protein, the inactive variant, Ttll6ApΔ$_{710}$-E422G-GFP, was expressed at a similar level (FIG. 9F) and localized to the same types of MT organelles. However, neither increase in tubulin glutamylation (FIG. 9F), nor alteration of cell growth or motility were observed (FIG. 9H, I), confirming that excessive glutamylation was responsible for the observed effects of Ttll6Ap overproduction.

Conclusion. The simplest interpretation of all our data is that TTLL1/Ttll1p and Ttll6Ap are two types of tubulin glutamylase catalytic components with distinct tubulin subunit preferences. The neuronal TTLL1 as well as Ttll1p have a preference for α-tubulin, while Ttll6Ap preferentially glutamylates β-tubulin. Unlike Ttll6Ap, Ttll1p (and its murine ortholog) did not increase glutamylation in vitro and in vivo upon overproduction. However, TTLL1 exists in a protein complex and additional subunits may be required for its activity and could be limiting in vivo. Indeed, immunoprecipitation of Ttll1p-GFP from overproducing *Tetrahymena* cells led to a recovery of glutamylase activity.

Ttll6Ap is a much larger protein (116 kDa) compared to TTLL1 (49 kDa) and Ttll1p (42 kDa) and may contain all properties required for autonomous glutamylase activity. The four non-catalytic subunits identified in the neuronal TTLL1 complex may be involved in tubulin substrate recognition, regulation of the enzymatic activity, or subcellular localization as suggested for PGs 1 (Regnard et al., *J Cell Sci* 116, 4181 (2003)). It is likely that Ttll1p is also in a complex, as is the murine homolog. Except for PGs4, we could not identify homologs of the other subunits of the neural complex (PGs1, PGs2, PGs5) outside of vertebrates, including *Tetrahymena*, indicating that variations in composition of non-catalytic subunits occur across phyla.

The unusually large number of TTLL genes in *Tetrahymena* and the lack of a detectable loss of function phenotype for TTLL1 suggests functional redundancy. In contrast, a mutation in the PGs1 component of the murine TTLL 1-complex lead to defective sperm axonemes and changes in animal behavior (Campbell et al., *Genetics* 162, 307 (2002)). In *C. elegans*, RNAi depletion of C55A6.2 (a TTLL5 type) causes embryonic lethality and sterility (Maeda et al., *Curr Biol* 11, 171 (2001)). Depletion of TTLL1 mRNA in PC12-E2 cells inhibited neurite outgrowth, suggesting an essential function in neurogenesis. The phylogenetic association of TTLL1, TTLL9, TTLL4, TTLL6, TTLL5 and TTLL15 protein types (86% bootstrap value; FIG. 8) suggests that these protein types are all involved in glutamylation of tubulin or possibly other proteins such as NAPs (Regnard et al., *J Biol Chem* 275, 15969 (2000)). Other members of the TTLL family may catalyze different types of posttranslational addition of an amino acid, such as polyglycylation.

Materials and Methods

Purification and Identification of Mouse Brain Glutamylase

Glutamylase was partially purified (400×) from 200 3 day-old mouse brains and immunoprecipitated with mAb 206 linked to protein G magnetic beads as described Regnard et al. (*J Cell Sci* 116, 4181 (2003)). The precipitated proteins were analyzed by two-dimensional (2D) polyacrylamide gel electrophoresis (PAGE). For the first dimension, non-equilibrium pH gradient electrophoresis (NEPHGE; O'Farrell et al. (1977) *Cell* 12, 1133) and for the second PAGE dimension, an acrylamide gradient (8-13%) were applied. Proteins were stained with Coomassie brilliant blue (Serva) and all visible protein spots (apart from two large spots corresponding to the heavy and light chain of mAb 206) were excised and submitted to in-gel digestion by trypsin. Extracted peptides were analyzed by nano-LC-MS-MS on a Q-TOF 2 mass spectrometer (Micromass Ltd., Manchester, UK) and identified using the Mascot software (Fraering et al. (2004) *Biochemistry* 43, 9774).

*Tetrahymena* Cell Extracts

To prepare extracts for glutamylase activity assays, cells were lysed in the T buffer (Tris-HCl 50 mM pH 8.0, NaCl 0.2 M, EGTA 1 mM, MgCl$_2$ 1 mM, NP-40 0.5%) containing protease inhibitors (leupeptin 0.5 E-64 10 μg/ml, chymostatin 10 μg/ml, antipain 12.5 μg/ml, according to Chilcoat et al. (*J Cell Biol* 135, 1775 (1996)). Total extracts were either directly analyzed or centrifuged at 50,000×g. The supernatant constituted the soluble fraction. The cytoskeletal fraction was obtained by resuspending and sonicating the pellet in T buffer.

To prepare whole cytoskeletons for western blots, 10$^7$ *Tetrahymena* cells were spun down and processed according to Williams et al. (*Methods Cell Biol* 47, 301 (1995)) with some modifications. Cells were resuspended in 2 ml of 10 mM Tris-HCl, pH 7.5 with protease inhibitors and incubated on ice for 5 min. An equal volume of 2× lysis buffer with protease inhibitors was added (1% Triton-X100 final concentration) and after 1 min on ice, cytoskeletons were collected by centrifugation (10 min, 16,000 g at 4° C.). Pellets were resuspended in a phosphate buffer and protein concentration was determined using the BCA TM Protein Assay (Pierce). Eight μg of protein was loaded per lane, separated on a 12% SDS-PAGE gel and processed for western blotting.

Size Exclusion Chromatography

A soluble extract of Ttll6ApΔ$_{710}$-GFP producing cells was fractionated on an HPLC TSK G300 SWXL, 7.8×300 mm column (TosoHaas, PA, USA) in MES 50 mM pH 6.9, EGTA 1 mM, MgCl$_2$ 1 mM, NaCl 0.35 M, Triton-X100 0.1%, at a flow rate of 0.8 ml/min. Fractions of 0.4 ml were collected. Protein standards used for calibration were thyroglobulin (669 kDa), aldolase (158 kDa), transferrin (81 kDa), hemoglobin (32 kDa) and cytochrome C (12.4 kDa).

Glutamylase Assay

The tubulin glutamylase activity was measured as described Regnard et al. (*Biochemistry* 37, 8395 (1998)). Briefly, reaction mixtures (20 μl) containing 50 mM Tris-HCl pH 9.0, 2 mM ATP (equilibrated to pH 7.0 with NaOH), 12 mM $MgCl_2$, 2.5 mM DDT, 10 μM taxotere, ι-[$^3$H]-glutamate (45-55 Ci/mmol, Amersham, UK) and 0.1 mg/ml taxotere-stabilized MTs, were incubated at 30° C. for 40 min. In some cases, to increase the radioactive signal, ι-[$^3$H]-glutamate was concentrated by centrifugation under vacuum and added at a final concentration of up to 25 μM. Protein fractions to be tested were added at a maximal final concentration of 0.5 mg/ml. The taxotere-stabilized mouse brain MTs were prepared as described Regnard et al. (*J Cell Sci* 112, 4281 (1999)). The salt concentration was maintained at ≦20 mM to avoid inhibition of the enzyme activity (Regnard et al. (1998) *Biochemistry* 37, 8395). Quantifications were done by scintillation counting of the α- and β-tubulin bands after SDS-PAGE and electro-transfer onto nitrocellulose, as described Regnard et al. (*Biochemistry* 37, 8395 (1998)). The specificity of glutamylation to tubulins was verified by submitting the reaction mixtures to SDS-PAGE and fluorography. Exposures were performed at −80° C. using Kodak (Rochester, N.Y.) XAR-5 films after enhancement with Amplify (Amersham). As noted before (Regnard et al. (2003) *J Cell Sci* 116, 4181), bead fractions obtained after immunoprecipitation have a disproportionally low activity compared to the input or unbound fractions, presumably because the beads hinder proper interactions between the glutamylase and the MT substrate. Therefore, 10-20 times more of the bead material was used compared to the equivalent amount of unbound and input material, but the levels of activity remained relatively low. Thus, the glutamylase assays of bead fractions cannot be considered as quantitative; they only provide qualitative information about the type of activity present. However, relevant quantitative information can be deduced from the comparison of the activities in the input and unbound material.

Antibodies

Mouse monoclonal antibodies (mAbs) used were mAb 206 (Regnard et al. (2003) *J Cell Sci* 116, 4181), GT335 (anti-glutamylation; Wolff et al., *Eur J Cell Biol* 59, 425 (1992)), ID5 (anti-glutamylation; Rüdiger et al., *Eur J Cell Biol* 78, 15 (1999)), 12G10 (anti-α-tubulin, from J. Frankel).

Polyclonal rabbit Abs were anti-Arp1 (courtesy of R. Melki), anti-CF Im25 (courtesy of S. Dettwiler and W. Keller), anti-GFP (Torrey Pines Biolabs, Houston, Tex.), polyE anti-glutamylation (serum 2303) and polyG anti-polyglycylation (serum 2301), the latter two courtesies of M. Gorovsky.

Laboratory-made rabbit polyclonal Abs were L26 (anti-p24/PGs5), L83 (anti-p32/PGs1; Regnard et al. (2003) *J Cell Sci* 116, 4181), L91 (anti-p33/PGs2 anti-peptide Ab), L90 (anti-p49/PGs3) and L80 (anti-p79/PGs4 anti-peptide Ab).

Secondary antibodies used were: HRP-labeled donkey anti-rabbit Ig 1:10,000, HRP-labeled protein A 1:5,000 (Amersham Pharmacia Biotech), goat-anti-mouse FITC and goat-anti-rabbit FITC (Zymed).

Immunoprecipitation

For immunoprecipitation, antibodies (FIGS. 5, 7, 14) were pre-incubated with protein G magnetic beads (Dynal Biotech), washed in PBS with 0.05% Tween-20 and incubated with the input material for 3 hrs at 4° C. The beads were extensively washed with Tris-HCl 50 mM pH 8.0, NaCl 0.5 M, NP-40 0.1% before analysis.

Western Blotting

Figure 5:
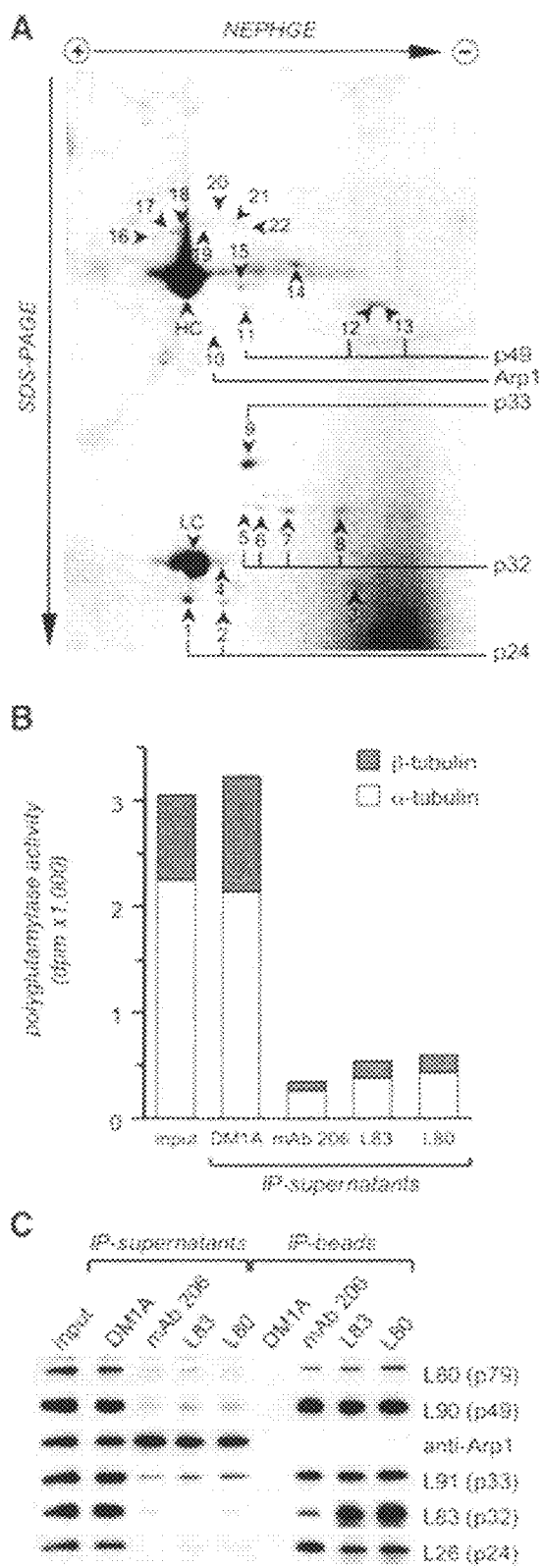
FIG. 5 shows characterization of the neuronal glutamylase. (A) A Coomassie Brilliant Blue stained NEPHGE 2D gel of a purified glutamylase fraction, immunoprecipitated from 200 3-day old mouse brains using mAb 206. All numbered protein spots were identified by nano-LC-MS-MS (Table I). "HC" and "LC" mark the positions of heavy and light chains of mAb 206. (B) Immunoprecipitations with mAb 206, L83 (anti-p32/PGs1; Regnard et al., *J Cell Sci* 116, 4181 (2003)), L80 (anti-p79) and DM1A (Mab anti-α-tubulin) used as a control. Equal proportions of input and supernatants were assayed for glutamylase activity. (C) Input, supernatants and beads (equal proportions) were analyzed by western blotting. The glutamylase activity, and all 5 glutamylase complex subunits were strongly depleted from the supernatants. The proteins were quantitatively recovered with the beads of mAb 206, L83 and L80, but not of DM1A. Arp1 did not quantitatively co-purify with the enzyme.

For western blots shown in FIG. 5, antibodies were used at 0.5 μg/ml. For FIGS. 7 and 14, anti-GFP, GT335 and anti-polyE antibodies were diluted at 1:5,000, 1:20,000 and 1:3,000, respectively. For western blots presented in FIG. 9 antibodies were used at the following dilutions: ID5 (1:100), polyG 2301 (1:2,000), 12G10 (1:100), anti-GFP (1:1,000). Proteins were visualized with HRP-labeled donkey anti-rabbit Ig 1:10,000 or HRP-labeled protein A 1:5,000, followed by detection with chemo luminescence (Western Lightning Chemo-luminescence Reagent Plus, Perkin Elmer).

Modeling of the Structure of TTLL1

TTLL1 (PGs3) contains an ATP/$Mg^{2+}$-binding site typical of enzymes with an ATP-dependent carboxylate-amine/thiol ligase activity (Galperin et al. (1997) *Protein Sci* 6, 2639; Dideberg et al. (1998) *Trends Biochem Sci* 23, 57). These so-called ADP-forming enzymes catalyze ATP-dependent ligations of carboxyl group carbon atoms of the first substrate to an amino (or imino) acid group nitrogen atoms of the second substrate via the formation of acylphosphate intermediates, as glutamylation reaction is predicted to involve. Previous structural alignments of ADP-forming enzymes have identified three conserved sequence motifs that correspond to the ATP-binding cleft (Artymiuk et al. (1996) *Nat Struct Biol* 3, 128), which are also well conserved in TTLL1. In enzymes with a known structure, these conserved regions are located at the ATP/$Mg^{2+}$-binding sites. Nevertheless, about 85% of the sequence of the ATP/$Mg^{2+}$-binding regions of the structurally characterized enzymes differs from TTLL1. To test our hypothesis about the enzymatic function of TTLL1, we applied a combination of a structure-based alignment, sequence profile search and molecular modeling. Several structures of ADP-forming enzymes (pdb codes: 1GSA, 1BNC, 2DLN, 1MOW, 1EHI, 1JDB, 1EYZ) were superposed with the Insightll program (Dayring et al. (1986) *J Mol Graph* 4, 82). The initial CLUSTAL alignment of the enzyme sequences was manually improved according to structural superposition. The resulting sequence alignments served for the generation of sequences profiles with the generalized sequence profile method and the pftools package (Bucher et al. (1996) *Comput Chem* 20, 3). The probability of random alignment was calculated by analyzing the score distribution obtained from a profile search versus a regionally randomized version of the protein database, assuming an extreme value distribution (Hofmann et al. (1995) *Trends Biochem Sci* 20, 347). Apart from the central ATP-binding site, the structures of all analyzed enzymes did not match. This changed when the enzyme structures were divided into four sub-structures (N-terminal substrate-binding domain, part 1 of ATP-binding domain, part 2 of ATP-binding domain and C-terminal region; FIG. 11) and separately superimposed with each other, yielding four structure-based alignments with corresponding sequence profiles. These sequence profiles (Bucher et al. (1996) *Comput Chem* 20, 3) were then applied to the sequence of TTLL1.

The initial structure of TTLL1 was constructed using the HOMOLOGY module of InsightII program (Dayring et al. (1986) *J Mol Graph* 4, 82) based on the alignment of TTLL1 to the known 3D-structures of ADP-forming enzymes, but mainly to glutathione synthetase (pdb code: 1GSA; Hara et al., *Biochemistry* 35, 11967 (1996)). The resulting model was subjected to 300 steps of minimization based on the steepest descent algorithm with the backbone atoms of α-helical segments restrained to their starting positions with the force constant K=100. The next 500 steps of the refinement were performed without any restrictions, using conjugate gradients algorithm. The CHARMM force field (Brooks et al. (1983) *J*

Figure 6:
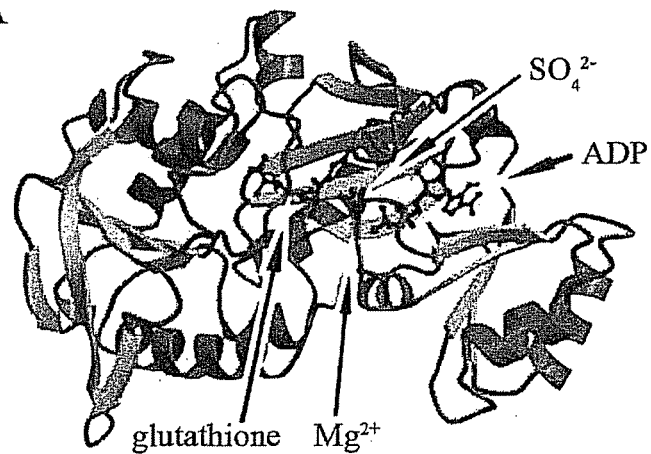
FIG. 6 shows a structural model of TTLL 1. (A) Crystal structure of glutathione synthetase from *E. coli* (pdb code 1GSA) in a complex with ADP, glutathione, $Mg^{2+}$ and sulphate (Hara et al., *Biochemistry* 35, 11967 (1996)). (B) A model of mouse TTLL1 (PGs3) in a complex with ATP, $Mg^{2+}$ and a protein substrate shown in ball-and-stick representation. The regions of TTLL1 that could not be modeled are drawn as thin lines. (C) A close-up view of the active center of TTLL 1. The protein substrate is a three-residue peptide with a central modified glutamate. The flanking amino acids are drawn only with Cβ atoms for clarity of the picture. The glutamate side chain contains two additional glutamate residues (Glu 1, Glu 2). The putative site for the next glutamate residue to be added to the side chain is indicated (Glu 3 site). All residues of the active site that are conserved with other ATP-dependent carboxylate-amine ligases are shown in dark green (see FIG. 11). Some positively charged amino acid residues (K 13, K 142 and K215 in light grey) that are specific to TTLL1 and close to the active site might be important for substrate binding. The proximity of the carboxyl group of Glu 2 and the phosphate of ATP could catalyze the formation of an acylphosphate intermediate (broken line).
Figure 6:
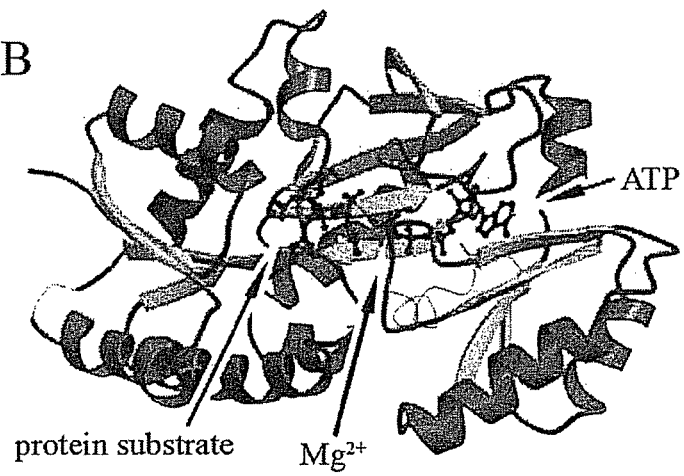
Figure 6:
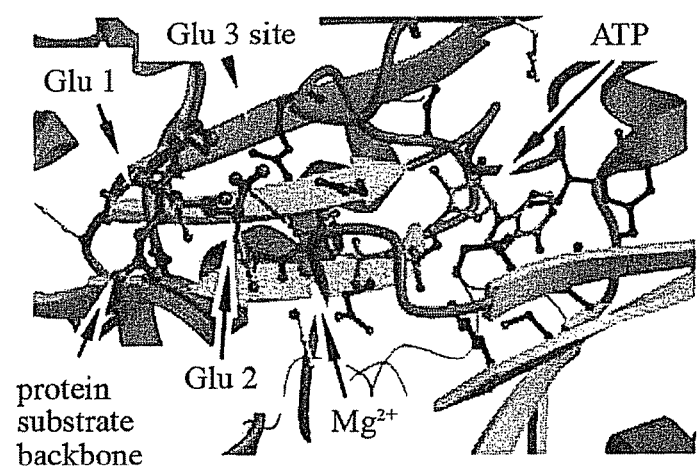

Comp Chem 4, 187) and the distance dependent dielectric constant were used for the energy calculations. The program PROCHECK (Laskowski et al. (1993) *J Appl Crystallog* 26, 282) was used to verify the quality of the modeled structure. The figures were generated with the programs Molscript and Raster3D (FIG. 6) (Kraulis et al. (1991) *J Appl Crystallog* 24, 946; Bacon et al. (1988) *J Mol Graph* 6, 219). As a result, we obtained an alignment of TTLL 1 not only in the previously mentioned ATP-binding regions, but also in all major parts of the protein (FIG. 11) with a structure highly similar to glutathione synthetase. ATP, $Mg^{2+}$ and a peptide with a glutamate side chain were docked into the model taking into consideration an analogous molecular co-crystallization with know ATP-dependent carboxylate-amine ligases (FIG. 6). For simplification of the model, we have fitted an A-E-A peptide modified on the central E into the structure, however, we have before shown that the flanking A residues could be replaced by others without changes for the fitting.

Searching of Genomes and Phylogenetic Analyses

The *Arabidopsis thaliana*, yeast, human and *Giardia lamblia* predicted TTL domain protein sequences were identified by BLAST searches of the NCBI databases (available on the world wide web at ncbi.nlm.nih.gov/BLAST/). The *Drosophila melanogaster* sequences were identified by BLAST searches at the FlyBase (available on the world wide web at flybase.bio.indiana.edu/). The *Caenorhabditis elegans*, and *Trypanosoma brucei* sequences were identified using The Sangers Institute (available on the world wide web at sanger.ac.uk/DataSearch/) and The Institute for Genomic Research (TIGR) databases for respective species (available on the world wide web at tigr.org). The *Tetrahymena thermophila* TTL domain sequences were identified by tBLASTn searches of the recently assembled macronuclear genome at the TIGR *Tetrahymena* blast server (available on the world wide web at tigrblast.tigr.org/er-blast/index.cgi?project=ttg) using genomic scaffolds of the November 2003 assembly. Using HsTTLL1 we first identified the *Tetrahymena* TTLL1 homolog gene and exhaustive searches of the *Tetrahymena* genome were continued using TTLL1 and several other TTL domain sequences. Starting from the region of homology to TTL domains of other organisms, the probable coding region was reconstructed based on the higher G/C content. The intron junctions were tentatively identified based on the known consensus splice sites (Wuitschick et al. (1999) *J Eukaryot Microbiol* 46, 239). As we have completed the manual prediction of the coding regions, the *Tetrahymena* Genome Project at TIGR has published the preliminary gene predictions based on gene finder programs. In general there was an agreement between the manual and software-based predictions. We verified each putative TTLL sequence by a reverse BLASTp of the NCBI databases. A cDNA sequence of TTLL4A was kindly provided by Drs. Kathleen Clark and Martin Gorovsky (University of Rochester, N.Y.). The cDNA plasmid of TTLL14F was kindly provided by Dr. Aaron Turkewitz (University of Chicago, Ill.).

The ends of the transcribed regions of TTLL1 and TTLL6A genes were identified by PCR of cDNAs pools or cDNA libraries from *Tetrahymena* cells grown under several different conditions. Total RNA was isolated using the modified TRI Reagent procedure (MRC; Chomczynski et al. (1995) *Biotechniques* 19, 942). cDNA was synthesized using primers of the SMART cDNA library construction kit and the PowerScript Reverse Transcriptase (Clontech). One pg of total RNA was used for the first strand cDNA synthesis (1.5-2 hrs at 42° C.). Next, 1 µl of the first strand cDNA reaction mix was used for a PCR reaction with the same primers (extension step at 68° C. for 8 min). A cDNA from cilia-regenerating cells was used to construct a small cDNA library (43,000 clones) by cloning into a plasmid vector according to the Clontech kit instructions. The 5' end of TTLL1 UTR was determined by 5'RACE PCR of the cDNA library using a gene specific primer anchored inside the conserved region and the SMART IV primer (Clontech). The 3' end of the TTLL1 cDNA was identified by 3' RACE PCR using a gene-specific primer and the CDS III/3' primer (Clontech). The same 5' and 3' RACE strategy with the cDNA library as a template was used to obtain terminal fragments of cDNAs for TTLL6. The fragment of cDNA initially amplified for the 3' end of the TTLL6 UTR lacked a stop codon in the translational frame, suggesting that the cDNA template was truncated. The protein prediction TTLL6A produced by the TIGR gene finder software indicated that the coding region extends for another 286 codons. Using a primer walking strategy with a pool of cDNA we subsequently mapped the end of TTLL6A transcribed region at a more downstream position, consistent with the TIGR prediction.

The TTL domains of each predicted protein sequence were identified manually using highly conserved peptide motifs and a preliminary alignment was done using Clustal X 1.82 program (Jeanmougin et al. (1998) *Trends Biochem Sci* 23, 403) followed by extensive manual adjustment using the Seaview program (Galtier et al., (1996) *Comput Appl Biosci* 12, 543). Phylogenetic analyses were performed using the Phylip version 3.6 package (Felsenstein, (1997) *Syst Biol* 46, 101) using the following programs. One hundred replicates of the sequence set were created using SEQBOOT. The distances were calculated using PROTDIST, trees were reconstructed using NEIGHBOR. The Jones-Taylor-Thorton (JTT) substitution model was used. A consensus tree was obtained using CONSENSE and the tree was plotted using DRAWGRAM.

Gene Knockout in *Tetrahymena*

A 1.9 kb 5' untranslated region immediately upstream of the TTLL1 coding region was amplified using the KOS 1 (5'-ATTTTATGAGCTCCACCATCTTTTATTTTGCTTT-3') (SEQ ID NO:1) and KOA1 (5'-TAAATAAGGATCCA-CACAAAATAGATAAAAAGGAG-3') (SEQ ID NO:2) primers. SacI and BamHI restriction sites were introduced at the ends of the above primer sequences, respectively. The PCR product was digested with BamHI and SacI and cloned into the p4T2-1 plasmid on one side of the neo2 cassette. A 1.6 kb fragment of the 3' UTR of TTLL1 containing a part of TTLL1 coding region was amplified using the TTL-K02-F (5'-ATTTTATATCGATTTGTT AAACCAGCATCACGA-3') (SEQ ID NO:3) and TTL-KO2-R (5'-TAAATAACTC-GAGAAAATTAAATGTCTGGCTGGAT-3') (SEQ ID NO:4) primers. The ClaI and XhoI restriction sites were introduced at the ends of the primers and used for subcloning into the other side of the neo2 cassette of p4T21. The resulting gene knockout targeting plasmid named pTTLL1-KO was digested with SacI and XhoI to release the disruption fragment of TTLL1::neo2 from the plasmid backbone. The germline disruption of the TTLL1 gene was done by biolistic bombardment and the knockout heterokaryons were constructed as described in Cassidy-Hanley et al. (*Genetics* 146, 135 (1997)). Cells homozygous for the TTLL1 deletion were obtained by a cross of two TTLL1 knockout heterokaryons (Hai et al. (2000) *Methods Cell Biol* 62, 513).

Expression and Localization of GFP Fusion Proteins in *Tetrahymena*

The pMTT1-GFP-N vector suitable for expression of coding regions with an N-terminal GFP tag under control of the MTT1 promoter was constructed on the basis of the pMTT1-IFT52-GFP plasmid (Brown et al. (2003) *Mol Biol Cell* 14, 3192). The coding region of IFT52 of this plasmid was replaced by the coding region of GFP (Haddad et al. (1997) *Proc Natl Acad Sci USA* 94, 10675) using a forward primer with a HindIII site and a reverse primer with MluI-BamHI sites (and a TGA stop codon between these two sites). Subcloning a coding region between the HindIII and BamHI sites of the resulting pMTT1-GFP-N provides a fragment which can be integrated into the BTU1 locus of *Tetrahymena* and the coding region can be expressed using the MTT1 promoter fragment in response to cadmium (Shang et al. (2002) *Proc Natl Acad Sci USA* 99, 3734). To overexpress TTLL1, the entire predicted coding region of TTLL1 gene was amplified from a total genomic DNA with addition of an MluI site to the forward primer and a BamHI site to the reverse primer and subcloned into pMTT1-GFP-N to create pMTT1-GFP-TTLL1. The same strategy was used to amplify the predicted coding region of TTLL6A to create pMTT1-GFP-TTLL6L plasmid, except that the reverse primer was designed to anchor at the position of 390 by downstream of the predicted TGA stop codon. Thus, after integration into the *Tetrahymena* genome, using the pMTT1-GFP-TTLL6L fragment, the TTLL6A coding region is probably expressed using the native 3' nontranscribed region. To create a plasmid for expression of the truncated version of Ttll6Ap gene product (Ttll6ApΔ$_{710}$-GFP), the coding region encompassing the amino acid codons 1-710 was amplified with MluI and BamHI sites added at the ends of the primers and subcloned into pMTT1-GFP-N to create pMTT1-GFP-TTLL6S. To produce a plasmid for expression of the ATPase deficient form of Ttll6ApΔ$_{710}$-GFP, we changed the predicted codon 422 from glutamic acid to glycine using the QuickChange site-directed mutagenesis kit (Stratagene) and obtained the plasmid named pTTLL6Δ-GFP.

For expression of GFP fusion proteins in *Tetrahymena*, we used the negative selection method based on targeting to the BTU1 locus (Gaertig et al. (1999) *Nat Biotechnol* 17, 462). All plasmids used for expression of GFP fusions had fragments of the BTU1 locus flanking sequences for homologous targeting. Following biolistic bombardment of starved CU522 cells, transformants with integrations into the BTU1 locus were selected with 20 μM paclitaxel and the presence of a transgene was confirmed by PCR using total genomic DNA. The expression of the transgene was induced by adding 2.5 μg/ml cadmium chloride to the medium and cells were analyzed microscopically or biochemically 2-4 hrs later.

Immunofluorescence and Microscopy

For immunofluorescence, cells were processed as described in Thazhath et al. (*Nat Cell Biol* 4, 256 (2002)) with modifications. Briefly, we hand-picked 50-100 cells using a pipette, washed cells by releasing into a drop of 10 mM Tris-HCl, pH 7.5 buffer on a cover slip. Cells were permeabilized on cover slips for 45-60 sec by exposure to 10 μl of 0.5% Triton-X100 in the PHEM buffer (Gaertig et al. (1992) *Protoplasma* 167, 74), followed by addition of 15 μl of 2% paraformaldehyde in the PHEM buffer. The fixed cells were air-dried and coverslips incubated for 10 min in the blocking solution (3% bovine serum albumin (BSA) in phosphate-buffered saline (PBS) with 0.1% Tween-20) and incubated for a few hours at room temperature (or overnight at 4° C.) in primary antibodies in PBS with 3% BSA and 10% normal goat serum. The following primary antibodies were used at the indicated dilutions: anti-GFP (1:100), and ID5 (1:10). The cover slips were washed 3 times for 5 min by immersion in PBS using small staining jars followed by incubation in the secondary antibodies diluted 1:100 for 1 hr at room temperature. After 3 washes cover slips were mounted as described in Gaertig et al. (*Protoplasma* 167, 74 (1992)). To visualize only Ttll6Ap-GFP fluorescence, cells were fixed as described above and analyzed directly. Images were collected using a Leica TCS SP2 Spectral Confocal Microscope with Coherent Ti: sapphire multiphoton laser (Mira Optima 900-F). Usually a series of optical sections was obtained and the top half of the sections was assembled into a composite image.

Figure 10:
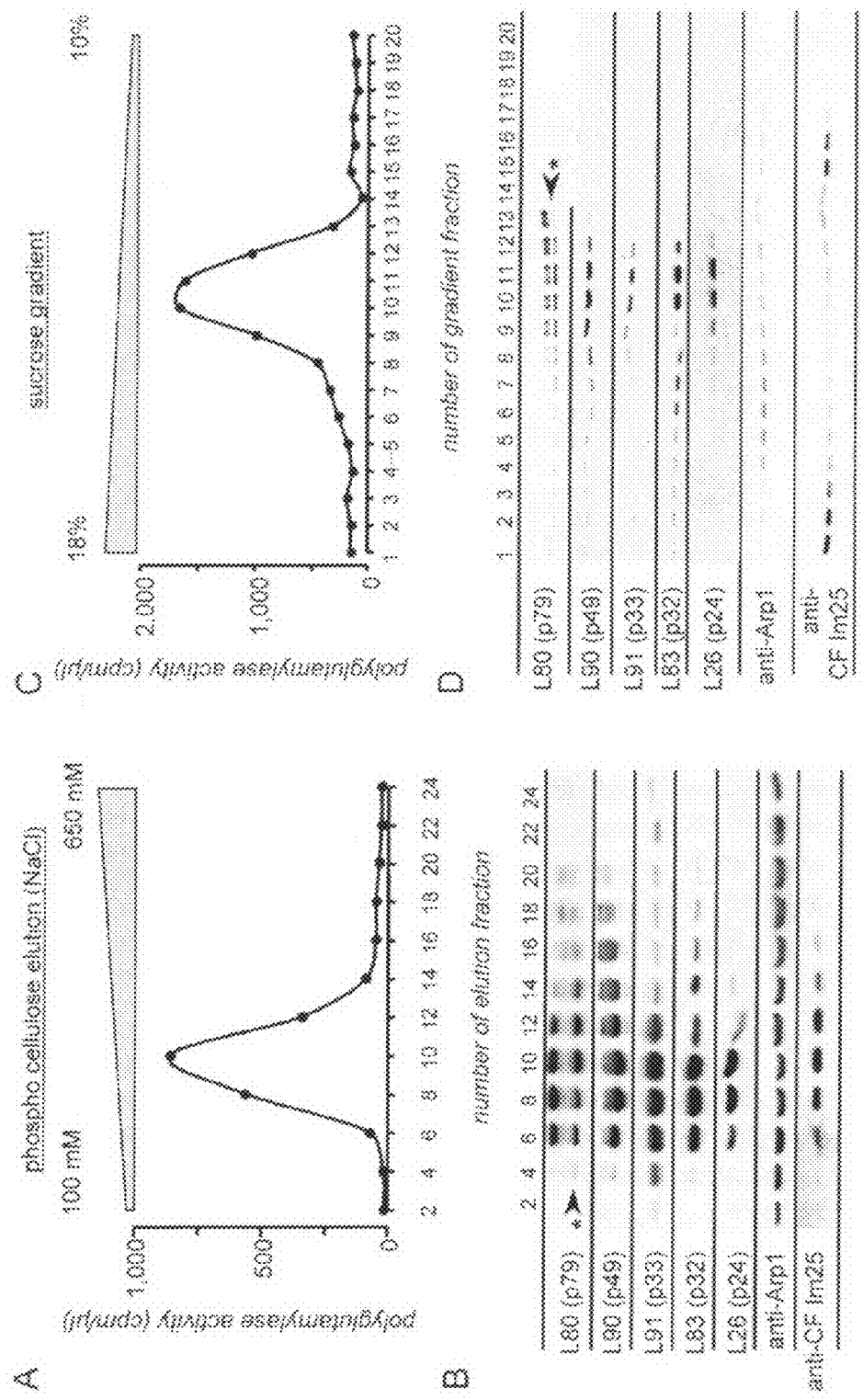
FIG. 10 shows co-purification of the glutamylase subunits and enzymatic activity.

FIG. 10 describes co-purification of the glutamylase subunits and enzymatic activity. Fractions of the two main purification steps of glutamylase from brain extract, phospho cellulose chromatography (A, B) and sucrose gradient centrifugation (C, D), are analyzed for glutamylase activity (A, C) and by western blot for the proteins p24, p32, p33, p49, p'79, Arp1 and CF Im25 (B, D). The five subunits p24 to p79 all eluted together with the peaks of enzymatic activity (A, C). CF Im25 and Arp1 show partial co-elution with glutamylase in the phospho cellulose step, but were mostly recovered in other fractions of the sucrose gradient. Note that L80 cross-reacts on western blots with another protein band of slightly higher apparent mass than p79, which is not immunoprecipitated (* the arrow points to the specific protein band for p79).

FIG. 11 shows a sequence profile alignment for TTLL1 modeling. The sequences of glutathione synthetase from *E. coli* (1GSA; SEQ ID NO:6) and TTLL1 from mouse (mT-TLL1; SEQ ID NO:7) have been aligned. The elements of the secondary structure, α-helices (turquoise arrows) and β-sheets (violet boxes), are shown above the alignment. Amino acids in lower case (mTTLL1) stand for regions that were not modeled. Red numbers indicate the beginning of four sub-domains: (1) N-terminal substrate-binding domain, (2) part 1 and (3) part 2 of the ATP-binding domain and (4) the C-terminal region. Residues that interact with ATP and Mg$^{2+}$ are in bold letters and the corresponding domains are outlined in yellow. All residues of the active site that are conserved with other ATP-dependent carboxylate-amine ligases are written in dark green (see FIG. 6C). Residues located in the proximity of the substrates are outlined in green. The E326 residue (mTTLL1) indicated by an arrowhead corresponds to the matched E422 residue of Ttll6Ap that has been mutated in Ttll6ApΔ$_{710}$-E422G.

FIG. 12 presents a phylogenetic analysis of predicted protein gene sequences containing a TTL domain. The TTL domains of each predicted protein sequence were aligned was using Clustal X 1.82 followed by manual adjustment in Sea-View. Phylogenetic analyses were performed using the Phylip version 3.6 package. One hundred replicates of the sequence set were created using SEQBOOT. The distances were calculated using PROTDIST, and trees were constructed using NEIGHBOR. The Jones-Taylor-Thorton (JTT) substitution model was used. A single consensus tree was obtained using CONSENSE. The yeast sequence was used as an outgroup. *Tetrahymena* has an extraordinarily large number of predicted TTL domain genes (50). Only one paralog of *Tetrahymena* is shown in each orthologous group and the number of additional paralogs is indicated in parentheses. The following are GenBank accession numbers of predicted protein sequences used in the analysis. Some sequences are not yet deposited in GenBank including some of the *Trypanosoma brucei* genes (whose sequences were derived from TIGR annotations) and most *Tetrahymena* sequences (also derived from the genomic sequences identified using the TIGR *Tetrahymena* blast server. *Homo sapiens*: TTL (Q8NG68), TTLL1 (NP_036395), TTLL2 (AAH30650), TTLL3 (T12515), TTLL4 (NP_055455), TTLL5 (NP_05587), TTLL6 (BACO5032), TTLL7 (AAH60878), TTLL8 (XP_104657), TTLL9 (XP_092778), TTLL10 (BAC85781), TTLL11 (AAM81328), TTLL12 (AAH01070), TTLL13 (XP_496092). Drosophila melanogaster: CG32238 (NP_729025), CG31108 (NP_733081), CG16833 (NP_723643), CG16716 (NP_725916), CG11201 (NP_609068), CG11323 (NP_609069), CG8918 (NP_573197), CG5987 (NP_651549), CG4089 (NP_650021), CG3964 (NP_722946), CG1550 (NP_610325), *Saccharomyces cerevisiae*: Ybr094wp (NP_009652.1). *Arabidopsis thaliana*: Atlg77550 (NP_177879.2). *Trypanosoma brucei*: Tb927.1.1550 (CAB95431), Tb927.2.5250 (XM_340623) Tb05.6E7.820 (TIGR annotation 314.m00409), Tb06.2N9.120 (TIGR 315.m00360) Tb03.5L5.580 (TIGR 312.m00548), Tb09.211.1170 (TIGR 320.m00798) Tb11.02.4640 (322.m00560), Tb10.61.3050 (TIGR 319.m01288) Tb11.02.0020 (322.m00126). *Caenorhabditis elegans*: F25C8 (part of the F25C8 cosmid, Sanger Institute, UK), C55A6.2 (NP_505918), ZK1128.6 (CAA87425), I-123L24.3 (AAL06035), K07C5.7 (CAA94900), D2013.9 (CAA87783). *Giardia lamblia*: GLP_43_54366_55577 (EAA40434), GLP_43_15991_17301 (EAA40412.1), GLP_618_12970_14472 (EAA38012.1), GLP_205_13412_15397 (EAA38969.1), GLP_223_2566_4779 (EAA37058.1), GLP_251_3885_7112 (EAA38326.1), GLP_203_36475_34136 (EAA39544.1).

The following are scaffold designations for the *Tetrahymena* TTLL gene sequences using the November 2003 assembly of the *Tetrahymena* macronuclear genome by TIGR: TTLL1 (8254582), TTLL2 (8254617), TTLL3A (8254579), TTLL3B (8254645), TTLL3C (8254670), TTLL3D (8254548), TTLL3E (8254652), TTLL4A (8254630), TTLL4B (8254717), TTLL4C (8254496), TTLL4D (8254359), TTLL4E (8254495), TTLL6A (8254600), TTLL6B (8254747), TTL6C (8254577), TTLL6D (8254607), TTLL6E (8254650), TTLL6F (8254010), TTLL9 (8254449), TTLL10A (8254580), TTLL10B (8254751), TTLL10C (8254034), TTLL10D (8254666), TTLL10E (8254504), TTLL10F (8254563), TTLL12A (8254576), TTLL12B (8254820), TTLL14A (8254487), TTLL14B (8254479), TTLL14C (8254589), TTLL14D (8254379), TTL14E (8254555), TTLL14F (8254814), TTLL14G (8253864), TTLL14H (8254469), TTLL14I (8254688), TTLL14J (8254798), TTLL14K (8254403), TTLL14L (8254823), TTLL14M (8254557), TTLL14N (8254748), TTLL14O (8254609), TTLL14P (8254819), TTL14Q (8254545), TTLL14R (8254737), TTLL14S (8254811), TTLL14T (8254373), TTLL15A (8254385), TTLL15B (8254460), TTLL15C (8254459).

FIG. 13 shows a multiple sequence alignment of TTL domains (SEQ ID NOs:8-65) of TTL and TTLL proteins. This alignment was used to construct the tree shown in FIGS. 8 and 12. Regions with low homology were not included in the alignment. Shaded regions indicate either amino acid identity or amino acid similarity (Clustal X alignment was colored with BoxShade and is available on the world wide web at ch.embnet.org/software/BOX_form.html). At: *Arabidopsis thaliana*, Ce: *Caenorhabditis elegans*, Dm: *Drosophila melanogaster*, Gl: *Giardia lamblia*, Hs: *Homo sapiens*, Sc: *Saccharomyces cerevisiae*, Tb: *Trypanosoma brucei*, Tt: *Tetrahymena thermophila*. TTL domains represented in FIG. 13 are *Homo sapiens*: TTL (SEQ ID NO:31), TTLL1 (SEQ ID NO:10), TTLL2 (SEQ ID NO:44), TTLL3 (SEQ ID NO:33), TTLL4 (SEQ ID NO:25), TTLL5 (SEQ ID NO:43), TTLL6 (SEQ ID NO:22), TTLL7 (SEQ ID NO:45), TTLL8 (SEQ ID NO:32), TTLL9 (SEQ ID NO:15), TTLL10 (SEQ ID NO:57), TTLL11 (SEQ ID NO:53), TTLL12 (SEQ ID NO:37), TTLL13 (SEQ ID NO:63); *Drosophila melanogaster*: CG32238 (SEQ ID NO:9), CG31108 (SEQ ID NO:41), CG16833 (SEQ ID NO:26), CG16716 (SEQ ID NO:20), CG11201 (SEQ ID NO:49), CG11323 (SEQ ID NO:39), CG8918 (SEQ ID NO:11), CG5987 (SEQ ID NO:21), CG4089 (SEQ ID NO:56), CG3964 (SEQ ID NO:27), CG1550 (SEQ ID NO:36); *Saccharomyces cerevisiae*: Ybr094wp (SEQ ID NO:62); *Arabidopsis thaliana*: Atlg77550 (SEQ ID NO:64); *Trypanosoma brucei*: Tb927.1.1550 (SEQ ID NO:50), Tb927.2.5250 (SEQ ID NO:30), Tb05.6E7.820 (SEQ ID NO:13), Tb06.2N9.120 (SEQ ID NO:51), Tb03.5L5.580 (SEQ ID NO:48), Tb09.211.1170 (SEQ ID NO:58), Tb11.02.4640 (SEQ ID NO:59), Tb10.61.3050 (SEQ ID NO:60), Tb11.02.0020 (SEQ ID NO:61); *Caenorhabditis elegans*: F25C8 (SEQ ID NO:16), C55A6.2 (SEQ ID NO:42), ZK1128.6 (SEQ ID NO:24), H23L24.3 (SEQ ID NO:52), K07C5.7 (SEQ ID NO:65), D2013.9 (SEQ ID NO:38); *Giardia lamblia*: EAA40434 (SEQ ID NO:12), EAA40412.1 (SEQ ID NO:17), EAA38012.1 (SEQ ID NO:19), EAA38969.1 (SEQ ID NO:54); *Tetrahymena*: TTLL1 (SEQ ID NO:8), TTLL2 (SEQ ID NO:46), TTLL3B (SEQ ID NO:55), TTLL4A (SEQ ID NO:23), TTLL6A (SEQ ID NO:18), TTLL6E (SEQ ID NO:40), TTLL9 (SEQ ID NO:14), TTLL10A (SEQ ID NO:34), TTLL12A (SEQ ID NO:35), TTLL14A (SEQ ID NO:28), TTLL14H (SEQ ID NO:29), TTLL1 SC (SEQ ID NO:47). Amino acid sequences within a conserved region located within the ATP-binding region and in close proximity to a substrate include subsequences NHFPGMFSLARK (SEQ ID NO:66) from *T. thermophila* Ttll6Ap and NHFPNHYELTRK (SEQ ID NO:67) from *T. thermophila* Ttll1 at amino acid positions 58-69 in FIG. 13A. A generic subsequence showing highly conserved amino acids, based on SEQ ID NO:67 from TtTtll1 as the reference subsequence, is NHFPXXXXLXRK (SEQ ID NO:68).

Figure 14:
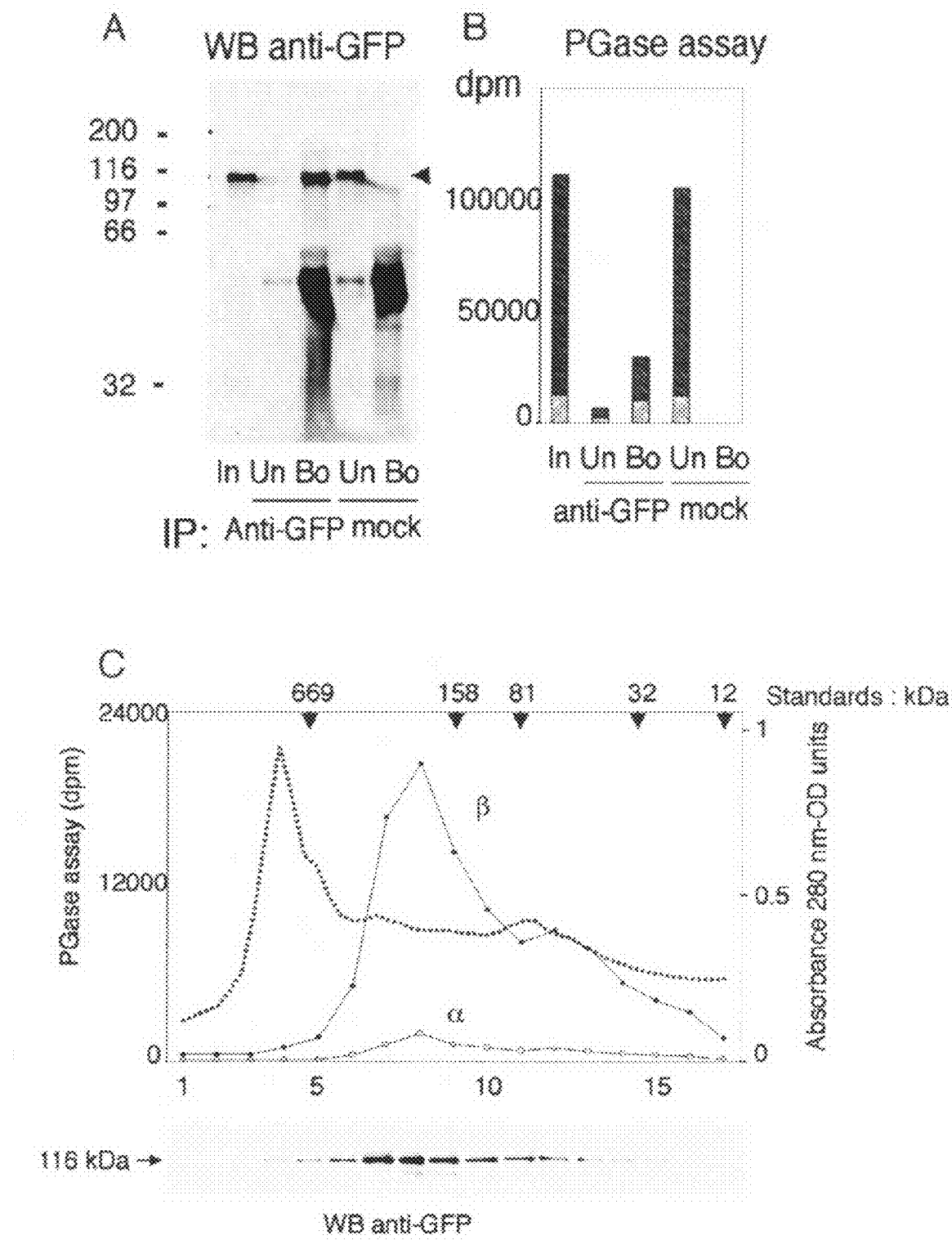
FIG. 14 shows glutamylation activity of Ttll6Ap in vitro.

FIG. 14 shows glutamylation activity of Ttll6Ap in vitro. Glutamylase activity co-purified with Ttll6ApΔ$_{710}$-GFP protein under all conditions tested, including immunoprecipitation (A, B), phosphocellulose (results not shown) and size exclusion chromatography (C). A-B. Soluble extracts of Ttll6ApΔ$_{710}$-GFP expressing cells were submitted to immunoprecipitation with anti-GFP antibodies or unrelated rabbit antibodies (mock). The input (In) as well as the unbound (Un) and bound (Bo) fractions were analyzed by western blot with anti-GFP antibody (A) and assayed for tubulin glutamylase activity (B). Equal proportions of input, unbound and bead fractions were analyzed by western blotting, while 10 times more bead fraction was assayed for glutamylase activity. C. Size exclusion chromatography using a soluble fraction of cells expressing Ttll6ApΔ$_{710}$-GFP. A soluble extract (4 mg of protein) of induced Ttll6ApΔ$_{710}$-GFP expressing cells was fractionated on an HPLC TSK column. Each fraction was analyzed by western blotting with anti-GFP antibodies (lower panel) and assayed for tubulin glutamylase activity using adult brain MTs as substrate (radioactive glutamate concentration 5 μM). The results are expressed as dpm incorporated into α- (open circles) and β-tubulin (filled circle). The absorbance profile at 280 nm is shown (dashed line). Arrowheads indicated the elution peak position of standard proteins used for calibration. The enzymatic activity and Ttll6ApΔ$_{710}$-GFP co-eluted in a peak of 180 kDa, while the expected size of Ttll6ApΔ$_{710}$-GFP is 116 kDa. It is possible that the Ttll6ApΔ$_{710}$-GFP is a homodimer, especially because the N-terminal region of the predicted peptide sequence contains a coiled-coil region.

TABLE I

Identification of all proteins precipitated with mAb 206 (see FIG. 5A).

| spot N[a)] | identified protein[b)] | Genebank accession N[b)] | recovered sequence[b)] | MASCOT score[b)] | protein identity |
|---|---|---|---|---|---|
| p79[c)] | D430025H09Rik protein | 16741525 | 26% | 622 | p79/PGs4 |
| 1 | nicolin 1[d)] | 13384852 | 42% | 315 | p24/PGs5 |
| 2 | nicolin 1[d)] | 13384852 | 48% | 404 | p24/PGs5 |
| 3 | cleavage and polyadenylation specific factor 5, 25 kD subunit | 13386106 | 23% | 190 | CF Im25 (Ruegsegger et al., Mol Cell 1, 243 (1998)) |
| 3 | complement component 1, q subcomponent, gamma polypeptide | 6671652 | 33% | 236 | non-specific |
| 4 | chain A, IgG2a Fab fragment | 640171 | 15% | 198 | non-specific |
| 5 | gene trap ROSA b-geo 22 | 22507341 | 32% | 496 | p32/PGs1 |
| 6 | gene trap ROSA b-geo 22 | 22507341 | 34% | 496 | p32/PGs1 |
| 7 | gene trap ROSA b-geo 22 | 22507341 | 57% | 607 | p32/PGs1 |
| 8 | gene trap ROSA b-geo 22 | 22507341 | 38% | 572 | p32/PGs1 |
| 9 | RIKEN cDNA 5730494M16 | 25029762 | 43% | 384 | p33/PGs2 |
| 10 | ARP1 actin-related protein 1 homolog A, centractin alpha | 5031569 | 20% | 287 | Arp1 (Holleran et al., J Cell Biol 135, 1815 (1996); Schafer et al., J Cell Biol 126, 403 (1994)) |
| 11 | tubulin tyrosine ligase-like 1 | 30725861 | 18% | 321 | p49/PGs3 |
| 12 | tubulin tyrosine ligase-like 1 | 30725861 | 30% | 428 | p49/PGs3 |
| 13 | tubulin tyrosine ligase-like 1 | 30725862 | 45% | 531 | p49/PGs3 |
| 14 | similar to Ig gamma-2B chain C region secreted form | 28523035 | 35% | 156 | non-specific |
| 14 | fibrinogen, B beta polypeptide | 20872398 | 44% | 665 | non-specific |
| 15 | immunoglobulin heavy chain constant region | 14091948 | 21% | 198 | non-specific |
| 15 | fibrinogen, B beta polypeptide | 20872398 | 30% | 552 | non-specific |
| 16 | chaperonin subunit 8 (theta) | 6753328 | 43% | 1110 | TRIC component (Lopez-Fanarraga et al., J Struct Biol 135, 219 (2001); Leroux et al., Curr Biol 10, R260 (2000)) |
| 17 | chaperonin containing TCP-1 theta subunit | 5295992 | 23% | 531 | TRIC component (Lopez-Fanarraga et al., J Struct Biol 135, 219 (2001); Leroux et al., Curr Biol 10, R260 (2000)) |
| 18 | chaperonin subunit 5 (epsilon) | 6671702 | 10% | 225 | TRIC component (Lopez-Fanarraga et al., J Struct Biol 135, 219 (2001); Leroux et al., Curr Biol 10, R260 (2000)) |
| 19 | keratin 1 | 17318569 | 25% | 620 | contamination |
| 20 | matricin | 631730 | 30% | 640 | TRIC component (Lopez-Fanarraga et al., J Struct Biol 135, 219 (2001); Leroux et al., Curr Biol 10, R260 (2000)) |
| 21 | chaperonin subunit 6a (zeta); chaperonin containing TCP-1 | 6753324 | 25% | 678 | TRIC component (Lopez-Fanarraga et al., J Struct Biol 135, 219 (2001); Leroux et al., Curr Biol 10, R260 (2000)) |
| 22 | chaperonin subunit 6a (zeta); chaperonin containing TCP-1 | 6753324 | 27% | 594 | TRIC component (Lopez-Fanarraga et al., J Struct Biol 135, 219 (2001); Leroux et al., Curr Biol 10, R260 (2000)) |

[a)] numbering according to excised spots from 2D-gel, FIG. 5A.
[b)] obtained with: MASCOT Matrix science, available on the world wide web at matrixscience.com.
[c)] identified from one-dimensional SDS-PAGE as shown in FIG. 6A (C. Regnard et al., J Cell Sci\ 116, 4181 (2003)).
[d)] protein of unknown function named nicolin (Backofen et al., Eur J Biochem 269, 5240 (2002)).

Example II

Biological Assay for Glutamylase Inhibition

The invention provides a phenotype-based assay for inhibitors of tubulin glutamylation. The assay is a biological assay; that is, it is performed in a host cell, preferably *Tetrahymena*. It is also referred to herein as an "in vivo" assay or "Assay I."

Overproduction of the truncated Ttll6Ap-GFP under cadmium-inducible promoter (at 2.5 µg/ml $CdCl_2$) caused a tight arrest in cell multiplication of *Tetrahymena*. Decreasing the concentration of cadmium allowed for more growth while increasing it two-fold was lethal within 18 hours. Thus, the extent of growth inhibition by Ttll6Ap is dependent on its intracellular concentration (which in turn is dependent on cadmium concentration). The presence of a compound which inhibits Ttll6Ap activity should partly or completely rescue the cell growth arrest. A preferred embodiment of the in vivo assay is outlined in FIG. 3 (left panel). The assay involves adding $CdCl_2$ to *Tetrahymena* cells in which Ttll6Ap expression is controlled by the cadmium-dependent microtubule T1 promoter, distributing cells into wells with compounds, incubating for a time required for uninhibited cells to grow, and reading a fluorescent signal that reflects cell density. Previous studies have established that there is an approximately linear response in the level of protein production using the microtubuleT1 promoter within the range of 0.25-5 µg/ml of $CdCl_2$ (Shang et al. (2002). Proc Natl Acad Sci 99, 3734-3739). A range of cadmium concentrations is used to create a spectrum of target/inhibitor ratios.

Figure 4:
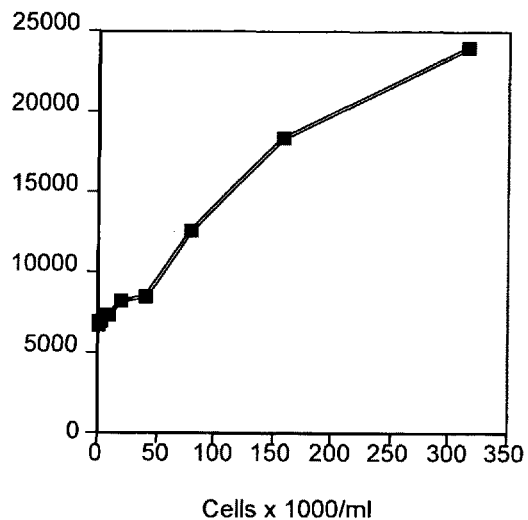
FIG. 4 shows fluorescence intensity as a function of *Tetrahymena* cell concentration; cells with MTT1-driven GFP, 100 μl/well, 96 well black plastic optical bottom plates, 485/530 nm.

The in vivo assay can be optimized as follows:

1) A strain with a red fluorescent protein (RFP) reporter is constructed so that cell density can be determined instantly using plate reader (e.g., BMG Fluorostar Optima reader). Fluorescence is beneficial over alternative readout types because there is no need to add detection substrates. In a pilot experiment and without any optimization we were able to detect a signal in living highly mobile GFP-expressing *Tetrahymena* cells above 10,000 cells/ml (FIG. 4). A simultaneous quantification of RFP and Ttll6Ap-GFP will help in sorting the primary hits. First, a strain that has RFP coding region stably integrated under a strong promoter whose activity is known to reflect cell proliferation (nonessential histone locus HHT1) is constructed. Next, a microtubuleT1-driven Ttll6Ap-GFP transgene is introduced into the nonessential BTU1 locus using a negative selection method (Gaertig et al. (1999) Nat. Biotech. 17, 462-465; U.S. Pat. No. 6,846,481, issued Jan. 25, 2005). As a control, a similar strain containing a version of Ttll6Ap that is inactive due to a mutation in the ATP-binding site (RFP, Ttll6Ap-G422-GFP) is prepared. The simultaneous use of this strain is valuable as a counterscreen for unrelated growth stimulators and compounds that are highly toxic. Our data indicate that Ttll6Ap-overproducing cells upon induction with 2.5 µg/ml $CdCl_2$ at density of ~104 cells/ml divide only once and do not proliferate for at least 12 hrs while controls undergo between 4-5 doublings (Janke et al. (2005) Science 308, 1758-1762 (see Example I)). Thus, the signal to noise ratio could theoretically be ~20 but the signal could be amplified by RFP fluorescence.

2) Assay conditions can be established for the following parameters:

a) Cadmium concentration and exposure time. An important aspect is the titration of potential inhibitory compounds. As discussed, the presence of a compound at a concentration that depletes the overproduced enzyme should promote cell growth. However, a relevant compound is likely to inhibit cell growth at its higher concentration that also depletes the endogenous glutamylases. This will especially be the case of potential broad specificity inhibitors that affect both TTLL6 and TTLL1 type glutamylases β-tubulin and α-tubulin preferring, respectively). The issue of titration could be dealt with by using compounds in several different concentrations as it is done routinely in HTS. Alternatively, Ttll6Ap can be induced at several levels by varying the cadmium concentration. This could lower the cost of screened compounds especially if the assay volume can also be reduced (see below). Using 96-well plates, the most optimal range of $CdCl_2$ concentration to produce the desired signal/noise ratio can be determined. Three concentrations can be chosen: 1) the lowest, 2) mid-range and 3) highest concentration of $CdCl_2$ that inhibit the multiplication of RFP, Ttll6Ap-GFP cells for a period sufficient to give a signal/noise ratio above 5. If needed, the exposure time can be increased to allow uninhibited cells to produce stronger readout signal.

b) Cell concentration. The lower the initial cell concentration, the lower the background but potentially longer time of incubation may be needed to produce a sufficiently strong signal.

c) Assay volume. The smaller the volume, the smaller the required quantities of screened chemicals. Furthermore, *Tetrahymena* cells grow faster and to higher densities in smaller drops due to increase aeration, which may increase the signal/noise ratio.

d) DMSO. DMSO is commonly used as a solvent for compounds. Published data indicate that *Tetrahymena* tolerates well DMSO at up to 2.5% (Nilsson et al. (1974) J Cell Sci 16, 39-47.

e) Assay sensitivity. Assay sensitivity can be evaluated by running assays on plates and including control wells with a series of $CdCl_2$ concentrations that are progressively lower. Lowering the cadmium concentration will mimic the Ttll6Ap activity-depleting action of an inhibitory compound. The actual effect of lowering $CdCl_2$ on the level of Ttll6Ap-GFP can be evaluated quantitatively by western blotting (using purified Ttll6Ap as a standard). Thus, we can determine the minimal depletion in the Ttll6Ap activity that can be detected using our assay.

If this assay is used as a primary screen, two secondary screens for hit validation can be used: 1) immunofluorescence and western blotting of compound-treated cells with anti-glutamylation antibodies will determine whether the compound affects the level and pattern of tubulin glutamylation; microscopic observations of treated cells will also determine whether the compound's action gives phenotypic changes that are consistent with deficiency in tubulin, and 2) an in vitro assay with purified enzyme will determine whether the compound directly inhibits the glutamylase enzyme activity. Further assays can be used to determine whether the enzyme is a broad or selective inhibitor and whether it can act on mammalian enzymes.

Example III

Cell-Free Assay for Glutamylase Inhibition

The assay is an "in vitro" assay; that is, it is performed in a cell-free environment. The in vitro assay is referred to herein as "Assay II." An in vitro assay is useful for hit validation (secondary screen) or possibly also as a primary high throughput screen. Assay for the purpose of a secondary screen is described first. The in vivo screen described (Assay I) could identify a large number of compounds. Several mechanisms could give a positive readout: 1) direct inhibition of glutamylases, 2) inhibition of an activator of glutamylases, 3) inhibition of an effector of microtubule glutamylation, 4) stimulation of a tubulin deglutamylase (there is evidence that reverse enzymes exist (Audebert et al. (1993) Mol. Biol. Cell 4, 615-626), 5) inhibition of expression by the MTT1 promoter, 6) growth stimulation by unrelated mechanisms, 7) intrinsic fluorescence of a compound. If we simultaneously read the RFP and GFP signals, we should eliminate compounds which affect the MTT1-driven expression. Compounds that promote growth non-specifically will show an increase in RFP signal in the counterscreen with cells expression inactive glutamylase. Compounds with intrinsic fluorescence will increase signal in the counterscreen as well. Compounds of type 1) (direct inhibitors) can be identified using an in vitro reaction with a purified Ttll6Ap. A reliable in vitro assay has been established for Ttll6Ap using a crude or purified Ttll6Ap, taxol-stabilized brain microtubules, ATP, and tritiated glutamic acid (Janke et al. (2005) Science 308, 1758-1762 (see Example I)). Following the reaction in vitro, products are separated by 1D SDS-PAGE, blotted onto nitrocellulose and the level of incorporation of tritiated E into $\alpha$- and $\beta$-tubulin is determined for excised bands using liquid scintillation counting. A fairly large number of compounds can be readily screened with a crude cytosolic assay. While this will eliminate some compounds, a relatively pure enzyme will be needed to identify compounds that are direct inhibitors (although compounds that are in categories 2-4 are also of great interest in long-term). Ttll6Ap has been partially purified from cytosol of overproducing cells by a phosphocellulose chromatography and gel filtration (Janke et al. (2005) Science 308, 1758-1762 (see Example I)). An alternative method for purifying the enzyme is possible using a modification of the tandem affinity purification (TAP) method (O'Connor et al. (2005) J Biol Chem 280, 17533-17539, Prathapam et al. (2005) Nat Struct Mol Biol 12, 252-257). The batch-purified enzyme can be used for validation of primary hit compounds using our established (radioactive) assay. The assay is time-consuming (1 day) but highly reliable and suitable as a validation screen.

Because TTLL6Ap is an ATPase, another assay is possible based on the production of ATP-dependent luminescence by luciferase with luciferin substrate. This assay measures the amount of ATP left after the reaction with an ATP consuming-enzyme and the level of luminescence is inversely proportional to the measured enzyme activity. The assay is widely used with kinases and has been used with other ATPases such as myosin (Cheung et al. (2002) Nat Cell Biol 4, 83-88). The assay is shown in in FIG. 3 (right panel). The ATP concentration is first optimized using a standard assay with radiolabelled glutamate. Next, a relatively low ATP concentration (micromolar range) is used, under which the reaction is still robust, to determine the timing of the reaction under which most of ATP is depleted by the activity of the TTLL6Ap. Once these conditions are established, the reaction is performed at 95% of ATP hydrolysis with luciferin and luciferase, and the luminescence signal is measured using the Lmax luminescence plate reader. The reliability and sensitivity of this assay can be determined by running test reactions in the presence of tritiated glutamic acid and analyzing products by both luminescence and liquid scintillation counting. Many parameters of the assay can be optimized, including the enzyme and substrates concentration, pH, Mg2+ concentration. One modification which could substantially lower the cost of high throughput screening is the potential use of ciliary axonemes as a microtubule substrate, in place of standard taxol-stabilized brain microtubules. Tetrahymena microtubules are certainly a formidable substrate in vivo (FIG. 2) and ciliary microtubules can be easily purified at extremely low cost. The assay sensitivity to inhibitors can be determined by using different ratios of ATP and nonhydrolyzable analog, AMP-PNP.

If the in vitro assay (Assay II) is used as a primary screen, the following secondary screens can be used for validation: 1) an in vitro activity assay with purified enzyme and tritiated glutamate; 2) immunofluorescence and western blotting of treated cells with anti-glutamylation antibodies to determine whether the compound affects the level of tubulin glutamylation in vivo (and causes anticipated types of phenotypic changes) which would indicate that it can penetrate the plasma membrane. Finally, using an overexpression in vivo assay (Assay I) we can determine whether the compound inhibition can be relieved by mild overproduction of Ttll6Ap.

Example IV

Hyperglutamylation of Tubulin Can either Stabilize or Destabilize Microtubules in the Same Cell In most eukaryotic cells, tubulin is subjected to posttranslational glutamylation, a conserved modification of unclear function. The glutamyl side chains form as branches of the primary sequence glutamic acids in two biochemically distinct steps: initiation and elongation. The length of the glutamyl side chain is spatially controlled and microtubule type specific. In this example, we probe the significance of the glutamyl side chain length regulation in vivo by overexpressing a potent side chain elongase enzyme, Ttll6Ap, in Tetrahymena. Overexpression of Ttll6Ap caused hyperelongation of glutamyl side chains on the tubulin of axonemal, cortical, and cytoplasmic microtubules. Strikingly, in the same cell, hyperelongation of glutamyl side chains stabilized cytoplasmic microtubules and destabilized axonemal microtubules. Our observations suggest that the cellular outcomes of glutamylation are mediated by spatially restricted tubulin interactors of diverse nature.

Microtubules are dynamic elements of the cytoskeleton that are assembled from heterodimers of $\alpha$- and $\beta$-tubulin. Once assembled, tubulin subunits undergo several conserved posttranslational modifications (PTMs) that diversify the external and luminal surfaces of microtubules (Verhey and Gaertig. 2007. Cell Cycle 6:2152-2160). Two tubulin PTMs, glycylation and glutamylation, collectively known as polymodifications, form peptide side chains that are attached to the $\gamma$-carboxyl groups of glutamic acids in the primary sequence of the C-terminal tails (CTTs) of $\alpha$- and $\beta$-tubulin (Eddé et al., 1990. Science 247:83-85; Redeker et al., 1994. Science 266:1688-1691). Glutamylated microtubules are abundant in projections of neurons (Eddé et al., 1990. Science 247:83-85), axonemes (Bré et al., 1994. Cell Motil. Cytoskeleton 27:337-349; Fouquet et al., 1994. Cell Motil. Cytoskeleton 27:49-58; Gagnon et al., 1996. J. Cell Sci. 109(Pt. 6):1545-1553), and centrioles/basal bodies (Bobinnec et al., 1998. Cell Motil. Cytoskeleton 39:223-232; Million et al., 1999. J. Cell Sci. 112(Pt. 23):4357-4366) and are detectable in the mitotic spindle and on a subset of cytoplasmic network microtubules (Abal et al., 2005. Biol. Cell 97:425-434; Bobinnec et al., 1998. Cell Motil. Cytoskeleton 39:223-232). The modifying enzymes, tubulin glutamic acid ligases (tubulin E-ligases), belong to the family of proteins related to the tubulin tyrosine ligase (TTL), known as TTL-like (TTLL) proteins (Janke et al., 2005. Science 308:1758-1762; van Dijk et al., 2007. Mol. Cell 26:437-448; Wloga et al., 2008. Eukaryot. Cell 7:1362-1372). Tubulin glutamylation appears to be important in vivo. A knockdown of the TTLL7 E-ligase mRNA in cultured neurons inhibits the outgrowth of neurites (Ikegami et al., 2006. J. Biol. Chem. 281:30707-30716). A loss of PGs1, a protein associated with TTLL1 E-ligase (Janke et al., 2005. Science 308:1758-1762; Regnard et al., 2003. J. Cell Sci. 116:4181-4190), disorganizes sperm axonemes in the mouse (Campbell et al., 2002. Genetics 162:307-320), and a morpholino knockdown of TTLL6 E-ligase expression in zebrafish inhibits the assembly of olfactory cilia (Pathak et al., 2007. Mol. Biol. Cell 18:4353-4364). The biochemical consequences of tubulin glutamylation in vivo are poorly understood, but the emerging model is that this PTM regulates interactions between microtubules and microtubule-associated proteins (MAPs) (Bonnet et al., 2001. J. Biol. Chem. 276:12839-12848; Boucher et al., 1994. Biochemistry 33:12471-12477; Ikegami et al., 2007. Proc. Natl. Acad. Sci. U. S. A. 104:3213-3218; Larcher et al., 1996. J. Biol. Chem. 271:22117-22124).

The ciliate *Tetrahymena thermophila* has 18 types of diverse microtubules that are all assembled in a single cell. Although most, if not all, of these microtubules are glutamylated, the length of glutamyl side chains is spatially regulated (Bré et al., 1994. Cell Motil. Cytoskeleton 27:337-349; Wloga et al., 2008. Eukaryot. Cell 7:1362-1372). Minimal side chains composed of a single glutamic acid (monoglutamylation) are present on the cytoplasmic and nuclear microtubules, whereas elongated side chains are present on the basal bodies and axonemes (Wloga et al., 2008. Eukaryot. Cell 7:1362-1372). In *Tetrahymena*, Ttll6Ap is a β-tubulin-preferring E-ligase (Janke et al., 2005. Science 308:1758-1762), with a strong if not exclusive, side chain elongating activity (van Dijk et al., 2007. Mol. Cell 26:437-448). Here, by overproducing Ttll6Ap in vivo, we explore the consequences of glutamyl side chain hyper-elongation. Unexpectedly, we show that in the same cells, hyperelongation of glutamyl side chains stabilizes cell body and destabilizes axonemal microtubules. The simplest explanation of these data is that, in vivo, the cellular outcomes of tubulin glutamylation are mediated by diverse microtubule type-specific MAPs. To our knowledge, we are first to report that excessive tubulin glutamylation can either stabilize or destabilize microtubules in the same cell.

Materials and Methods

Strains, culture, and green fluorescent protein (GFP) tagging. *Tetrahymena* cells were grown in the SPP medium (Gorovsky et al., 1975. Methods Cell Biol. 9:311-327) supplied with the antibiotic-antimycotic mix (Invitrogen, Carlsbad, Calif.). To overexpress Ttll6Ap variants tagged at the N terminus with GFP, fragments of the coding region of TTLL6A were amplified with addition of MluI and BamHI sites at the 5' and 3' ends, respectively, and cloned into pMTT1-GFP plasmid (Wloga et al., 2006. Mol. Biol. Cell 17:2799-2810). The primers are listed in Table 2. The transgenic strains were constructed and induced as described previously (Janke et al., 2005. Science 308:1758-1762; Wloga et al., 2008. Eukaryot. Cell 7:1362-1372).

TABLE 2

Primers used for overexpression plasmids.

| Name | Sequence | Seq ID |
|---|---|---|
| Tt116A-forward | 5' AATAAACGCGTCATGTCATAGAAAGATATATAT 3' | 69 |
| Tt116A-M241-forward | 5' AATAAACGCGTCATG-GATAATAAATAAAGTGATATA 3' | 70 |
| Tt116A-A327-forward | 5' ATATACGCGTCGCCTAGTTGTTAAAAAAAAG 3' | 71 |
| Tt116A-E337-forward | 5' AATAAACGCGTCGAGTAGGCAAAGAAGCAATAAG 3' | 72 |
| Tt116A-R712-forward | 5' AATTACGCGTCAGAGTTTTGACTGGTAAAAAGTG 3' | 73 |
| Tt116A-1781-forward | 5' TTTAAACGCGTCATTAGAAGAAATA-CAAAAAGGTC 3' | 74 |
| Tt116A-R924-forward | 5' AATTACGCGTCAGAGTAGCAATAGGAGTCAAAAG 3' | 75 |
| Tt116A-reverse | 5' ATATAGGATCCATACATACATACATCCATTCA 3' | 76 |
| Tt116A-K1116-reverse | 5' TTTATGGATCCTCACTTTATTGTCACTCGTTTATC 3' | 77 |
| Tt116A-V929-reverse | 5' TTATTGGATCCTTGACTCCTATTGCTACTCTG 3' | 78 |
| Tt116A-Q828-reverse | 5' AATTGGATCCTCAAGTCTAAGAATTAGGCTT 3' | 79 |
| Tt116A-E725-reverse | 5' TTTATGGATCCTCATTCTTCAGGTGTGTACTTC 3' | 80 |

Immunofluorescence and electron microscopy. GFP-Ttll6Ap-expressing cells were grown in SPP with 0.5 to 2.5 µg of $CdCl_2$/ml for 2 to 4 h. For GFP-Ttll6Ap localization, a 10-µl drop of cells was placed on a coverslip, followed by the addition of 20 µl of 2% paraformaldehyde in PHEM buffer (Schliwa and van Blerkom. 1981. J. Cell Biol. 90:222-235) and, after 20 s, the addition of 10 µl of 0.5% Triton X-100 in PHEM. The cells were subjected to immunofluorescence (Janke et al., 2005. Science 308:1758-1762) with the following primary antibodies: 12G10, an anti-α-tubulin monoclonal antibody (MAb) (Jerka-Dziadosz et al., 1995. Dev. Biol. 169: 644-661) at 1:50; MAb ID5 (40), which in *Tetrahymena* is specific to polyglutamylated tubulin (Wloga et al., 2008. Eukaryot. Cell 7:1362-1372), at 1:50; poly(E) antipolyglutamic acid antibodies (1:100) (Shang et al., 2002. J. Cell Biol. 158:1195-1206); TAP952, an anti-monoglycylated tubulin MAb (1:5,000) (Bré et al., 1998. Mol. Biol. Cell 9:2655-2665; Callen et al., 1994. Biol. Cell 81:95-119); and 6-11 B-1, an anti-acetyl-K40 α-tubulin MAb (1:200) (LeDizet and Piperno. 1991. Methods Enzymol. 196:264-274). The secondary goat antibodies were as follows: anti-mouse-FITC, anti-mouse-Cy3, anti-rabbit-Cy3, and anti-rabbit-Cy5 (Zymed) at 1:200 dilutions. Cells were viewed under either Leica TCS SP or Zeiss LSM 510 VIS/META confocal microscopes. To measure the length of the cilia, the cells were labeled with MAb 12G10, [and, in some experiments, double labeled with poly(E) antibodies]. Confocal images were recorded with a 0.8-µm distance between z-sections, and sets of two to four z-sections were merged. The lengths of the cilia were measured by using ImageJ 1.37. For transmission electron microscopy (TEM), the cells were prepared as described previously (Jerka-Dziadosz et al., 2001. Protist 152:53-67).

Figure 15:
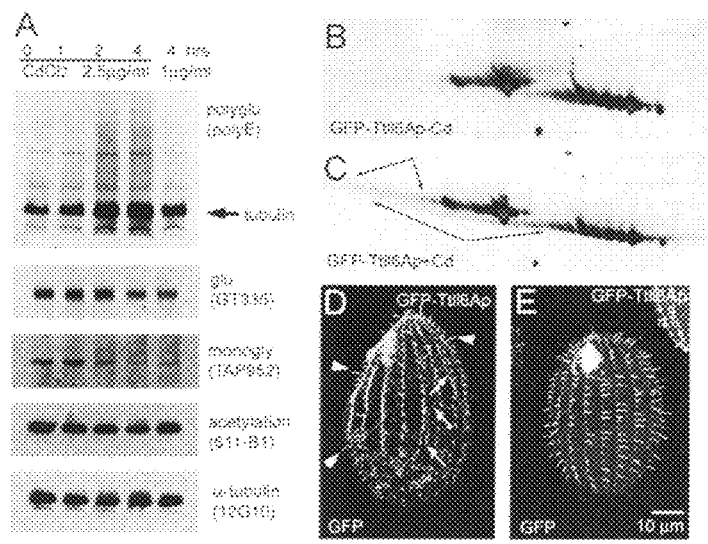
FIG. 15 shows overproduction of GFP-Ttll6Ap causes elongation of glutamyl side chains on tubulin in vivo. (A) Western blots of total proteins from GFP-Ttll6Ap-expressing cells that are either uninduced (0 h) or induced for 1, 2, or 4 h with either 1 or 2.5 μg of CdCl2/ml. (B and C) 2D silver-stained protein gels containing cytoskeletons of uninduced (B) or induced (C) GFP-Ttll6Ap cells. The arrows point at strings of highly acidic protein isoforms that appear at the mass level of the main spots of α- and β-tubulin upon induction of GFP-Ttll6Ap. (D to E) Confocal fluorescence images of the GFP signal in growing (D) and cilia regenerating (E) GFP-Ttll6Ap cells induced with 2.5 μg of CdCl$_2$/ml for 3 h. Note the increase of the signal of GFP-Ttll6Ap in short growing cilia (arrowheads) and on subcortical microtubules (arrows). Bar, 10 μm.

Western blots and 2D gels. For a two-dimensional (2D) separation of tubulin isoforms, cytoskeletons were prepared as described previously (Janke et al., 2005. Science 308: 1758-1762) from uninduced or induced GFP-Ttll6Ap-expressing cells and washed with the lysis buffer without Triton X-100. A 100-µg portion of the cytoskeletons (15 µl) was separated by isoelectric focusing on 18-cm Immobiline dry strips (4.5-5.5), followed by SDS-PAGE (10%) and silver staining. For Western blots, total extracts from 5 x $10^3$ cells were separated by SDS-8% PAGE (Janke et al., 2005. Science 308:1758-1762). The primary antibodies were used as follows at the indicated concentrations: 12G10 (1:10,000), poly (E) (1:2,000), GT335 anti-glutamylation MAb (1:1,000) (55), TAP952 (1:10,000), and 6-11 B-1 (1:10,000).
Results Overproduction of Ttll6Ap hyperelongates glutamyl side chains on axonemal and cell body microtubules. Ttll6Ap of *Tetrahymena* is a potent E-ligase (Janke et al., 2005. Science 308:1758-1762) with strong side chain-elongating activity on β-tubulin (van Dijk et al., 2007. Mol. Cell 26:437-448). Here, we explore the consequences of deregulation of the glutamyl side chain length by overexpression of Ttll6Ap in *Tetrahymena*. We overexpressed Ttll6Ap as an N-terminal GFP fusion using the strong cadmium-dependent MTT1 promoter (Janke et al., 2005. Science 308:1758-1762; Shang et al., 2002. Proc. Natl. Acad. Sci. U. S. A. 99:3734-3739). A Western blot with the anti-polyglutamic acid antibody, poly(E), which recognizes elongated glutamyl side chains (>=3E), showed that overexpression of GFP-Ttll6Ap increased the levels of polyglutamylation of proteins in the tubulin size range, whereas the levels of other proteins recognized by the same antibody (likely glutamylated nontubulin proteins), remained unchanged (FIG. 15A). 2D SDS-PAGE showed that overproduction of GFPTtll6Ap led to appearance of strings of highly acidic isoforms migrating near the main spots of α- and β-tubulin (FIGS. 15B and C, arrows). The levels of tubulin glutamylation detected by GT335, an antibody that recognizes a glutamyl side chain of any length (Wolff et al., 1992. Eur. J. Cell Biol. 59:425-432), were unchanged or slightly lower in overexpressing cells (FIG. 15A). Thus, in vivo, overexpressed Ttll6Ap appears to have primarily a side chain-elongating activity on tubulin.

GFP-Ttll6Ap localized mainly to a subset of short, most likely assembling cilia (see FIGS. 16A and B [arrows]). Consistently, when GFP-Ttll6Ap was overproduced in cilium-regenerating cells, the transgenic protein was targeted to most if not all cilia (FIG. 15E). Overproduction of increased duration (or increased strength) resulted in colocalization of GFP-Ttll6Ap to subcortical and cytoplasmic microtubules (FIG. 15D, arrows), in addition to cilia (FIG. 15D, arrowheads) (Janke et al., 2005. Science 308:1758-1762).

Figure 17:
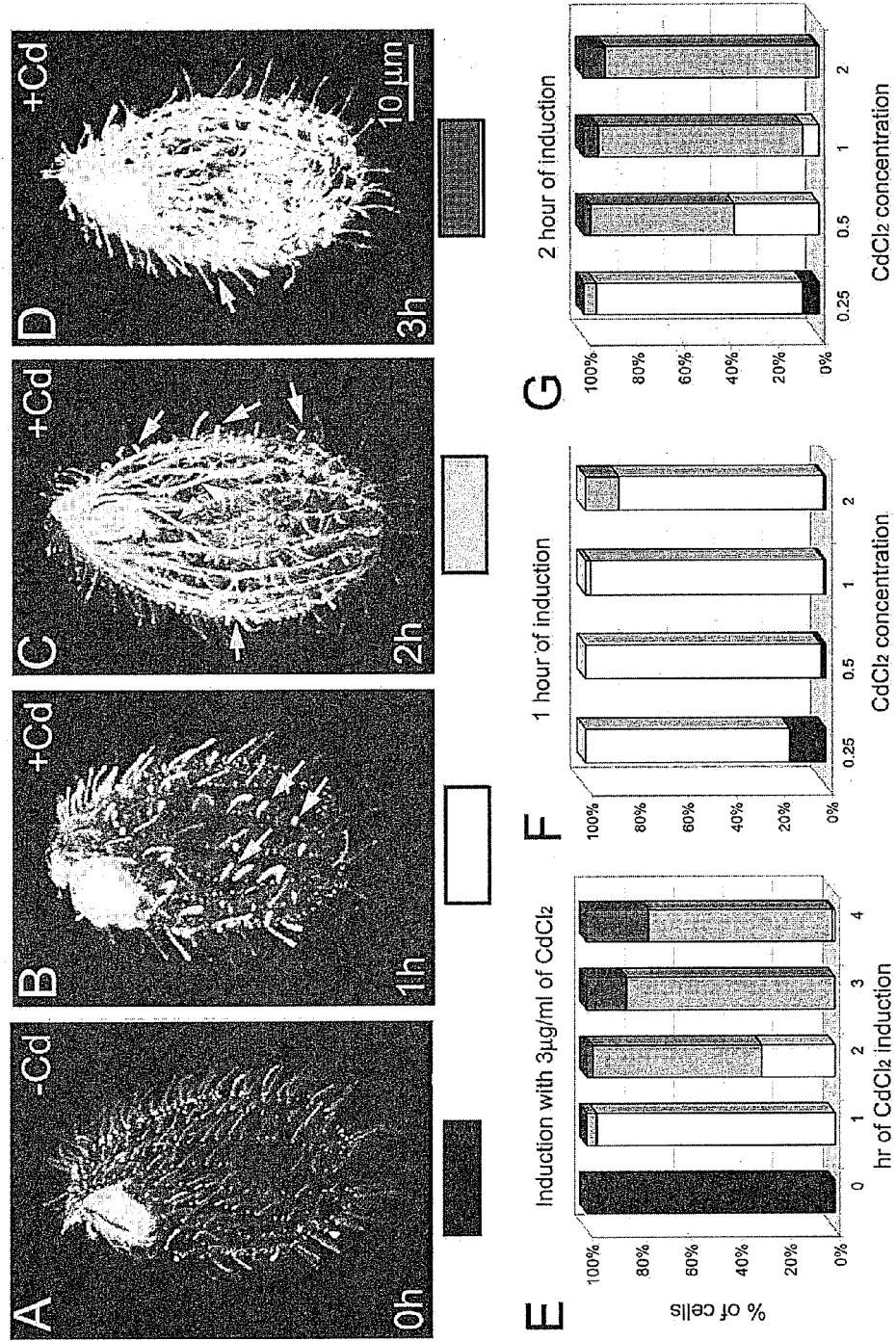
FIG. 17 shows overproduced GFP-Ttll6Ap increases the levels of tubulin polyglutamylation on ciliary and cell-body microtubules in a time- and overexpression strength-dependent manner. (A to D) Confocal fluorescence images of GFP-Ttll6Ap cells that are untreated (A) or induced with 2.5 µg of $CdCl_2$/ml for 1 (B), 2 (C), or 3 h (D) and subjected to immunofluorescence with a MAb that recognized polyglutamylation (ID5). We reduced the gain levels in B to D to avoid overexposure. Arrows point to short hyperglutamylated cilia, arrowheads points to hyperglutamylated cell body microtubules. Bar, 10 µm. (E to G) Graphs that document the distribution of cells with distinct pattern of tubulin hyperglutamylation as shown in panels A to D, as a function of either cadmium concentration or duration of induction with cadmium.
Figure 18:
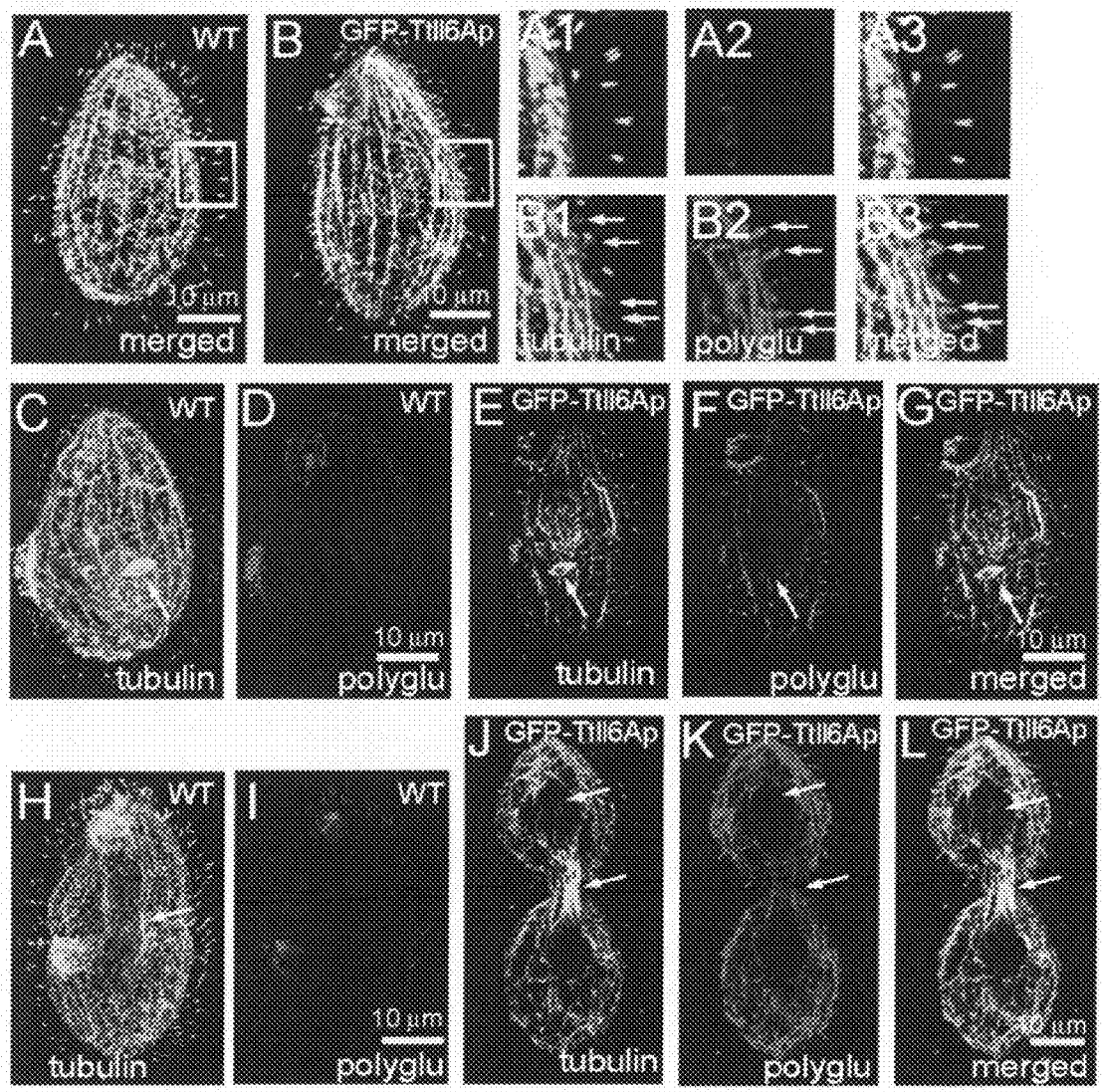
FIG. 18 shows overproduction of GFP-Ttll6Ap results in formation of short, hyperglutamylated axonemes and hypeglutamylation of cytoplasmic, subcortical and spindle microtubules. Microtubules in wild-type (A, A1-A3, C, D, H, I) and GFP-Ttll6Ap overproducing cells (B, B1-B3, E-G, J-L) induced for 3 hr with 2.5 µg/ml $CdCl_2$ and stained with anti-α-tubulin antibodies (A1, B1, C, E, H, J) and polyE antibodies (A2, B2, D, F, I, K). A, A3, B, B3, G, L represent merged images. Note short hyperglutamylated cilia in GFP-Ttll6A cells (B1-B3, arrows), hyperglutamylated spindle in the micronucleus (F, arrow), intranuclear microtubules in the dividing macronucleus (K, arrows) and bundles of hyperglutamylated subcortical and cytoplasmic microtubules. Bar, 10 µm.

Overproduction of GFP-Ttll6Ap strongly increased the levels of tubulin polyglutamylation on ciliary, cell body, and nuclear microtubules (FIGS. 17 and 18). The pattern of accumulation of tubulin polyglutamylation was dependent on the time and strength of overexpression of GFP-Ttll6Ap (FIGS. 15A and 17). A 1-h induction of GFP-Ttll6Ap with 2.5 µg of $CdCl_2$/ml or induction for a longer time by a lower cadmium concentration increased the level of tubulin polyglutamylation mainly in assembling axonemes (FIGS. 17A and B). This indicates that cilia are the primary site of the native Ttll6Ap activity. Functional studies agree with this hypothesis: deletion of TTLL6A and a closely related TTLL6F led to a loss of ciliary motility and deletion of additional paralogs (TTLL6B and 6D) led to shortening of cilia (Examples V and VI). The hyperglutamylated axonemes in GFP-Ttll6Ap cells were shorter than axonemes in untreated cells (FIG. 17B and FIG. 18B1 to B3). With longer induction period or increased strength of induction (cadmium concentration), tubulin polyglutamylation accumulated on cortical and cytoplasmic microtubules (FIGS. 17C and D [arrowheads] and FIG. 17E to G).

Figure 16:
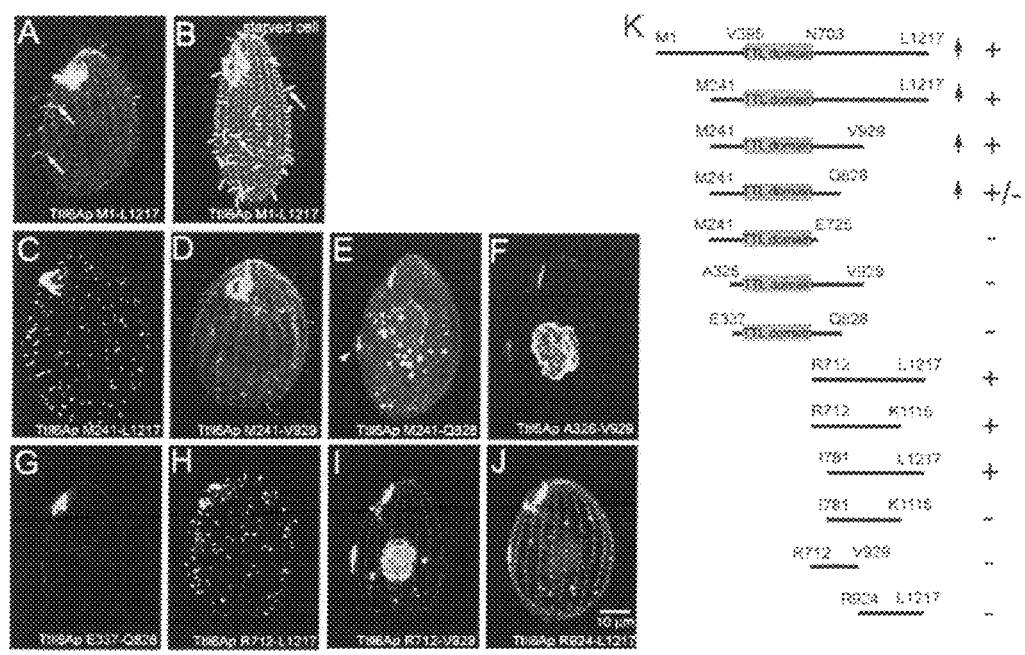
FIG. 16 shows Imaging of *Tetrahymena* cells expressing either full length or truncated GFP-Ttll6Ap. (A, B) Fluorescence confocal images of GFP-Ttll6Ap overexpressed in a growing cell induced for 2 hr with 2.5 μg/ml CdCl$_2$ (A) or in a starved cell induced for 2 hr with 0.05 μg/ml CdCl$_2$ (B). Note predominant localization of GFP-Ttll6Ap to short assembling cilia (arrows) and weaker signal in the full length cilia. (C-J) Fluorescence confocal images of GFP in cells overproducing truncated variants of GFP-Ttll6Ap after 3 hr of 2.5 μg/ml CdCl$_2$ induction. Bar=10 μm. Note that the variant lacking the 240 N-terminal amino acids (Ttll6Ap M241-L1217) showed increased ciliary signal, and accumulated at the tips of cilia (C). An enrichment at the ciliary tips was also observed for a fragment with a larger N-terminal deletion that lacked the TTL-like catalytic domain, R712-L1217 (H). Furthermore, shortening of the M241-L1217 protein from the C-terminal end (M241-V929 and M241-Q828) resulted in a localization pattern that was similar to the localization pattern of the full length protein (D, E compare to FIG. 15D) however note that the majority of GFP-Ttll6Ap-M241-Q828 is associated with cytoplasmic microtubules and only weak signal is observed in growing oral cilia (arrowhead). Thus, the N-terminal 240 (M1-E240) and the C-terminal 288 (K930-L1217) amino acids appear to contain determinants that promote and inhibit uniform ciliary localization of Ttll6Ap, respectively. Note also that further deletions of the C-terminal, microtubule targeting fragment from either protein end created fragments (R712-V929 (I) and R924-L1217 (J)) that failed to localize to cilia. Thus, either multiple parts of the R712-L1217 region are required for ciliary localization or deletions at both ends of this fragment affect its conformation in the context of ciliary targeting. (K) A scheme illustrating the organization of amino acid sequences of expressed variants. The arrows pointing up mark enzymatically active proteins. The "+" or "−" mark presence or absence of the Ttll6Ap variant in the cilia.
Figure 19:
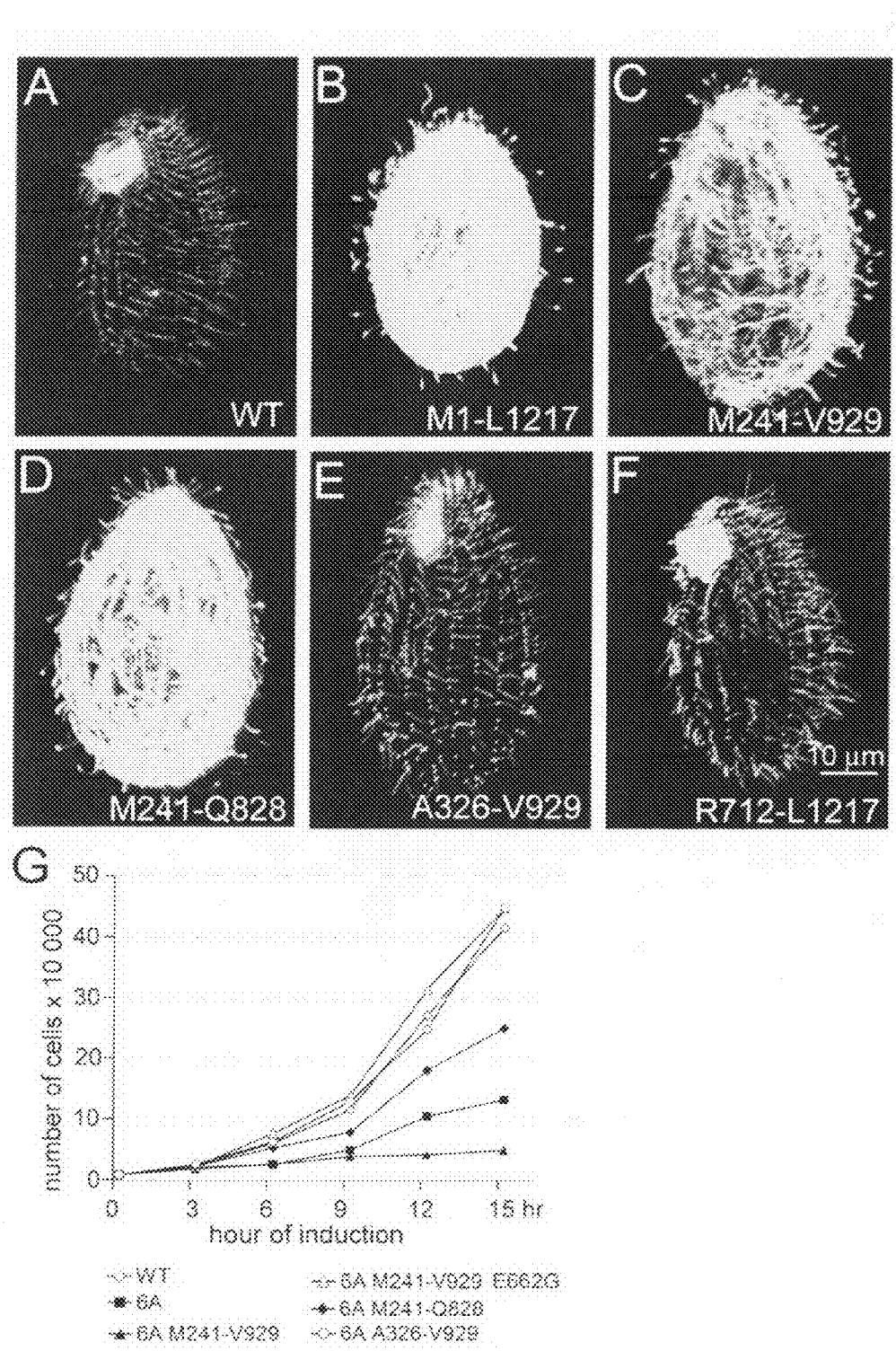
FIG. 19 shows mapping the minimal domain of Ttll6Ap that is required for E-ligase activity. (A-F) Immunofluorescence images of cells labeled for polyglutamylation with ID5 mAb that are either wild-type (A) or express specific truncated versions of GFP-Ttll6Ap (B-F) as indicated in the panels. By comparing the signal of ID5 mAb, it is apparent that the only proteins expressed in cells shown in panels B-D are enzymatically active. All images were obtained using the same gain level and consequently the images in shown in B-D are overexposed. Bar=10 µm. (G) Growth rate of wild type cells (+Cd) and cells overexpressing truncated GFP-Ttll6Ap as indicated in the legend.

To determine which parts of Tll6Ap are required for ciliary localization and enzymatic activity, we overexpressed truncated variants of Ttll6Ap as GFP fusions (see FIGS. 16 and 19). The predicted Ttll6Ap is composed of 1,217 amino acids with the conserved TTL-like domain located between V395 and N703 (based on SMART prediction [Letunic et al., 2009. Nucleic Acids Res. 37:D229-D232]). Truncations of the C-terminal portion of the protein beyond Q828 residue resulted in increased retention of the fusion protein in the cell body (see FIG. 16). On the other hand, the fragment R712-L1217 lacking the TTL-like domain was sufficient to target GFP to cilia (see FIG. 16H). Thus, the R712-L1217 region contains determinants involved in targeting of Ttl6Ap to cilia.

Truncation of 240 amino acids on the N-terminal side and 390 amino acids on the C-terminal side of the TTL-like domain (GFP-Ttll6Ap-M241-Q828 variant) had an E-ligase activity in vivo (see FIG. 19A to D). Further deletions on either the N- or C-terminal side (resulting in fragments E337-Q828, M241-E725, and A326-V929) abolished the E-ligase activity in vivo (see FIG. 19E). Therefore, among the tested variants, the M241-Q828 fragment is the smallest enzymatically active protein. The TTL homology domain is contained between V395 and N703. Thus, less conserved amino acids adjacent to the TTL-like homology domain contribute to the enzymatic activity, as seen earlier for mammalian E-ligases (van Dijk et al., 2007. Mol. Cell 26:437-448). The majority of GFP-Ttll6Ap-M241-Q828 was associated with cytoplasmic microtubules, and only weak signal was observed in growing cilia during the formation of new oral apparatus prior to cell division (see FIG. 16E [arrowhead]). In vegetatively growing GFP-Ttll6Ap-M241-Q828-overexpressing cells, short hyperglutamylated cilia were rarely observed but bundles of hyperglutamylated cell body microtubules were abundant (see FIG. 19D). In contrast to GFP-Ttll6Ap and GFPTtll6Ap-M241-V929-overexpressing cells that gradually loose motility (Janke et al., 2005. Science 308:1758-1762), GFP-Ttll6Ap-M241-Q828-overexpressing cells remained motile. Thus, GFP-Ttll6Ap M241-Q828 acts primarily in the cell body. We used truncated variants of GFP-Ttll6Ap to selectively drive tubulin hyperglutamylation in the cell body (see below). The growth rate of cells overexpressing either full-length or enzymatically active fragments of GFP-Ttll6Ap was reduced compared to wild-type cells treated with the same cadmium concentration (see FIG. 19G), suggesting that hyperglutamylation of cell body microtubules is deleterious for cell growth.

Figure 20:
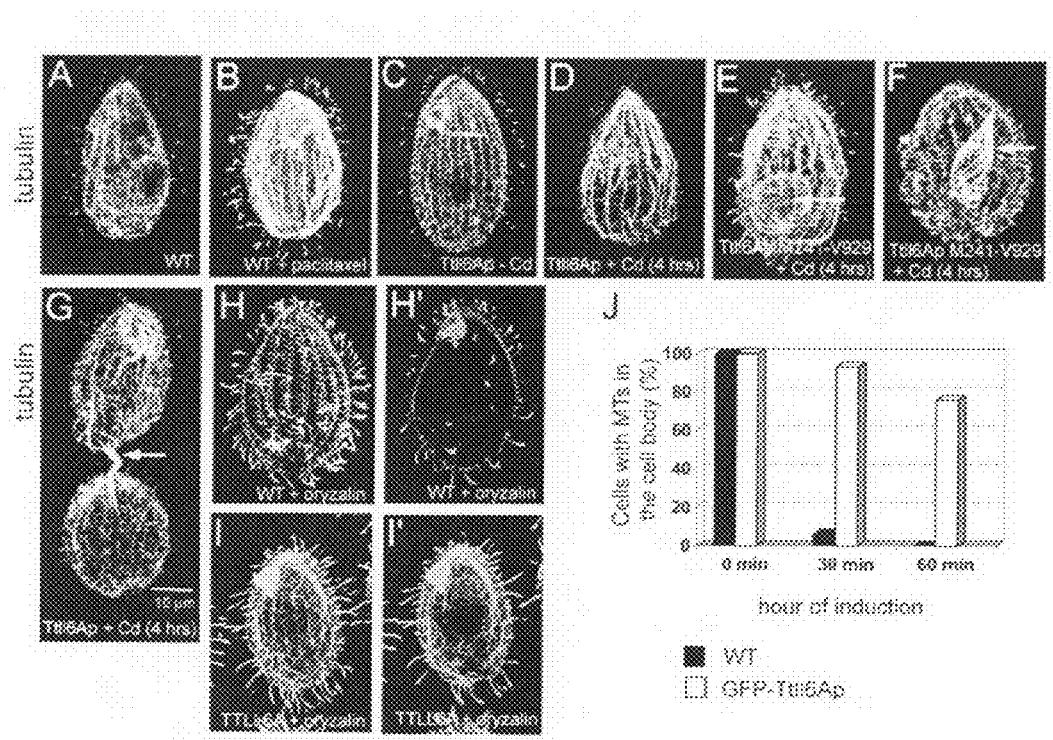
FIG. 20 shows tubulin hyperglutamylation stabilizes cell body microtubules. (A to I') Confocal microscopic images of cells stained with anti-α-tubulin MAb 12G10. (A and B) Wild-type cells grown without (A) or with (B) 40 µM paclitaxel. Note the appearance of thick bundles of subcortical microtubules in the drug-treated cells. (C to G). Cells expressing GFP-Ttll6Ap or its truncated variant M241-V929 that are uninduced (C) and induced with cadmium (D to G). Note the appearance of bundles of microtubules in the cell body and macronuclei (arrow) in the overproducing cell. (H to I') Overexpression of GFP-Ttll6Ap protects subcortical and cytoplasmic microtubules against oryzalin-induced depolymerization. Wild-type (H and H') and GFP-Ttll6Ap-overexpressing (I and I') cells grown for 4 h in the presence of 2.5 µg of $CdCl_2$/ml were treated for 30 min with 10 µM oryzalin. Panels H' and I' show the internal sections of cells shown in panels H and I, respectively. Note the nearly complete depolymerization of cell body microtubules in the wild-type cells but not in Ttll6Ap-overproducing cells. Bar, 10 µm. (J) A graph documents the percentages of wild-type and GFP-Ttll6Ap cells with cytoplasmic microtubules during oryzalin treatment.
Figure 21:
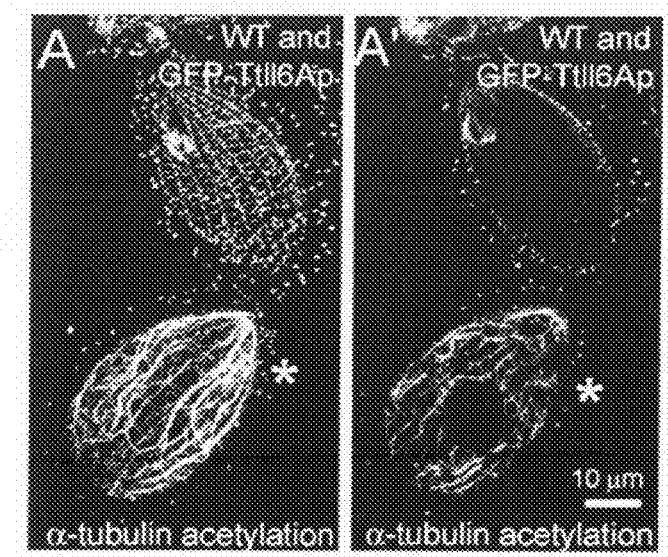
FIG. 21 shows hyperelongation of glutamyl side chains in the cell body causes accumulation of α-tubulin K40 acetylation. (A) Wild-type and GFP-Ttll6Ap cells (indicated by the asterisk) were grown for 4 h in the presence of 2.5 µg of $CdCl_2$/ml and labeled side-by-side with antiacetylated tubulin antibodies (6-11 B-1). (A) Projection image of z-section from the top half of the cell; (A') section showing the middle part of the cell. Bar, 10 µm.

Tubulin hyperglutamylation increases the abundance and stability of cell body microtubules. In wild-type *Tetrahymena* cells, the length of the glutamyl side chains on tubulin is spatially regulated. The cell body microtubules (cytoplasmic, subcortical, and nuclear) have tubulin subunits with side chains limited to a single E (monoglutamylated) except for the postoral fiber microtubules that carry biglutamylated side chains (Wloga et al., 2008. Eukaryot. Cell 7:1362-1372). Within the cell cortex, axonemes and basal bodies contain mono- and polyglutamylated microtubules (with biglutamylated or longer side chains), whereas cortical bundles have side chains limited to a single E (Wloga et al., 2008. Eukaryot. Cell 7:1362-1372). Overproduction of GFPTtll6Ap resulted in the polyglutamylation of diverse microtubules in the cell body, which in wild-type cells are only monoglutamylated, including cytoplasmic network and nuclear microtubules (see FIG. 18C to). Moreover, in GFP-Ttll6Ap-overexpressing cells, anti-α-tubulin antibodies revealed abnormally thick bundles of subcortical and nuclear microtubules (FIG. 20C to G and see FIG. 18C to L). In dividing cells, abnormally thick bundles of intramacronuclear microtubules were present around and within the cytoplasmic bridge connecting the future daughter cells (FIG. 20G, arrow). Bundling of nuclear microtubules was especially apparent in the GFP-Ttll6Ap-M241-V929 cells, and this was likely due to the increased presence of this variant in the cell body (see FIG. 16D; FIGS. 20E and F, arrows). The increased abundance, bundling, and curvature of microtubules indicated that hyperglutamylated microtubules are excessively stable. For example, similar curved bundles of microtubules appear in *Tetrahymena* cells treated with the microtubule stabilizing drug, paclitaxel (Fujiu and Numata. 2000. Cell Motil. Cytoskeleton 46:17-27) (FIGS. 20A and B) and in cells with a K350M mutation in β-tubulin that confers paclitaxel sensitivity (Smith et al., 2004. Eukaryot. Cell 3:1217-1226). To probe the stability of cell body microtubules, we treated the wild-type and GFP-Ttll6Ap-overexpressing cells with the microtubule-destabilizing compounds, nocodazole (40 µM) and oryzalin (10 µM). Although these drugs caused rapid depolymerization of cytoplasmic microtubules in wild-type cells (FIGS. 20H, H', and J), similarly treated GFPTtll6Ap-overexpressing cells retained abundant cell body microtubules (FIGS. 20I, I', and J). Next, we investigated the levels of α-tubulin K40 acetylation in GFP-Ttll6Ap-overproducing cells, since this PTM accumulates on long-lived microtubules (Piperno et al., 1987. J. Cell Biol. 104:289-302). Although wild-type cells had a strong K40 acetylation signal that was limited to the stable microtubules of cell cortex and cilia, the GFP-Ttll6Ap-overproducing cells showed abundant K40 acetylation on cytoplasmic microtubules, a finding consistent with increased stability of these microtubules (FIG. 21). Cells overexpressing a variant of GFP-Ttll6Ap that lacks enzymatic activity due to a mutation in the catalytic domain (Janke et al., 2005. Science 308:1758-1762) had a wild-type organization of cell body and cortical microtubules and a normal the pattern of K40 acetylation. Thus, hyperelongation of glutamyl side chains stabilizes at least a subset of cell body microtubules.

Figure 22:
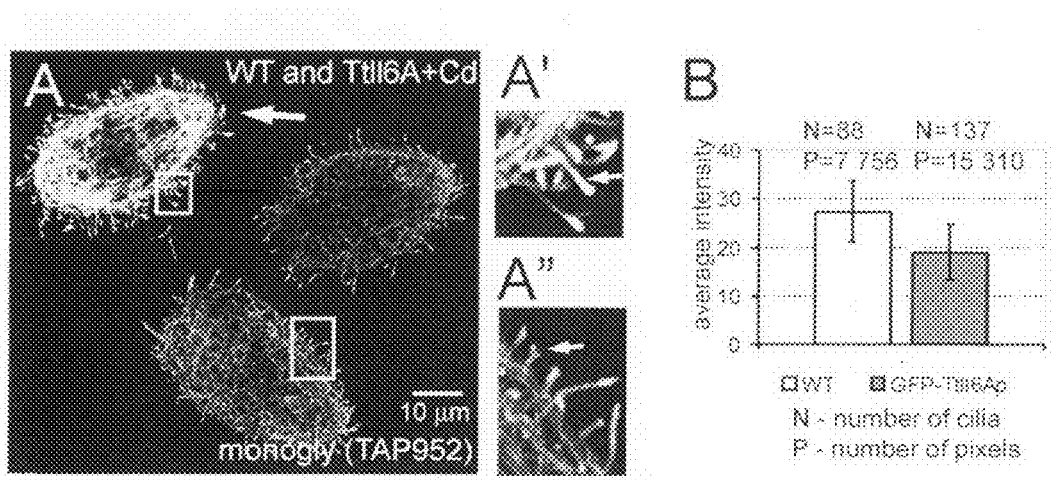
FIG. 22 shows Overproduction of GFP-Ttll6Ap caused decrease in the levels of tubulin monoglycylation. (A-A") levels of tubulin monoglycylation detected by TAP952 antibodies in wild-type (arrow) and GFP-Ttll6Ap cells induced with 2.5 µg/ml $CdCl_2$ for 4 hr. (A', A") Inserts showing higher magnification of cilia in wild-type (A') and GFP-Ttll6Ap cells (A"), both regions marked in A with white frame. Note that growing cilia in wild-type cell has higher levels of tubulin monoglycylation than full length cilia (A', arrow) while short cilia in GFP-Ttll6Ap cells have similar levels of tubulin monoglycylation as full length cilia (A", arrow). Bar=10 µm. (B) Quantitative immunofluorescence analysis showing average intensity of tubulin monoglycylation detected by TAP952 antibodies in cilia in wild-type and GFP-Ttll6Ap overproducing cells. Bars represent standard deviation.

GFP-Ttll6Ap-overproducing cells also had reduced levels of tubulin monoglycylation on stabilized cytoplasmic and cortical microtubules (FIG. 15A and see FIG. 22). Similar observations were made for tubulin polyglycylation. We have previously documented that the two tubulin polymodifications, glutamylation and glycylation, inhibit each other, and we suggested that this mutual inhibition can be explained either by competition for the same modification sites or steric inhibition of adjacent sites (Wloga et al., 2009. Dev. Cell 16:867-876). Overproduction of GFP-Ttll6Ap does not lead to an increase in the total number of glutamyl side chains on tubulin (based on Western blots with GT335 MAb that recognizes a side chain of any length [FIG. 15A]). Thus, it is more likely that elongation of glutamyl side chains sterically inhibits the activity of tubulin G-ligases (TTLL3 [Ikegami and Setou. 2009. FEBS Lett. 583:1957-1963; Rogowski et al., 2009. Cell 137:1076-1087; Wloga et al., 2009. Dev. Cell 16:867-876]) on adjacent polymodification sites.

Figure 23:
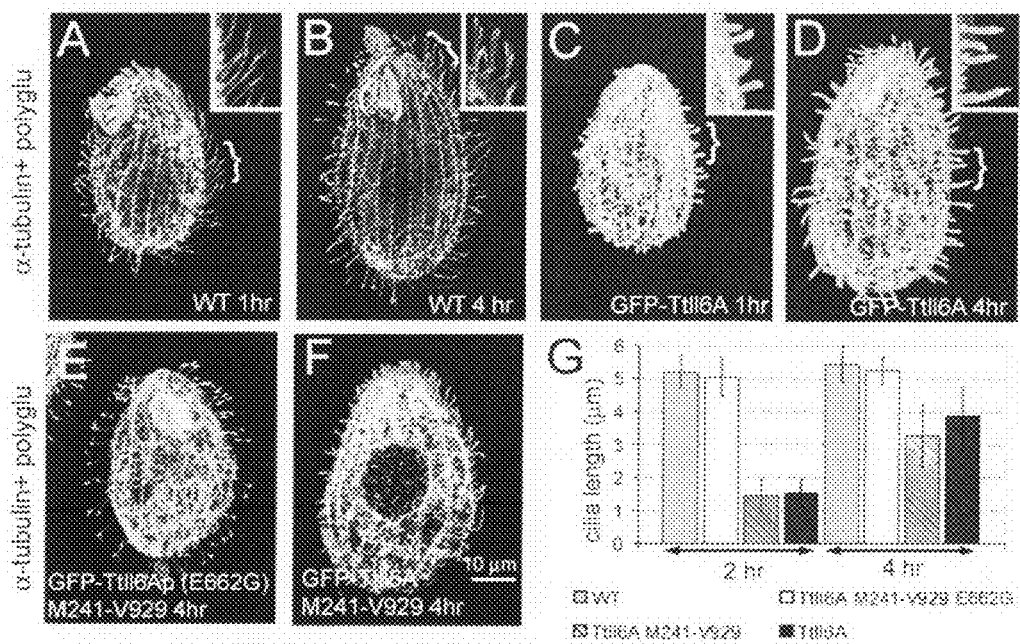
FIG. 23 shows hyperelongation of glutamyl side chains delays cilium regeneration. (A to F) Confocal immunofluorescence images of wild-type (A and B) and GFP-Ttll6Ap (C and D), GFP-Ttll6Ap-M241-V929-E662G (E)-, and GFP-Ttll6Ap-M241-V929 (F)-overexpressing cells that regenerated cilia for 1 (A and C), 2 (E and F), or 4 h (B and D) after deciliation. Cells were costained with anti-α-tubulin 12G10 MAb and the anti-polyglutamylation antibody poly(E). Note the shorter size of cilia of GFP-Ttll6Ap cells. Insets show cilia at higher magnifications from the areas indicated by a bracket. (G) A graph shows the average lengths of cilia as a function of time of cilium regeneration. Bar, 10 µM.

Hyperglutamylation destabilizes microtubules in axonemes. GFP-Ttll6Ap-overexpressing cells contained both excessively short hyperglutamylated cilia (in which GFP-Ttll6Ap accumulates) and unaffected cilia (with a low GFP-Ttll6Ap signal; FIG. 15D, FIGS. 16A and B, and FIG. 18B). The short, hyperglutamylated cilia observed within 1 to 4 h after induction of GFP-Ttll6Ap overexpression could be assembling cilia that had failed to elongate or preexisting cilia that had undergone shortening (or both). Since mildly overproduced GFP-Ttll6Ap is preferentially targeted to assembling cilia (FIG. 15E), hyperglutamylation could primarily affect axonemes during their assembly. To test this hypothesis, we deciliated wild-type and GFP-Ttll6Ap-overproducing cells and examined the lengths of the cilia during regeneration. While at 1 h after deciliation wild-type cells had regenerated cilia to 85% of the original length (4.32±0.57 µm, n=30), during the same period the GFP-Ttll6Ap-overexpressing cells regenerated significantly shorter cilia (1.07±0.35 µm, n=50 [FIGS. 23A and C]). The GFP-Ttll6Ap-overexpressing cells maintained short hyperglutamylated cilia even 4 h after deciliation (3.88±0.89 µm, n=82; wild-type cells 5.43±0.59 µm, n=60 [FIGS. 23B, D, and G]).

Figure 24:
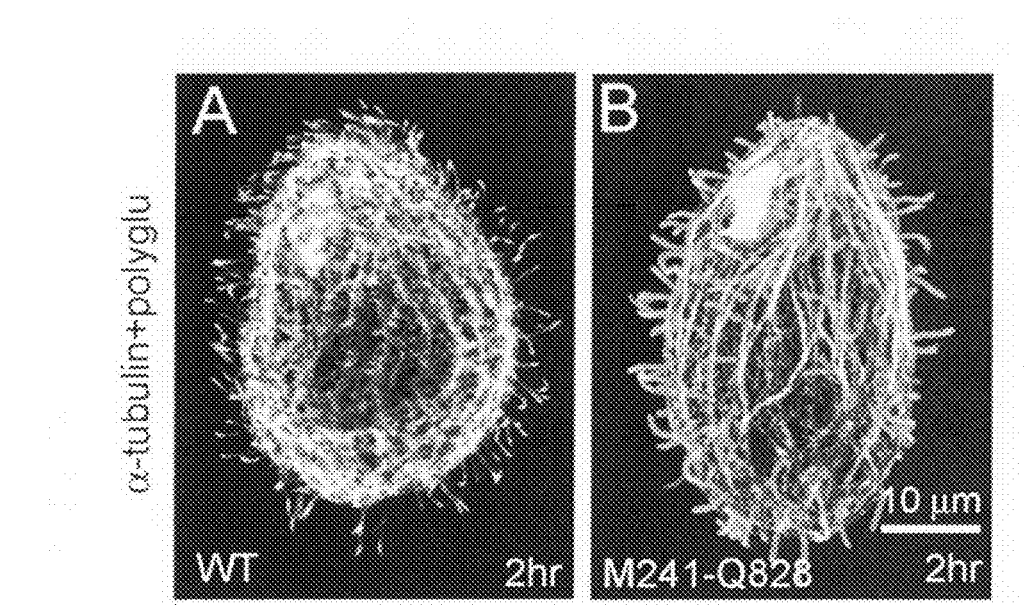
FIG. 24 shows tetrahymena cells overexpressing M241-Q828 GFP-Ttll6A regenerate cilia with the rate similar to wild-type cells. Confocal immunofluorescence images of wild-type (A) and GFPTtll6Ap M241-Q828 overexpressing cells (B) that regenerated cilia for 2 hr in culture medium supplied with 2.5 µg/ml cadmium chloride. Cells were costained with anti-α-tubulin 12G10 mAb and anti-polyglutamylation antibodies polyE. Note the similar length of cilia of wild-type and GFP-Ttll6Ap M241-Q828 overexpressing cells. Bar, 10 µm.

The failed elongation of regenerating cilia in cells overproducing GFP-Ttll6Ap could be caused either by the physical presence of GFP-Ttll6Ap or by tubulin hyperglutamylation. To distinguish between these two effects, we compared the lengths of cilia in *Tetrahymena* cells overexpressing either an enzymatically active and cilium-targeted enzyme (GFP-Ttll6Ap-M241-V929) or an inactive enzyme with an amino acid substitution in the ATP-binding site (GFP-Ttll6Ap-M241-V929-E662G [Janke et al., 2005. Science 308:1758-1762]). Whereas cells overproducing an active enzyme regenerated excessively short axonemes (1.44±0.49, n=62, after 2 h [FIGS. 23F and G]), cells overexpressing an inactive enzyme assembled normal length axonemes (5.05±0.59 µm, n=40, after 2 h [FIGS. 23E and G]) despite the fact that the inactive enzyme is targeted to cilia (Janke et al., 2005. Science 308:1758-1762). Cells overexpressing GFP-M241-Q828 that localizes mainly to cell bodies, regenerated cilia at the rate similar to that of wild-type cells (see FIG. 24). Thus, most likely, the inhibitory effect of GFPTtll6Ap on the elongation of axonemes is mediated by hyperelongation of glutamyl side chains on axonemal tubulin.

Figure 25:
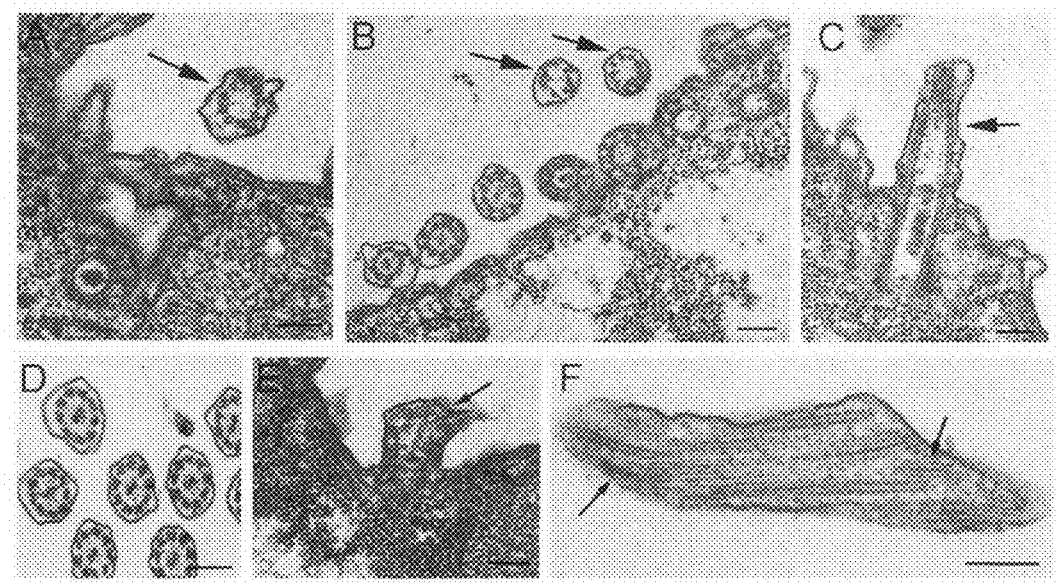
FIG. 25 shows hyperglutamylation of ciliary microtubules results in structural defects in axonemes. TEM cross-sections (A, B, and D) and longitudinal sections (C, E, and F) of cilia in wild-type (D) and GFP-Ttll6Ap-overproducing (A to C, E, and F) cells. Note that short cilia (A to C) lack a central pair (90, arrows) and that broken microtubules are visible (E and F, arrows). Bar, 200 nm.

The TEM analysis of vegetatively growing cells overproducing GFP-Ttll6Ap (FIG. 25) revealed two types of axonemes: unaffected 92 axonemes and structurally defective mostly 90 axonemes. The intact 92 axonemes are likely present in the nonassembling cilia that do not accumulate GFP-Ttll6Ap. The defective axonemes frequently lacked a central pair (FIG. 25A to C) and had broken outer doublets (FIGS. 25E and F). These observations indicate that, in GFP-Ttll6Ap-overproducing cells, assembling axonemes are unstable.

Figure 26:
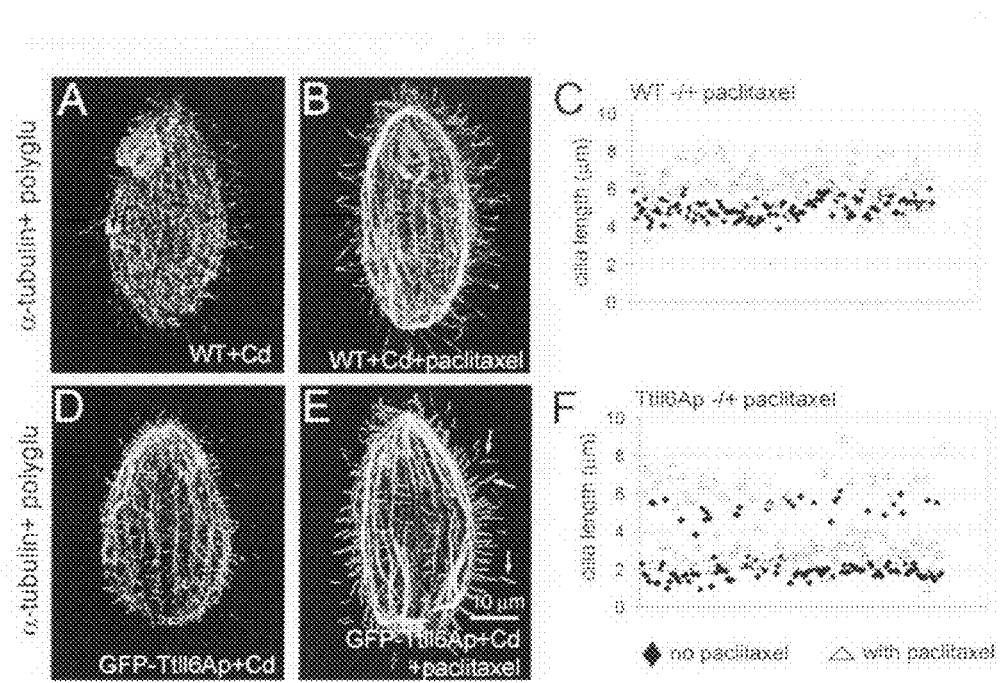
FIG. 26 shows paclitaxel partly rescues the destabilizing effect of hyperglutamylation on elongation of assembling cilia in vegetatively growing *Tetrahymena*. Confocal immunofluorescence images of wild-type (A and B) and GFP-Ttll6Ap-overexpressing (D and E) cells grown without (A and D) or with (B and E) 40 µM paclitaxel. Cells were costained with anti-α-tubulin antibodies and anti-poly(E) antibodies. The arrows in panel E point to hyperglutamylated distal segments. Bar, 10 µm. (C and F) A graph documents the distribution of cilium length in wild-type (C) and GFP-Ttll6Ap-overexpressing (F) cells. Black diamonds indicate the cilium lengths in cells grown without drug, and open triangles represent the cilium lengths in cells grown in the presence of paclitaxel.
Figure 27:
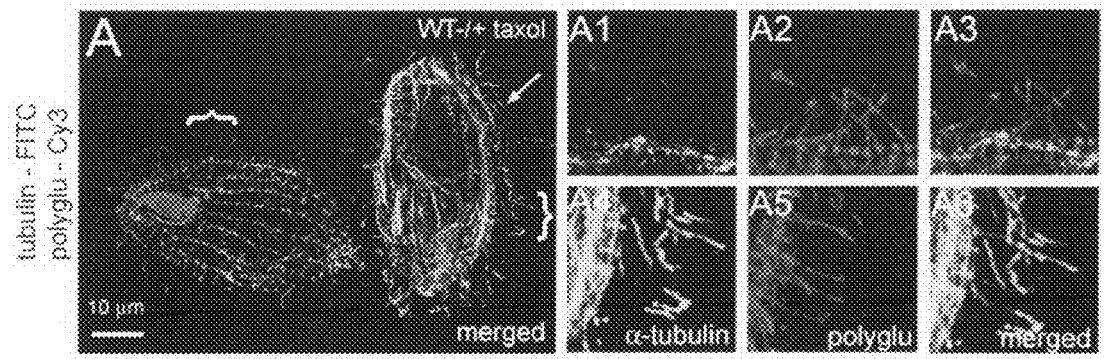
FIG. 27 shows Levels of tubulin glutamylation in cilia in wild-type cells treated with paclitaxel. (A) Confocal microscope image of mixed population of wild-type cells (cell on the left) and wildtype cells grown for 4 hr in the presence of 40 μM paclitaxel (cell on the right, indicated by arrow) showing α-tubulin (12G10) in green and levels of tubulin polyglutamylation with polyE in red; (A1-A6) Magnified images of cilia from area indicated by brackets in wild-type cells grown without paclitaxel (A1-A3) or wild-type cells grown in the presence of paclitaxel (A4-A6). Bar, 10 μm.

In an attempt to probe how the dynamic properties of axonemal microtubules change as a function of glutamyl side chain hyper-elongation, we treated control and GFP-Ttll6Ap-overproducing cells with 40 µM paclitaxel for 3 h. As previously described in wild-type cells (Wloga et al., 2009. Dev. Cell 16:867-876), paclitaxel increased the average axoneme length by 20% (length before treatment, 5.02±0.52 µm, n=129; length after treatment, 6.05±1.12 µm, n=173 [FIGS. 26A to C]). In GFP-overproducing cells, the assembling cilia were 44% treated GFP-Ttll6Ap-overproducing cells (no drug, 1.87±0.36 µm; paclitaxel treated, 2.7±0.6 µm [FIGS. 26D to F]). Furthermore, the assembling cilia in GFPTtll6Ap-overproducing, paclitaxel-treated cells had elevated levels of tubulin polyglutamylation comparable to those in axonemes of the untreated GFP-Ttll6Ap-overproducing cells. The simplest explanation of these observations is that hyperelongation of glutamyl side chains on the tubulin of assembling axonemal microtubules makes them unstable and that this effect can be counteracted by paclitaxel. Interestingly, in GFPTtll6Ap-overexpressing paclitaxel-treated cells, preexisting cilia underwent elongation by 22% by forming a hyperglutamy-lated distal segment (before treatment, 5.25±0.5 µm; paclitaxel treated, 6.39±0.82 µm [FIGS. 26E and F, arrows]). In wild-type cells treated with paclitaxel the distal segments of preexisting elongated axonemes had lower levels of tubulin polyglutamylation compared to the preexisting proximal axoneme segment (see FIG. 27). This argues again that the destabilizing effects of hyperglutamylation in the axoneme are counteracted by paclitaxel.

Discussion

The polymeric character of glycylation and glutamylation, as well as the fact that these PTMs affect multiple modification sites within the tubulin CTTs and can coexist on the same tubulin proteins, generates an exceptionally large number of tubulin isoforms. The polymodification sites on β-tubulin are required for axoneme assembly (Thazhath et al., 2002. Nat. Cell Biol. 4:256-259). Functional studies on the E- and G-ligases indicate that both glutamylation and glycylation on tubulin are important and contribute to either the assembly or the stability of microtubules, including those present in neural extensions (Ikegami et al., 2006. J. Biol. Chem. 281:30707-30716), and axonemes (Pathak et al., 2007. Mol. Biol. Cell 18:4353-4364; Rogowski et al., 2009. Cell 137:1076-1087; Wloga et al., 2009. Dev. Cell 16:867-876). However, it is not known what the structural consequences of tubulin polymodifications on microtubules are.

The length of the polymodification side chain is spatially regulated and dependent on the microtubule type and possibly on the position of tubulin subunits within the microtubule (Bré et al., 1994. Cell Motil. Cytoskeleton 27:337-349; Wloga et al., 2008. Eukaryot. Cell 7:1362-1372). Moreover, in multicellular organisms, the glutamyl side chain length changes during organismal development (Audebert et al., 1994. J. Cell Sci. 107(Pt. 8):2313-2322; Ikegami et al., 2006. J. Biol. Chem. 281:30707-30716). Among the mechanisms that regulate the side chain length could be (i) temporal and spatial regulation of the initiation and elongation steps performed by E-ligases and (ii) selective shortening of glutamyl side chain by deglutamylases (Audebert et al., 1994. J. Cell Sci. 107(Pt. 8):2313-2322). Whereas some E-ligases, such as the murine TTLL7, can both initiate and elongate the side chains (Mukai et al., 2009. Biochemistry 48:1084-1093), the majority of studied E-ligases have a bias for either chain elongation or initiation (Janke et al., 2005. Science 308:1758-1762; van Dijk et al., 2007. Mol. Cell 26:437-448; Wloga et al., 2008. Eukaryot. Cell 7:1362-1372). Ttll6Ap is a strong elongate for β-tubulin (van Dijk et al., 2007. Mol. Cell 26:437-448; this example). We have studied here the consequences of hyperelongation of glutamyl side chain in vivo by overexpressing Ttll6Ap. Although the activity mediated by GFP-Ttll6Ap on the nonciliary microtubules could be nonphysiological, this ectopic activity gave us a tool to investigate the importance of the side chain length regulation on multiple types of microtubules within the same cell.

We show that the consequences of overexpression of Ttll6Ap depend on the cellular context. Hyperelongation of glutamyl side chains on cell body microtubules increased the density and bundling of microtubules, resistance to depolymerizing drugs, and α-tubulin K40 acetylation. These effects are consistent with an increased stability of hyperglutamylated cell body microtubules. In wild-type *Tetrahymena* cells, the most dynamic microtubules (e.g., the cytoplasmic network, micronuclear spindle, and macronuclear and longitudinal cortical microtubules) have tubulin subunits with side chains limited to monoglutamylation (Bré et al., 1994. Cell Motil. Cytoskeleton 27:337-349; Wloga et al., 2008. Eukaryot. Cell 7:1362-1372). In contrast, basal bodies and axonemes have elongated glutamyl side chains, and these microtubules are known to be extremely stable (turnover slowly and resist standard depolymerizing treatments) (Thazhath et al., 2004. Mol. Biol. Cell 15:4136-4147). We speculate that the physiological elongation of glutamyl side chains on tubulin of basal body and axonemal microtubules contributes to their increased stability. Indeed, deletion of some TTLL6 genes led to shortening of axonemes (Example VI). In GFP-Ttll6Ap-overproducing cells, hyperelongation of the cell body microtubules could lead to capture of axoneme-stabilizing MAPs that are in transit to cilia. A model that elongation of the glutamyl side chains stabilizes microtubules by recruiting MAPs likely applies to other contexts. In neurons, the accumulation of tubulin polyglutamylation during differentiation correlates with increased stability of microtubules and the accumulation of MAP2 in dendrites and the cell body (Ikegami et al., 2006. J. Biol. Chem. 281:30707-30716). Moreover, knockdown of TTLL7 E-ligase inhibited the formation of MAP2-positive neurites in PC-12 cells (Ikegami et al., 2006. J. Biol. Chem. 281:30707-30716). In vitro studies show that the levels of tubulin glutamylation affect the binding of certain structural MAPs and motor proteins to microtubules (Bonnet et al., 2001. J. Biol. Chem. 276:12839-12848; Boucher et al., 1994. Biochemistry 33:12471-12477; Ikegami et al., 2007. Proc. Natl. Acad. Sci. U. S. A. 104:3213-3218; Larcher et al., 1996. J. Biol. Chem. 271:22117-22124). Future studies in vitro based on microtubule polyglutamylation with purified E-ligases should shed light on the mechanism of polyglutamylation-induced microtubule stabilization and, in particular, should reveal whether polyglutamylation has a direct effect on the microtubule dynamics or acts via MAPs.

Given the apparent stabilizing effect of the hyperelongation of glutamyl side chains on the cell body microtubules and the fact that native axonemes have relatively long glutamyl side chains, it was surprising that we observed a seemingly opposite effect of hyperglutamylation on axonemes. It appears that the destabilizing effects of overexpressed Ttll6Ap on axonemes are largely autonomous and cannot be explained by the retention of stabilizing axonemes-destined MAPs in the cell body. The shortening of axonemes could be explained by inhibition of the intraflagellar transport (IFT) pathway, a motility mechanism that moves precursors required for cilia assembly along growing outer doublet microtubules (Kozminski et al., 1993. Proc. Natl. Acad. Sci. U.S.A. 90:5519-5523). However, the defect in the elongation of axonemes in GFP-Ttll6Ap cells is partly rescuable by paclitaxel, suggesting that the elongation of glutamyl side chains destabilizes axonemal microtubules. Moreover, paclitaxel failed to rescue an axoneme assembly defect caused by a loss of function of IFT in the DYF1 knockout strain of Tetrahymena (Dave et al., 2009. Eukaryot. Cell 8:1397-1406).

Hyperelongation of glutamyl side chains on tubulin could affect the dynamics of microtubules. This model agrees with the observation that the removal of CTTs by proteolysis with subtilisin increases the resistance of microtubules to depolymerization by high salt and cold (Bhattacharyya et al., 1985. J. Biol. Chem. 260:10208-10216; Sackett et al., 1985. J. Biol. Chem. 260:43-45), although other studies disagree with this conclusion (Knipling et al, 1999. Cell Motil. Cytoskeleton 43:63-71; Saoudi et al., 1995. J. Cell Sci. 108(Pt. 1):357-367). CTTs are highly negatively charged and could interact with the positively charged surface of the tubulin dimer (Priel et al., 2005. Eur.Biophys. J. 35:40-52). Glutamylation further increases the negative charge of CTTs. The bonds between the dimers could be weakened by charge repulsion, especially if CTTs of neighboring tubulin subunits can interact with each other. However, we would need to assume that in GFPTtll6Ap-overproducing cells, and specifically in the cell body, the lattice-weakening effects of glutamylation are counteracted by stabilizing MAPs that preferentially bind to hyperglutamylated microtubules.

Alternatively, the restriction of the destabilizing effect of hyperglutamylation to the axoneme could result from differential utilization of tubulin subunits. In vitro studies showed that Ttll6Ap prefers β-tubulin (Janke et al., 2005. Science 308:1758-1762), but the same enzyme, when overexpressed in vivo, modified both α- and β-tubulin (FIG. 15C). Thus, some differences in the consequences of excessive activity of Ttll6Ap could result from the differential utilization of α- and β-tubulin subunits in different microtubules, which in turn could be caused by competing MAPs that selectively hinder one of the two tubulin subunits.

However, another explanation of the restriction of destabilizing influence of hyperglutamylation to axonemes is that this effect is mediated by axoneme-restricted factors that are regulated by polyglutamylation. Specifically, in assembling axoneme, hyperelongation of glutamyl side chains could increase the activity of factors that promote microtubule depolymerization. A microtubule-severing protein, katanin, plays a prominent role in the axoneme assembly. Katanin localizes to cilia in Tetrahymena and Chlamydomonas (Dymek et al., 2004. Eukaryot. Cell 3:870-879; Sharma et al., 2007. J. Cell Biol. 178:1065-1079). The presence of CTTs is required for the katanin-mediated microtubule-severing activity in vitro (McNally and Vale. 1993. Cell 75:419-429). Knockouts of katanin subunit genes in Tetrahymena phenocopy the substitutions of glutamic acids that undergo polymodifications in the CTT of β-tubulin (Sharma et al., 2007. J. Cell Biol. 178:1065-1079). The activity of spastin, another microtubule-severing protein, is blocked by an antibody that recognized a terminal glutamic acid, a finding consistent with a requirement of either detyrosination or polyglutamylation (or both) for severing activity (Roll-Mecak and Vale. 2008. Nature 451:363-367). In the axoneme, tubulin hyperglutamylation could cause an excessive activity of severing factors such as katanin, specifically during axoneme assembly, and this could prevent axoneme elongation and assembly of central microtubules. Interestingly, the levels of tubulin glutamylation appear to change during axoneme assembly in wild-type cells. The short assembling cilia label more strongly with antibodies that recognize elongated glutamyl side chains. The signal of polyglutamylation decreases as cilia mature, while the levels of polyglycylation increase in these cilia (Sharma et al., 2007. J. Cell Biol. 178:1065-1079). Thus, axonemal microtubules undergo remodeling of the PTM composition as part of the polymer maturation. It is possible that some glutamyl side chains are trimmed down or completely removed by deglutamylating enzymes (Audebert et al., 1993. Mol. Biol. Cell 4:615-626) and are replaced by glycyl side chains. Thus, tubulin glutamylation could play distinct roles during and after assembly of the axoneme. In a growing axoneme, tubulin polyglutamylation could promote polymer turnover, whereas in the mature axoneme the modification could contribute to increased stability of the polymer.

To summarize, this example shows that the effects of tubulin hyperglutamylation are subcellular context specific. In the same cells, hyperglutamylation stabilizes cell body microtubules and destabilizes axonemes. We propose that the differential effects of hyperglutamylation are mediated by nonuniformly distributed MAPs.

Example V

Tubulin Glutamylation Regulates Ciliary Motility by Altering Inner Dynein Arm Activity How microtubule-associated motor proteins are regulated is not well understood. A potential mechanism for spatial regulation of motor proteins is provided by post-translational modifications of tubulin subunits that form patterns on microtubules. Glutamylation is a conserved tubulin modification (Edde et al., 1990. Science 247, 83-85) that is enriched in axonemes. The enzymes responsible for this PTM, glutamic acid ligases (E-ligases), belong to a family of proteins with a tubulin tyrosine ligase (TTL) homology domain (TTL-like or TTLL proteins) (Janke et al. 2005. Science 308, 1758-1762). We show that in cilia of Tetrahymena, TTLL6 E-ligases generate glutamylation mainly on the B-tubule of outer doublet microtubules, the site of force production by ciliary dynein. Deletion of two TTLL6 paralogs caused severe deficiency in ciliary motility associated with abnormal waveform and reduced beat frequency. In isolated axonemes with a normal dynein arm composition, TTLL6 deficiency did not affect the rate of ATP-induced doublet microtubule sliding. Unexpectedly, the same TTLL6 deficiency increased the velocity of microtubule sliding in axonemes that also lack outer dynein arms, in which forces are generated by inner dynein arms. We conclude that tubulin glutamylation on the B-tubule inhibits the net force imposed on sliding doublet microtubules by inner dynein arms.

Results and Discussion

Figure 28:
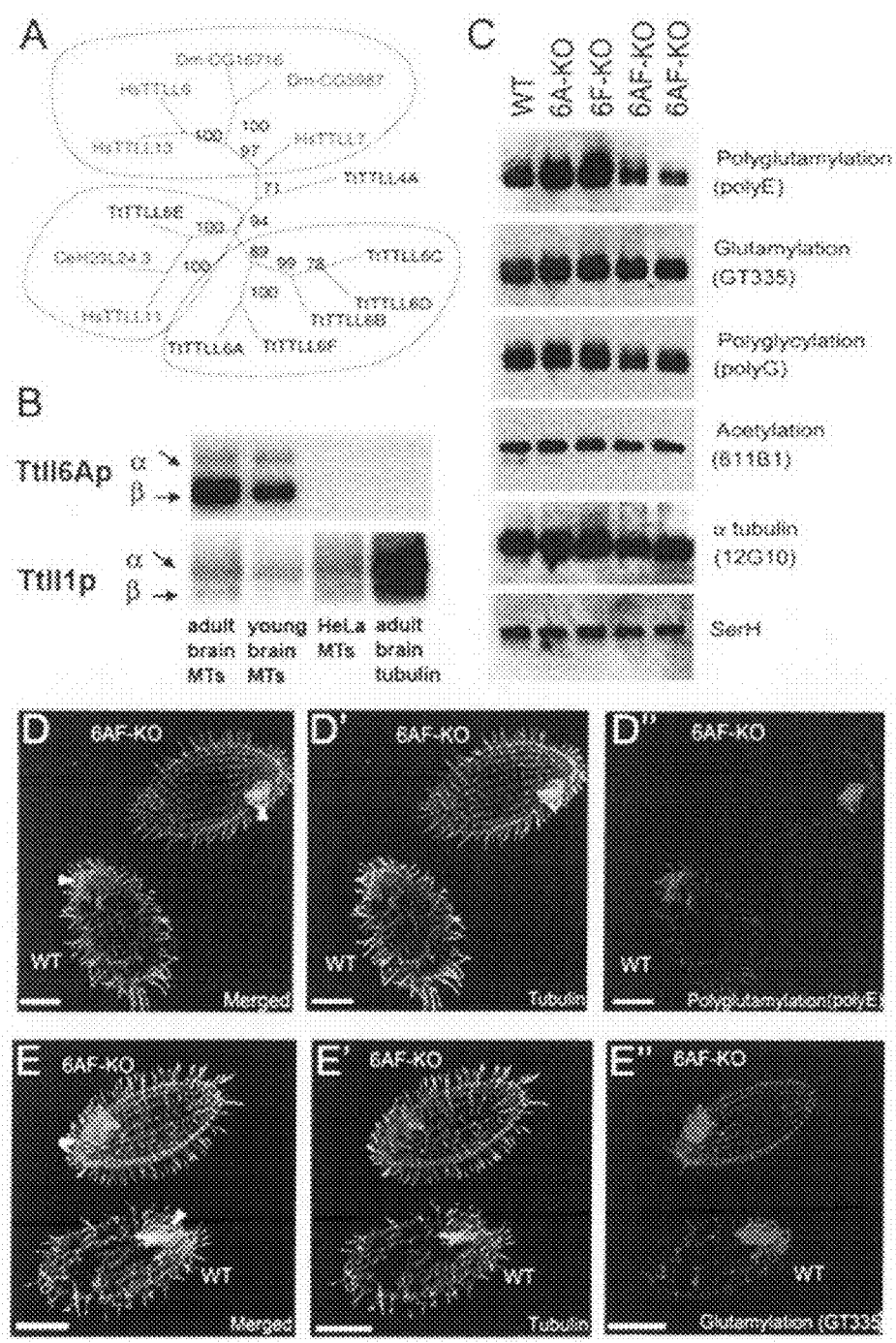
FIG. 28 shows deletion of Ttll6Ap and Ttll6Fp leads to a loss of tubulin glutamylation in cilia (A) A neighbor-joining phylogenetic tree based on the catalytic domain of TTLL6 E-ligases (Wloga et al. 2008. Eukaryot Cell 7, 1362-1372). Tt-Ttll4Ap was used as an outgroup. Abbreviations of species: Hs, *Homo sapiens*; Ce, *Caenorhabditis elegans*; Dm, *Drosophila melanogaster*; Tt, *Tetrahymena thermophila*. (B) A fluorogram of mammalian microtubule proteins (20 μg) separated by SDS-PAGE after in vitro glutamylation with partially purified GFP-Ttll6Ap and GFP-Ttll1p, ATP and $^3$H-glutamate. (C) A western blot of cilia proteins. The anti-SerH antigen antibodies were used as a loading control. (D-E") Immunofluorescence images of pairs of wildtype and 6AF-KO cells imaged side by side. Wildtype cells were prefed with India Ink to reveal dark food vacuoles. Cells were labeled with 12G10 anti-α-tubulin mAb and polyE anti-polyglutamylation antibodies (D-D") or with SG anti-total tubulin antibodies and GT335 anti-glutamylated tubulin mAb (E-E"). Arrowheads mark oral membranelles. Bar, 10 μm. Quantitative data are shown in FIG. 29A.

TTLL6 enzymes generate tubulin polyglutamylation in cilia. The genome of Tetrahymena contains 6 genes encoding TTLL6 paralogs, namely, Ttll6Ap through Ttll6Fp (FIG. 28A). Ttll6Ap is targeted to cilia (Janke et al. 2005. Science 308, 1758-1762; Wloga et al., 2010. Eukaryot Cell. 9,184-193). To characterize the enzymatic properties of Ttll6Ap, we overexpressed GFP-Ttll6Ap in Tetrahymena, partially purified and assayed the enzyme for glutamylation of microtubules in vitro. Glutamylation involves two distinct steps: initiation and elongation. To distinguish between the two reactions, we used microtubules with varying levels of pre-existing glutamylation: high (adult murine brain tubulin), intermediate (young murine brain tubulin) and low (HeLa tubulin) (Regnard et al., 2003. J Cell Sci 116, 4181-4190). Enriched GFP-Ttll6Ap strongly modified microtubules made of adult brain tubulin, less efficiently microtubules made of young brain tubulin, and failed to detectably modify microtubules made of HeLa tubulin (FIG. 28B). The activity was primarily on β-tubulin as seen earlier (Janke et al. 2005. Science 308, 1758-1762). Moreover, enriched GFP-Ttll6Ap did not modify unpolymerized adult brain tubulin (FIG. 28B). As a control, we used another partially purified E-ligase, Ttll1p, (Wloga et al. 2008. Eukaryot Cell 7, 1362-1372) with the same microtubule substrates, and detected a distinct enzymatic profile (FIG. 28B). These and earlier studies (Wloga et al., 2010. Eukaryot Cell. 9,184-193; van Dijk et al., 2007. Mol Cell 26, 437-448) are consistent with Ttll6Ap acting primarily as a glutamyl side chain elongase for β-tubulin in microtubules.

Figure 29:
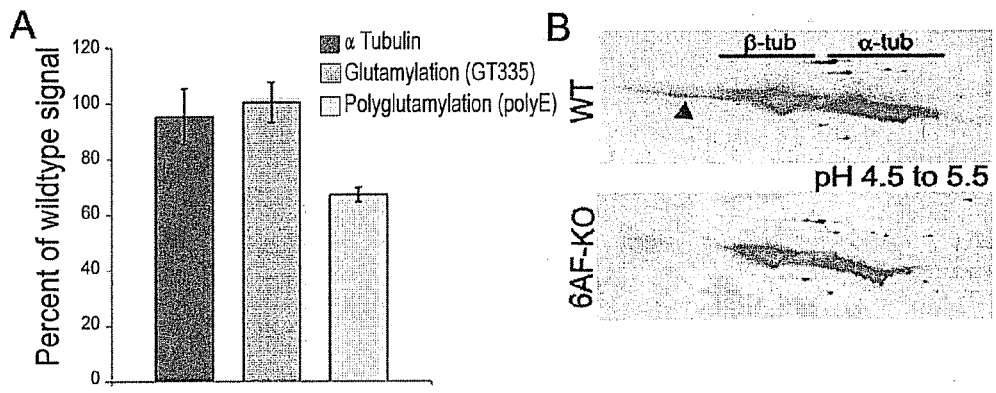
FIG. 29 shows loss of Ttll6Ap and Ttll6Fp leads to a loss of elongated glutamyl side chains in axonemes. (A). A histogram that documents the average intensity of fluorescence signals detected for antibodies against tubulin or glutamylated tubulin using quantitative immunofluorescence. Wild type (labeled with India ink) and 6AF-KO cells were mixed and processed for double immunofluorescence for total tubulin and glutamylated tubulin (using either GT335 or polyE antibodies). Confocal images were obtained of pairs of wild type and mutant cells located near each other. Signal intensities were measured for individual axonemes using ImageJ. A total of 4 images (8 cells) were analyzed, Between 73 and 196 axonemes were measured for antibody. For any given pair of cells, the mutant signal average was calculated as a percentage of the adjacent wild type cell signal. The histogram contains an average of each image value. Error bars represent standard errors. (B) Images of portions of tubulin regains of 2D gels of axonemal proteins. The arrowhead marks a region that contains a string of highly acidic protein forms migrating near the main spots of tubulin in the wild type that are missing in the 6AF-KO cilia. Note that on SDS-PAGE, ciliate tubulin migrates in an inverted order as compared to most other species (β-tubulin migrates more slowly).

In *Tetrahymena*, glutamylation occurs on most types of microtubules, but the length of the glutamyl side chain is spatially regulated (Wloga et al. 2008. Eukaryot Cell 7, 1362-1372), presumably by localized activities of elongases such as Ttll6Ap. While the modification is detectable on most if not all microtubules, only microtubules of cilia and basal bodies are labeled by the polyE antibodies that recognize elongated (poly)glutamyl side chains ((Wloga et al. 2008. Eukaryot Cell 7, 1362-1372) and FIG. 28D'). Knocking out the TTLL6A gene by DNA homologous recombination neither changed the levels of tubulin glutamylation (FIG. 28C) nor affected the gross phenotype. TTLL6F encodes a close paralog (FIG. 28A). Cells with a deletion of TTLL6F showed no reduction in the levels of tubulin glutamylation (FIG. 28C). However, a double knockout strain, 6AF-KO, had strongly reduced levels of elongated side chains recognized by polyE antibodies (FIG. 28C), indicating that Ttll6Ap and Ttl1Fp act synergistically. Consistent with this result, 2D gel electrophoresis of axonemal proteins showed a prominent reduction in the abundance of protein isoforms migrating as a smear on the more acidic side of the major β-tubulin spots in 6AF-KO cilia (FIG. 29B). Immunofluorescence with polyE antibodies showed a decrease in tubulin polyglutamylation signal in cilia and basal bodies of 6AF-KO cells imaged side by side with wild type cells (FIG. 28D-D"). The levels of tubulin glutamylation recognized by the GT335 antibody that detects an epitope at the base of the glutamyl side chain and probably recognizes side chains of any length (Wolff et al., 1992. Eur J Cell Biol 59, 425-432) appeared unchanged in 6AF-KO cilia based on immunofluorescence (FIG. 28E-E", FIG. 29A) and western blotting (FIG. 28C). These data indicate that, the absence of Ttll6Ap and Ttll6Fp leads to shortening but not complete loss of glutamyl side chains, which agrees with the enzymatic profile of Ttll6Ap obtained in vitro. In cilia of 6AF-KO cells, the levels of tubulin acetylation and glycylation appeared nearly normal (FIG. 28C). Thus, Ttll6Ap and Ttll6Fp together contribute to β-tubulin glutamylation in cilia and are responsible primarily if not exclusively for the chain elongation in vivo.

Figure 30:
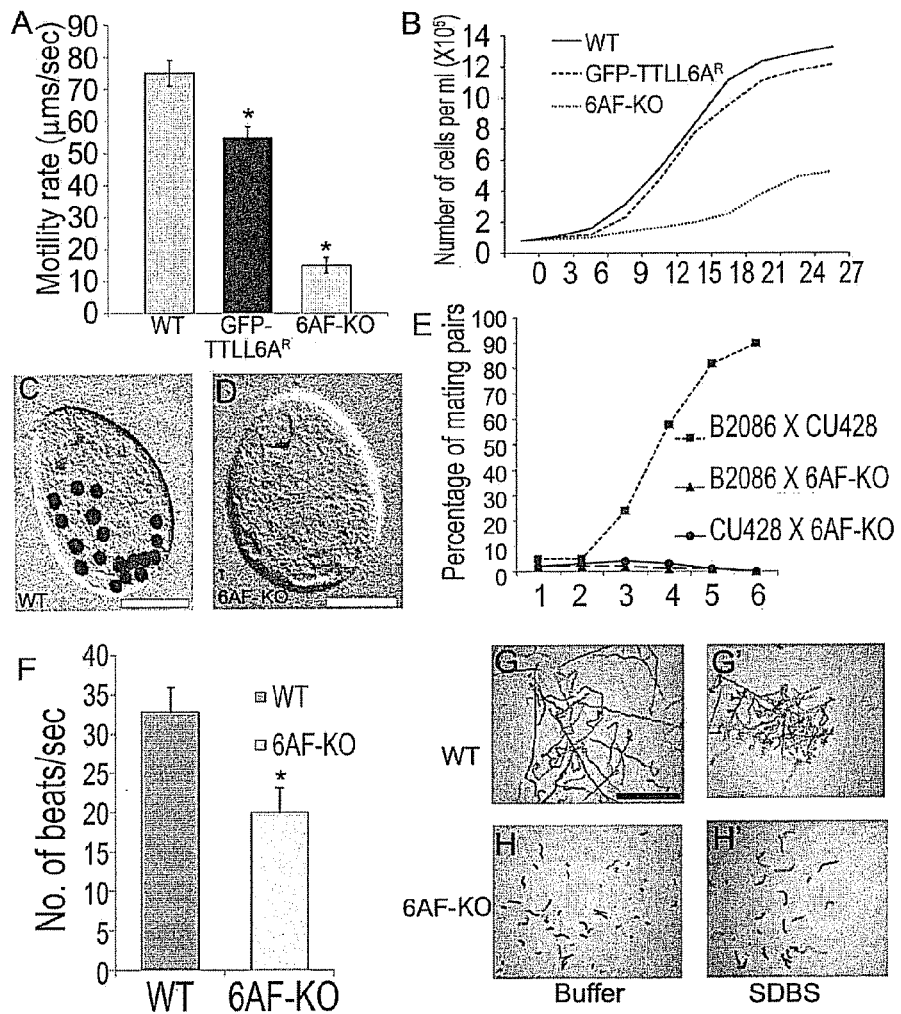
FIG. 30 shows cells lacking Ttll6Ap and Ttll6Fp display a loss of cilia-dependent functions. (A) A histogram shows the average linear cell motility rate during 5 sec for wild type, 6AF-KO and 6AF-KO cells rescued with a GFP-Ttll6Ap transgene (6AF-KO$^R$) (n=40 for each strain). Bars represent standard deviations. *p<0.001. (B) Culture growth curves. (C-D) Images of a wild type (C) and 6AF-KO (D) cell exposed to India ink for 30 min. Bar, 20 μm. (E) The graph shows the percentage of paired cells following mixing of either two starved wild type strains (CU428 and B2086) or 6AF-KO cells with either of the two wild type strains. (F) The average ciliary beat frequency for wild type (n=27) and 6AF-KO cells (n=27, p<0.0001). Error bars represent standard deviations. (G-H'). Swimming responses to SDBS. Wild type (G-G') or 6AF-KO (H-H') cells were exposed to either a buffer alone or SDBS (20 μg/ml), and the paths of live cells were recorded for 1 sec. Bar, 1 mm.

Ttll6Ap and Ttll6Fp affect ciliary motility. The 6AF-KO cells have a normal density of cilia that appear only slightly shorter than wild type cilia (wild type 5.6±0.8 µm, n=150; 6AF-KO, 5.0±0.5 µm, n=150). However, the 6AF-KO cells moved at only ⅕ of wild type rate (FIG. 30A). In ciliates, phagocytosis requires the motility of ciliary membranelles that sweep food particles into the oral cavity. Although, the 6AF-KO cells assemble oral membranelles (arrowheads, FIG. 28D,E), they exhibited a greatly reduced rate of formation of food vacuoles (FIG. 30C,D), consistent with malfunction of oral cilia. 6AF-KO cells also showed a reduced rate of multiplication (FIG. 30B). *Tetrahymena* cells require motile cilia for conjugation (our unpublished data). When starved 6AF-KO cells (earlier grown for over 100 generations to reach sexual maturity) were mixed with wild type cells, few pairs formed and these pairs dissociated quickly (FIG. 30E). Thus, all functions dependent on normal ciliary motility appear to be severely affected in 6AF-KO cells.

Biolistic bombardment of 6AF-KO cells with a GFP-Ttll6Ap transgene (targeted to an unrelated locus) resulted in the appearance of cells with vigorous motility (at the frequency of 0.014%), and no such cells were found in the mock-transformed population (n=$10^7$). The rescued cells had a GFP signal in cilia and basal bodies (results not shown) and recovered a nearly normal rate of motility, multiplication (FIG. 30A,B), and phagocytosis (Table 3). Thus, the dramatic loss of ciliary functions seen in 6AF-KO cells is caused by the loss of TTLL6 protein activity.

TABLE 3

Phagocytic activity is restored by re-introduction of GFP-Ttll6Ap transgene into 6AF-KO cells.

|  | Wild Type | 6AF-KO | GFP-TTLL6A$^R$ |
| --- | --- | --- | --- |
| Average number of labeled food vacuoles/cell | 42.8 | 0 | 36.3 |
| Standard deviation | 3.7 | — | 3.5 |
| N = | 25 | 25 | 25 |

Food vacuoles were labeled with India ink for 30 min, cells were fixed and the average number of food vacuoles per cell was determined.

High-speed video microscopy showed that in wild type cells, locomotory cilia had an asymmetric waveform and rows of cilia were engaged in metachronal. In contrast, in 6AF-KO cells, many cilia appeared straight and some were seen rotating around a central pivot point, often colliding with each other in an uncoordinated motion. Furthermore, immunofluorescence images indicate that 6AF-KO cilia are more straight than wild type (FIG. 28D,E). In some 6AF-KO cultures grown for over 480 generations, the waveform was partly restored to normal. In these "adapted" 6AF-KO cells (6AF-KO$^4$), the beat frequency could be measured, and was found to be ~60% of wild type (FIG. 30F).

Figure 31:
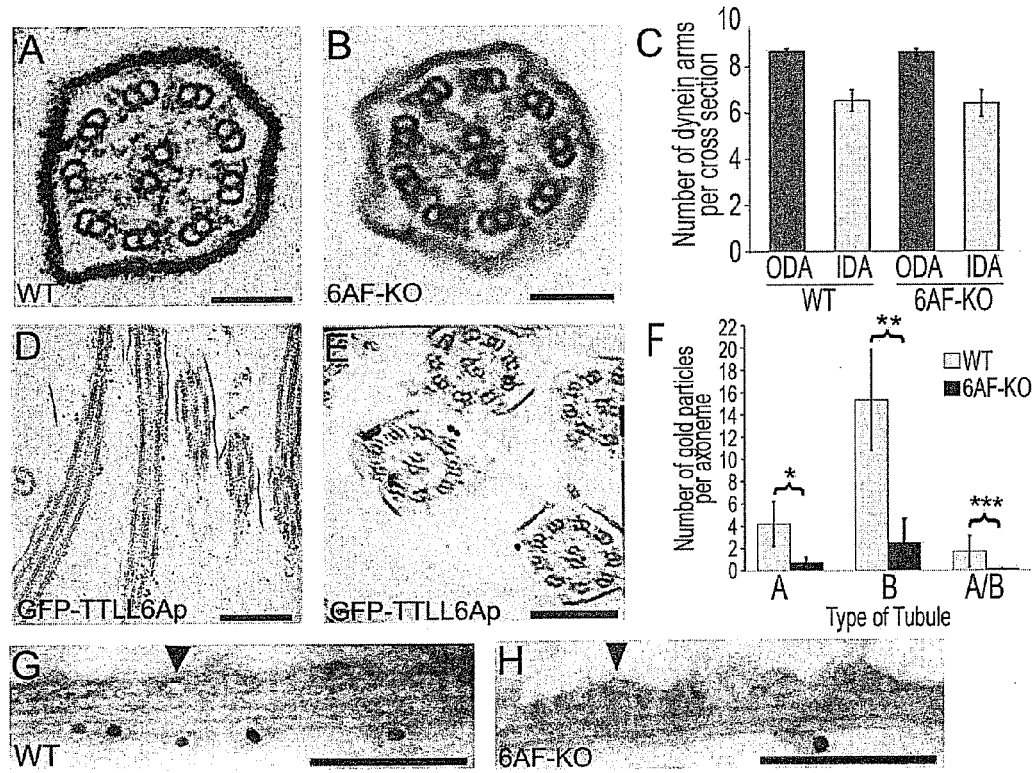
FIG. 31 shows Ttll6Ap and Ttl6Fp generate polyglutamylation primarily on B-tubule of outer microtubules. (A-B) Cross sections of wild type (A) and 6AF-KO (B) cilia of cells grown at 30° C. Bar, 100 nm (C) A graph that documents the average number of IDAs and ODAs per axoneme cross-section (wild type n=27; 6AF-KO n=27). Error bars represent standard errors. (D-E) Sections of cells expressing GFP-Ttll6Ap that were labeled with anti-GFP antibodies using immunogold TEM. Bar in D, 750 nm. Bar in E, 250 nm. (F) A graph that quantifies the localization of polyglutamylated tubulin epitopes in doublet microtubules labeled by whole mount immunogold microscopy (shown in G, H and FIG. 32) using polyE antibodies and anti-rabbit IgG 10 nm gold conjugates. Each gold particle was scored as associated more closely with either the A- or B-tubule, or the intertubule junction (A/B). Error bars represent standard deviations. *p=0.0001, p<0.0001, *p=0.0085. Twelve wild type and 12 6AF-KO axonemes were scored (G, H) Examples of isolated doublet microtubules of wild type (G) and 6AF-KO origin (H) analyzed by whole mount immunogold microscopy using polyE antibodies. Arrowheads mark the A-tubule covered with dynein arms. Additional images are shown in FIG. 32. Bar, 100 nm.

Exposure of wild type *Tetrahymena* cells to 20 µg/ml of sodium dodecyl benzene sulfonate (SDBS), causes rapid avoidance reaction associated with backward motility, likely by depolarizing the ciliary plasma membrane. While wild type cells showed rapid SDBS-induced avoidance responses (based on deviations from the linearity of swimming paths), the 6AF-KO cells failed to swim backwards, and instead slightly increased the rate of forward motility (FIG. 30G,H). The responses of 6AF-KO cells to other plasma membrane-depolarizing treatments (1 mM Ba$^{++}$, 20 mM Ca$^{++}$) were similar to SDBS. At the time of addition of SDBS, some 6AF-KO cells showed a slight turn, indicating that the signal detection pathways that regulate motility are at least partly functional. These data suggests that the response to signals, that requires proper modulation of activity of dynein arms, is affected. However, ultrastructural studies revealed that 6AF-KO axoneme cross-sections have a normal morphology (FIG. 31A,B, n=209). No difference was found in the frequency of outer (ODA) and inner dynein arms (IDA) on wild type and 6AF-KO axoneme cross-sections (FIG. 31C). Thus, we considered that TTLL6 enzymes, via tubulin glutamylation, could be affecting the activity ciliary dyneins.

Figure 32:
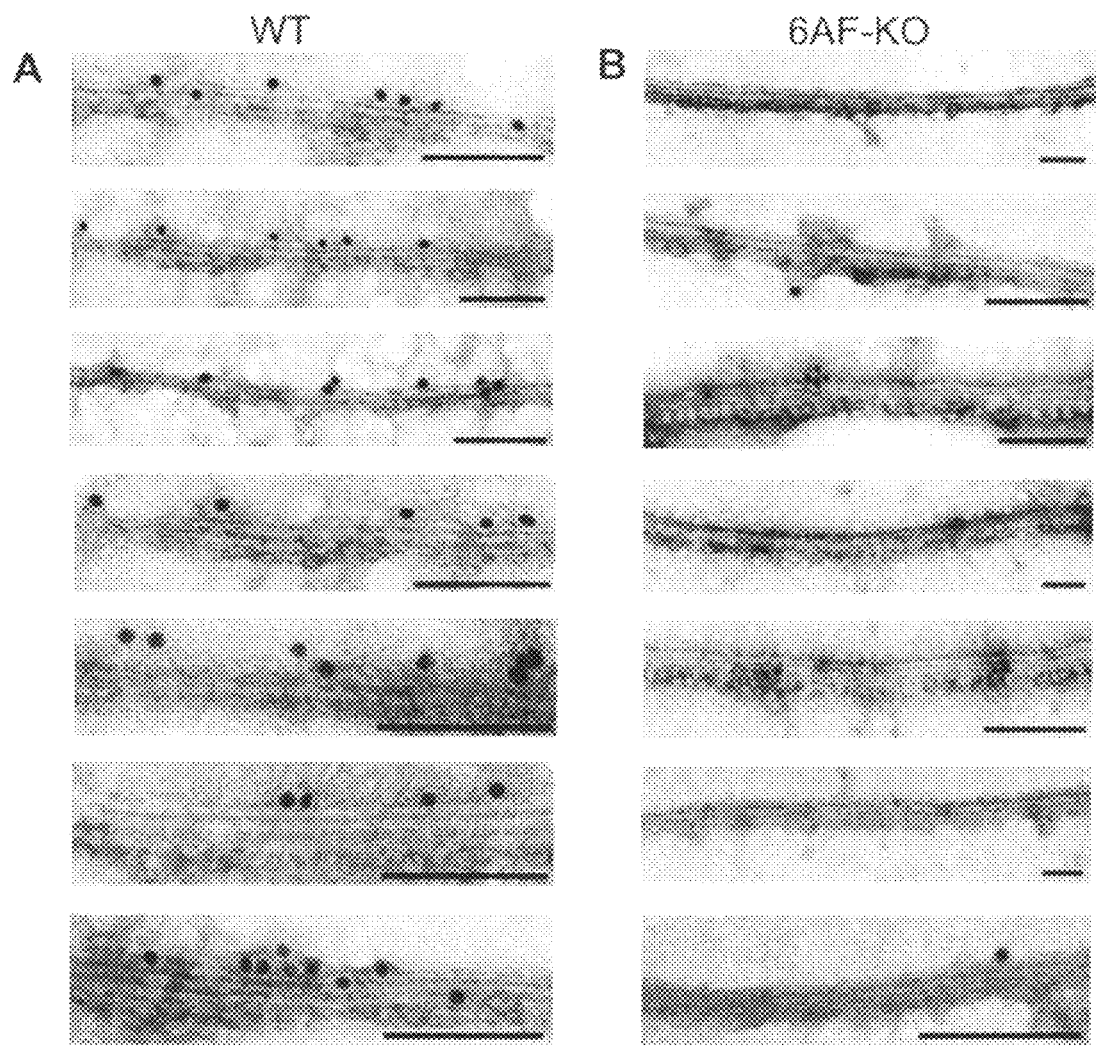
FIG. 32 shows Ttll6Ap and Fp primarily affect the polyglutamylation levels on the B-tubule or outer doublets. Images of negatively stained immunogold-labeled (using polyE antibodies) wildtype and 6AF-KO axonemes. Bar, 100 nm.

Ttll6Ap and Ttll6Fp primarily modify the B-tubule of outer microtubules. Immunogold TEM studies showed that overexpressed GFP-Ttll6Ap localized to the outer doublets and not to central microtubules in all of cross-sections examined (FIG. 31D,E n=38). We evaluated the distribution of polyglutamylated (polyE) epitopes on isolated doublet microtubules that were extruded from the axoneme with 40 μM ATP (see below). In negatively stained doublet microtubules viewed on edge, the A-tubule can be identified based on its increased width (as compared to the B-tubule), and dynein arms projecting from its surface (arrowhead, FIG. 31G,H). In wild type doublets, the majority of gold particles were detected in proximity of the B-tubule (FIG. 31F,G, FIG. 32) and the signal was dramatically reduced in 6AF-KO axonemes (FIG. 31F,H, FIG. 32). Thus, Ttll6Ap and Ttl1Fp primarily generate glutamylation on the B-tubule. Our observations are consistent with earlier microscopic and biochemical studies showing enrichment of tubulin glutamylation on the B-tubule (Kann et al., 1995. Tissue Cell 27, 323-329; Lechtreck and Geimer, 2000. Cell Motil Cytoskeleton 47, 219-235; Multigner et al., 1996. Biochemistry 35, 10862-10871). Since the B-tubule serves as a track for ciliary dynein, the primary role of tubulin glutamylation in cilia could be to regulate the motor activity of ciliary dynein.

Figure 33:
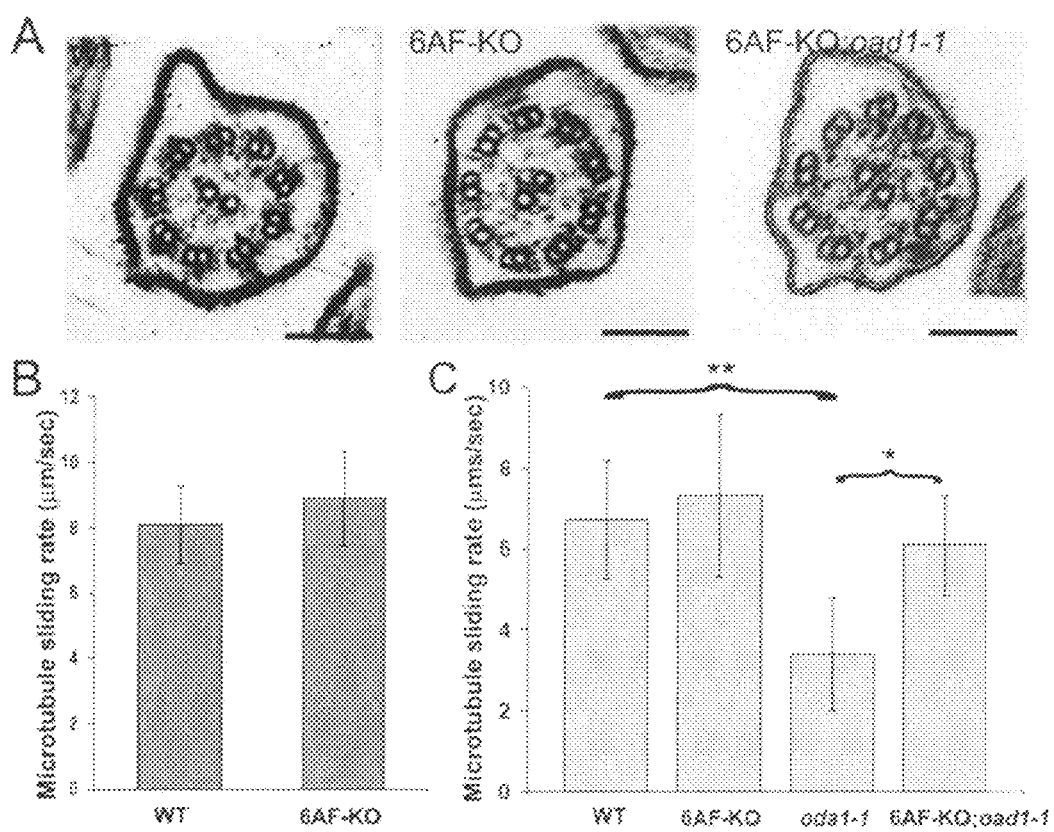
FIG. 33. Tubulin glutamylation regulates the velocity of inner dynein arm driven microtubule sliding in axonemes in vitro. (A) TEM cross-sections of wildtype, 6AF-KO and 6AF-KO; oad1 axonemes grown for 12 hr at 38° C. Bar=125 nm. The average numbers of dynein arms on scored axoneme cross-sections were as follows: 6AF-KO: 8.6+/−0.2 ODA, 6.4+/−0.6 IDA per section, n=15; 6AF-KO; oad1-1: 2.8+/− 0.5 ODA, 6.5+/−0.2 IDA per section, n=15. (B) A graph shows the average sliding velocity of wild type (n=40) and 6AF-KO (n=40) axonemes obtained from cells grown at the standard temperature (30° C.). Error bars represent standard deviations. Data were collected in 3 independent experiments. (C) A graph that documents the average sliding velocity of wild type (n=74), oad1-1 (n=41) 6AF-KO (n=73), and 6AF-KO;oad1-1 (n=46) axonemes obtained from cells grown at the 38° C., to induce the loss of ODAs in cells that are homozygous for the oad1-1 allele. Error bars represent standard deviations. *p<0.0001 for 6AF-KO;oad1-1 vs wildtype; **p<0.0001 for oad1-1 vs wildtype. Data were collected in 3 independent experiments.

Tubulin glutamylation strongly affects the inner dynein arm-driven microtubule sliding in isolated axonemes in vitro. When isolated *Tetrahymena* axonemes are exposed to ATP, outer doublet microtubules undergo unconstrained dynein-driven microtubule sliding (rather than reactivated bending) and the velocity of ATP-induced axonemal microtubule sliding can be used to assay the activity of ciliary dynein in situ (Summers Gibbons, 1971. Proc Natl Acad Sci U S A 68, 3092-3096; Okagaki and Kamiya, 1986. J Cell Biol 103, 1895-1902; Sale and Satir, 1977. Proc Natl Acad Sci U S A 74, 2045-2049). With 1 mMATP, microtubules underwent sliding at similar rates in wildtype and 6AF-KO axonemes (FIG. 33B). In wild type axonemes, the microtubule sliding velocity is believed to be primarily determined by the activity of ODAs (reviewed in Kamiya, 2002. Int Rev Cytol 219, 115-155). To test whether the TTLL6-mediated tubulin glutamylation affects the microtubule sliding generated specifically by IDAs, we constructed a strain that lacks TTLL6A and TTLL6F and is homozygous for the temperature-sensitive oadl-1 allele. When oadl-1 mutants are grown at restrictive temperature (38° C.), ODAs fail to assemble and cells are nearly paralyzed (Ludmann, 1993. J Eukaryot Microbiol 40, 650-660; Attwell et al., 1992. J Protozool 39, 261-266). We assessed microtubule sliding in axonemes isolated from wildtype, oadl-1, 6AF-KO and 6AF-KO;oadl-1 triple mutant cells, all grown for 12 hr at 38° C. We confirmed that 6AF-KO;oadl-1 cells had fewer ODAs as compared to 6AF-KO cells grown at the same temperature (FIG. 33A). As reported (Seetharam and Satir, 2005. Cell Motil Cytoskeleton 60, 96-103), oadl-1 axonemes showed a decreased rate of microtubule sliding as compared to wild type (FIG. 33C) while wild type and 6AF-KO axonemes showed nearly the same microtubule sliding velocity, as seen earlier for axonemes from cells grown at the standard temperature (compare FIG. 33B, C). Unexpectedly, the 6AF-KO;oadl-1 axonemes showed a nearly two-fold increase in the rate of microtubule sliding as compared to oadl-1 axonemes (FIG. 33C). These data indicate that tubulin glutamylation generated on the B-tubule by Ttll6Ap and Ttll6Fp has a restraining effect on the microtubule sliding velocity generated by the net activity of IDAs.

To conclude, we report that tubulin polyglutamylation generated by TTLL6 enzymes plays a major role in ciliary motility, and that the mechanism appears to involve regulation of inner dynein arm activity. Earlier studies have implicated tubulin glutamylation in axoneme assembly (Campbell et al. 2002. Genetics 162, 307-320; Pathak et al., 2007. Mol Biol Cell 18, 4353-4364). Deletion of additional TTLL6 paralogs in *Tetrahymena* led to major shortening of the axoneme (Example VI). Thus, tubulin glutamylation affects both axoneme assembly and motility and the latter function may require a higher dose of TTLL6 activity. A recent study of a *Chlamydomonas* mutant defective in TTLL9, an α-tubulin-preferring E-ligase, also revealed that tubulin polyglutamylation controls ciliary motility by affecting inner dynein arm activity (Kubo et al., 2009. Tubulin polyglutamylation regulates axonemal motility by changing activities of inner arm dyneins. Submitted). Thus, both studies link tubulin glutamylation, mediated by two conserved E-ligases on either α- or β-tubulin, to regulation of IDA activity. The abnormal waveform and lack of ciliary reversals that we observed in the 6AF-KO cells are also consistent with malfunctioning IDAs in *Tetrahymena* (Wood et al., 2007. J Cell Sci 120, 3075-3085; Hennessey et al., 2002. Cell Motil Cytoskeleton 53, 281-288). The mechanochemical properties of ODAs and IDAs are distinct but the underlying structural basis is not well understood (reviewed in Kamiya, 2002. Int Rev Cytol 219, 115-155). For example, in *Tetrahymena*, the 22S dynein fraction from the salt extract of axonemes (mainly ODAs) produces a linear gliding of microtubules at the rate of 8 μm/s, while the 14S dynein fraction (presumably IDAs) produces a motility at the rate of 4 μm/s associated with microtubule rotation (Vale and Toyoshima, 1988. Cell 52, 459-469). Importantly, two IDA subtypes that were studied in *Chlamydomonas* (dynein c and f/I1) display processive movements along microtubules (Sakakibara et al., 1999. Nature 400, 586-590; Kotani et al., 2007. Biophys J 93, 886-894). Kotani and colleagues proposed that in the bending cilium, processive IDAs, acting simultaneously with faster ODAs, impose a drag on sliding microtubules and could increase the axoneme curvature (Kotani et al., 2007. Biophys J 93, 886-894). We speculate that tubulin glutamylation is important for the processive motility of IDAs. One unusual feature of dynein motor domain is that it contacts the microtubule track by a conserved stalk domain (Gee et al., 1997. Nature 390, 636-639). Recent studies indicate that the stalk acts as a tether that allows for pulling of parts of the dynein molecule toward the microtubule during the power stroke (Ueno et al., 2008. Proc Natl Acad Sci U S A 105, 19702-19707; Carter et al., 2008. Science 322, 1691-1695). Thus, tubulin glutamylation could regulate the affinity of the stalk in inner dynein arms to the B-tubule. The patterns of glutamylation vary between axonemes of different species (Hoyle et al., 2008. Cell Motil Cytoskeleton 65, 295-313). Thus, specific beating patterns could be dependent on diverse patterns of tubulin glutamylation.

Experimental Procedures

Phylogenetic analyses. Sequences of TTLL6 protein homologs were obtained from NCBI databases. Conserved catalytic domains were aligned and neighbor-joining trees constructed as previously described (Edde et al., 1990. Science 247, 83-85).

Germ line-based targeting. The gene targeting plasmids were made based on the macronuclear genome sequence of *Tetrahymena thermophila*, available at the *Tetrahymena* Genome Database (Janke et al. 2005. Science 308, 1758-1762). Two fragments of macronuclear DNA were amplified for each locus. The fragments were designed to flank the genomic sequence that encodes the catalytic domain of TTLL6

TABLE 4

Primers used for construction of targeting fragments.

| Gene | Primers sequence (5'-3') | Restriction sites used to release the targeted fragment | Size of targeting fragment | Selectable cassette | TTLL catalytic domain region replaced | Seq. ID |
|---|---|---|---|---|---|---|
| TTLL6A | Forward ATATTGGGCCCGAGGAAGATGATGATGAGA | ApaI/SacI | 1.5 kb | Neo3 | 926 bp | 81 |
| | Reverse: ATAAACCCGGGGCTAAAGAAAACATACCAG | | | | | 82 |
| | Forward AATTTACTAGTAGCCATGGGTTTTAGAAGT | | 1.45 kb | | | 83 |
| | Reverse: ATTATGAGCTCCTTTTGGAAGTAATGICAG | | | | | 84 |
| TTLL6F | Forward: ATATTGGGCCCGAGCTAATCAAACATACGA | ApaI/SacII | 1.47 kb | mtt1-rp1291.6kb | | 85 |
| | Reverse: ATTATATCGATTTCCTAGCTATTCTGGTTA | | | | | 86 |
| | Forward: ATATTCCCGGGAAAAAGCCTGATGTTGAAG | | 1.44 kb | | | 87 |
| | Reverse: ATATTCCGCGGGGCTACAAATAAAGTCCAT | | | | | 88 |

(Table 4). Fragments were subcloned on either side of a selectable drug resistance cassette (neo3 (Wloga et al., 2010. Eukaryot Cell. 9,184-193) or mtt1-rp129. The cassette was embedded in a reverse transcriptional orientation. The targeting fragments were separated from the rest of the plasmid using restriction enzymes and transformed biolistically into mating CU428 and B2086 strains (Regnard et al., 2003. J Cell Sci 116, 4181-4190) at 3, 3.5 and 4 hr after mixing. After shooting, cells were incubated in SPP and 2.5 µg/ml CdCl$_2$ for 3 hr, and transformants were selected with appropriate drugs (neo3, paramomycin-100 µg/ml with CdCl$_2$ 2.5 µg/ml; mtt1-rp129, cycloheximide 15 µg/ml with CdCl$_2$ 2.5 µg/ml). Putative germline transformants were identified by co-resistance to 15 µg/ml 6-methylpurine. Knockout heterokaryons were generated by allowing the disrupted alleles to assort from the macronucleus via phenotypic assortment and by making the micronucleus fully homozygous using a star cross (Wloga et al. 2008. Eukaryot Cell 7, 1362-1372). Double knockout strains were made by multiple rounds of standard crosses. Total homozygotes were created by crossing appropriate heterokaryons and isolating progeny. The absence of the targeted genomic regions in the homozygote was confirmed by PCR of genomic DNA with primers designed to amplify junctions between selectable cassettes and the nontargeted gene specific regions (Table 5).

TABLE 5

Diagnostic primers used for verification of gene disruptions (amplify deleted regions)

| Type of gene | | Seq. ID |
|---|---|---|
| TTLL6A | Forward 5'-TATCTTTTGGACTGATAATGCT-3' | 89 |
| | Reverse 5'-CTCTTAATATCTTTCCACAG-3' | 90 |
| TTLL6F | Forward 5'-AGATCTCTAAAGGAAAATGC-3' | 91 |
| | Reverse 5'-TTCATGTAGTTATCTGGTTG-3' | 92 |

To construct a triple mutant strain, 6AF-KO;oadl-1, a 6AF-KO heterokaryon was crossed to an oadl-1 germline mutant strain (van Dijk et al., 2007. Mol Cell 26, 437-448), triple heterozygotes were matured and drug resistance was lost from the macronucleus by phenotypic assortment. Strain with homozygous micronuclei were made by a cross to A*III. Specific heterokaryons that were homozygous for both gene disruptions and the oadl-1 allele were identified by an outcross to an oadl-1 homozygote strain, and identification their progeny that was resistant to paromomycin, cycloheksimide in the presence of cadmium and displayed ciliary paralysis after incubation at 38° C.

For rescue, vegetatively growing 6AF-KO cells were biolistically transformed with a fragment encoding MTT1-GFP-TTLL6A targeted to BTU1 (Janke et al. 2005. Science 308, 1758-1762). A strain lacking TTLL6A and TTLL6F and homozygous the oadl-1 mutation (Attwell et al., 1992. J Protozool 39, 261-266) was constructed by standard crosses.

Phenotypic studies. The multiplication, cell motility and phagocytosis rates were measured as described (Wloga et al. 2008. Eukaryot Cell 7, 1362-1372). To assay swimming behavior, 2 ml of cells ($2 \times 10^5$ cells/ml) were added to 100 ml of wash buffer (10 mM Tris, 50 µM CaCl$_2$, MOPS pH 7.2), centrifuged at 1000×g for 2 min and suspended in 2 ml. After 30 min of adaptation, cells were assayed in 70 µl drop on a two-ring slide, with or without SDBS (20 µg/ml) and video recordings were done under a dissecting microscope with a Moticam 480 digital camera. To measure the beat frequency, cells ($2 \times 10^5$ cells/ml) were recorded at 500 frames/sec by a Photronics 1280 PCI FastCam on a Nikon Eclipse E600 microscope.

Biochemical studies. Partial purifications of Ttll6Ap and Ttlllp from overproducing Tetrahymena strains and in vitro glutamylation assays with taxotere—stabilized microtubules made of the murine brain and HeLa tubulin were performed as described (Wloga et al. 2008. Eukaryot Cell 7, 1362-1372).

To purify cilia, Tetrahymena cells were grown to a density of $3 \times 10^5$ cells/ml in 500 ml of SPP, washed with 10 mM Tris pH 7.5 and suspended in 40 ml of 10 mM Tris, 50 mM sucrose, 10 mM CaCl$_2$ with protease inhibitors (Complete, Roche). Deciliation was initiated by adding 600 µl of 0.5 M acetic acid, after 2 min followed by 550 µl of 0.6M KOH. Cell bodies were removed (1860×g, 5 min) and cilia were collected (23,300×g, 15 mM, 4° C.) and suspended in 500µ of the axoneme buffer (20 mM potassium acetate, 5 mM MgSO$_4$, 0.5 mM EDTA, 20 mM HEPES, pH 7.6).

Microtubule sliding in isolated axonemes. Cilia were suspended at 0.1 mg protein/ml in the axoneme buffer (without protease inhibitors). For experiments on axonemes purified from strains carrying the oadl-1 mutation, all strains were grown for 12 hr at 38° C. with inocula adjusted according to individual growth rates to collect cells at 3×10$^5$ cells/ml. Cilia were suspended at 0.1 mg protein/ml in 500 µl of the motility buffer (1 mM DTT, 50 mM potassium acetate, 5 mM MgSO4, 1 mM EGTA, 30 mM HEPES, PEG 1%, pH 7.6). To demembranate, 10 µl of 1% NP-40 in motility buffer was added to 50 µl of diluted cilia. The axoneme suspension was pipetted into a perfusion chamber constructed with a glass slide and cover slip separated by double stick tape. The perfusion chamber was washed with 50 µl of axoneme buffer followed by perfusion with 50 µl of 1 mM of ATP, in the motility buffer. The sliding of microtubules was recorded on a Zeiss Axiovert 35 microscope equipped with dark field optics (40×PlanApo), on a silicon-intensified camera (VE-1000, Dage-MTI, Michigan City, Ind.). The video images were converted to a digital format using Labview 7.1 software (National Instruments, Austin, Tex.). The sliding velocity was determined manually by measuring microtubule end displacement, as a function of time, on tracings calibrated with a micrometer (Okagaki and Kamiya, 1986. J Cell Biol 103, 1895-1902).

Immunofluorescence and western blotting. The cells were stained by immunofluorescence as described in (Wolff et al., 1992. Eur J Cell Biol 59, 425-432) with the following primary antibodies: 12G10 (1:50), GT335 (1:100), SG polyclonal anti-total tubulin (1:600) and polyE (1:100).

For western blotting, 5 µg of cilia protein per lane were separated on a 10% SDS-PAGE and western blots were done as described (Kann et al., 1995. Tissue Cell 27, 323-329), with the primary antibodies at the following dilutions: GT335 anti-glutamylated tubulin mAb (1:1,000) (Lechtreck and Geimer, 2000. Cell Motil Cytoskeleton 47, 219-235), 12G10 anti-α-tubulin mAb (1:10,000) (Developmental Studies Hybridoma Bank), polyE anti-polyglutamic acid antibodies (1:1,000) (Wloga et al., 2010. Eukaryot Cell. 9,184-193), polyG, anti-polyglycine antibodies (Multigner et al., 1996. Biochemistry 35, 10862-10871), 6-11 B-1 anti-acetyl-K40 on α-tubulin (Summers Gibbons, 1971. Proc Natl Acad Sci U S A 68, 3092-3096), and anti-SerH surface antigen antibodies (Okagaki and Kamiya, 1986. J Cell Biol 103, 1895-1902).

Electron microscopy. For standard transmission electron microscopy (TEM), cells were fixed as described (Sale and Satir, 1977. Proc Natl Acad Sci U S A 74, 2045-2049). For immunogold TEM, cells carrying an MTT1-GFP-TTLL6A transgene were grown in 5 ml of SPP medium (2×10$^5$ cells/ml) and induced with 2.5 µg/ml CdCl$_2$ for 3 hr, gently spun down briefly, fixed in an Eppendorf tube and stained as described above for immunofluorescence with anti-GFP antibodies (Abcam, 1:10,000) overnight followed by anti-rabbit IgG-10 nm gold (1:60) (Amersham Pharmacia) for 2 hr at room temperature. Cells were concentrated by centrifugation to 100 µl and post-fixed with 1 ml of 2% glutaraldehyde (in 0.1M sodium cacodylate buffer, p117.2) on ice for 1 h. Cells were washed 5 times in cold sodium cacodylate buffer (10 min each on ice) and fixed with 1 ml of 1% osmium tetroxide for 1 hour on ice. The pellet was washed 5 times in water, followed by dehydration in ethanol concentration/water series and embedding in Epon. Ultrathin sections were stained with uranyl acetate and lead citrate and analyzed on JEOL 1200 EX transmission electron microscope. For immunogold whole mount TEM, cilia were purified from 50 ml of cells (3×10$^5$ cells/ml) and demembranated in 500 µl of 1% NP40 in the axoneme buffer. After 5 min on ice, axonemes were collected at 23,000 g (15 min, 4° C.), washed with 1 ml of axoneme buffer and, centrifuged and suspended in the axoneme buffer at 10 mg tight pellet/ml of. To initiate sliding of axonemal microtubules, 0.5 µl of 2 mM ATP was added to 50 µl of axonemal suspension (final concentration 40 µM). After incubation for 3 min at room temperature, 10 µl of suspension was placed onto a formvar-coated grid for 1 min and the excess was absorbed by filter paper. Grids were processed for immunogold TEM (Kamiya, 2002. Int Rev Cytol 219, 115-155) as described below and stained using uranyl acetate.

For immunogold whole mount TEM, axonemes were purified and reactivated with ATP as described in the main text, and labeled with antibodies according to (Kamiya, 2002. Int Rev Cytol 219, 115-155) with minor modifications. Ten µl of the ATP-reactivated axonemes were placed on top of a formvar-coated copper EM grid, allowed to settle for 1 min, the excess of liquid was drained with a filter paper and the material was immediately fixed by floating the grid on top of a 50 µl drop of 2% paraformaldehyde in PHEM buffer. The grids were washed by dipping in 10 mM HEPES (pH 7.4) about 15 times and blocked by covering with 10 µl of 3% BSA, 0.01% Tween20 in PBS for 15 min. The grids were incubated in 50 µl drops of primary antibodies (1:100 polyE in the blocking buffer). The grids were washed by dipping in PBS about 15 times, incubated in 50 µl drops of the secondary antibody, anti-rabbit IgG-10 nm gold (GE Healthcare) (1:60 in the blocking buffer), washed 15 times in PBS, and negatively stained with 2% uranyl acetate.

Example VI

*Tetrahymena* Strains Lacking Paralogs of the TTLL6 Gene Demonstrate Reduced Glutamylation Methods described in detail in Example V were used to obtain strains of *Tetrahymena thermophila* lacking 4 or 5 paralogs of TTLL6 gene family. Deletion of additional TTLL6 paralogs (on top of TTLL6A and TTLL6F genes that were deleted earlier and are described in Example V) led to further reduction in the levels of tubulin polyglutamylation but the reduction in the levels of total glutamylation is less pronounced. As a result, axonemes of cilia of deletion mutants have shortened glutamyl side chains. Such axonemes can potentially be used for an in vitro tubulin glutamylation assay with Ttll6Ap or similar enzymes that act mainly as glutamyl ligases with chain elongation activity.

Figure 34:
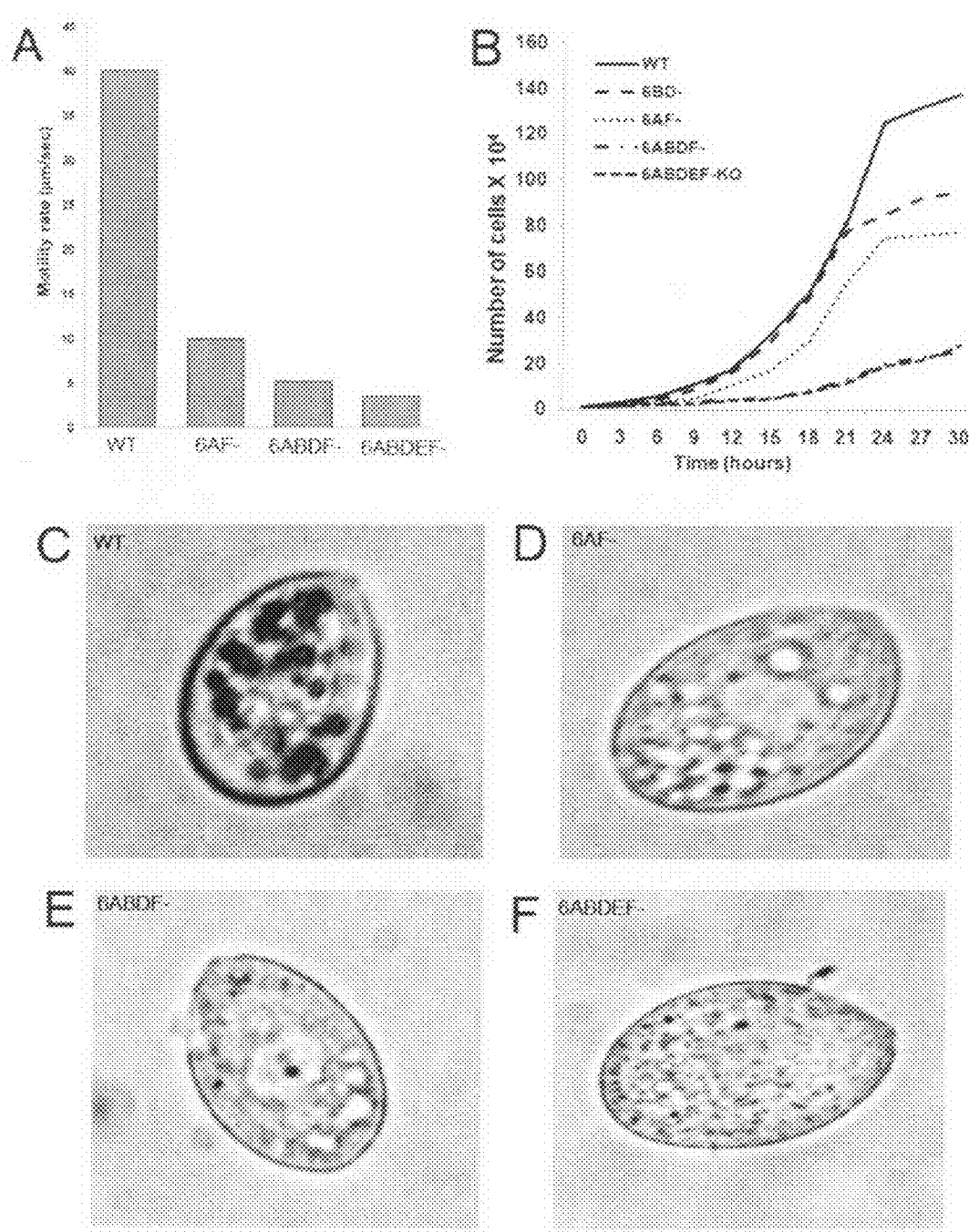
FIG. 34 shows deletion of multiple paralogs genes of TTLL6 progressively reduces the rate of growth, phagocytosis and cell motility.

Deletion of multiple paralogs genes of TTLL6 progressively reduces the rate of growth, phagocytosis and cell motility. In all panels of FIG. 34, WT designates a wild type strain while 6AF-, 6BD-, 6ABD-F, and 6ABDEF- designate strains lacking from 2 to 5 paralogous genes in the TTLL6 family (TTLL6A, TTLL6B, TTLL6D, TTLL6E, TTLL6F). FIG. 34A shows motility rates. FIG. 34B shows culture growth rates. FIG. 34C-D shows images of cells fed with India ink to evaluate the ability to perform phagocytosis. Note that ink-filled food vacuoles are present only in WT cells.

Figure 35:
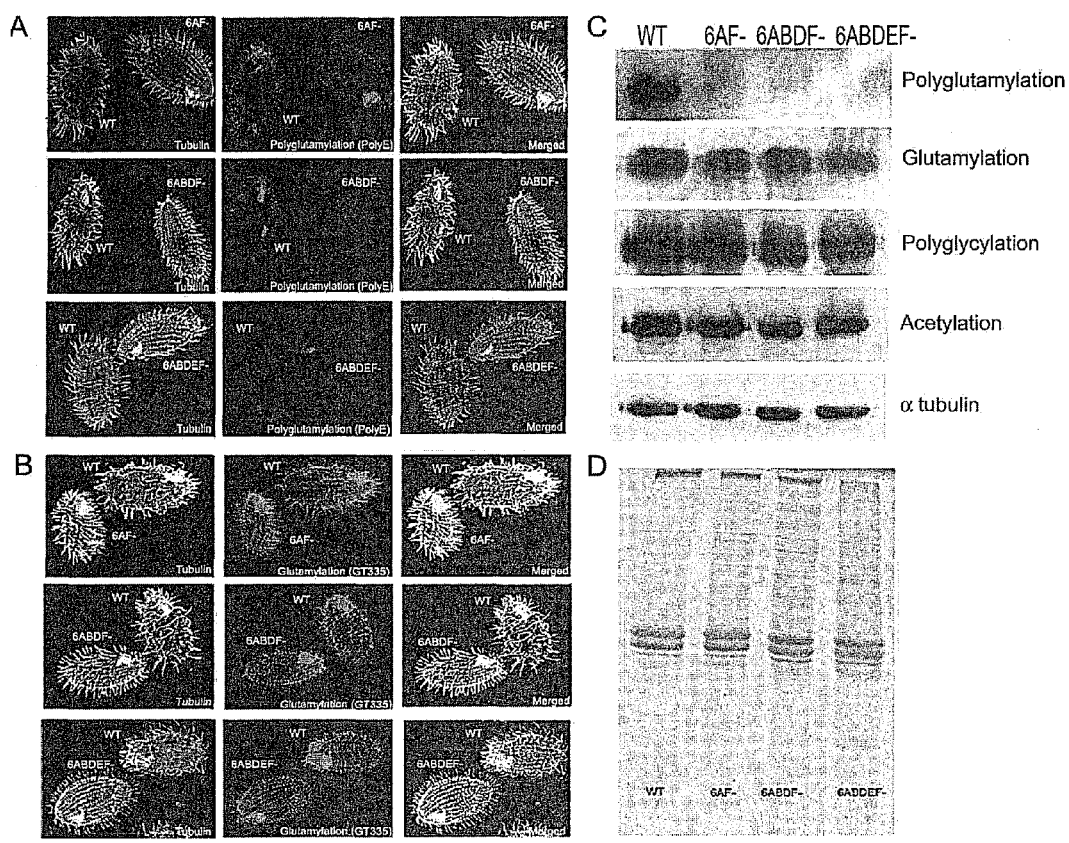
FIG. 35 shows deletion of multiple TTLL6 paralog genes leads to a progressive loss of tubulin polyglutamylation.

Deletion of multiple TTLL6 paralog genes leads to a progressive loss of tubulin polyglutamylation. In all panels of FIG. 35, WT designates a wild type strain while 6AF-, 6BD-, 6ABD-F, and 6ABDEF- designate strains lacking from 2 to 5 paralogous genes in the TTLL6 family (TTLL6A, TTLL6B, TTLL6D, TTLL6E, TTLL6F). FIG. 35A shows immunofluorescence images of a pair of cells imaged side by side. One of the cells is WT and another lacks two or more TTLL6 paralog genes. The left row contains images of cells labeled by an anti-tubulin antibody, 12G10. The middle row contains the same cells labeled by antibodies against polyglutamylation (polyE). The right row contains images of merged signals shown in the other two rows. Note a progressive loss of tubulin polyglutamylation along with the deletion of TTLL6 paralog genes. FIG. 35B shows immunofluorescence images of a pair of cells images side by side. One of the cells is WT and another lacks two or more TTLL6 paralog genes. The left row contains images of cells labeled by an anti-tubulin antibody, 12G10. The middle row contains the same cells labeled by antibodies against tubulin glutamylation (GT335). The right row contains images of merged signals shown in the other two rows. Note that the signals are similar in WT and TTLL6 knockout cells. Thus, the loss of TTLL6 paralogs leads to polyglutamylation side chain shortening and not its complete loss. FIG. 35C shows a western blot of total ciliary proteins isolated from WT and TTLL6 knockout strains. The following antibodies were used: polyE (anti-polyglutamylation), GT335 (tubulin glutamylation), polyG (anti-polyglycylation), 6-11 B-1 (anti-acetyl-K40 of α-tubulin), 12G10 (anti-α-tubulin). FIG. 35D shows a Coomassie Blue stained SDS-PAGE gel of protein samples used in FIG. 35C as a control for equal loading.

Figure 36:
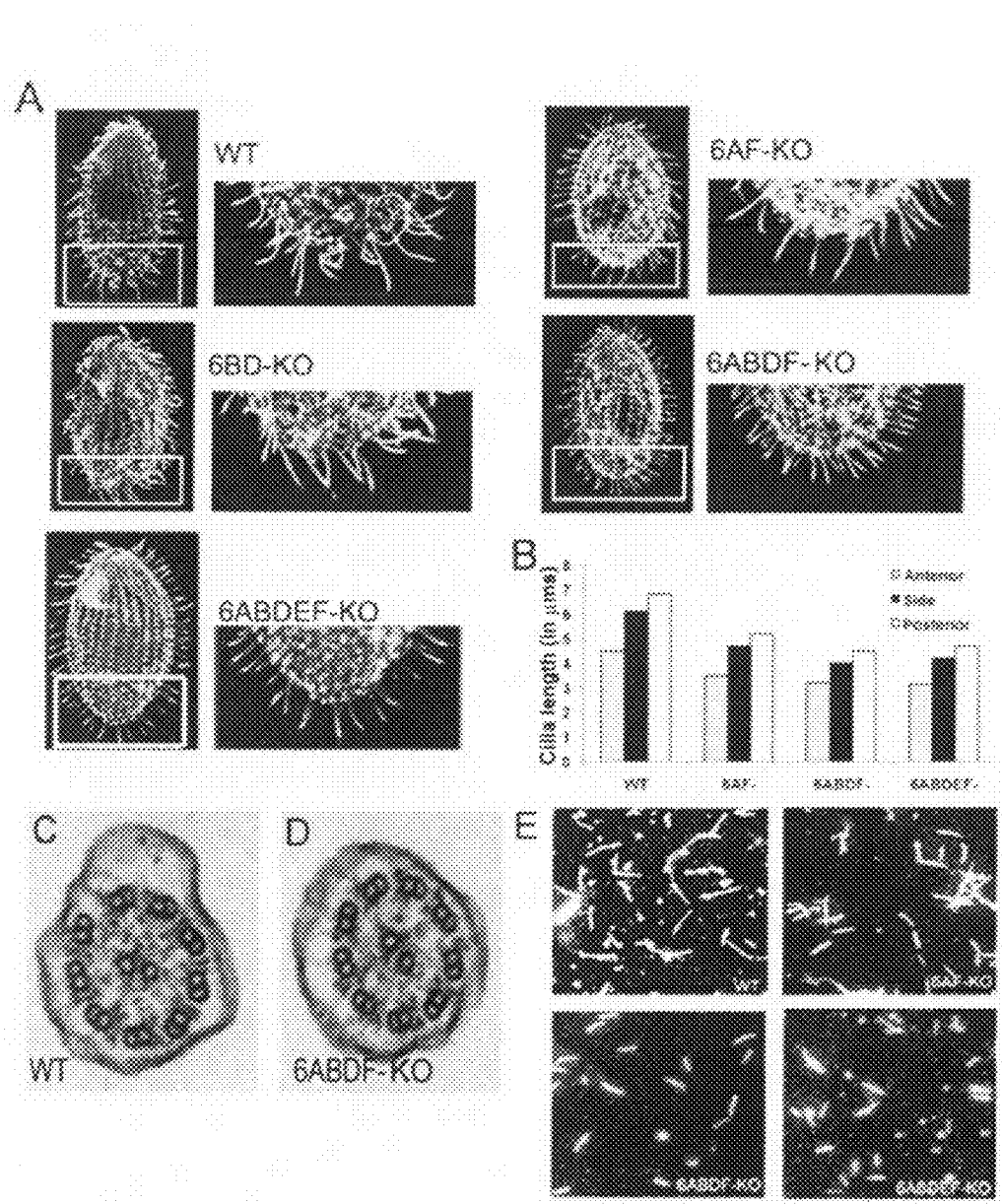
FIG. 36 shows deletion of multiple TTLL6 paralog genes leads to progressive shortening of cilia.

Deletion of multiple TTLL6 paralog genes leads to progressive shortening of cilia. FIG. 36A shows immunofluorescence images of cells labeled by 12G10 anti-α-tubulin antibodies. FIG. 36B shows a histogram that documents the distribution of ciliary length obtained by measurements of cilia of cells labeled by immunofluorescence. FIG. 36C-D shows electron micrographs of axoneme cross-sections of a WT and knockout cell which demonstrate that the axoneme structure is normal despite its shortening. FIG. 36E shows immunofluorescence images (with anti-α-tubulin antibodies) of isolated cilia.

Example VII

TTLL3 is a Tubulin Glycine Ligase that Regulates the Assembly of Cilia

In most ciliated cell types, tubulin is modified by glycylation, a posttranslational modification of unknown function. This example shows that the TTLL3 proteins act as tubulin glycine ligases with chain-initiating activity. In *Tetrahymena*, deletion of TTLL3 shortened axonemes and increased their resistance to paclitaxel-mediated microtubule stabilization. In zebrafish, depletion of TTLL3 led to either shortening or loss of cilia in several organs, including the Kupffer's vesicle and olfactory placode. This example also shows that, in vivo, glutamic acid and glycine ligases oppose each other, likely by competing for shared modification sites on tubulin.We propose that tubulin glycylation regulates the assembly and dynamics of axonemal microtubules and acts either directly or indirectly by inhibiting tubulin glutamylation. Wloga et al., "TTLL3 is a Tubulin Glycine Ligase that Regulates the Assembly of Cilia," Jun. 16, 2009, *Developmental Cell* 16:867-876.

In a typical motile cilium, its microtubular scaffold, the axoneme, is built around a framework of nine outer and two central microtubules. The axoneme is composed of several hundred different proteins (Pazour et al., 2005. J. Cell Biol. 170, 103-113; Smith et al., 2005. J. Proteome Res. 4, 909-919). In most cell types, ciliogenesis involves the delivery of precursors to the tips of growing axonemes by the intraflagellar transport (IFT) pathway (Kozminski et al., 1995. J. Cell Biol. 131, 1517-1527). However, how the axoneme assembles once the precursors are delivered to cilia is poorly understood.

Ciliary tubulin is marked by conserved posttranslational modifications (PTMs), that could play a role in assembly of the axoneme (Verhey and Gaertig 2007. Cell Cycle 6, 2152-2160). Two types of tubulin PTMs, known as polymodifications—glutamylation (Eddé et al., 1990. Science 247, 83-85) and glycylation (Redeker et al., 1994. Science 266, 1688-1691)—are peptide branches made of either glutamyl or glycyl residues that are attached to the g-carboxyl group of glutamic acids of the C-terminal tail domains (CTTs) of α- and β-tubulin. Recently, we have identified the tubulin glutamic acid ligase enzymes as proteins related to tubulin tyrosine ligase (Ersfeld et al., 1993. J. Cell Biol. 120, 725-732), known as TTL-like (TTLL) proteins (Janke et al., 2005. Science 308, 1758-1762). Studies on several glutamic acid ligases (E-ligases) indicate that tubulin glutamylation is important for assembly of axonemes. The loss of the noncatalytic subunit of TTLL1 E-ligase led to defective sperm axonemes and male sterility in mice (Campbell et al., 2002. Genetics 162, 307-320), and depletion of TTLL6 inhibited assembly of olfactory cilia in zebrafish (Pathak et al., 2007. Mol. Biol. Cell 18, 4353-4364).

The role of tubulin glycylation remains unknown, mainly because the modifying enzymes are yet to be discovered. Here we use *Tetrahymena* to identify TTLL3 as a tubulin glycine ligase (G-ligase) with a chain-initiating activity. *Tetrahymena* cells lacking all TTLL3 genes have shortened axonemes that are resistant to paclitaxel, indicating that tubulin glycylation changes the lattice properties of axonemal microtubules. Next, we use zebrafish to study the significance of TTLL3 during vertebrate development. Morpholino (MO)-based depletion studies indicate that TTLL3 is required for either elongation or stability of axonemes. In both organisms, a reduction in tubulin glycylation led to hyperglutamylation. Thus, glycylation could act by competing with glutamylation for shared modification sites on tubulin.

Results

TTLL3 Homologs of *Tetrahymena* are Required for Initiation of Glycyl Side

Chains on Tubulin. The TTLL superfamily includes proteins that mediate the ligation of amino acids to proteins, including enzymes that catalyze tubulin tyrosination (Ersfeld et al., 1993. J. Cell Biol. 120, 725-732) and glutamylation (Janke et al., 2005. Science 308, 1758-1762). The murine TTLL10 glycylates NAP1 (Ikegami et al., 2008. FEBS Lett. 582, 1129-1134), but it is not known whether any TTLL glycylates tubulin. TTLL3 sequences (Janke et al., 2005. Science 308,1758-1762) are present in organisms that have tubulin glycylation (Bré et al., 1996. J. Cell Sci. 109, 727-738; Bressac et al., 1995. Eur. J. Cell Biol. 67, 346-355), but are absent in *Trypanosoma* and Plasmodium that lack this PTM (Fennell et al., 2008. Int. J. Parasitol. 38, 527-539; Schneider et al., 1997. J. Cell Sci. 110, 431-437). Thus, TTLL3 could be a G-ligase for tubulin.

Figure 37:
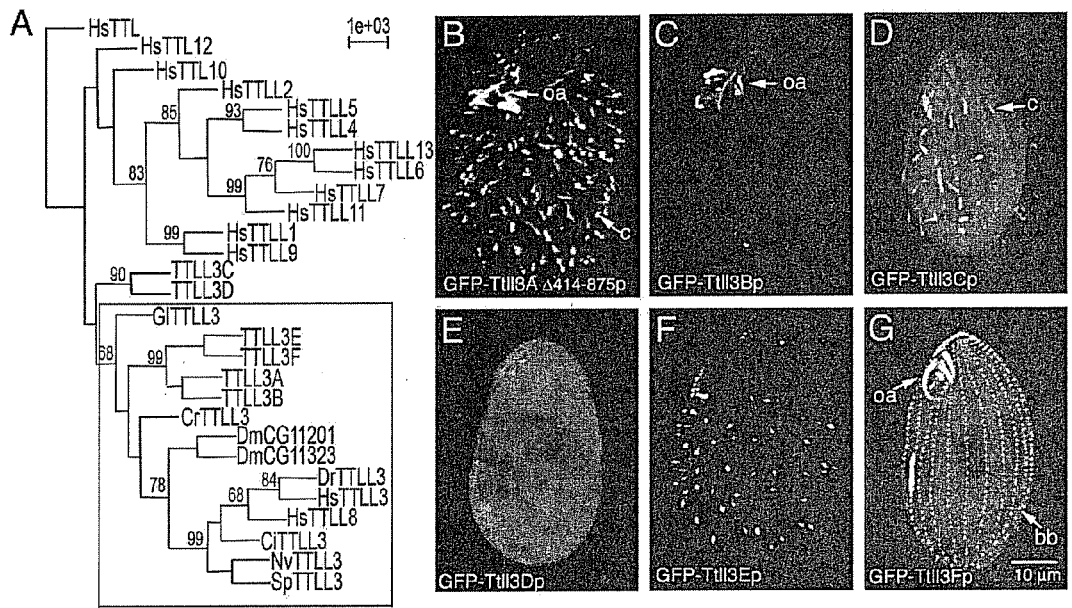
FIG. 37A shows a phylogenetic tree of TTLLs calculated using the conserved catalytic TTL domain by a neighbor-joining method and HsTTL as an outgroup. All known human proteins that have a TTL catalytic domain are included. From other organisms, sequences that were best matches for HsT-TLL3 and identified as TTLL3 type sequence in a reverse BLASTp were included. TTLL sequences were obtained from National Center for Biotechnology Information (NCBI), *Tetrahymena* genome database (available on the worldwide web at ciliate.org/), *Ciona intestinalis* and *Chlamydomonas reinhardtii* from DOE Joint Genome Institute (available on the worldwide web at genome.jgipsf.org/ciona4/ciona4.home.html). Abbreviations and accession numbers: Ci, *Ciona intestinalis*; Cr, *Chlamydomonas reinhardtii* (C_540087); Dm, *Drosophila melanogaster* (CG11323 and CG11201); Dr, *Danio rerio* (AAI17657.1); Gl, *Giardia lamblia* (XP_001708169.1); Hs, *Homo sapiens* (TTL, NP_714923.1; TTLL1, CAG30485.1; TTLL2, AAK20169.1; TTLL3, NP_056459.3; TTLL4, Q14679.2; TTLL5, Q6EMB2.1; TTLL6, BAC05032.1; TTLL7, NP_078962.4; TTLL8, XP_943304.2; TTLL9, EAW76406.1; TTLL10, Q6ZVT0.2; TTLL11, NP_919228.2; TTL12, NP_055955.1; TTLL13, NP_001025135.2); Nv, *Nematostella vectensis* (XP_001636414.1); Sp, *Strongylocentrotus purpuratus* (X_784103.1); Tt, *Tetrahymena thermophila* (Ttll3Ap, TTHERM_00666600; Ttll3Bp, TTHERM_00125600; Ttll3Cp, TTHERM_00378750; Ttll3Dp, TTHERM_00196050; Ttll3Ep, TTHERM_00770730; Ttll3Fp, TTHERM_00316230).
FIG. 37B-G shows fluorescence confocal images of GFP in cells overproducing GFP-tagged Ttll3Ap-A414-875 (a fragment lacking the catalytic domain and C-terminal part) (B), GFP-Ttll3Bp (C), GFPTtll3Cp (D), GFP-Ttll3Dp, (E) GFP-Ttll3Ep (F) and GFP-Ttll3Fp (G) after 3 hrs of 2.5 μg/ml cadmium chloride induction. Abbreviations: bb, basal body; c, cilium; oa, oral apparatus. Bar, 10 μm.

*Tetrahymena thermophila* has four genes encoding members of the conserved TTLL3 clade: TTLL3A through TTLL3D, and two genes encoding divergent TTLL3-like proteins, TTLL3E and TTLL3F (see FIG. 37). All these proteins have peptide signatures in the ATPase domain that are diagnostic of the TTLL3 clade. Ectopic GFP-Ttll3Ap, Bp, Cp, and Ep localized mainly to cilia, with GFP-Ttll3Ap and Ep present mainly in locomotory and oral cilia (FIG. 37F and FIG. 38C), Bp in oral cilia, and Cp in assembling locomotory cilia (FIGS. 37C-D). The N-terminal noncatalytic domain of Ttll3Ap was sufficient for ciliary localization (FIG. 37B). GFPTtll3Dp remained in the cell body, while 3Fp was enriched in the basal bodies (FIGS. 37E-G).

Figure 38:
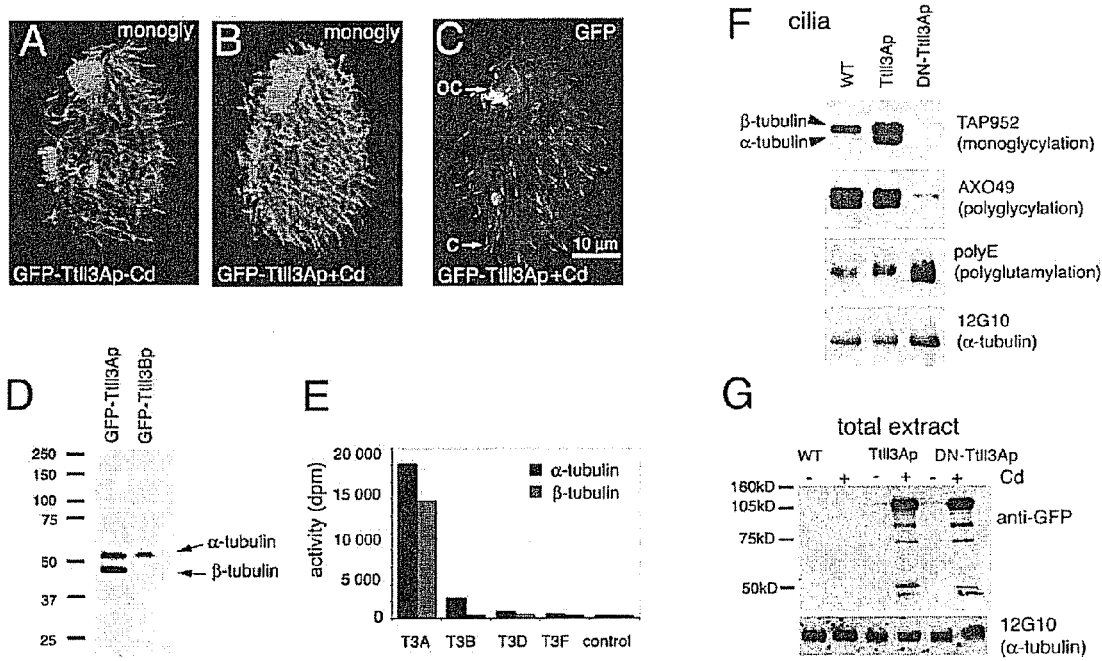
FIG. 38 shows TTLL3 enzymes increase tubulin monoglycylation in *Tetrahymena*.
Figure 39:
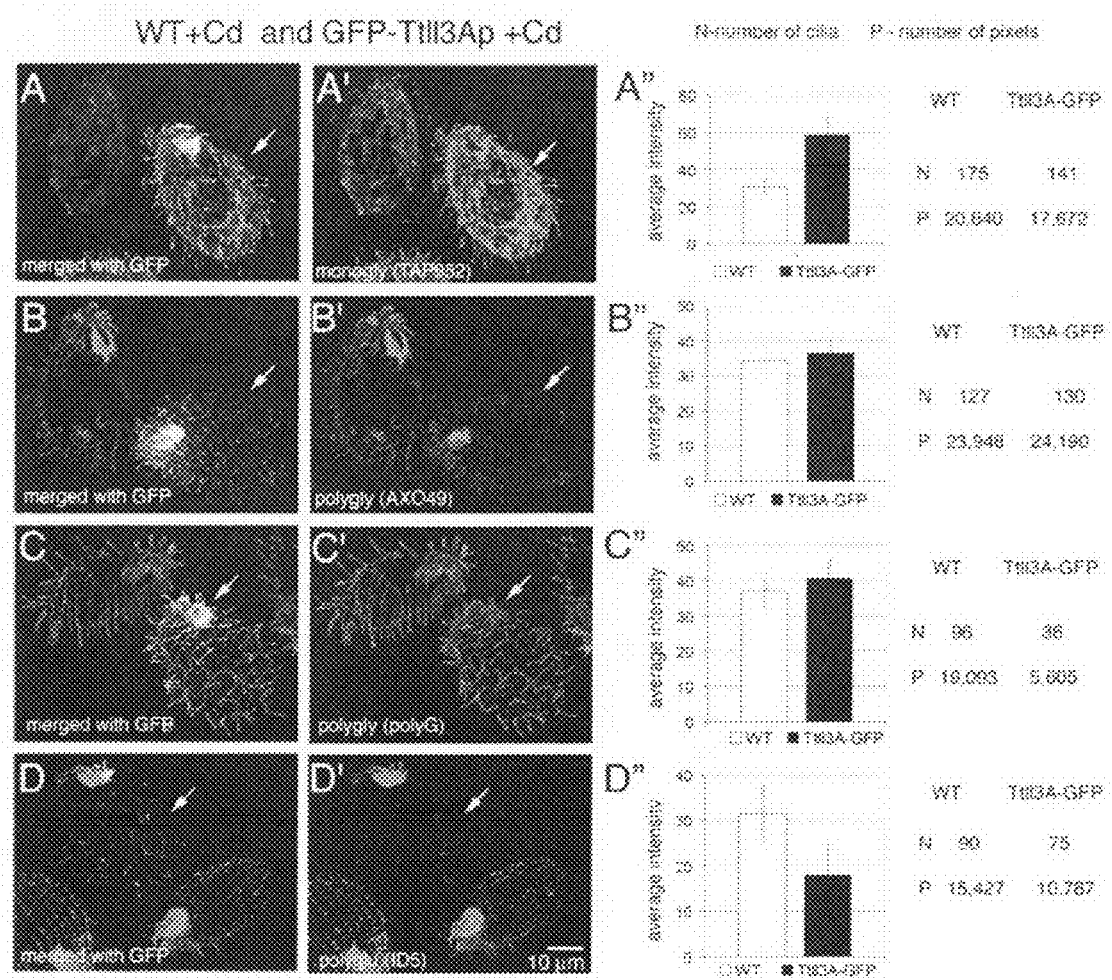
FIG. 39 shows overproduction of GFP-Ttll3Ap increases tubulin monoglycylation and reduces tubulin glutamylation.

We measured the tubulin glycylation activity in cytoplasmic fractions of *Tetrahymena* overproducing specific paralogs. A GFP-Ttll3Ap-enriched extract showed a strong increase in glycylation activity on α- and β-tubulin, while the GFP-Ttll3Bp-enriched extract had increased activity on α-tubulin (FIGS. 38D-E). The TAP952 monoclonal antibody (mAb) recognizes monoglycylated sites on tubulin, while the AXO49 mAb (Bré et al., 1998. Mol. Biol. Cell 9, 2655-2665) and polyG antibodies (Duan and Gorovsky, 2002. Curr. Biol. 12, 313-316) recognize elongated side chains (polyglycylation). Expression of GFP-Ttll3Ap increased the levels of tubulin monoglycylation, but not polyglycylation in cilia based on immunofluorescence (FIGS. 38A-B and FIGS. 39A-C") and Western blots (FIG. 38F). Thus, Ttll3Ap mediates glycyl side chain initiation activity.

Figure 40:
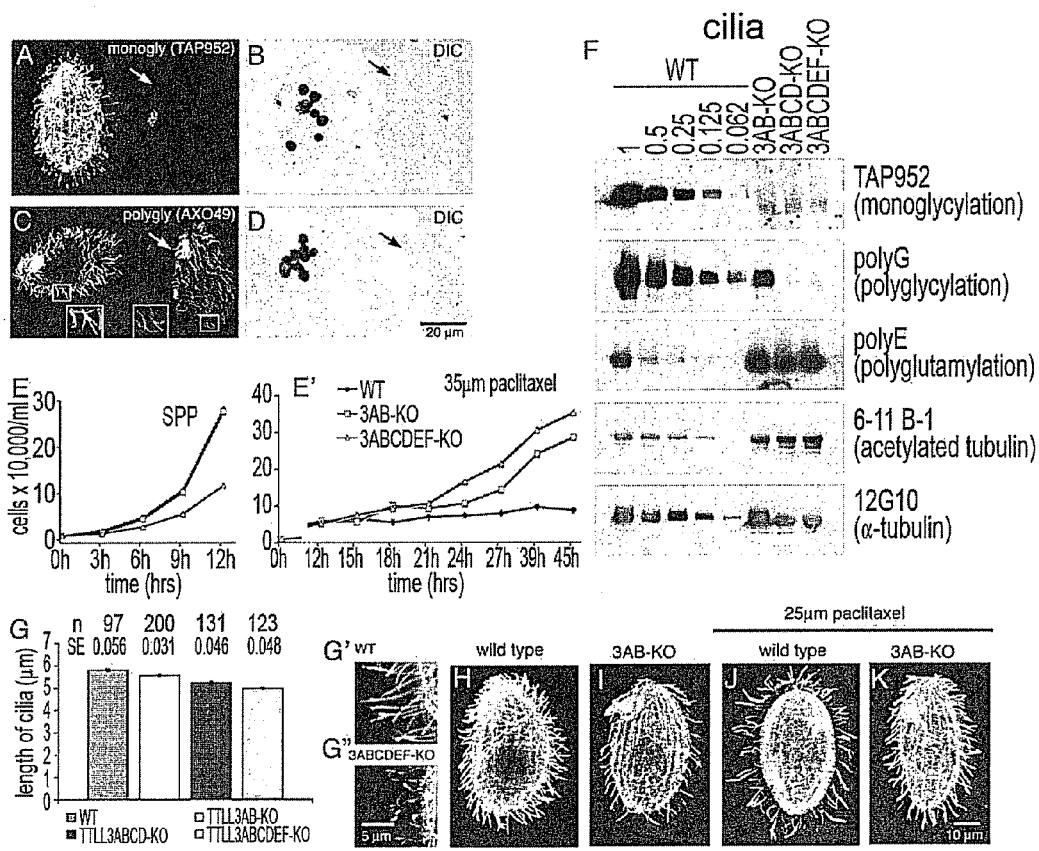
FIG. 40 shows disruption of TTLL3 genes reduces tubulin glycylation and increases tubulin glutamylation.
Figure 41:
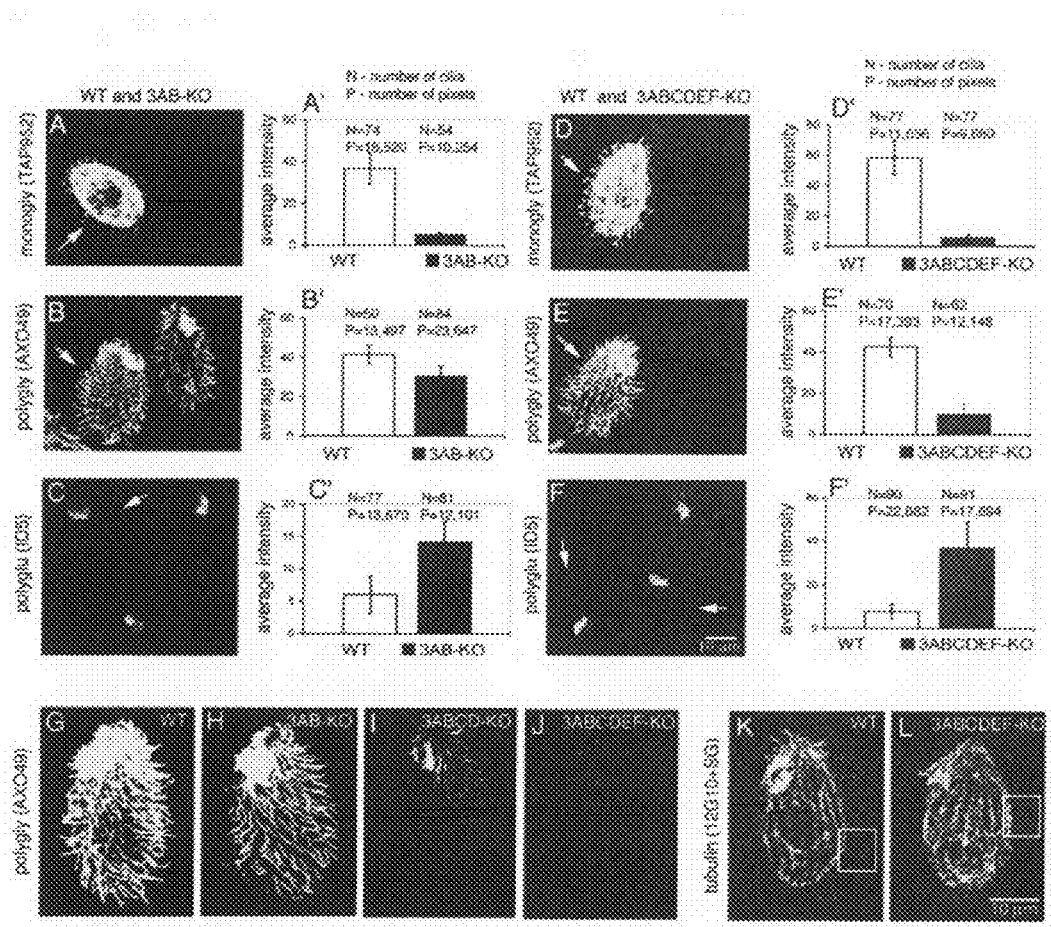
FIG. 41 shows knockouts of TTLL3 genes reduce the levels of tubulin glycylation and increase the levels of tubulin glutamylation.
Figure 42:
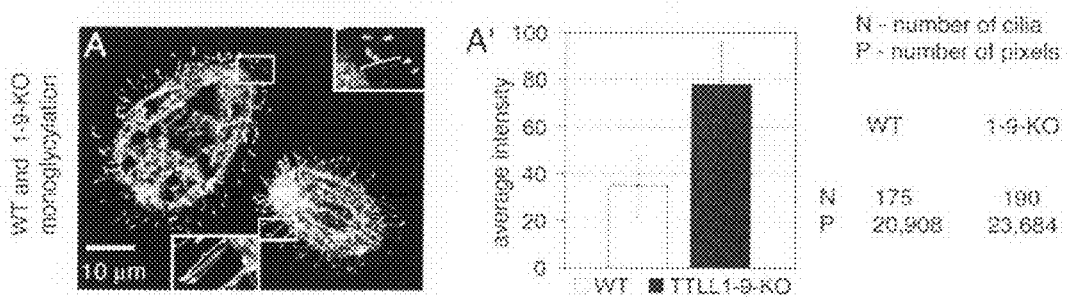
FIG. 42 shows a knockout of TTLL1 and TTLL9 genes that encode α-tubulin preferring glutamic acid ligases (Wloga et al. 2008. Eukaryot. Cell 7, 1362-1372) reduces the signal of tubulin glutamylation and increases the signal of tubulin monoglycylation in cilia. TTLL1 and TTLL9 knockout cells were mixed with wild type cells (earlier fed with India ink) and stained with TAP952 antibodies to detect monoglycylation (A). A graph representing the quantitative immunofluorescence analysis of the intensity of cilia staining in WT and TTLL1/9 knockout cells; the intensity of staining was measured in the part of cilia indicated by parenthesis (A').

Next, using homologous DNA recombination, we disrupted TTLL3A and TTLL3B genes that encode ciliary paralogs with a significant activity in vitro. In 3AB-KO cells, the levels of monoglycylated tubulin were strongly reduced (FIGS. 40A-B, and 40F; FIGS. 41A-A') and the levels of tubulin polyglycylation were moderately reduced (FIGS. 40C-D, F; FIGS. 41B, B', and H). Strikingly, the levels of tubulin glutamylation in cilia were increased by ~3-fold (FIG. 40F; FIGS. 41C-C'). Additional experiments indicate that, under a variety of conditions, the levels of tubulin glycylation and glutamylation are inversely correlated. For example, overexpression of GFP-Ttll3Ap decreased tubulin glutamylation in cilia (FIG. 39D-D"), and conversely, axonemes from a strain lacking two E-ligases—Ttll1p and Ttll9p (Wloga et al. 2008. Eukaryot. Cell 7, 1362-1372)—have increased levels of tubulin glycylation (FIG. 42). Thus, the two polymodifications negatively regulate each other.

A transmission electron microscopy (TEM) analysis did not reveal any defects in 3AB-KO axonemes (FIG. 43M). The 3AB-KO cells grew at a normal rate on standard medium (FIG. 40E), but multiplied faster than wild-type in the presence of the microtubule stabilizing drug, paclitaxel (FIG. 40E'). In wild-type cells, paclitaxel induced a remarkable elongation of axonemes, but this effect was not observed in 3AB-KO cells (FIGS. 40H-K). Thus, 3AB-KO cells and specifically axonemes are resistant to paclitaxel.

Next, we constructed strains lacking either four conserved (3ABCD-KO), or all six TTLL3 genes (3ABCDEF-KO; FIG. 44). The quadruple and sextuple knockout strains showed further reduction in the levels of tubulin glycylation in cilia, including a strong reduction in polyglycylation (FIG. 40F; FIGS. 41D-E' and G-J). Thus, in contrast to Ttll3Ap and Bp, the activity of the remaining TTLL3 paralogs is closely coupled to chain elongation. However, even cells lacking all TTLL3 genes (3ABCDEF-KO) had a residual glycylation signal in the tubulin region of a Western blot of ciliary proteins (estimated as ~8% of the wild-type level for mono- and <1% for polyglycylation [FIG. 40F]) and in axonemes of fixed cells (FIGS. 41D-E' and J). Thus, it appears that another enzyme(s) distinct from TTLL3 also generates tubulin glycylation. Based on immunofluorescence, 3ABCDEF-KO cells had higher levels of tubulin polyglutamylation than the 3AB-KO cells (compare FIGS. 41F-F' to FIGS. 41C-C'). The quadruple and sextuple KO strains grew more slowly as compared with wild-type and 3AB-KO cells (FIG. 40E), and the level of paclitaxel resistance in the 3ABCDEF-KO strain was higher as compared with the 3AB-KO strain (FIG. 40E'). Thus, there is correlation between the loss of TTLL3 function and the levels of hyperglutamylation and paclitaxel resistance.

The increased paclitaxel resistance suggests that hypoglycylated microtubules are more dynamic. Surprisingly, axonemes in TTLL3 knockout strains consistently had moderately elevated levels of K40 acetylation on α-tubulin, a marker of long-lived microtubules (FIG. 40F) (LeDizet and Piperno 1991. Meth. Enzymol. 196, 264-274). This suggests that glycylation promotes subunit turnover of axonemal microtubules. The 3ABCDEF-KO axonemes were normal at the ultrastructural level (FIG. 43N). However, the loss of TTLL3 function led to a progressive shortening of the axonemes; in 3ABCDEF-KO cells, axonemes are 15% shorter than wild-type (FIGS. 40G-G"; FIGS. 41K and L). Thus, in *Tetrahymena*, TTLL3 is required for the vast majority of tubulin glycylation and promotes axoneme elongation.

A Dominant-Negative Mutation of TTLL3 Causes Severe Defects in Axoneme Assembly in *Tetrahymena*. If TTLL3 is a G-ligase, its activity should be blocked by a mutation that affects the ATPase domain. Using a cadmium-dependent promoter (MTT1), we overexpressed an active GFP-Ttll3Ap and an inactive GFP-Ttll3Ap, with an E818G mutation (GFPDN-Ttll3Ap) that was predicted to block the ATPase activity (Janke et al., 2005. Science 308, 1758-1762). Both proteins accumulated to similar levels (FIG. 38G) and localized to cilia (FIG. 38C and FIG. 45A). In cells overproducing GFP-Ttll3Ap, there was a moderate reduction in the length of cilia (from 5.2±0.7 to 4.9±0.9 mm [FIGS. 45D, E, and J]). In GFP-DN-Ttll3Ap cells, at 6 hr, most cilia were extremely short (2.1±0.8 mm), while some cilia were exceptionally long (7±0.9 mm [FIGS. 45C, F, and K]), and the proportion of short cilia increased after 11 hr (FIG. 45L). GFPDN-Ttll3Ap was enriched in short cilia and in the distal segments of long cilia (FIGS. 45A-C). The levels of mono- and polyglycylation were moderately reduced in GFP-DN-Ttll3Ap, even without induction of transgene expression, due to the basal expression of the MTT1. Moreover, in induced cells, segments of cilia with that accumulated GFP-DN-Ttll3Ap had extremely low levels of tubulin monoglycylation (FIG. 46) and polyglycylation (FIGS. 45A-C and F). As expected, the hypoglycylated segments of axonemes enriched in GFP-DNTtll3Ap had strongly increased levels of glutamylation (FIGS. 45G-I').

It is most likely that short cilia are those that have assembled during induced GFP-DN-Ttll3Ap expression, while the long cilia arose by distal extension of pre-existing units. Indeed, GFPDN-Ttll3Ap-overexpressing cells that were subjected to complete deciliation could regenerate only excessively short cilia (FIG. 47).

TEM analysis showed that cells expressing GFP-Ttll3Ap had no apparent defects in the axonemes (FIG. 43H). In GFP-DN-Ttll3Ap cells, 60% of axoneme cross-sections lacked the central microtubules (FIGS. 43B, D, F, G, and I; and Table 6). Some peripheral doublets were rotated (FIGS. 43B and F) or absent (FIG. 43E). Rarely, abnormal peripheral triplet microtubules were present in the axoneme (FIG. 43G). Many axoneme cross-sections had ectopic singlet microtubules (FIGS. 43B, C, and E). Since such microtubules were not present in axonemes of cilia-regenerating cells (Table 6), we conclude that ectopic singlets form at the distal ends of the pre-existing cilia. Indeed, many longitudinal cilia sections in vegetatively growing GFPDN-Ttll3Ap cells had ectopic, disordered singlet microtubules, primarily in the distal regions (FIGS. 43K and L). These data suggest that the hypoglycylated/ hyperglutamylated segments added to ends of pre-existing motile axonemes are unstable.

TABLE 6

Axoneme cross-sections of wild-type and GFP-Ttll3Ap-E818G Tetrahymena cells that are either growing vegetatively or regenerating cilia.

| | 9 + 2 | 9 + 2 with twisted doublets | 9 + 0 | 9 + 0 with twisted doublets | singlet ectopic MTs | Two axoneme profiles// cilium | Peripheral triplets | Fewer Doublets | n |
|---|---|---|---|---|---|---|---|---|---|
| Growing WT somatic cilia | 99.57% (229) | 0% (0) | 0.43% (1) | 0% (0) | 0% (0) | 0% (0) | 0% (0) | 0% (0) | 230 |
| Growing WT oral cilia | 100% (158) | 0% (0) | 0% (0) | 0% (0) | 0% (0) | 0% (0) | 0% (0) | 0% (0) | 158 |
| Growing Ttll3Ap-E818G (somatic cilia) | 26.19 (33) | 1.59% (2) | 42.87% (54) | 9.52% (12) | 5.55% (7) | 11.9% (15) | 0% (0) | 2.38% (3) | 126 |
| Growing Ttll3Ap-E818G (oral cilia) | 60.65% (259) | 0% (0) | 37.87% (159) | 0% (0) | 0.7% (3) | 0% (0) | 1.41% (6) | 0% (0) | 427 |
| Cilia regenerating WT (30 min) | 95.82% (275) | 0% (0) | 3.14% (9) | 1.04% (3) | 0% (0) | 0% (0) | 0% (0) | 0% (0) | 287 |
| Cilia regenerating Ttll3Ap-E818G (30 min) | 39% (78) | 0.5% (1) | 55% (110) | 5.5% (11) | 0% (0) | 0% (0) | 0% (0) | 0% (0) | 200 |
| Cilia regenerating Ttll3Ap-E818G (60 min) | 41.81% 92 | 0.46% 1 | 53.64% (118) | 4.09 (9) | 0% (0) | 0% (0) | 0% (0) | 0% (0) | 220 |

Immunogold TEM shows that both active and DN forms of the enzyme localized to the peripheral doublets (FIGS. 43H-J). Moreover, in wild-type cells, mono- and polyglycylation were detected exclusively on outer doublets in 98% (FIG. 30; n=93) and 100% (FIG. 43P; n=100) cross-sections, respectively. Thus, TTLL3 proteins act primarily by modifying tubulin of the outer microtubules, and the effects of DN-Ttll3Ap on the central pair assembly are probably indirect.

Knockdown of Ttll3 in Zebrafish Affects Ciliary Assembly and Cilia in Developing Embryos. Next, we addressed the significance of TTLL3 in a vertebrate. Zebrafish has a single TTLL3 gene, ttll3 (gi:113671247) (FIG. 37A). Immuno-fluorescence of zebrafish embryos (n=57) using TAP952 revealed monoglycylated tubulin in cilia of the olfactory placode (FIG. 48H), otic vesicle (FIGS. 49A and A'), spinal cord, hypochord (FIG. 49G), pronephric ducts (FIG. 49C and FIG. 50E), and neuromast hair cells (FIG. 50I). Cilia in the nasal epithelium (FIG. 48J), neuromasts, and the medial section of the pronephros stained with AXO49, indicating the presence of polyglycylation. Thus, the pattern of tubulin glycylation is tissue dependent.

To reduce ttll3 function, we used antisense MOs to block either the translation initiation (TTLL3-ATG) or splicing at the intron 10/exon 11 junction (TTLL3-SP) of ttll3 mRNA. Injection of 1 ng of TTLL3-ATG MO greatly reduced tubulin monoglycylation in multiple types of cilia at 72 hpf (compare FIG. 48H with FIG. 48I; FIGS. 49A-D, G, H; FIGS. 50E, F, I, and L). In TTLL3-ATG MO embryos, the TAP952 signal was not detected in the cilia of the spinal cord (in 89% of morphants), the medial (61%), and the distal part of pronephric duct (98%) (n=46). TTLL3-SP MOs (3 ng) reduced tubulin monoglycylation in cilia of the olfactory placode, otic vesicle, spinal cord, and hypochord in all analyzed embryos (n=8). In morphants, in the olfactory placode, the levels of polyglycylation (using AXO49) were also reduced (FIGS. 48J and K). No change in the levels of tubulin glycylation was detected in multiple types of cilia in embryos injected with control (random sequence) MOs (n=5; FIG. 51). Since the two ttll3 MOs contain no overlapping sequences, yet produce similar effects on tubulin glycylation, and similar phenotypic defects (see below), we conclude that the reduction in glycylation in the morphants is due to a specific reduction in ttll3 function.

In control embryos, the GT335 antibody detected glutamylated tubulin in all types of cilia that also had glycylated tubulin (n=14). Despite the reduction of monoglycylation in ttll3 morphants, most cilia types maintained a strong GT335 signal (FIGS. 49I and J). Moreover, the polyE antibody that recognizes polyglutamylation (Shang et al., 2002. J. Cell Biol. 158, 1195-1206) detected an increased signal in cilia of the olfactory placode and neuromasts in morphants (FIGS. 48H'-I"; FIGS. 50J, K, M, and N). Thus, in some zebrafish tissues, tubulin glycylation may inhibit tubulin glutamylation as it does in Tetrahymena. However, cilia in the distal parts of pronephric duct were either GT335 negative (n=7) or had very short GT335-positive segments (n=5) (FIGS. 49E and F). It is thus possible that depletion of ttll3 inhibits the assembly of a subset of pronephric cilia.

The majority of morphant embryos had a "curly tail" (FIGS. 48A-D; FIGS. 50A-C; TTLL3-ATG: 76%; n=128; TTLL3-SP: 64.3%; n=84). For unclear reasons, embryos that were manually released from the chorion at 24 hpf had curled-up tails, whereas those released at 48 hr had curled-down tails (FIGS. 50A-C). The curly tail phenotype is often associated with ciliary deficiencies (Sun et al., 2004. Development 131, 4085-4093).

Defective cilia disrupt fluid flow in the kidney and brain, resulting in severe distensions of these organs that manifest as hydrocephaly and cystic kidneys (Kramer-Zucker et al., 2005. Development 132, 1907-1921). Some ttll3 morphants were hydrocephalic (81% of TTLL3-SP, n=37; 10% of TTLL3-ATG, n=30) (FIGS. 48E and F). We did not observe kidney cysts, despite the dramatic reduction of glycylation in cilia of the pronephric duct (FIGS. 49C and D; FIGS. 50E and F).

TABLE 7

Heart position in zebrafish control and TTLL3 morphant embryos obtained by scoring either live embryos or those subjected to in situ hybridization using clm1 probe.

|  |  | left | middle | right | N |
|---|---|---|---|---|---|
| control | live | 58 (93.6%) | 4 (6.4%) | 0 (0%) | 62 |
|  | hybridization | 13 (92.9%) | 1 (7.1%) | 0 (0%) | 14 |
| control MO | live | 76 (93.8%) | 5 (6.2%) | 0 (0%) | 81 |
| TTLL3-ATG-MO | live | 56 (50%) | 33 (29.5%) | 23 (20.5%) | 112 |
|  | hybridization | 21 (50%) | 7 (16.7%) | 14 (33.3%) | 42 |
| TTLL3-SP-MO | live | 21 (64%) | 8 (24%) | 4 (12%) | 33 |
|  | hybridization | 23 (57.5%) | 6 (15%) | 11 (27.5%) | 40 |

In vertebrate embryos, motile cilia are required to establish the left-right (LR) axis at the end of gastrulation (Burdine and Schier, 2000. Genes Dev. 14, 763-776). In zebrafish, the first cilia form in a tissue called the Kupffer's vesicle (KV), which is analogous to the mouse node (Essner et al., 2005. Development 132, 1247-1260). Disruptions of the KV cilia result in a complete reversal of the LR axis, known as situs inversus, or in a randomized LR axis, called heterotaxia (Burdine and Schier, 2000. Genes Dev. 14, 763-776). During normal development, the developing heart is located on the left side of the embryo, as revealed by expression of cardiac myosin light chain 2 (cmlc2) (FIG. 52E) (Yelon, 2001. Dev. Dyn. 222, 552-563). In ttll3 morphants, by contrast, hearts were often located on the right side of the embryo, or along the midline (Table 7). Consistent with this, cmlc2 (FIGS. 52F-H; Table 7) and lefty2 (Table 8) were often abnormally expressed on the right side, along the midline, or bilaterally. In zebrafish, asymmetry in the brain is revealed by lefty1, which is expressed on the left side of the epiphysis, a structure in the diencephalon that gives rise to the pineal gland (FIG. 52A [Liang et al., 2000]). In ttll3 morphants; by contrast, lefty1 mRNA was often present on the left side, bilaterally, or on the right side of the epiphysis, indicating that asymmetry in the brain was also disrupted (FIGS. 52B-D). The nodal-related gene, southpaw (spaw), is the earliest marker of LR asymmetry and is normally expressed in the left lateral plate mesoderm (Long et al., 2003). In ttll3 morphants, spaw was often expressed bilaterally or in the right lateral plate mesoderm (Table 8). Injection of control random sequence MOs did not lead to patterning defects (Table 7). Injection of MOs designed to deplete non-TTLL3 TTLLs (TTLL10 and -12) have produced a distinct combination of defects, and none these MOs affected the LR asymmetry. These results suggest that tubulin glycylation is needed either for assembly or function of KV cilia. Indeed, we found that morphants had fewer and shorter KV cilia as compared with control embryos, as revealed by staining with the 6-11 B-1 antibody, which recognizes α-tubulin with acetyl-K40 (LeDizet and Piperno 1991. Meth. Enzymol. 196, 264-274; FIGS. 52I-K).

In addition to KV, the assembly of cilia in other tissues is also affected by Ttll3 depletion. Based on the staining with 6-11 B-1 mAb, cilia in the neuromasts cells were shorter in ttll3 morphants (FIGS. 50G and H). In the wild-type nose, the 6-11 B-1-positive cilia were densely packed around the edge of the olfactory placode (FIGS. 48G

TABLE 8

Expression patterns of lefty2 and southpaw in zebrafish control and TTLL3 morphant embryos.

| | Pattern of Expression | | | | |
|---|---|---|---|---|---|
| | No specific signal | left | Bilatera or midline | right | N |
| *lefty2* | | | | | |
| Control | 1 (7%) | 13 (93%) | 0 (0%) | 0 (0%) | 14 |
| TTLL3-ATG-MO | 8 (19%) | 15 (35.7%) | 5 (11.9%) | 14 (33.4%) | 42 |
| TTLL3-SP-MO | 16 (38.1%) | 21 (50%) | 2 (4.8%) | 3 (7.1%) | 42 |
| *southpaw* | | | | | |
| Control | 3 (8.8%) | 31 (91.2%) | 0 (0%) | 0 (0%) | 34 |
| TTLL3-ATG-MO | 19 (24.3%) | 14 (17.9%) | 34 (43.7%) | 11 (14.1%) | 78 |
| TTLL3-SP-MO | 6 (14.6%) | 12 (29.3%) | 22 (53.7%) | 1 (2.4%) | 41 | and L). In the placodes of morphants, there were large gaps lacking 6-11 B 1-positive cilia (FIG. 48M). To rule out the possibility that K40 α-tubulin acetylation is reduced in the morphants without a loss of the axoneme, we examined the olfactory cilia by SEM. In wild-type, the olfactory placode is an oval structure filled with cilia (FIGS. 48N and O; n=7). In all ttll3 morphants examined, the density of cilia was reduced, and many of the remaining cilia were truncated (FIGS. 48P and R; n=7). TEM analysis of the olfactory placode in the wildtype embryo revealed the presence of axonemes with either 9+0 or 9+2 organization (the latter were usually close to the placode rim [Hansen and Zeiske, 1993. J. Comp. Neurol. 333, 289-300]) (FIGS. 53A-D and I). Most 9+2 axoneme cross-sections had dynein arms, but some axonemes lacked dynein arms (FIG. 53B). The distal ends of axonemes contained singlet A-subfiber extensions lacking projections (FIG. 53D). Morphant cilia appeared normal (FIGS. 53E-H and K), but longitudinal sections showed that many morphant cilia were excessively short and some had swollen tips (FIG. 48S and FIG. 53J). Thus, the main effect of Ttll3 depletion in zebrafish is shortening and loss of axonemes.

Discussion

We show that TTLL3 proteins are required for tubulin glycylation in a protist and in a vertebrate. Overproduction of TTLL3 in *Tetrahymena* led to a strong increase in tubulin monoglycylation, but not polyglycylation, consistent with chain-initiating activity. A mutation that inactivates the ATPase domain of TTLL3 inhibited its G-ligase activity. In a separate study, Rogowski et al. show that the mammalian and Drosophila TTLL3 proteins mediate G-ligase/initiase activity (Rogowski et al., 2009. Cell, 137, 1076-1087). The simplest explanation of all these data is that TTLL3 is a conserved tubulin G-ligase with a chain-initiating activity.

Loss of TTLL3 proteins led to dramatic reduction in the levels of tubulin glycylation in cilia of *Tetrahymena* and zebrafish. However, *Tetrahymena* mutants lacking all TTLL3 genes have residual tubulin glycylation signal in cilia. The mammalian TTLL10 mediates glycine side chain elongation activity on tubulin (Rogowski et al., 2009. Cell, 137, 1076-1087). However, TTLL10 can directly glycylate a recombinant NAP1, indicating an ability to initiate (Ikegami et al., 2008. FEBS Lett. 582, 1129-1134). Thus in *Tetrahymena*, TTLL10 enzymes could initiate side chains on tubulin, perhaps only in the absence of TTLL3. Alternatively, yet-uncharacterized TTLL types (e.g., TTLL14 or TTLL15) could act as G-ligases.

*Tetrahymena* cells lacking TTLL3 assembled shorter cilia. In zebrafish, lack of TTLL3 activity leads to dramatic shortening or complete loss of cilia. Thus, the zebrafish and *Tetrahymena* phenotypes are consistent, although cilia are less affected in *Tetrahymena*, possibly due to action of non-TTLL3 G-ligases. In *Tetrahymena*, besides tubulin, the only immunologically detectable glycylated protein is Pgp1p, which is targeted to the endoplasmic reticulum (Xie et al., 2007. Eukaryot. Cell 6, 388-397). Thus, the effects of TTLL3 deficiencies on cilia assembly and function are likely mediated by tubulin glycylation. In Drosophila, several nontubulin proteins undergo TTLL3-dependent glycylation (Rogowski et al., 2009. Cell, 137, 1076-1087). Drosophila may be unusual, because this species lacks TTLL10, and thus all protein glycylation may be dependent on TTLL3. We can not exclude, however, the possibility that a protein distinct from tubulin undergoes glycylation mediated by TTLL3 and contributes to ciliogenesis in *Tetrahymena* and zebrafish.

Overproduction of an ATPase-deficient form of Ttll3Ap in *Tetrahymena* led to shortening of the axoneme and structural defects, including lack of assembly of central microtubules. These effects can be explained either by competitive inhibition of TTLL3 and non-TTLL3 G-ligases that act on tubulin, or by disturbance of another function of CTT, such as glutamylation. Consistent with the latter hypothesis, strong overexpression of a ciliary E-ligase, Ttll6Ap resulted in a phenotype that strongly resembles that of cells overexpressing DN-Ttll3Ap. Interestingly, the expression of GFPDN-Ttll3Ap inhibited the assembly of central microtubules, while the enzyme itself and tubulin glycylation appear restricted to outer microtubules. This observation indicates that the assembly of central microtubules is dependent on the properties of outer doublets.

This example shows that TTLL3, most likely by modifying tubulin, is of critical importance for assembly of cilia. It remains to be determined how tubulin glycylation affects ciliary microtubules at the molecular level. This PTM is present primarily on the outer axonemal microtubules, and therefore its absence could inhibit IFT (Kozminski et al., 1995. J. Cell Biol. 131, 1517-1527). A reduction in the rate of IFT motors could explain the shortening of cilia caused by deficiencies in TTLL3 in both *Tetrahymena* and zebrafish. Indeed, a mutation of a subset of polymodification sites on the CTT of β-tubulin in *Tetrahymena* led to accumulation of electron-dense materials near outer microtubules in the cilia (Redeker et al., 2005. J. Biol. Chem. 280, 596-606). However, the sperm axoneme in *Drosophila* is strongly glycylated (Bressac et al., 1995. Eur. J. Cell Biol. 67, 346-355), but assembles without IFT (Han et al., 2003. Curr. Biol. 13,1679-1686). Thus, the evolutionary conservation of tubulin glycylation is probably based on a function distinct from IFT.

TTLL3-null cells (and specifically axonemes) showed increased resistance to paclitaxel, a microtubule-stabilizing agent. While paclitaxel binds inside the microtubule lumen (Nogales et al., 1998. Nature 391, 199-202), there are interactions between the microtubule lumen and its surface (Raff et al., 2008. Curr. Biol. 18, 911-914). Thus glycylation of CTTs could indirectly affect the paclitaxel binding site in the lumen. However, TTLL3-deficient axonemes are excessively short, suggesting that glycylation affects turnover rate or stability of axonemal microtubules. In mammalian cells, paclitaxel resistance is associated with increased dynamics of cytoplasmic microtubules (Barlow et al., 2002. J. Cell Sci. 115, 3469-3478). The axonemal microtubules exchange subunits even when fully assembled (Wloga and Gaertig 2008. Ciliary tubulin and its post-translational modifications. In *Ciliary Function in Mammalian Development*, Yoder (ed.), San Diego: Academic Press, pp. 83-109). Unexpectedly, axonemes deficient in glycylation show a moderate increase in the K40 acetylation, a marker of long-lived microtubules (LeDizet and Piperno 1991. Meth. Enzymol. 196, 264-274), arguing that lack of glycylation increases, rather than decreases, the residence time for tubulin subunits. To reconcile these data, we can consider that lack of tubulin glycylation makes axonemal microtubules less dynamic and, at the same time, limits the access of paclitaxel to its luminal binding sites. Paclitaxel diffuses across the microtubule walls via small fenestrations (Nogales et al., 1998. Nature 391, 199-202; Ross and Fygenson 2003. Biophys. J. 84, 3959-3967). The lack of tubulin glycylation on CTTs could reduce the size of these fenestrations. As the axonemal microtubules are coated with protein complexes and their plus ends are capped (Dentler, 1980. J. Cell Sci. 42, 207-220), diffusion across the microtubule wall could be rate limiting for buildup of paclitaxel concentration inside the lumen. A tighter microtubule lattice could also reduce the level of axoneme dynamics, and promote accumulation of K40 acetylation. A lack of proper turnover of axonemal microtubules could, in turn, lead to shorter size of cilia. While counterintuitive, there is already evidence that katanin, a factor that promotes turnover of microtubules by severing, is required for assembly of axonemes, and interacts with posttranslationally modified tubulin (Dymeket al., 2004. Eukaryot. Cell 3,870-879; Sharma et al., 2007. J. Cell Biol. 178, 1065-1079).

Further evidence that the status of polymodifications affects the axonemal lattice organization is provided by the results of overexpression of GFP-DN-Ttll3Ap. In these cells, distal segments of pre-existing cilia that elongated using hypoglycylated tubulin were apparently unstable. Since the pre-existing cilia were initially motile, their movement could lead to breakage of the newly assembled distal hypoglycylated/hyperglutamylated segments. Thus, axonemes with an abnormal composition of polymodifications could be more fragile, possibly due to reduced flexibility. The mechanical properties of the lattice could be important to both cilia with intrinsic motility and primary cilia that bend passively in response to flow of fluid in the extracellular space in mammals. In support of this idea, tubulin glycylation has been detected in both motile (Redeker et al., 1994. Science 266, 1688-1691) and primary cilia (Davenport et al., 2007. Curr. Biol. 17, 1586-1594). Some protists, like *Trypanosoma*, are endowed with motile cilia and 9+2 axonemes and lack tubulin glycylation (Schneider et al., 1997. J. Cell Sci. 110, 431-437), but these organisms assemble a paraflagellar rod, which could affect the mechanical properties of the flagellum.

This example shows that G- and E-ligases oppose each other on tubulin. A reduction of tubulin glycylation increased the levels of tubulin glutamylation and, conversely, a reduction of tubulin glutamylation increased the levels of tubulin glycylation. Moreover, overexpression of TTLL3 reduced the levels of tubulin glutamylation (this example) and overexpression of the TTLL6 E-ligase reduced the levels of tubulin glycylation. Both polymodifications occur on the glutamic acids of the CTTs and can coexist on the same tubulin CTTs (Redeker et al., 2005. J. Biol. Chem. 280, 596-606). In ciliates, glycylation occurs on several adjacent glutamic acids on the CTT of b-tubulin (Vinh et al., 1999. Biochemistry 38, 3133-3139), but the sites of glutamylation have not been mapped. In other organisms, glutamylation sites are located at glutamic acids adjacent to or overlapping with the glycylation sites on the CTT (Popodi et al., 2005. Cell Motil. Cytoskeleton 62, 48-64). It is thus likely that G- and E-ligases compete for the same sites or influence each other by sterically blocking adjacent sites. In contrast to tubulin glutamylation, which may be present in all organisms with axonemes, a few lineages (e.g., *Trypanosoma* and Plasmodium) lack glycylation despite the presence of axonemes (Fennell et al., 2008. Int. J. Parasitol. 38, 527-539; Schneider et al., 1997. J. Cell Sci. 110, 431-437). It is tempting to speculate that tubulin glutamylation is directly involved in the axoneme properties, while tubulin glycylation acts as competitive inhibitor of tubulin glutamylation. The few lineages that lack tubulin glycylation could use other means to decrease the levels of tubulin glutamylation, including unidentified enzymes that trim the glutamyl side chains (Audebert et al., 1993. Mol. Biol. Cell 4, 615-626).

Experimental Procedures

Cultures. *Tetrahymena* thermophila cells were grown in SPP medium. To determine the growth rate, cells were diluted to $10^4$ cells/ml and grown in 10 ml of SPP in 150 ml flasks. In some experiments, paclitaxel (LC Laboratories, Woburn, Mass.) was added to the SPP medium. WT in Kalkutta and Tupfel longfin (commonly known as "WIK" and "TL", respectively) zebrafish were raised at 28° C. at 14 hr light/10 hr dark cycle. The embryos were cultured in egg water at 28° C.

GFP Tagging and Gene Disruptions in *Tetrahymena*. The coding regions (based on the *Tetrahymena* Gene Database) of TTLL3 paralogs were amplified from genomic DNA with primers listed in Table 9, and ligated into pMTT1-GFP (Wloga et al., 2006. Mol. Biol. Cell 17,2799-2810). A plasmid for expression of GFP-DN-Ttll3Ap was made by changing the E codon GAA 818 to a G codon GGT using PCR with overlapping primers. Plasmids were digested with ApaI and SacII, and 20 mg was used to transform CU522 cells. Transformants were subjected to phenotypic assortment to increase the copy number by culturing with 20 mM paclitaxel (Gaertig et al., 1999. Nat. Biotechnol. 17, 462-465).

TABLE 9

Primers used for amplification of the predicted coding regions of TTLL3 homologs in *Tetrahymena*.

| TTLL Primers | | Restriction sites added | Seq. ID |
|---|---|---|---|
| TTLL3A | 5' ATATACGCGTCATGTTCTAATAGAATTAGCAG 3' | MluI | 93 |
| | 5' ATAATGGATCCTCATTTTTATTCTCTATAGAT 3' | BamHI | 94 |
| TTLL3A | 5' ATATACGCGTCATGTTCTAATAGAATTAGCAG 3' | MluI | 95 |
| tail | 5' TATTGGATCCTCATTCTTTTAAGTAATTCTTGAG 3' | BamHI | 96 |
| TTLL3B | 5' TTTATACGCGTCATGTTTAGCATCGATATTTAAGG 3' | MluI | 97 |
| | 5' TTATTCTCGAGTCATTTTTTGTAAGAAGCTAGTAC 3' | XhoI | 98 |
| TTLL3C | 5' ATTATACGCGTCATGAGTTCTTTAGATGAAGGITTA 3' | MluI | 99 |
| | 5' TTTTTGGATCCTCATGAGAAATTAGGTTTTAGATT 3' | BamHI | 100 |
| TTLL3D | 5' ATATACGCGTCATGGATAAAAGTTACAATATA 3' | MluI | 101 |
| | 5' ATAATGGATCCTCACAATTTTTTACTACTTTAAGT 3' | BamHI | 102 |
| TTLL3E | 5' ATATACGCGTCATGATATTGC-CITTTGAATACTATTTT 3' | MluI | 103 |
| | 5' ATTTAGGATCCAACTGATTTATCGTTGATTGAGTG 3' | BamHI | 104 |
| TTLL3F | 5' ATATACGCGTCATGAGTGATCGAATATATCAT 3' | MluI | 105 |
| | 5' ATAATGGATCCTCATATTTTTTAATTTTCATTTTTC 3' | BamHI | 106 |

For gene disruptions, two fragments of a TTLL3 gene were amplified (Table 10) and cloned into a plasmid with a drug resistance cassette. The fragments were designed to flank the region encoding the catalytic domain. CU428 and B2086 mating cells were biolistically transformed (Cassidy-Hanley et al., 1997. Genetics 146, 135-147). The multiple knockout cells were obtained by crosses (Sharma et al., 2007. J. Cell Biol. 178, 1065-1079). Because multiple genes were disrupted using the same selectable marker, heterokaryons with a desired combination of alleles were identified by backcrosses and screening of progeny using PCR with primers that amplify specific disrupted loci.

TABLE 10

Primers and Resistance Cassettes Used to Prepare Plasmids for Gene Knockouts in Tetrahymena.

| Gene | Primers | Disruption cassette | Seq. ID |
|---|---|---|---|
| TTLL3A | F1-5' AAATAGGGCCCCTTAAACCAGCAGCAACAGAC 3' | Neo3 | 107 |
|  | R1-5' AAATACCCGGGCAAGACTCTCTGGATTAGGAT 3' |  | 108 |
|  | F2-5' AAATTATCGATTGATGTTTATCACAGGCTAAG 3' |  | 109 |
|  | R2-5' AAATTGAGCTCTGCTTTAGTTATGTTTAGAAC 3' |  | 110 |
| TTLL3B | F1-5' AAATAGGGCCCATCATAGTAGAGTAACAGCCT 3' | MTT1-RPL29 | 111 |
|  | R1-5' AAATAATCGATCTGGTGAATGTTTGGTTGTTG 3' |  | 112 |
|  | F2-5' AAAATCCCGGGTACCTTGTGTAAGTCCAGAAG 3' |  | 113 |
|  | R2-5' ATATTCCGCGGTCATTTTTTGTAA-GAAGCTAGTAC 3' |  | 114 |
| TTLL3C | F-5' TAAACCGCGGGATAGCCTGTCTTCTCCTCCA 3' | Neo3 | 115 |
|  | R-5' AATAGGGCCCGATACTTTAATATCAAATACTTGC 3' |  | 116 |
| TTLL3D | F1-5' AAATGGGCCCTAGATGACAGTATTGTTGATGC 3' | Neo3 | 117 |
|  | R1-5' AATTCCCGGGTTAGGTCTGCATTGTCAAACC 3' |  | 118 |
|  | F2-5' TTAAATCGATAGTTGAGATAATTGATCATGC 3' |  | 119 |
|  | R2-5' TTAAGAGCTCCTCATAAATAATCTACCACAC 3' |  | 120 |
| TTLL3E | F1-5' ATTTGGGCCCTTAGGGAGTTCTGCTGCTAAGAGT 3' | MTT1-RPL29 | 121 |
|  | R1-5' AATTAATCGATACTTGTAGTCATCATTTGAATC 3' |  | 122 |
|  | F2-5' ATTAACCCGGGCCATCTGCTAATTCAAGAGGA 3' |  | 123 |
|  | R2-5' ATTAAGAGCTCACTGATTTATCGTTGATTGAGTG 3' |  | 124 |
| TTLL3F | F1-5' AAAAAGGGCCCAACAACCATCCATATGACAGC 3' | Neo3 | 125 |
|  | R1-5' AAATTCCCGGGCCATCCTAGCTCAATTAGAAC 3' |  | 126 |
|  | F2-5' TATAATCGATAAGGCTTGCAGATAATGAGTG 3' |  | 127 |
|  | R2-5' TATAGAGCTCGGGAATTTGAACTTAACACAG 3' |  | 128 |

Immunofluorescence and Electron Microscopy of *Tetrahymena*. Immuno-fluorescence was done as previously described (Wloga et al., 2006. Mol. Biol. Cell 17, 2799-2810) and quantified using mixed mutant and WT cells (fed with India ink) imaged side by side. The average pixel intensity was determined for sections of axonemes from the base to below the tip using ImageJ. TEM was performed as previously described (Jerka-Dziadosz et al., 2001. Protist 152, 53-67). For immunoelectron TEM, cells were fixed as for immunofluorescence, reacted with anti-GFP antibodies (1:1000; Abcam) in 3% bovine serum albumin (BSA) in the PHEM buffer with 0.1% Tween-20 for 2 hr, followed by anti-rabbit IgG-10 nm gold antibodies (GE Healthcare) at 1:60 in 3% BSA in PBS for 1.5 hr. Cells were postfixed in 2.5% glutaraldehyde in PBS for 1 hr, followed by 1% osmium tetroxide in PBS for 1 hr. After washing, cells were dehydrated in an ethanol series, embedded in Epon, sectioned, and analyzed in a JEM 1210 electron microscope.

Western Blots. Total protein from 4 3 103 cells, or 4 mg of cilia, were used per lane and blots were prepared as previously described (Wloga et al. 2008. Eukaryot. Cell 7, 1362-1372) with the following mAbs: 12G10 anti-a-tubulin (1:20,000); 6-11 B-1 anti-acetylated α-tubulin (1:10,000) (LeDizet and Piperno 1991. Meth. Enzymol. 196, 264-274); TAP952 anti-monoglycylated tubulin (1:5000) (Bré et al., 1998. Mol. Biol. Cell 9, 2655-2665; Callen et al., 1994. Biol. Cell 81, 95-119); AXO49 anti-polyglycylated tubulin (1:10,000) (Bré et al., 1998. Mol. Biol. Cell 9, 2655-2665); and polyclonal antibodies polyE (1:1000) (Shang et al., 2002. J. Cell Biol. 158, 1195-1206), polyG (1:5000) (Duan and Gorovsky, 2002. Cum Biol. 12, 313-316), and anti-GFP (1:6,000) (Torrey Pines Biolabs).

In Vitro G-Ligase Assay. *Tetrahymena* strains expressing a TTLL3 homolog were grown to $2 \times 10^5$ cells/ml, induced with 2.5 mg/ml of $CdCl_2$ for 4 hr. The cells were lysed in the enzyme reaction buffer, ERB (50 mM Tris HCl [pH 8.0], 10% glycerol, 5 mM MgCl2, 1 mM EGTA) with 0.2% NP-40 (2 ml/g of cell pellet), centrifuged at 100,000 3 g, and the supernatant was assayed. The assay was performed in 50 ml of ERB with 2 mM ATP, 250 pmol [$^3$H]-glycine (5 ml of 20.0 Ci/mmol; GE Healthcare), and 10 ml of cell extract. Taxotere (20 mg)-stabilized brain microtubules were added and incubated at 30° C. for 4 hr. The reaction was stopped by the addition of the SDS sample buffer and boiling for 5 min at 95° C. The samples were subjected to 10% SDS-PAGE and electrotransferred onto nitrocellulose. The tubulin bands were visualized by Ponceau S, excised, and subjected to liquid scintillation counting. For fluorography, SDS-PAGE gels were stained with Coomassie blue, incubated in Amplify (GE Healthcare), dried, and subjected to autoradiography.

MO Knockdowns in Zebrafish Embryos. TTLL3-ATG MO (5' GTGTTGGTGCATGTTTGAGTTAACC 3'; SEQ ID NO:129) and TTLL3-SP MO (5' GATGTACAGAGCT-GAGATTGAAAAG 3; SEQ ID NO:130) were obtained from Open Biosystems (Huntsville, AL). TTLL3-ATG targets the translation initiation site of ttll3 mRNA. TTLL3-SP is predicted to prevent splicing of exon 11 and cause a frame shift in exon 12. This would eliminate the coding sequence downstream of exon 10, which includes a conserved catalytic domain-encoding region. To evaluate the effect of TTLL3-SP on ttll3 mRNA, total RNA was isolated with TRIzol reagent (Invitrogen, Inc., Carlsbad, Calif.) from embryos at 7 hpf: 50 uninjected control embryos, 40 embryos injected with 3 ng TTLL3-SP MO, or 30 embryos injected with 5 ng TTLL3-SP MO. Total RNA (1 mg) was used as a template for cDNA synthesis with random hexamers and oligo-dT primers and the iScript TM cDNA synthesis kit (Bio-Rad Laboratories, Hercules, Calif.). cDNA (2 ml) was amplified with the following primers spanning exon 11: TTLL3-splice F, 5'-CTTACTCCACTCATACGCTG-3' (exon 10; SEQ ID NO:131); TTLL3-splice R, 5'-GTCGAATGTTGATCACCTCC-3' (exon 12; SEQ ID NO:132). As expected, primers flanking exon 11 produced a shorter product in RT-PCR from embryos injected with TTLL3-SP than in controls (FIG. 50D). There was a dramatic reduction in the levels of endogenous TTLL3 mRNA in embryos injected with TTLL3-SP-MO, suggesting that this MO affects mRNA stability. As a negative control, we injected 25 base MOs with a random base mixture at each position (Gene Tools, Inc., Philomath, Oreg.).

Microscopy of Zebrafish. For whole-mount, in situ hybridization, embryos were fixed as previously described (Hagos and Dougan, 2007), stored in 100% methanol at −20° C., and stained with spaw, lefty1, lefty2, and cmlc2 probes (Yelon, 2001). Embryos were photographed under differential interference contrast with a Zeiss Axioplan 2 microscope with Slidebook (Intelligent Imaging Innovations, Denver, Colo.). For immunofluorescence, the embryos were manually dechorionated and fixed with 0.5% Triton X-100 and 4% paraformaldehyde in PBT (0.1% Tween-20 in PBS) at 4° C. overnight. After washing with PBT, embryos were dehydrated in methanol/PBT series and incubated overnight in 100% methanol at −20° C. After rehydration, embryos were blocked for 1-2 hr in 2% BSA, 0.5% normal goat serum, 1%DMSO, 0.5% Triton X-100 in PBS, and incubated overnight at 4° C. with one of the following antibodies: 6-11 B-1 (1:1000); TAP952 (1:2000); AXO49 (1:2000); and GT335 (1:1000); polyE (1:500). After washing 3×10 min with 0.5% Triton X-100 in PBS, embryos were incubated overnight at 4° C. in anti-mouse-IgG-FITC or anti-rabbit-IgG-Cy3 (1:500; Zymed), washed (3×10 min), mounted in 100 mg/ml of DABCO (Sigma-Aldrich) in PBS, and examined on a Leica TCS SP confocal microscope.

For electron microscopy, the dechorionated embryos were fixed at 4° C. overnight in 2.5% glutaraldehyde in 0.1Mcacodylate buffer (pH 7.2), postfixed for 1 hr on ice in 1% osmium tetroxide in 0.1 M cacodylate buffer, and dehydrated through ethanol series. For SEM, embryos were dried at a critical point using $CO_2$, sputter coated with gold, and observed in an SEM Leo982 microscope. For TEM, fixed embryos were dehydrated in 100% acetone, incubated in a mixture of acetone and Epon 812 (3:1, 1:1, and 1:3, 2 hr each) followed by overnight infiltration in 100% Epon 812. After transfer to fresh Epon 812, blocks were polymerized at 60° C.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A genetically engineered *Tetrahymena* cell comprising a deletion of at least two paralogs of TTLL6 or TTLL3; wherein said cell expresses tubulin exhibiting reduced polymodification compared to a wild-type *Tetrahymena* cell.

2. The *Tetrahymena* cell of claim 1 wherein the tubulin comprises shortened glutamyl side chains compared to wild-type *Tetrahymena* tubulin.

3. The *Tetrahymena* cell of claim 2 wherein at least a portion of the shortened glutamyl side chains contain less than 6 glutamic acid residues, and wherein the density of the glutamyl side chains containing less than 6 glutamic acid residues is increased relative to wild-type *Tetrahymena* tubulin.

4. The *Tetrahymena* cell of claim 2 wherein at least a portion of the shortened glutamyl side chains contain only one glutamic acid residue, and wherein the density of the glutamyl side chains containing only one glutamic acid residue is increased relative to wild-type *Tetrahymena* tubulin.

5. The *Tetrahymena* cell of claim 1 wherein the tubulin lacks glycyl side chains that are present in wild-type tubulin.

6. The *Tetrahymena* cell of claim 5 wherein the tubulin glycylation level is less than 90% of the tubulin glycylation level in wild-type *Tetrahymena* tubulin.

7. The *Tetrahymena* cell of claim 1 which is a TTLL6A/TTLL6F knockout cell.

8. The *Tetrahymena* cell of claim 1 wherein the two paralogs are selected from the group consisting of TTLL6A, TTLL6B, TTLL6C, TTLL6D, TTLL6E, and TTLL6F.

9. The *Tetrahymena* cell of claim 1 wherein the two paralogs are selected from the group consisting of TTLL3A, TTLL3B, TTLL3C, TTLL3D, TTLL3E, and TTLL3F.

10. The *Tetrahymena* cell of claim 1 which is selected from the group consisting of a TTLL6A/TTLL6F knockout cell, a TTLL6A/TTLL6B/TTLL6D/TTLL6F knockout cell, and a TTLL6A/TTLL6B/TTLL6D/TTLL6E/TTLL6F knock out cell.

11. The *Tetrahymena* cell of claim 1 which is selected from the group consisting of a TTLL3A/TTLL3B knockout cell, a TTLL3A/TTLL3B/TTLL3C/TTLL3D knockout cell, and a TTLL3A/TTLL3B/TTLL3C/TTLL3D/TTLL3E/TTLL3F knockout cell.

12. A method for identifying an inhibitor of a glutamic acid ligase, the method comprising:
    contacting a cellular component isolated from the *Tetrahymena* cell of claim 1 with a candidate inhibitor compound and a glutamic acid ligase; and
    detecting a change in glutamylation of the cellular component, wherein the absence of additional glutamylation is indicative of a compound that inhibits glutamic acid ligase.

13. The method of claim 12 wherein the cellular component is selected from the group consisting of an axoneme, a microtubule, a stabilized microtubule and a tubulin.

14. A method for identifying an inhibitor of a glycine ligase, the method comprising:
    contacting a cellular component isolated from the *Tetrahymena* cell of claim 1 with a candidate inhibitor compound and a glycine ligase; and
    detecting a change in glycylation of the cellular component, wherein the absence of additional glycylation is indicative of a compound that inhibits glycine ligase.

15. The method of claim 14 wherein the cellular component is selected from the group consisting of an axoneme, a microtubule, a stabilized microtubule and a tubulin.

16. A genetically engineered *Tetrahymena* cell comprising a disruption of at least two paralogs of TTLL6 or TTLL3; wherein the disruption is the result of homologous recombination, and wherein said cell expresses tubulin exhibiting reduced polymodification compared to a wild-type *Tetrahymena* cell.

* * * * *